(12) United States Patent
Kim et al.

(10) Patent No.: US 11,667,622 B2
(45) Date of Patent: Jun. 6, 2023

(54) ORGANIC LIGHT EMITTING COMPOUND AND ORGANIC ELECTROLUMINESCENCE DEVICE USING SAME

(71) Applicant: SOLUS ADVANCED MATERIALS CO., LTD., Iksan-si (KR)

(72) Inventors: Hongsuk Kim, Yongin-si (KR); Young Bae Kim, Yongin-si (KR); Hoe Moon Kim, Yongin-si (KR); Ho Jun Son, Yongin-si (KR); Hyungchan Bae, Yongin-si (KR)

(73) Assignee: SOLUS ADVANCED MATERIALS CO., LTD., Iksan-si (KR)

( * ) Notice: Subject to any disclaimer, the term of this patent is extended or adjusted under 35 U.S.C. 154(b) by 230 days.

(21) Appl. No.: 16/462,359

(22) PCT Filed: Nov. 21, 2017

(86) PCT No.: PCT/KR2017/013248
§ 371 (c)(1),
(2) Date: May 20, 2019

(87) PCT Pub. No.: WO2018/093231
PCT Pub. Date: May 24, 2018

(65) Prior Publication Data
US 2019/0367477 A1    Dec. 5, 2019

(30) Foreign Application Priority Data
Nov. 21, 2016   (KR) .................. 10-2016-0155319

(51) Int. Cl.
*C07D 401/10*    (2006.01)
*C07D 405/14*    (2006.01)
(Continued)

(52) U.S. Cl.
CPC ......... *C07D 401/10* (2013.01); *C07D 213/06* (2013.01); *C07D 401/04* (2013.01);
(Continued)

(58) Field of Classification Search
None
See application file for complete search history.

(56) References Cited

U.S. PATENT DOCUMENTS

2016/0351817 A1* 12/2016 Kim .................... H01L 51/006
2018/0226587 A1*  8/2018 Parham ............... C07D 409/04

FOREIGN PATENT DOCUMENTS

| CN | 101395105 A | 3/2009 |
| CN | 104428283 A | 3/2015 |

(Continued)

OTHER PUBLICATIONS

International Search Report for PCT/KR2017/013248 dated Feb. 22, 2018 [PCT/ISA/210].
(Continued)

*Primary Examiner* — Jay Yang
(74) *Attorney, Agent, or Firm* — Sughrue Mion, PLLC

(57) ABSTRACT

The present invention relates to a novel compound having excellent functions, such as electron injection and transport and light emission functions, and an organic electroluminescence device. By using the novel compound in an organic material layer of the organic electroluminescence device, properties of the device such a light emitting efficiency, driving voltage, and life can be improved.

10 Claims, 1 Drawing Sheet

(51) Int. Cl.
   *C07D 401/04* (2006.01)
   *C07D 409/04* (2006.01)
   *C07F 5/02* (2006.01)
   *C07D 409/10* (2006.01)
   *C07D 213/06* (2006.01)
   *C07D 405/04* (2006.01)
   *H01L 51/00* (2006.01)
   *H01L 51/50* (2006.01)

(52) U.S. Cl.
   CPC ......... *C07D 405/04* (2013.01); *C07D 405/14* (2013.01); *C07D 409/04* (2013.01); *C07D 409/10* (2013.01); *C07F 5/025* (2013.01); *H01L 51/0054* (2013.01); *H01L 51/0056* (2013.01); *H01L 51/0058* (2013.01); *H01L 51/0072* (2013.01); *H01L 51/5012* (2013.01); *H01L 51/5056* (2013.01); *H01L 51/5072* (2013.01); *H01L 51/5092* (2013.01)

(56) References Cited

FOREIGN PATENT DOCUMENTS

| | | |
|---|---|---|
| CN | 105321984 A | 2/2016 |
| CN | 106206964 A | 12/2016 |
| CN | 106206999 A | 12/2016 |
| EP | 2 983 227 A1 | 2/2016 |
| JP | 2015-216245 A | 12/2015 |
| KR | 10-2014-0012598 A | 2/2014 |
| KR | 10-2016-0055557 A | 5/2016 |
| WO | 2011/010843 A1 | 1/2011 |
| WO | 2014/061963 A1 | 4/2014 |
| WO | WO-2017/016667 A1 * | 2/2017 |

OTHER PUBLICATIONS

Office Action dated Nov. 5, 2021 from the China National Intellectual Property Administration in CN Application No. 201780071908.3.

* cited by examiner

ORGANIC LIGHT EMITTING COMPOUND AND ORGANIC ELECTROLUMINESCENCE DEVICE USING SAME

CROSS REFERENCE TO RELATED APPLICATIONS

This application is a National Stage of International Application No. PCT/KR2017/013248 filed Nov. 21, 2017, claiming priority based on Korean Patent Application Nos. 10-2016-0155319 filed Nov. 21, 2016.

TECHNICAL FIELD

The present disclosure relates to a novel organic light-emitting compound and an organic electroluminescent device using the same and, more particularly, to an anthracene-based compound having excellent electron injection and transport and light-emitting abilities, and an organic electroluminescent device containing the compound in at least one organic material layer thereof and having improved properties including emission efficiency, driving voltage, lifespan, etc.

BACKGROUND ART

In an organic electroluminescent element (hereinafter referred to as "organic EL device"), the application of a current or voltage across two opposite electrodes induces the injection of holes from the anode and electrons from the cathode into an organic material layer. The injected holes and electrons recombine with each other to generate excitons which then return to the ground state, emitting light. According to kinds of electron spin of the excitons formed, the organic electroluminescent elements may be classified into fluorescent light-emitting elements in which decay of singlet excitons contributes to the production of light through spontaneous emission and phosphorescent light-emitting elements in which decay of triplet excitons contributes to the production of light through spontaneous emission.

Electron spin of excitons formed by the recombination of electrons and holes may either be in a singlet state or a triplet state at a ratio of 25% singlet state:75% triplet state. Fluorescent EL devices in which light is emitted by singlet excitons, theoretically does not exceed 25% in internal quantum efficiency and 5% in external quantum efficiency, based on the formation rate of a singlet excitons. When using as a phosphorescent host a metal complex compound including a heavy transition-metal atoms, such as Ir, Pt, etc., phosphorescent EL devices in which light is emitted by triplet exciton can exhibit emission efficiency four times as high as that of fluorescent light-emitting elements.

Theoretically, phosphorescent EL devices are higher in emission efficiency than fluorescent EL devices, as described above. In contrast to green or read phosphorescent EL devices, a host that meets the color purity of deep blue, high efficiency, and broad energy gap required in blue phosphorescent EL devices is underdeveloped and has not yet been commercialized so that blue fluorescent EL devices rather than blue phosphorescent EL devices have predominantly been employed in products thus far. For conventional blue fluorescent EL devices, studies have been directed toward using a material having substituents introduced at various positions of benzene rings as a sole host and a sole dopant so as to improve the emission color of the device, carrier transport properties, the stability of the film. For instance, DPVBi developed by Idemitsu Kosan or dinaphtylanthracene developed by Kodak is known as a blue fluorescent light-emitting layer material. However, such conventional blue fluorescent light-emitting layer materials are under a satisfactory level in terms of thermal stability and emission efficiency. Therefore, there is a need for the development of a luminescent material having an excellent performance.

DETAILED DESCRIPTION OF THE INVENTION

Technical Problem

An object of the present disclosure is to provide a novel organic compound that has excellent electron injection ability, electron transport ability, and luminescence ability and can be thus used as a light-emitting layer material or an electron transport auxiliary layer.

Another object of the present disclosure is to provide an organic electroluminescent device comprising the novel organic compound and exhibiting a low driving voltage, high emission efficiency, and improved lifespan.

Technical Solution

In order to accomplish the above objects, the present disclosure provides a compound represented by the following Formula 1:

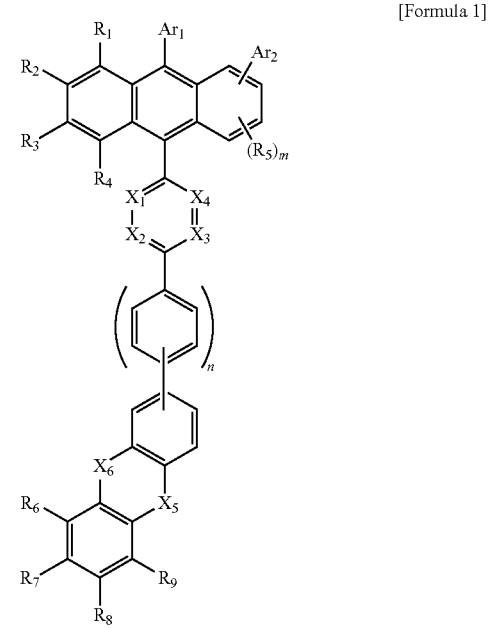

[Formula 1]

(wherein, $X_1$ to $X_4$, which are the same or different from each other, are each independently $C(Ar_3)$ or N, with the proviso that at least one of $X_1$ to $X_4$ is N, wherein when $Ar_3$ is present in a plural number, the plural $Ar_3$'s are the same or different from other;

n is an integer of 0 to 3;

$X_5$ is selected from the group consisting of S, O, $N(Ar_4)$, and $C(Ar_5)(Ar_6)$;

$X_6$ represents a single bond or is selected from the group consisting of S, O, $N(Ar_7)$, and $C(Ar_8)(Ar_9)$;

Ar$_1$ is selected from the group consisting of a C$_6$-C$_{60}$ aryl group and a heteroaryl group having 5 to 60 nucleus atoms, or may combines with an adjacent group to form a fused aromatic ring or fused heteroaromatic ring;

Ar$_2$ is selected from the group consisting of hydrogen, a C$_6$-C$_{60}$ aryl group, and a heteroaryl group having 5 to 60 nucleus atoms or combine with an adjacent group to form a fused aromatic ring or fused heteroaromatic ring;

Ar$_3$ to Ar$_9$, which are the same or different from each other, are each independently selected from the group consisting of hydrogen, deuterium (D), halogen, a cyano group, a nitro group, a C$_1$-C$_{40}$ alkyl group, a C$_2$-C$_{40}$ alkenyl group, a C$_2$-C$_{40}$ alkynyl group, a C$_3$-C$_{40}$ cycloalkyl group, a heterocycloalkyl group having 3 to 40 nucleus atoms, a C$_6$-C$_{60}$ aryl group, a heteroaryl group having 5 to 60 nucleus atoms, a C$_1$-C$_{40}$ alkyloxy group, a C$_6$-C$_{60}$ aryloxy group, a C$_1$-C$_{40}$ alkylsilyl group, a C$_6$-C$_{60}$ arylsilyl group, a C$_1$-C$_{40}$ alkylbron group, a C$_6$-C$_{60}$ arylboron group, a C$_6$-C$_{60}$ mono- or diarylphosphinyl group, and a C$_6$-C$_{60}$ arylamine group or each independently combine with an adjacent group to form a fused aromatic ring or fused heteroaromatic ring;

R$_1$ to R$_9$, which are the same or different, are each independently selected from the group consisting of hydrogen, deuterium (D), halogen, a cyano group, a nitro group, a C$_1$-C$_{40}$ alkyl group, a C$_2$-C$_{40}$ alkenyl group, a C$_2$-C$_{40}$ alkynyl group, a C$_3$-C$_{40}$ cycloalkyl group, a heterocycloalkyl group having 3 to 40 nucleus atoms, a C$_6$-C$_{60}$ aryl group, a heteroaryl group having 5 to 60 nucleus atoms, a C$_1$-C$_{40}$ alkyloxy group, a C$_6$-C$_{60}$ aryloxy group, a C$_1$-C$_{40}$ alkylsilyl group, a C$_6$-C$_{60}$ arylsilyl group, a C$_1$-C$_{40}$ alkylbron group, a C$_6$-C$_{60}$ arylboron group, a C$_6$-C$_{60}$ arylphosphine group, a C$_6$-C$_{60}$ mono- or diarylphosphinyl group, and a C$_6$-C$_{60}$ arylamine group or each independently combine with an adjacent group to form a fused aromatic ring or fused heteroaromatic ring; and m is an integer of 1 to 3;

wherein the aryl group and the heteroaryl group in Ar$_1$ and Ar$_2$ are each independently unsubstituted or substituted with one or more substituent selected from the group consisting of a C$_1$-C$_{40}$ alkyl group, a C$_6$-C$_{60}$ aryl group, and a heteroaryl group having 5 to 60 nucleus atoms wherein the two or more substituents, if present, are the same or different from each other).

In addition, the present disclosure provides an organic electroluminescent device comprising an anode, a cathode and at least one organic material layer interposed therebetween, wherein the at least one organic material layer includes the compound represented by Formula 1 therein.

According to an embodiment, the at least one organic material layer may comprise a hole injection layer, a hole transport layer, a light-emitting layer, an electron transport layer, and an electron injection layer wherein the light-emitting layer may include the compound represented by Formula 1.

According to another embodiment, the at least one organic material layer may comprise a hole transport layer, a hole injection layer, a light-emitting layer, an electron transport auxiliary layer, an electron transport layer, and an electron injection layer wherein the electron transport auxiliary layer may include the compound.

Advantageous Effects

Exhibiting excellent electron injection and transport and luminescence properties, the compound, represented by Formula 1, according to the present disclosure can be used as a material for an organic material layer in an organic electroluminescent device.

Employing the compound represented by Formula 1 as a fluorescent host material or an electron transport auxiliary layer material, the organic electroluminescent device according to the present invention exhibits a higher luminescence performance, a lower driving voltage, a higher emission efficiency, and a longer lifespan than those comprising conventional host materials and can thus improve the performance and lifespan of the full-color display panels.

MODE FOR CARRYING OUT THE INVENTION

Below, a detailed description will be given of the present invention.

<Novel Organic Compound>

The compound, represented by Formula 1, according to the present disclosure has an anthracene as a basic structure in which a heteroaromatic ring moiety or aromatic ring moiety consisting of three or more rings, such as a dibenzofuran moiety, a benzocarbazole moiety, a fluorene moiety, a dioxin moiety, etc. is introduced onto the carbon atom at position 10 in the anthracene moiety through a divalent linker comprising nitrogen (N)-containing six-membered heteroarylene group while an aromatic ring or heteroaromatic ring is directly connected to the carbon atom at position 9 in the anthracene moiety. The compound represented by Formula 1 is superior in terms of electron transport and injection ability and luminescence ability. When included in an organic electroluminescent device, therefore, the compound of Formula 1 can improve the device in driving voltage, emission efficiency, lifespan, etc. Here, numbering of the anthracene molecule is as follows:

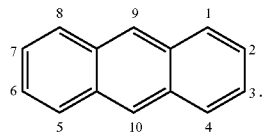

As the anthracene moiety has a broad bandgap, the compound represented by Formula 1 can be useful as a host material.

In addition, the compound represented by Formula 1 exhibits an excellent electron injection and transport performance because the heteroaromatic ring moiety or aromatic ring moiety consisting of three or more rings is coupled with the divalent linker comprising the N-containing six-membered heteroarylene group, which is an electron withdrawing group (EWG) with high electron absorption, therein.

Figure 1:
FIGS. 1 to 3 are diagrams illustrating electron distributions of compounds R95, C1, and C2, respectively.

Furthermore, the compound of Formula 1 to which the N-containing six-membered heteroarylene group is directly introduced at position 10 on the anthracene moiety has an electron distribution expanded to the heteroarylene group and is lower in LUMO energy, compared to a compound having an arylene group bonded to the carbon atom at position 10 on the anthracene moiety or a compound to which a heteroarylene group is bonded via a linker other than directly. For example, as shown in FIG. 1, compound R95

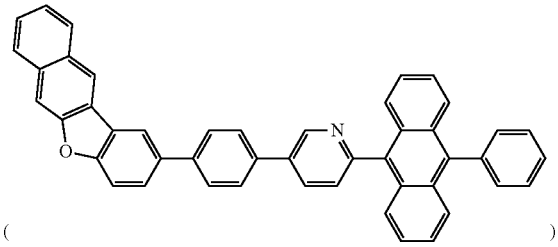 [SMILES: c1ccc(-c2c3ccccc3c(-c3ccc(-c4ccc(-c5ccc6oc7cc8ccccc8cc7c6c5)cc4)cn3)c3ccccc23)cc1]

exhibits an electron distribution expanded to the heteroarylene group and has a LUMO energy level of 1.66 eV and a HOMO e

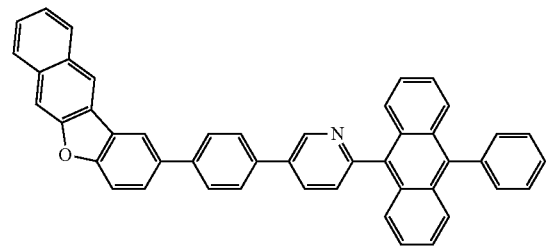 [SMILES: c1ccc(-c2c3ccccc3c(-c3ccc(-c4ccc(-c5ccc6oc7cc8ccccc8cc7c6c5)cc4)cn3)c3ccccc23)cc1]

nergy level of 1.73 eV. On the other hand, compound C1

Figure 2:
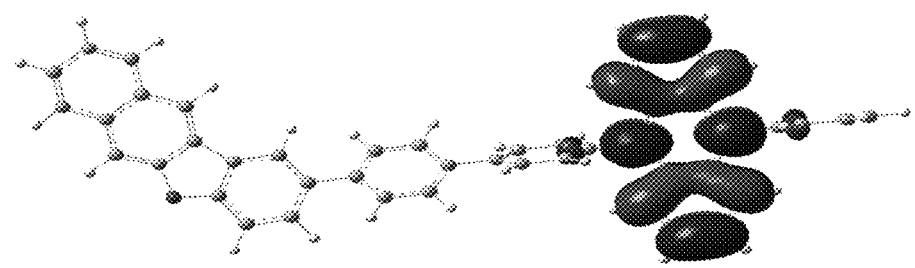
Figure 3:
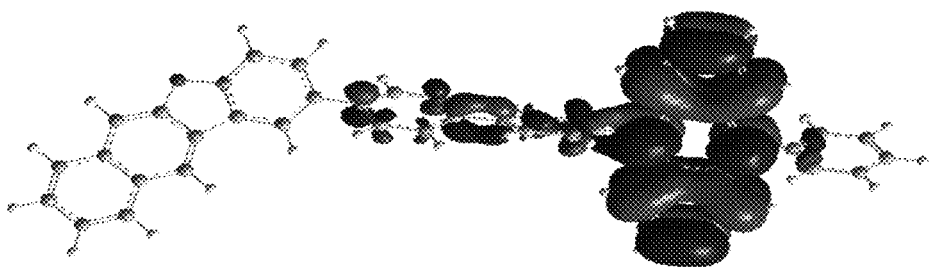


has a LUMO energy of 1.63 eV and a HOMO energy level of 1.73 eV and compound C2 has a LUMO energy level of 1.61 eV and a HOMO energy level of 1.71 eV (see FIGS. 2 and 3). Thus, when applied as an electron transport and injection layer to an organic luminescent device, the compound of Formula 1 can improve the device in driving voltage, emission efficiency, and lifespan.

Therefore, when the compound represented by Formula 1 is used as a light-emitting layer material (preferably, fluorescent host) or an electron transport auxiliary layer material in an organic electroluminescent device, recombination capability between holes and electrons in the light-emitting layer can be enhanced by the compound of Formula 1, thereby improving the device in driving voltage, emission efficiency, and lifespan and moreover maximizing the performance of the full-color organic EL panel.

In Formula 1, $X_1$ to $X_4$, which are the same or different, are each independently $C(Ar_3)$ or N, with the proviso that at least one of $X_1$ to $X_4$ is N; preferably one of $X_1$ to $X_4$ may be N and the others may be $C(Ar_3)$. In this regard, when $Ar_3$ is present in a plural number, they are the same or different from each other.

In Formula 1, n is an integer of 0 to 3 and preferably 0 or 1.

In Formula 1, $X_5$ is selected from the group consisting of S, O, $N(Ar_4)$, and $C(Ar_5)(Ar_6)$.

In Formula 1, $X_6$ represents a single bond or is selected from the group consisting of S, O, $N(Ar_7)$, and $C(Ar_8)(Ar_9)$, and preferably may represent a single bond.

In Formula 1, $Ar_1$ is selected from the group consisting of a $C_6$-$C_{60}$ aryl group and a heteroaryl group having 5 to 60 nucleus atoms or combine with an adjacent group to form a fused aromatic ring or fused heteroaromatic ring, preferably is selected from the group consisting of a $C_6$-$C_{60}$ aryl group and a heteroaryl group having 5 to 60 nucleus atoms and more preferably from the group consisting of a $C_6$-$C_{30}$ aryl group and a heteroaryl group of 5 to 30 nucleus atoms.

In Formula 1, $Ar_2$ is selected from the group consisting of hydrogen, a $C_6$-$C_{60}$ aryl group, and a heteroaryl group having 5 to 60 nucleus atoms or combine with an adjacent group to form a fused aromatic ring or fused heteroaromatic ring, preferably is selected from the group consisting of hydrogen, a $C_6$-$C_{60}$ aryl group, and a heteroaryl group having 5 to 60 nucleus atoms, and more preferably from the group consisting of hydrogen, a $C_6$-$C_{30}$ aryl group, and a heteroaryl group of 5 to 30 nucleus atoms.

In this regard, the aryl group and the heteroaryl group in $Ar_1$ and $Ar_2$ are each independently unsubstituted or substituted with one or more substituents selected from the group consisting of a $C_1$-$C_{40}$ alkyl group (preferably, a $C_1$-$C_{20}$ alkyl group), a $C_6$-$C_{60}$ aryl group (preferably, a $C_6$-$C_{30}$ aryl group), and a heteroaryl group having 5 to 60 nucleus atoms (preferably, a heteroaryl group of 5 to 30 nucleus atoms), wherein the two or more substituents, if present, are the same or different from each other.

In Formula 1, $Ar_3$ to $Ar_9$, which are the same or different from each other, are each independently selected from the group consisting of hydrogen, deuterium (D), halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nucleus atoms, a $C_6$-$C_{60}$ aryl group, a heteroaryl group having 5 to 60 nucleus atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylbron group, a $C_6$-$C_{60}$ arylboron group, a $C_6$-$C_{60}$ mono- or diarylphosphinyl group, and a $C_6$-$C_{60}$ arylamine group or each independently combine with an adjacent group to form a fused aromatic ring or fused heteroaromatic ring.

Preferably, $Ar_3$ to $Ar_9$ are each independently selected from the group consisting of hydrogen, deuterium (D), a $C_1$-$C_{40}$ alkyl group, a $C_6$-$C_{60}$ aryl group, and a heteroaryl group having 5 to 60 nucleus atoms or each independently combine with an adjacent group to form a $C_5$-$C_{30}$ fused aromatic ring or an O-, S-, or N-containing 5- to 30-membered fused heteroaromatic ring.

More preferably, $Ar_3$ to $Ar_9$ are each independently selected from the group consisting of hydrogen, deuterium (D), a $C_1$-$C_{20}$ alkyl group, a $C_6$-$C_{30}$ aryl group, and a heteroaryl group of 5 to 30 nucleus atoms or each independently combine with an adjacent group to form a $C_5$-$C_{30}$ fused aromatic ring or an O-, S-, or N-including 5- to 30-membered fused heteroaromatic ring. For instance, when $X_5$ is $C(Ar_5)(Ar_6)$, $Ar_5$ and $Ar_6$ may combine with each other to form a fused aromatic ring or fused heteroaromatic ring such as a spiro-acridine group, a spiro-fluorene group, a spiro-xanthene group, etc.

In Formula 1, $R_1$ to $R_5$, which are the same or different from each other, are each independently selected from the group consisting of hydrogen, deuterium (D), halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nucleus atoms, a $C_6$-$C_{60}$ aryl group, a heteroaryl group having 5 to 60 nucleus atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylbron group, a $C_6$-$C_{60}$ arylboron group, a $C_6$-$C_{60}$ arylphosphine group, a $C_6$-$C_{60}$ mono- or diarylphosphinyl group, and a $C_6$-$C_{60}$ arylamine group or each independently combine with an adjacent group to form a fused aromatic ring or fused heteroaromatic ring. In this regard, when $R_5$ is present in a plural number, they are the same or different from each other.

Preferably, $R_1$ to $R_5$ may each be independently selected from the group consisting of hydrogen, deuterium (D), a $C_6$-$C_{60}$ aryl group, and a heteroaryl group having 5 to 60 nucleus atoms and more preferably from the group consisting of hydrogen, deuterium (D), a $C_6$-$C_{30}$ aryl group, and a heteroaryl group of 5 to 30 nucleus atoms. In this regard, when $R_5$ is present in a plural number, they are the same or different from each other.

In Formula 1, $R_6$ to $R_9$, which are the same or different from each other, are each independently selected from the group consisting of hydrogen, deuterium (D), halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nucleus atoms, a $C_6$-$C_{60}$ aryl group, a heteroaryl group having 5 to 60 nucleus atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylbron group, a $C_6$-$C_{60}$ arylboron group, a $C_6$-$C_{60}$ mono- or diarylphosphinyl group, and a $C_6$-$C_{60}$ arylamine group or at least one pair of $R_6$ and $R_7$, $R_7$ and $R_8$, and $R_8$ and $R_9$ may combine with each other to form a fused aromatic ring or fused heteroaromatic ring.

Preferably, $R_6$ to $R_9$ may each be independently hydrogen or at least one pair of $R_6$ and $R_7$, $R_7$ and $R_8$, and $R_8$ and $R_9$ may combine with each other to form a $C_6$-$C_{60}$ fused aromatic ring or a 5- to 60-membered fused heteroaromatic ring.

More preferably, $R_6$ to $R_9$ may each be independently hydrogen or at least one pair of $R_6$ and $R_7$, $R_7$ and $R_8$, and $R_8$ and $R_9$ may combine with each other to form a $C_6$-$C_{30}$ fused aromatic ring or a 5- to 30-membered fused heteroaromatic ring.

m is an integer of 1 to 3.

The compound represented by Formula 1 may be exemplified by one of Formulas 2 to 5, but is not limited thereto:

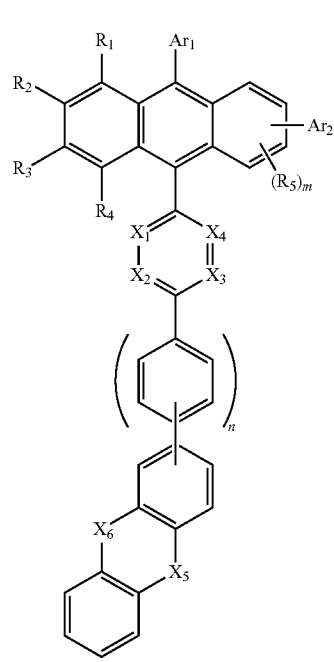

[Formula 2]

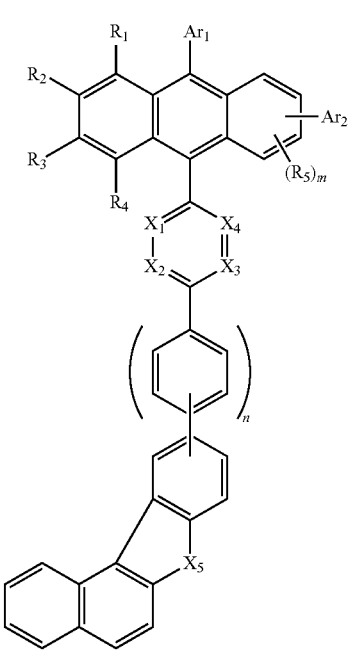

[Formula 3]

[Formula 4]

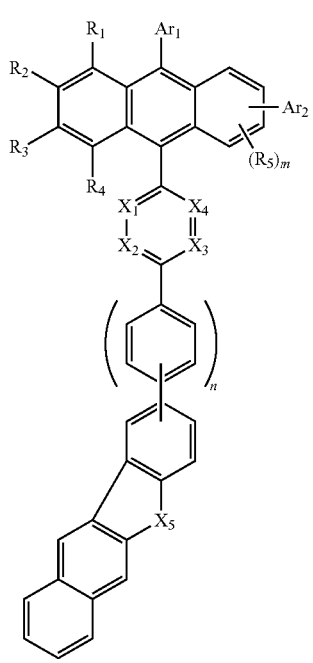

[Formula 5]

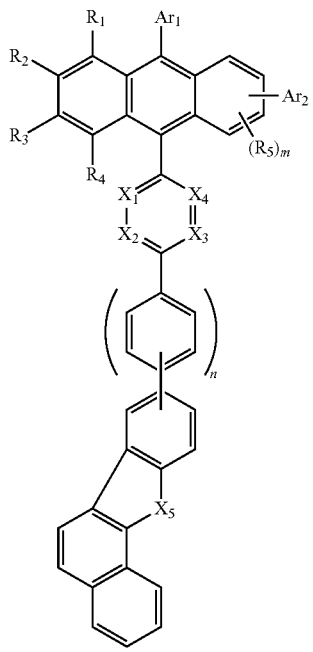

wherein,
R₁ to R₅, X₁ to X₅, Ar₁, Ar₂, m, and n are each the same as those defined in Formula 1.

Examples of the compound represented by Formula 2 include, but are not limited to, compound represented by the following Formula 6:

[Formula 6]

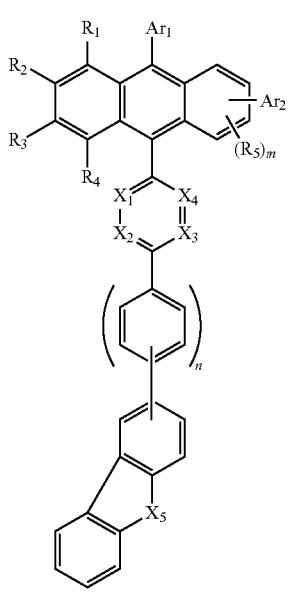

wherein,
$R_1$ to $R_5$, $X_1$ to $X_5$, $Ar_1$, $Ar_2$, m, and n are each the same as those defined in Formula 1.

Examples of the compound represented by Formula 6 include, but are not limited to, compound represented by the following Formula 7:

[Formula 7]

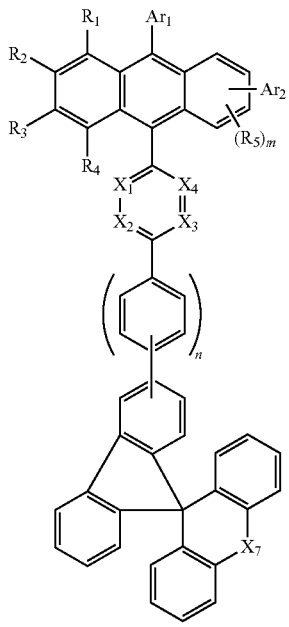

wherein,
$R_1$ to $R_5$, $X_1$ to $X_4$, $Ar_1$, $Ar_2$, m, and n are each the same as those defined in Formula 1, $X_7$ represents a single bond or is selected from the group consisting of S, O, $N(Ar_{10})$, and $C(Ar_{11})(Ar_{12})$, and $Ar_{10}$ to $Ar_{12}$, which are the same or different from each other, are each independently selected from the group consisting of hydrogen, deuterium (D), halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nucleus atoms, a $C_6$-$C_{60}$ aryl group, a heteroaryl group having 5 to 60 nucleus atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylbron group, a $C_6$-$C_{60}$ arylboron group, a $C_6$-$C_{60}$ mono- or diarylphosphinyl group, and a $C_6$-$C_{60}$ arylamine group.

Specific examples of the compound represented by Formula 1 of the present disclosure include Compounds R1 to R401 illustrated below, but are not limited thereto:

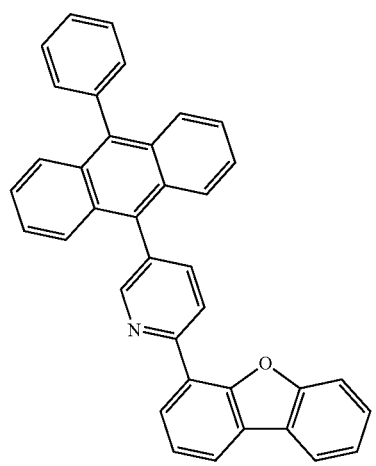

R1

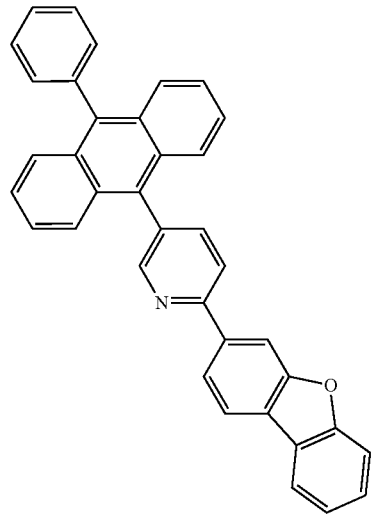

R2

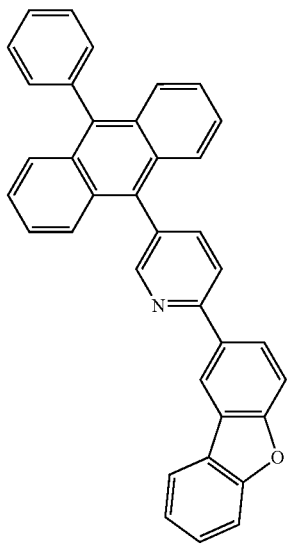

R3

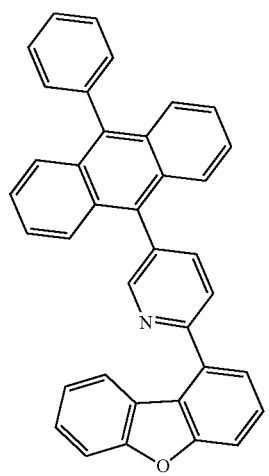

R4

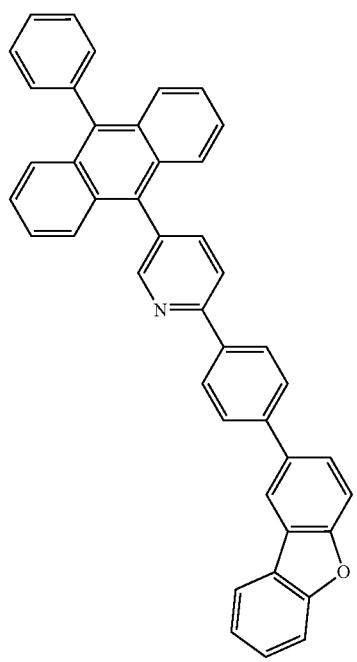

R5

R6
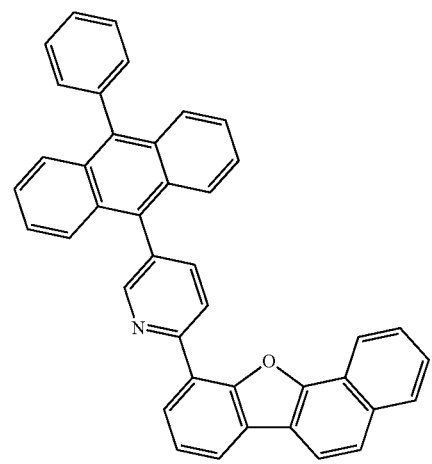
R7
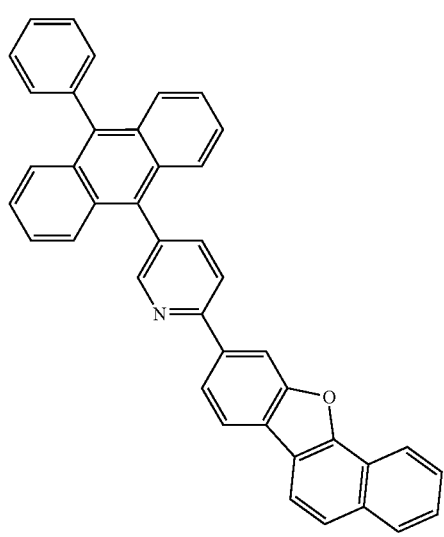
R8
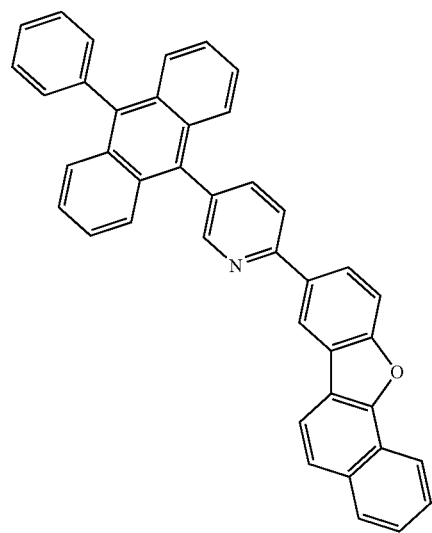
R9
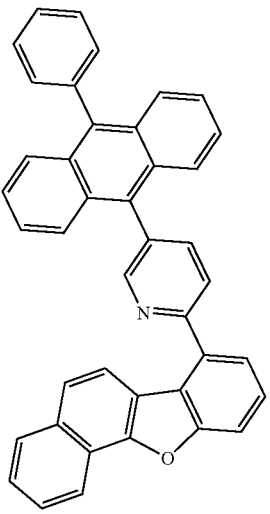
R10
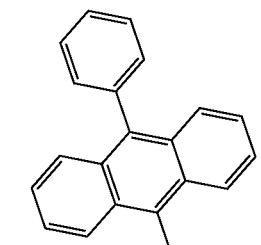
R11
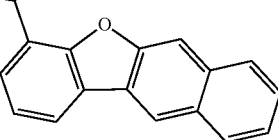

R12
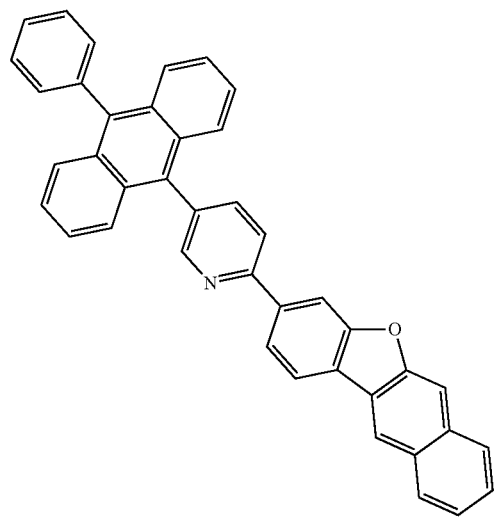
R13
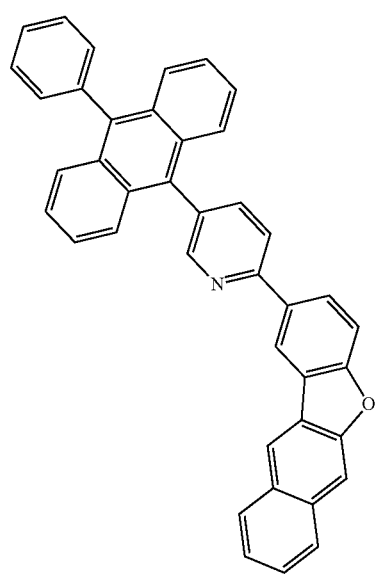
R14
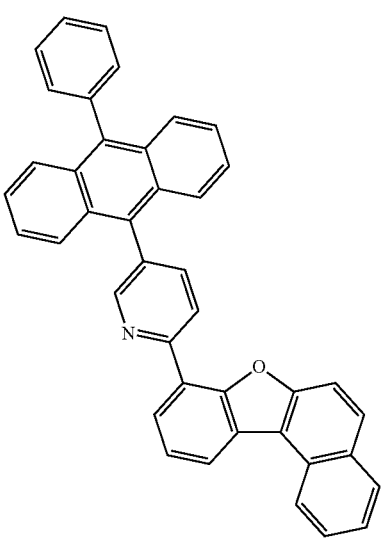
R15
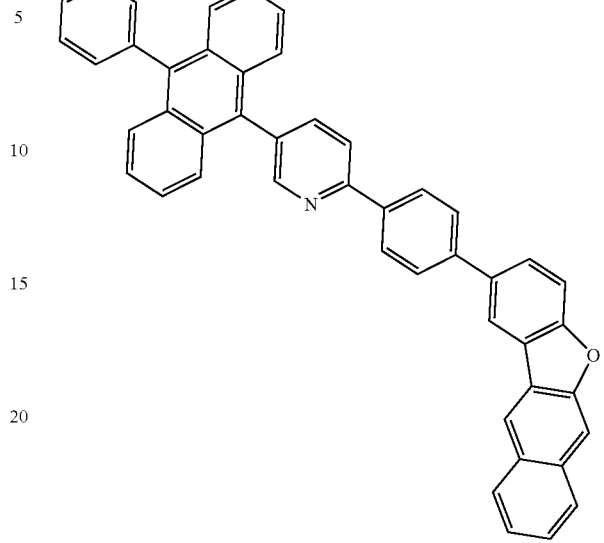
R16

R17
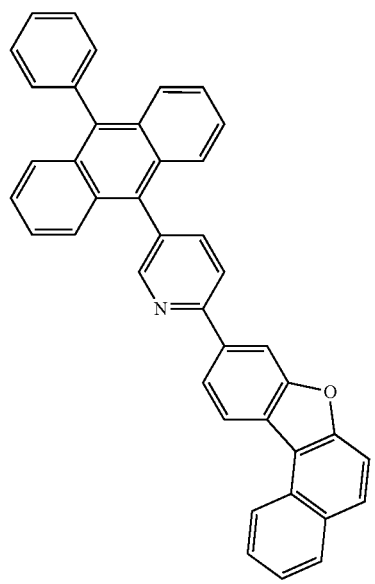
R18
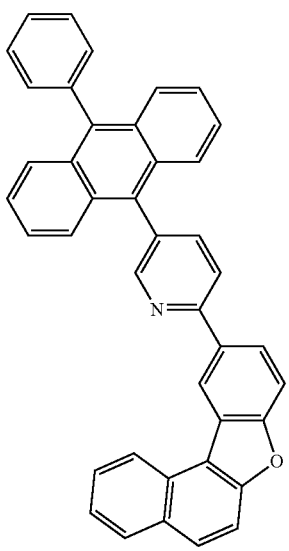
R19
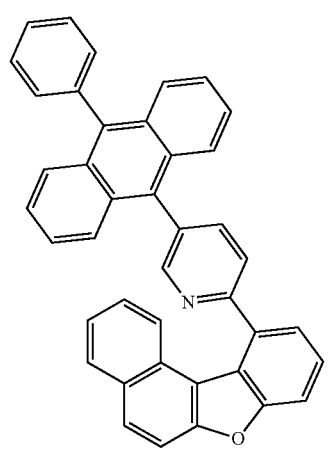
R20
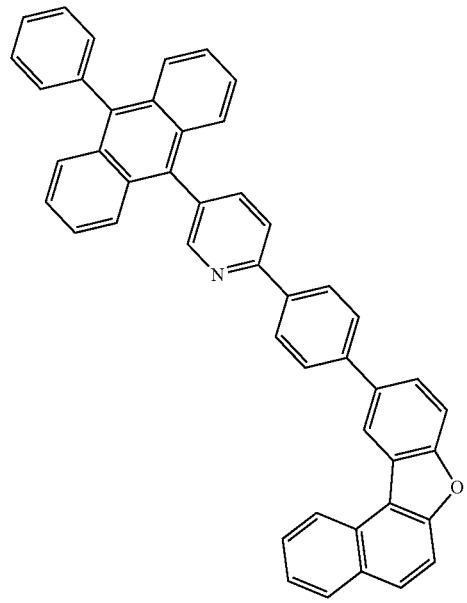
R21
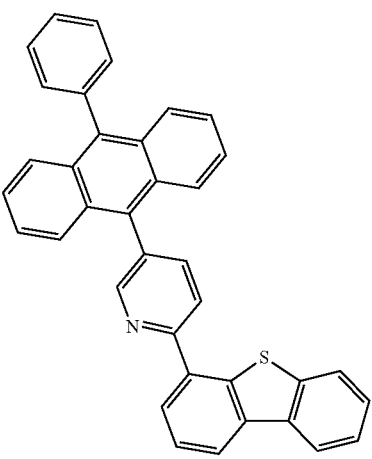
R22
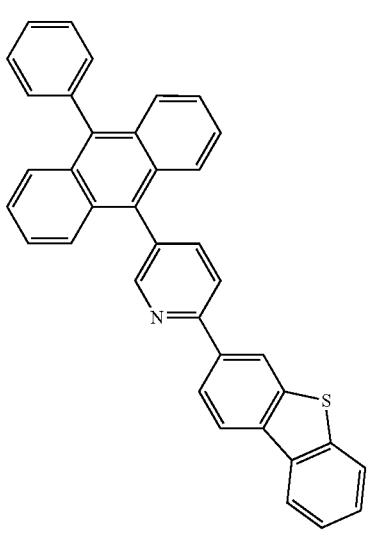

R23
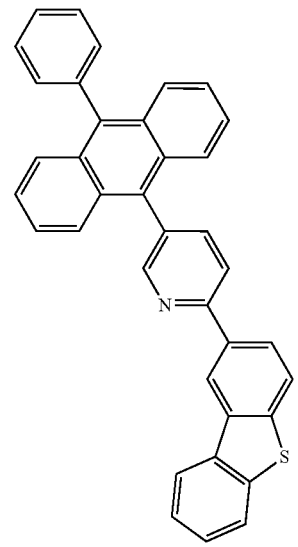
R24
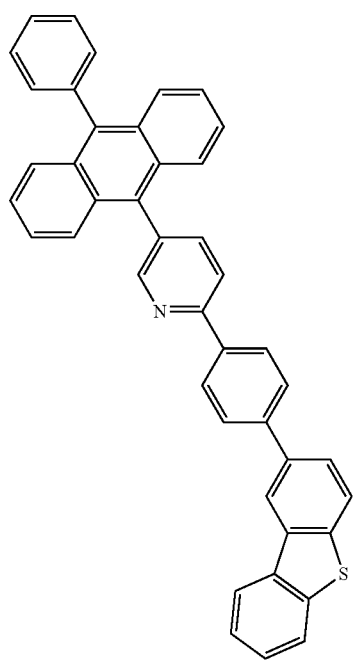
R25
R26
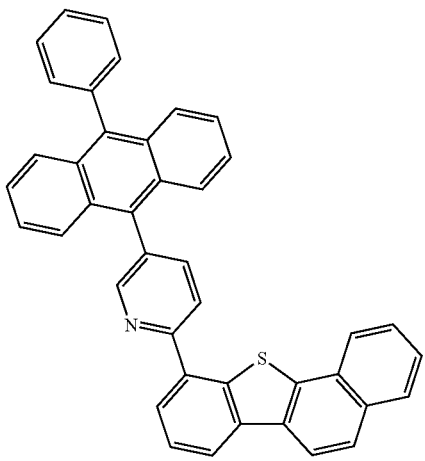
R27
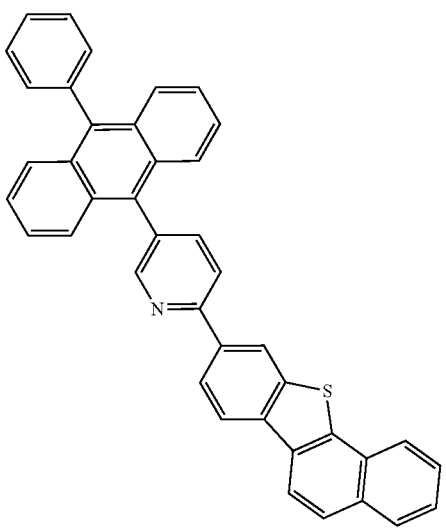
R28
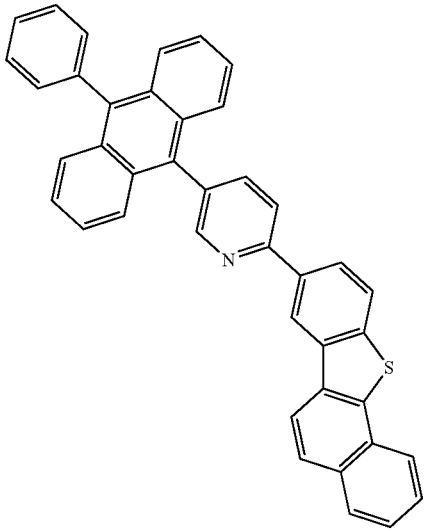

R29
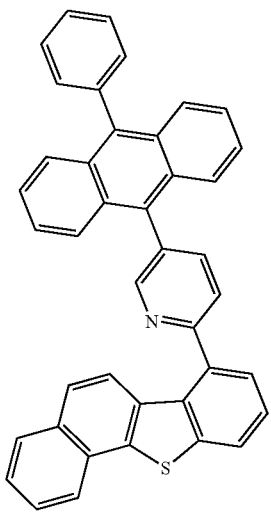
R30
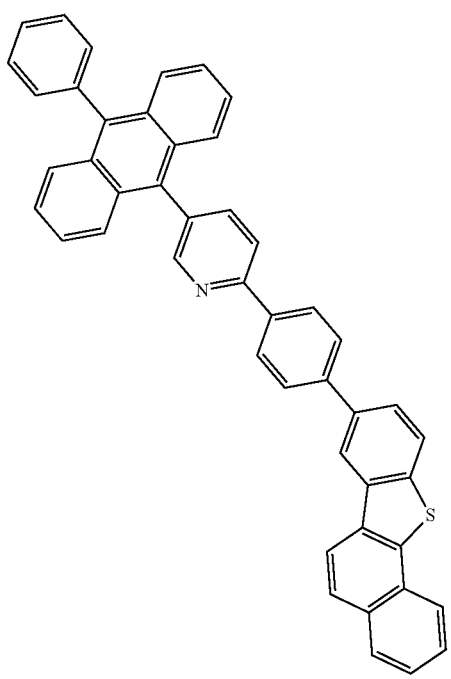
R31
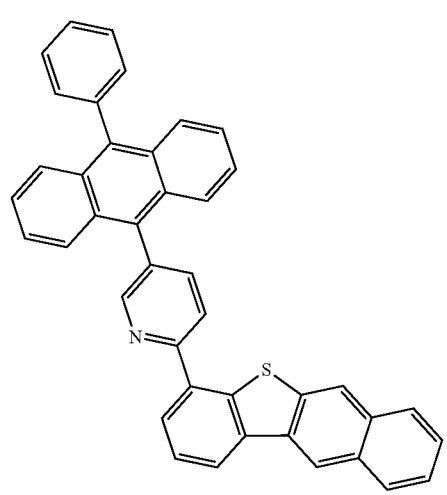
R32
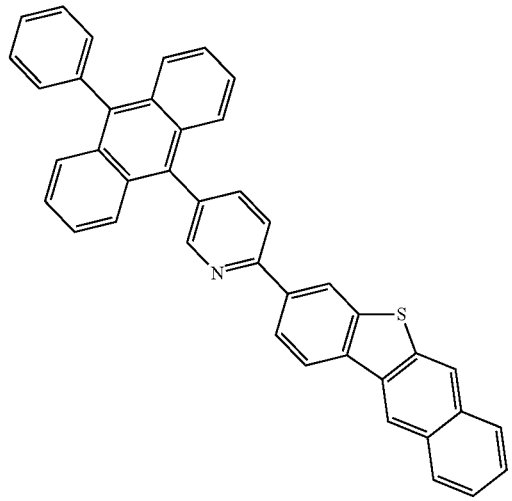
R33
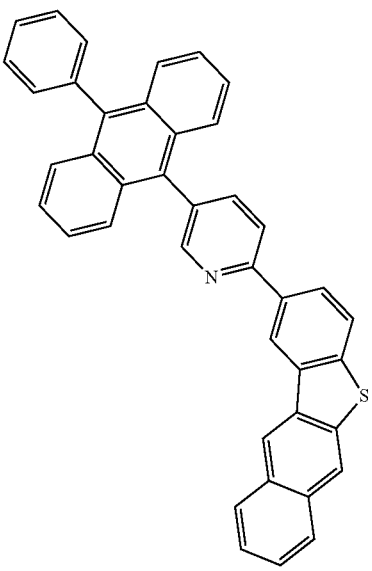
R34
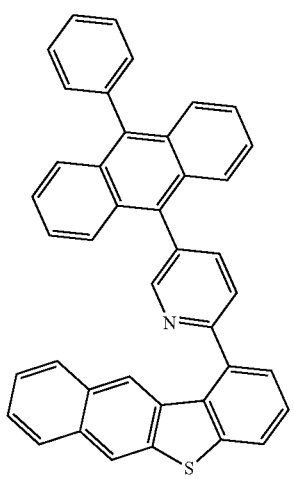

R35
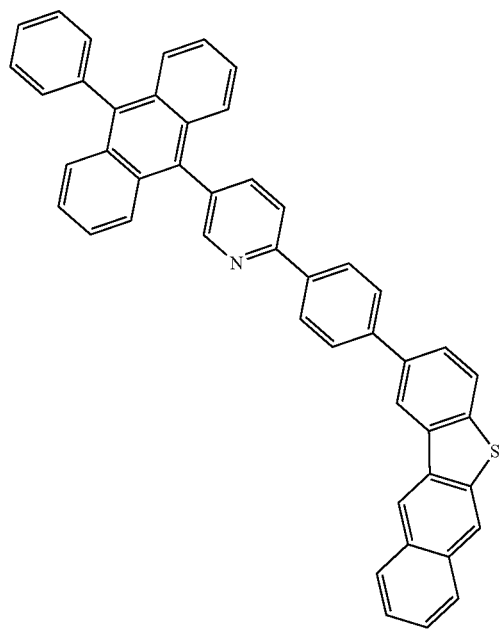
R36
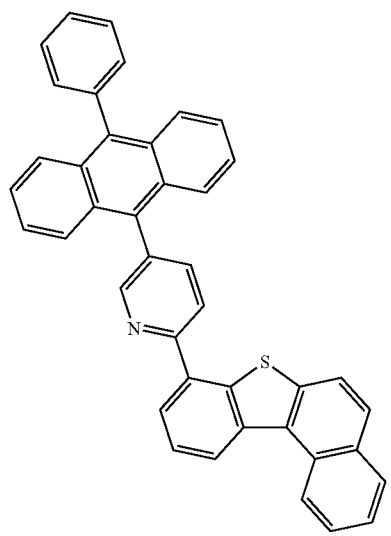
R37
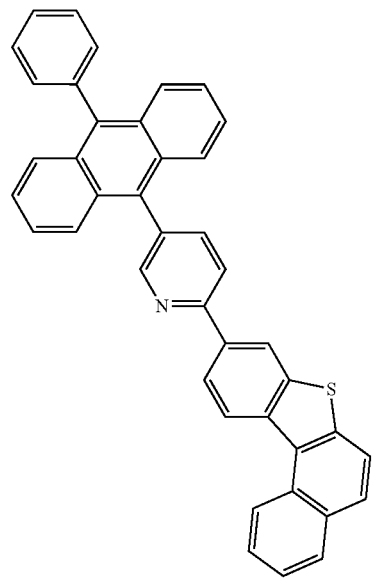
R38
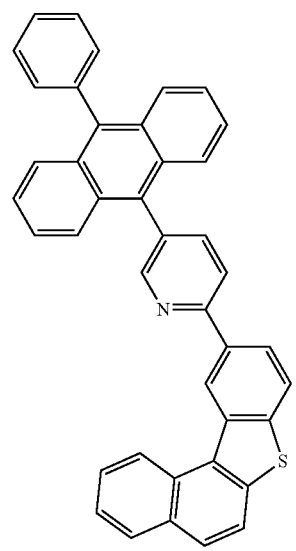
R39
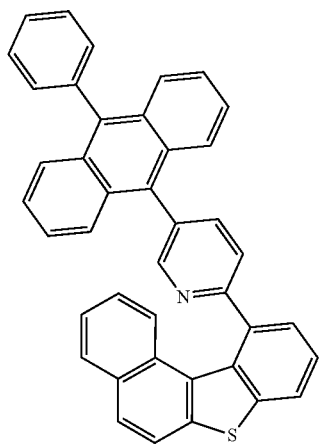

R40
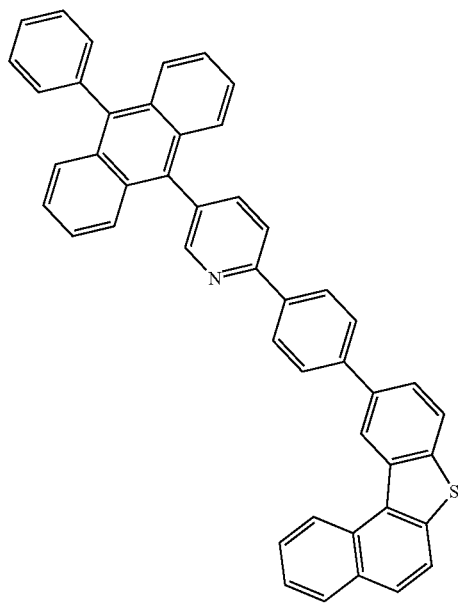
R41
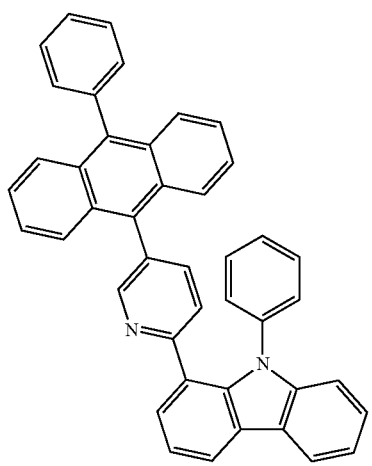
R42
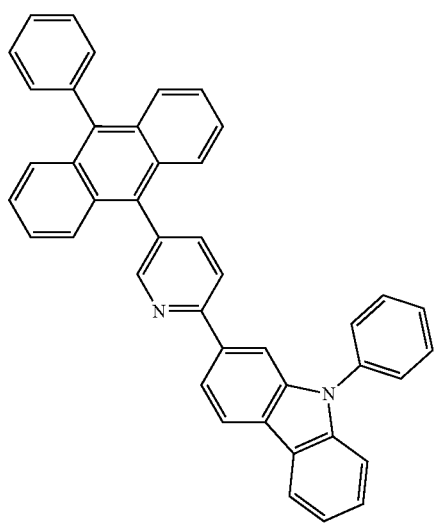
R43
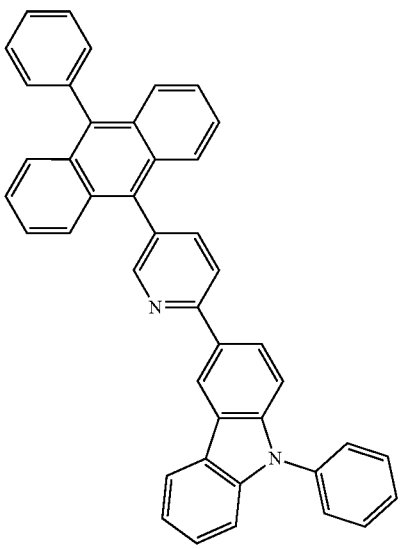
R44
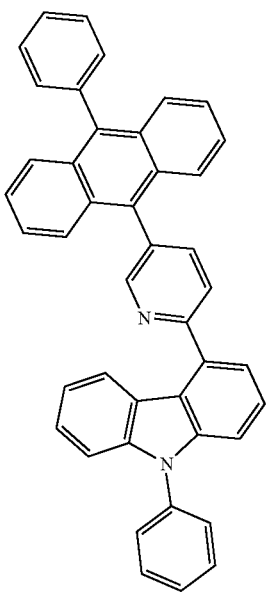

R45
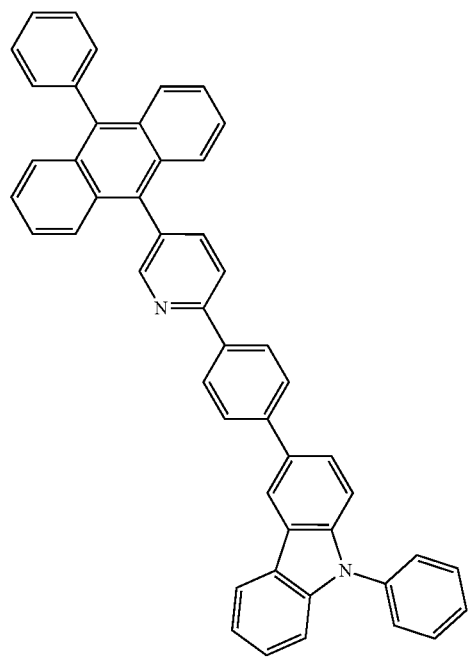
R48
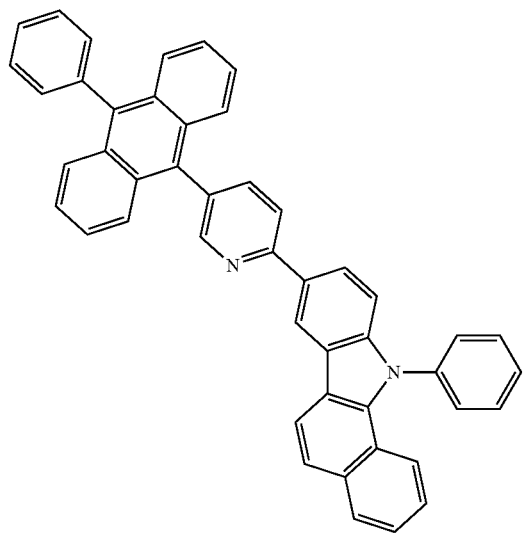
R46
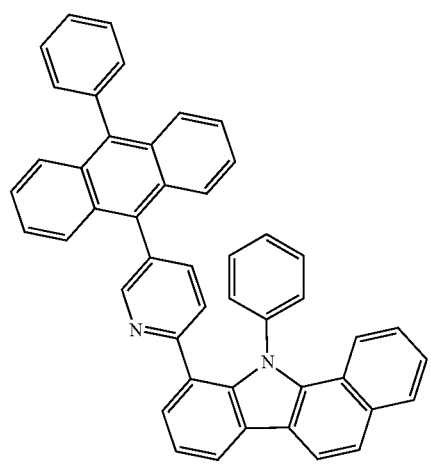
R47
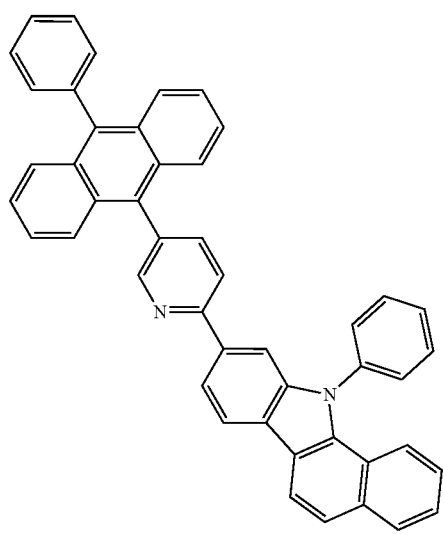
R49
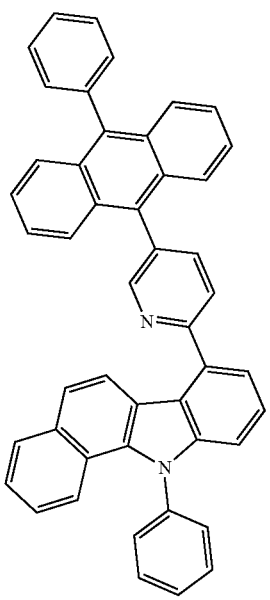

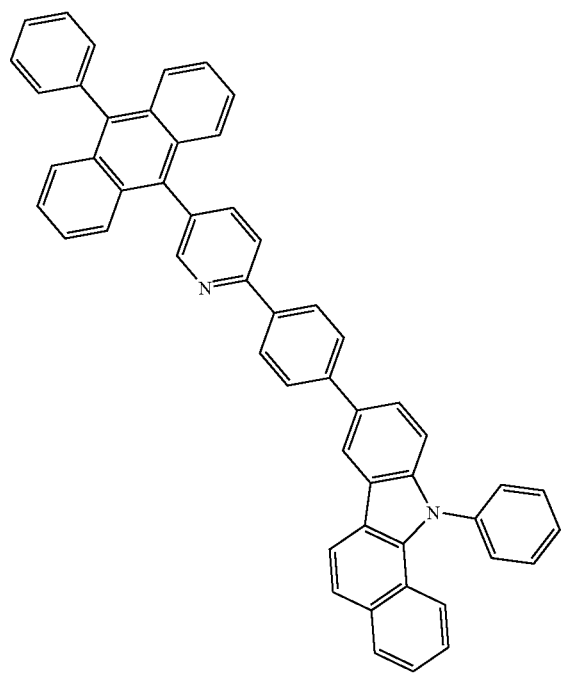
R50
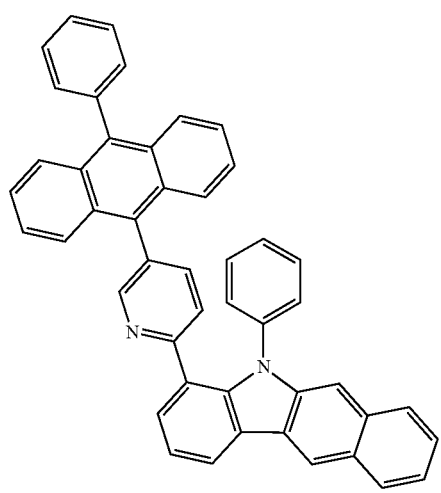
R51
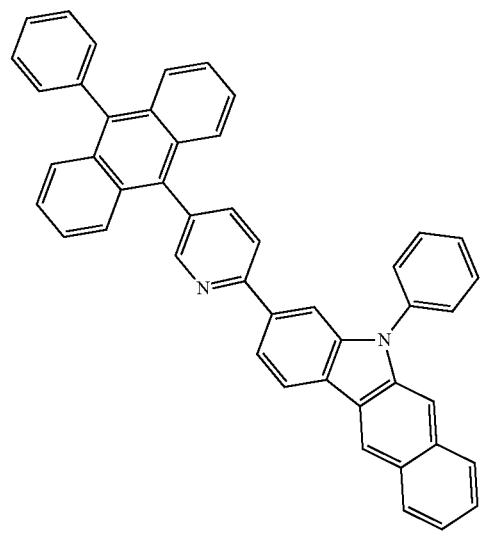
R52
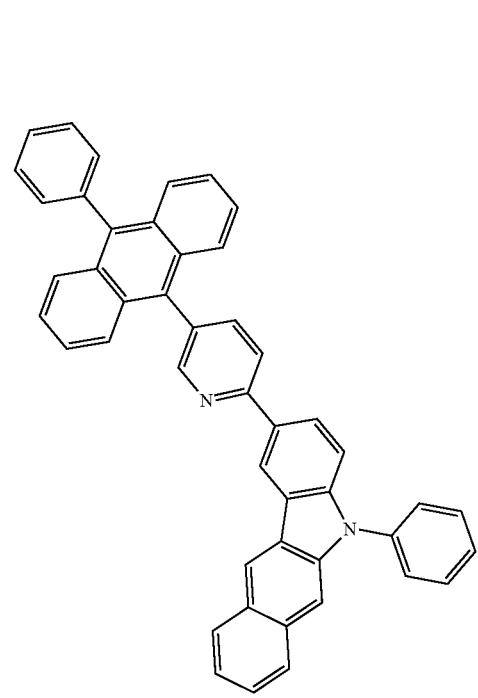
R53

R54
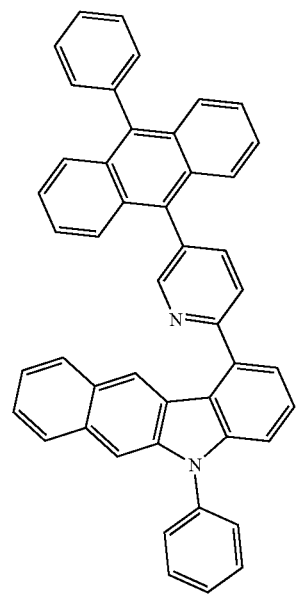
R55
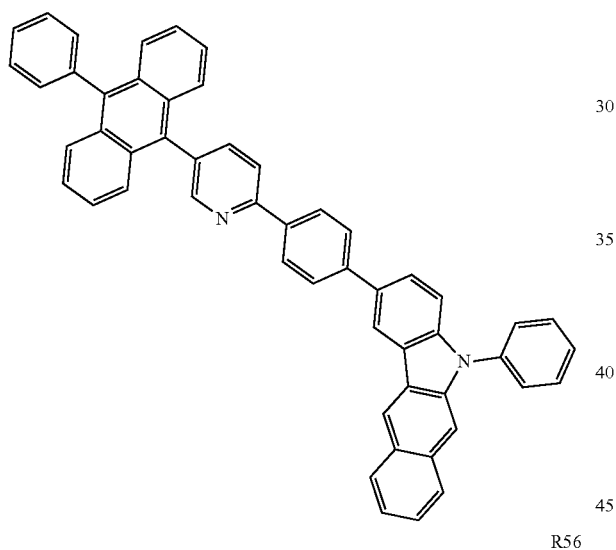
R56
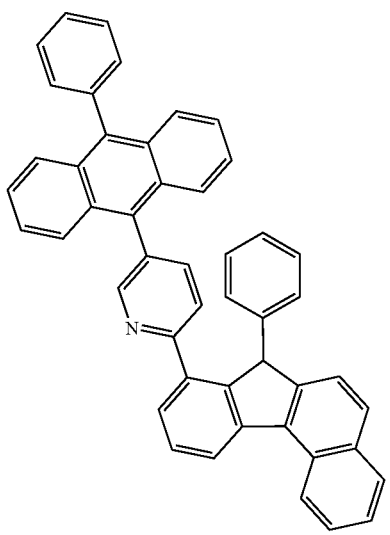
R57
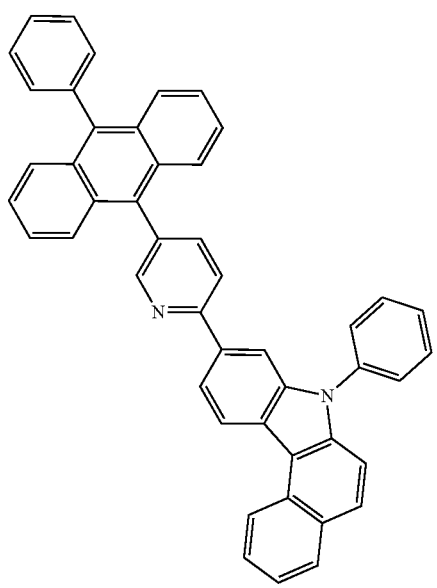
R58
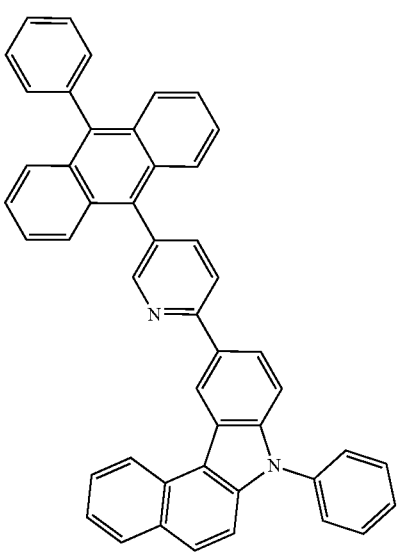

R59
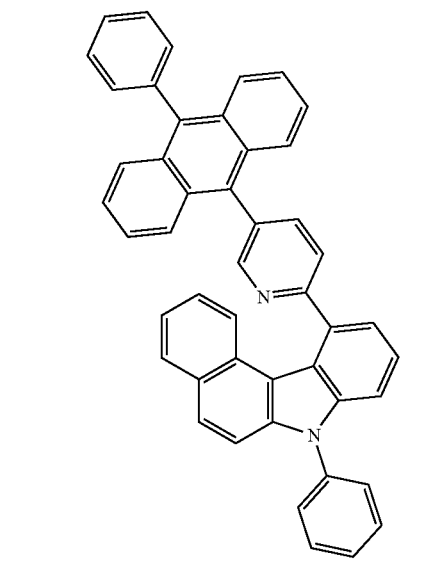
R60
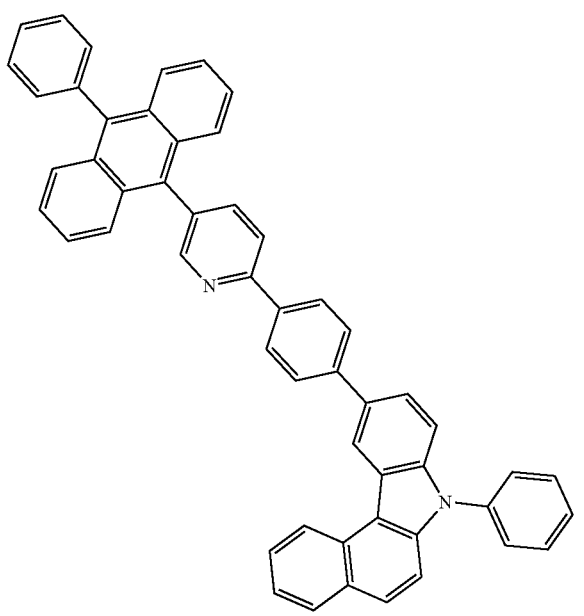
R61
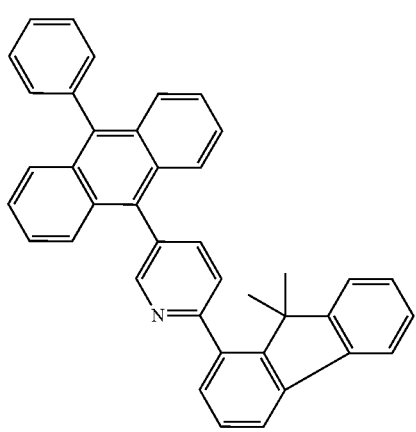
R62
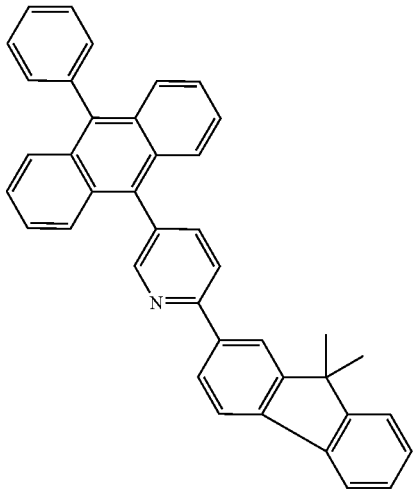
R63
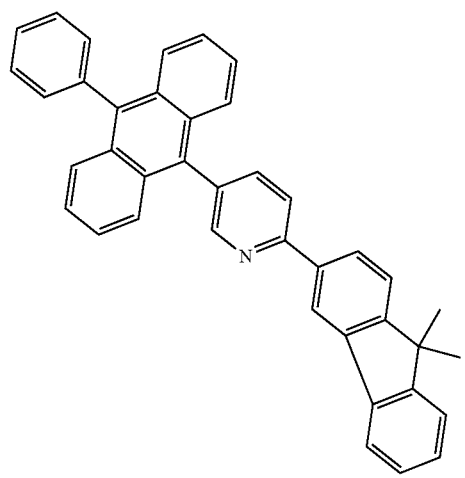
R64
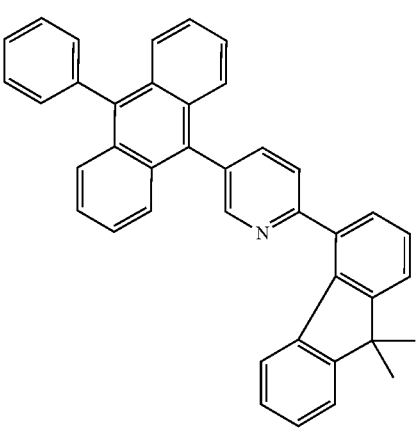

R65
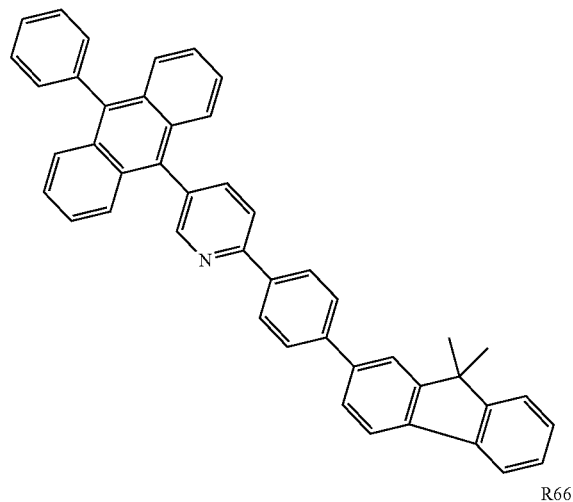
R66
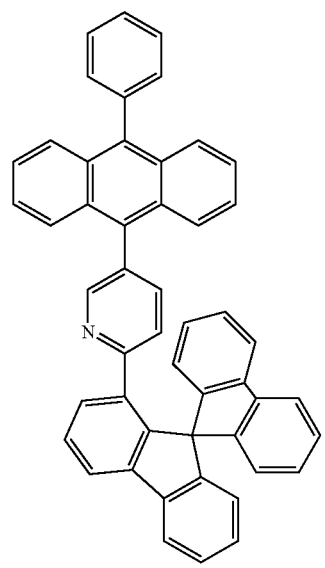
R67
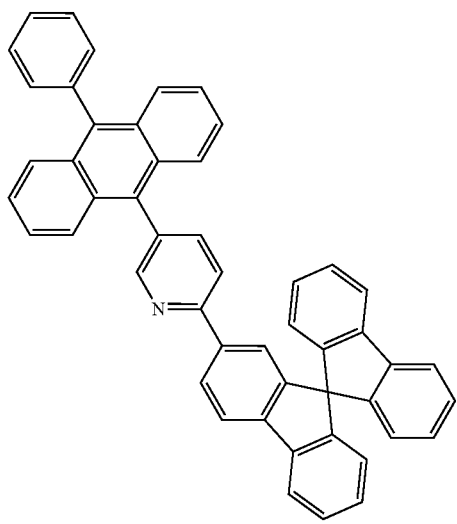
R68
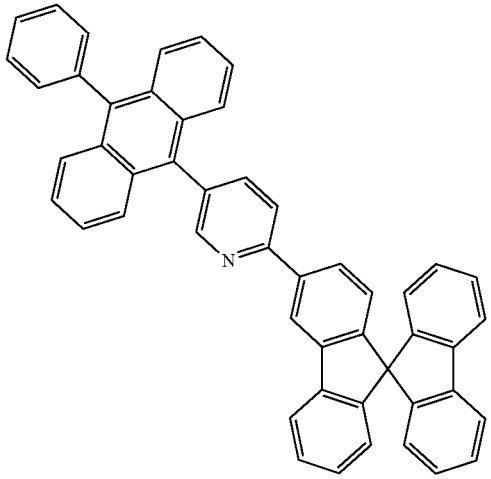
R69
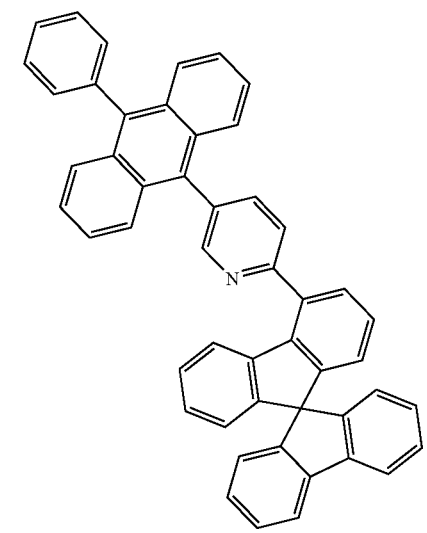
R70

R71
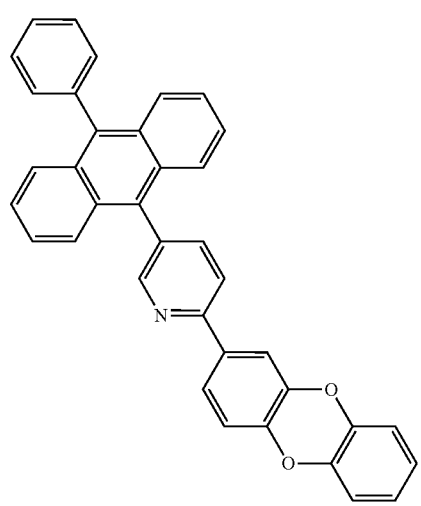
R72
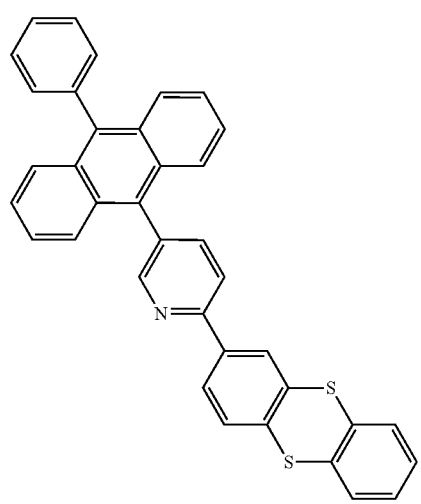
R73
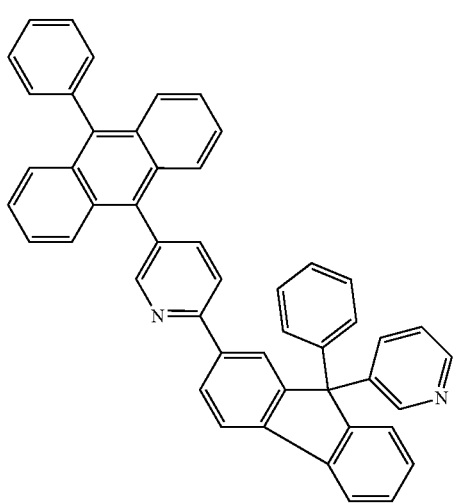
R74
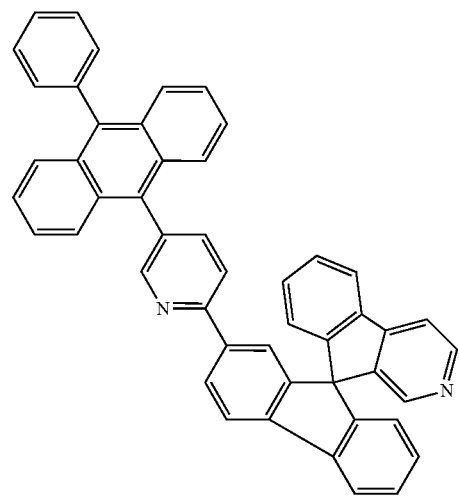
R75
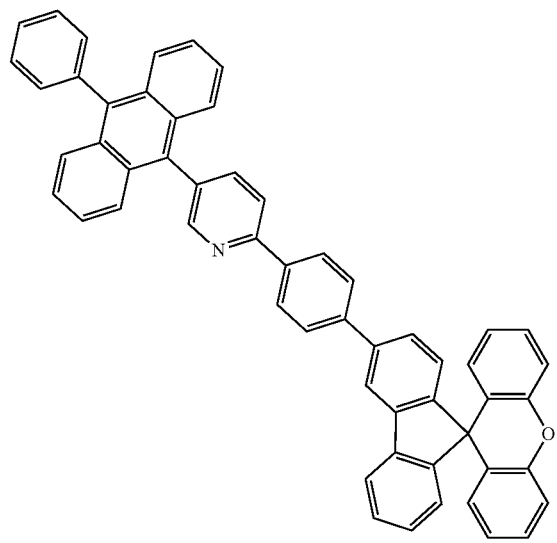
R76
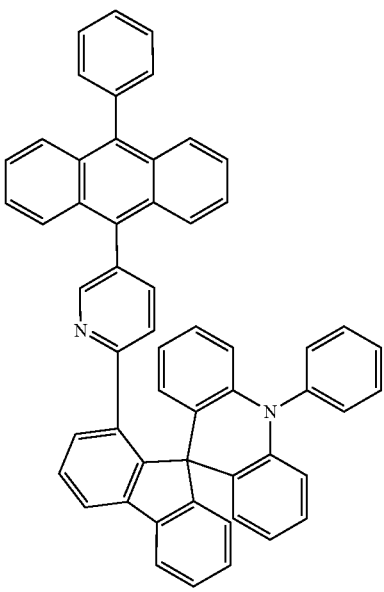

R77
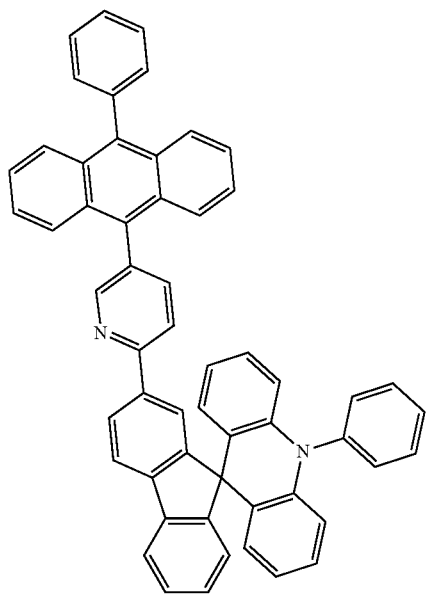
R79
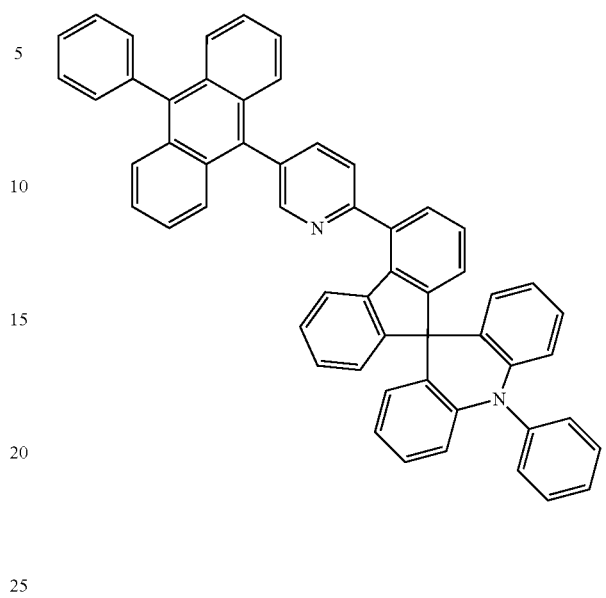
R80
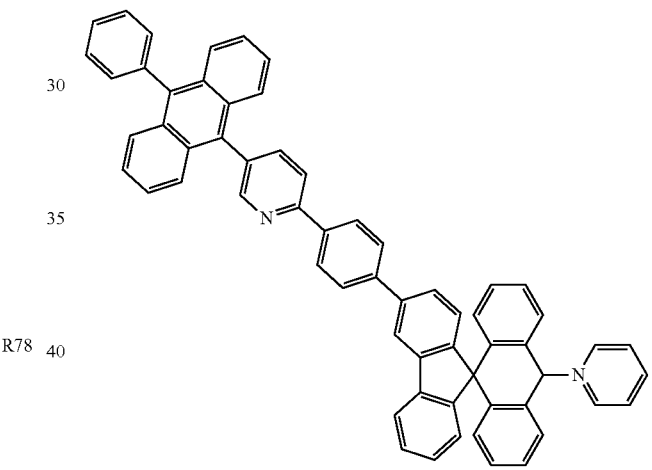
R78
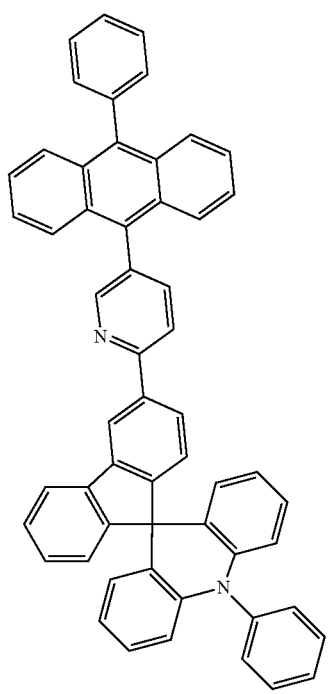
R81
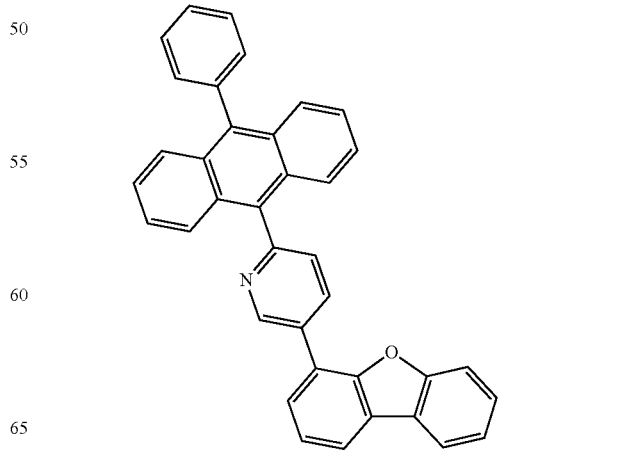

41
-continued
R82
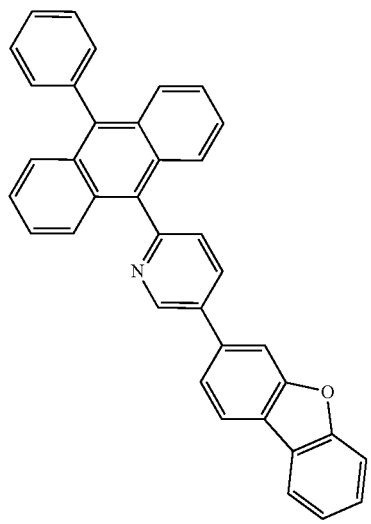
R83
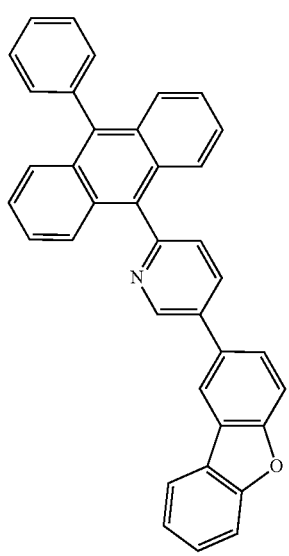
R84
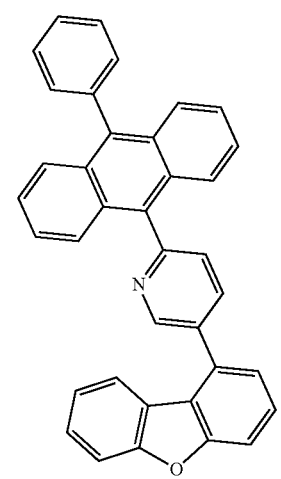
42
-continued
R85
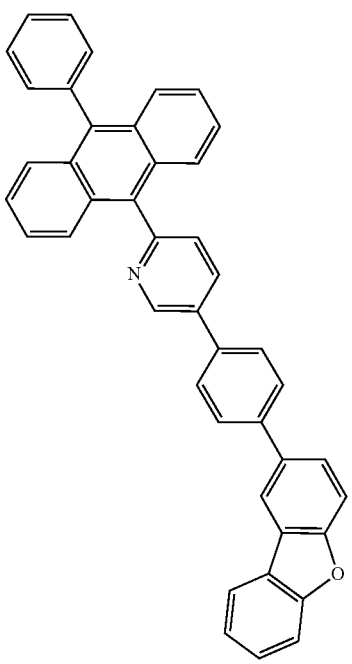
R86
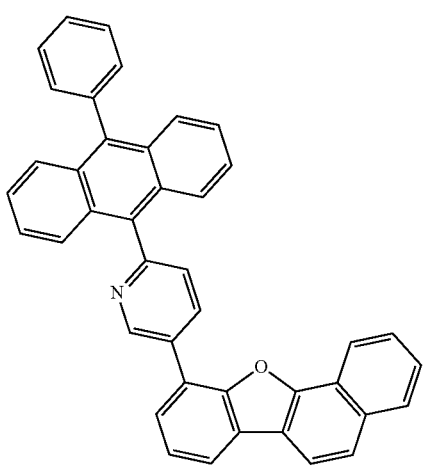
R87
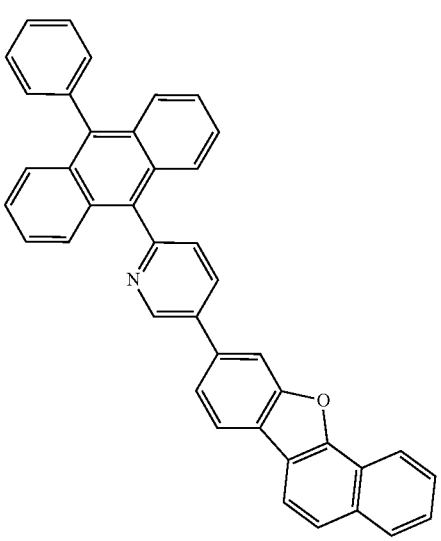

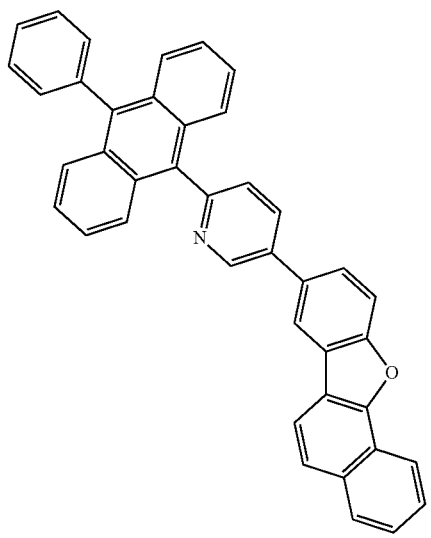 R88
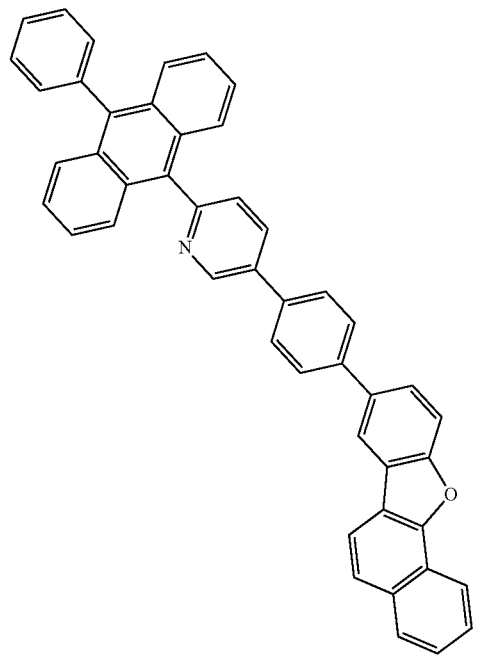 R90
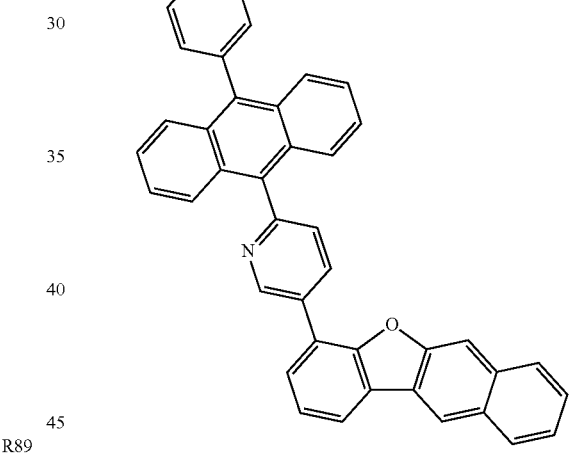 R91
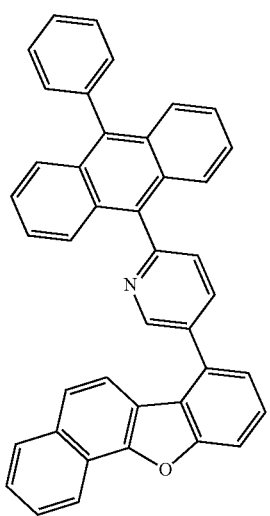 R89
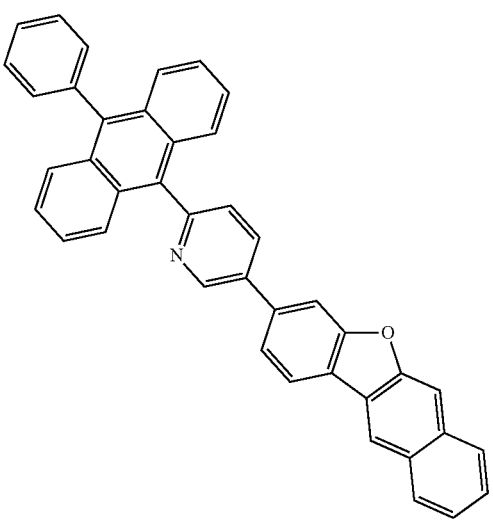 R92

45
-continued
R93
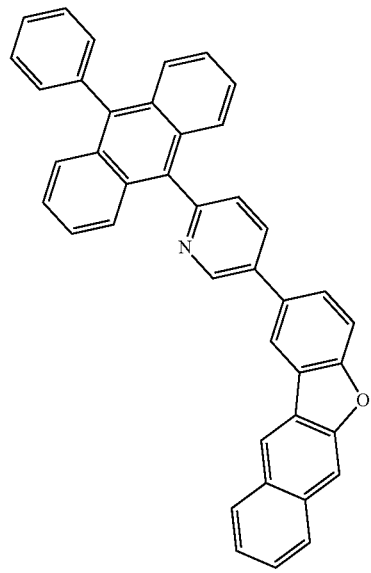
R94
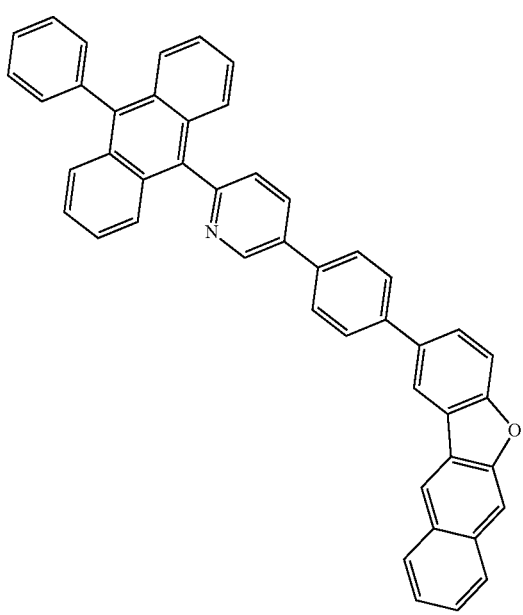
R95
46
-continued
R96
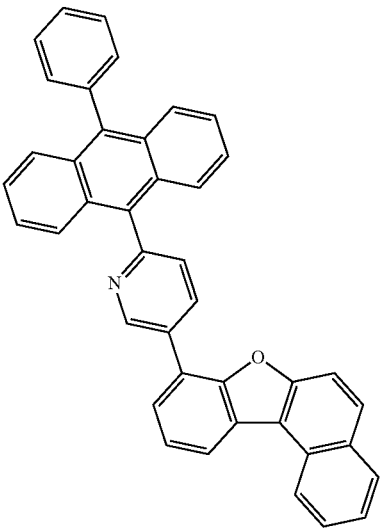
R97
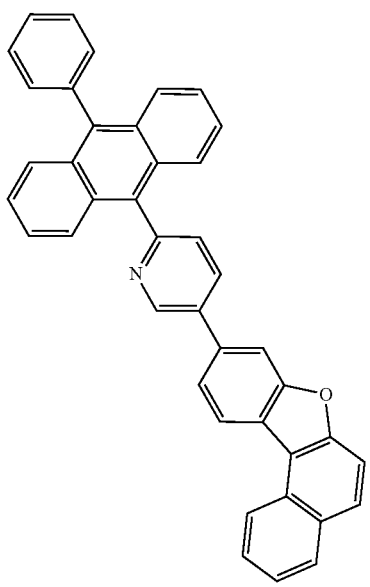
R98
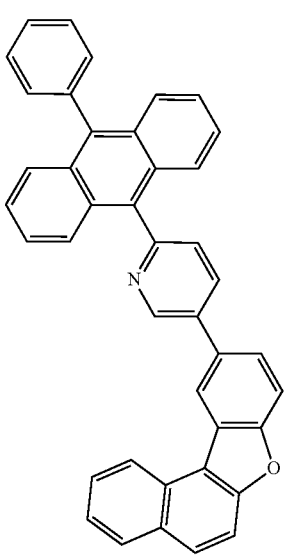

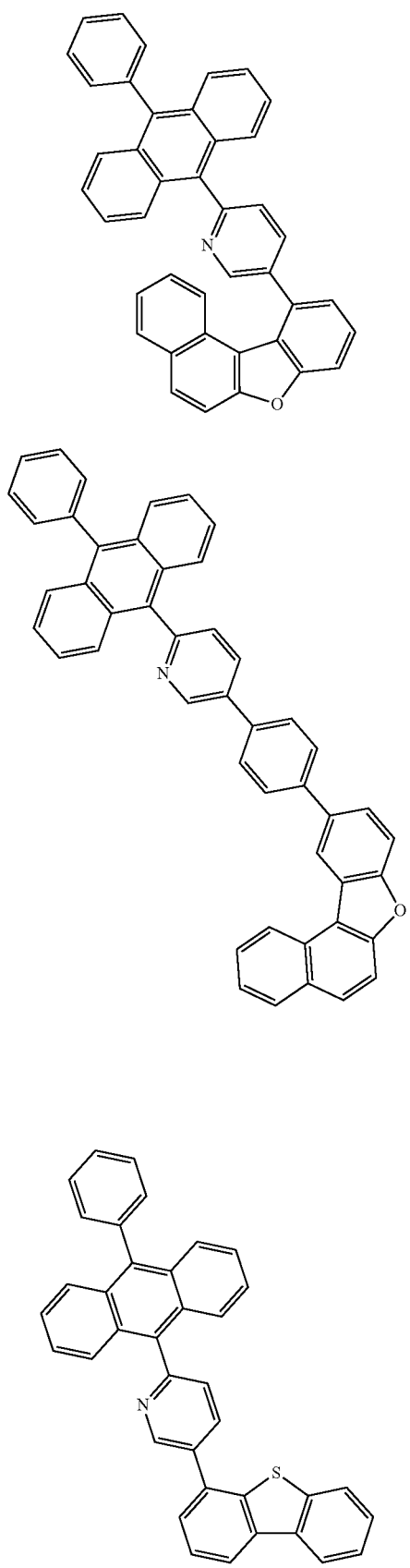
R99
R100
R101
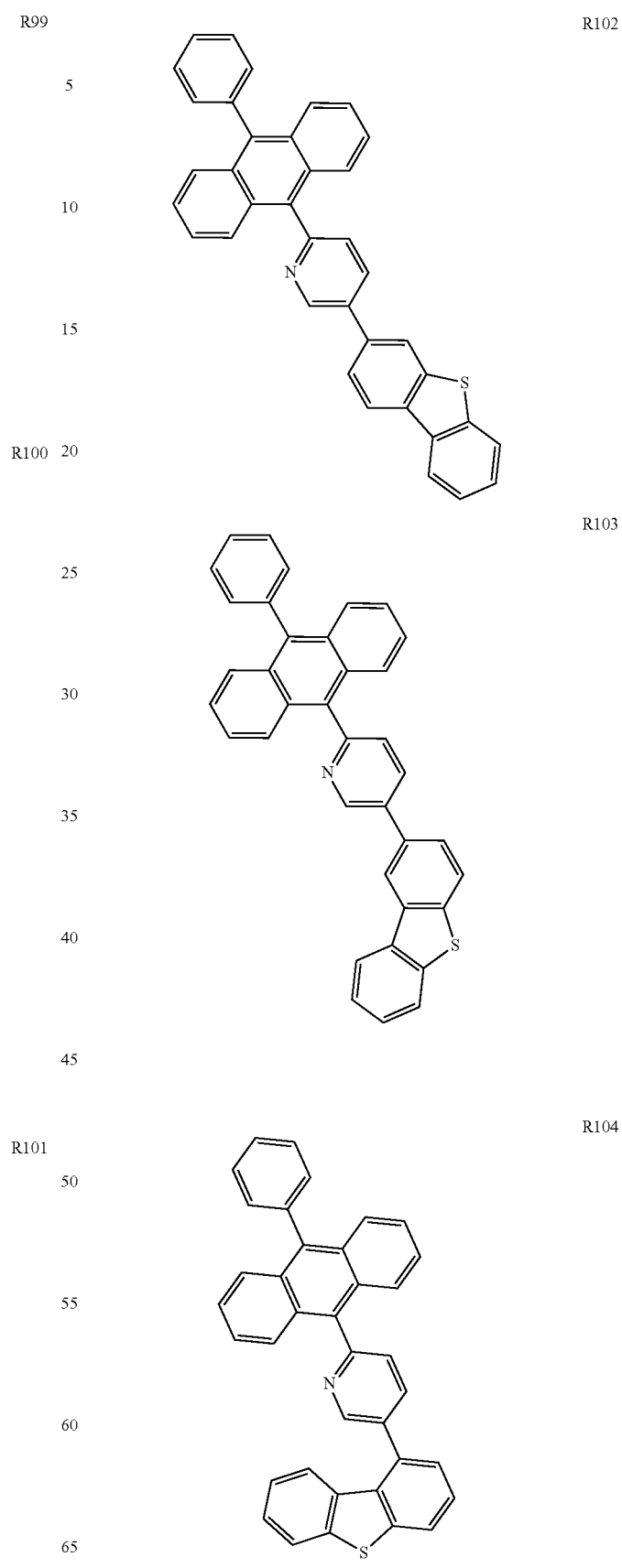
R102
R103
R104

R105
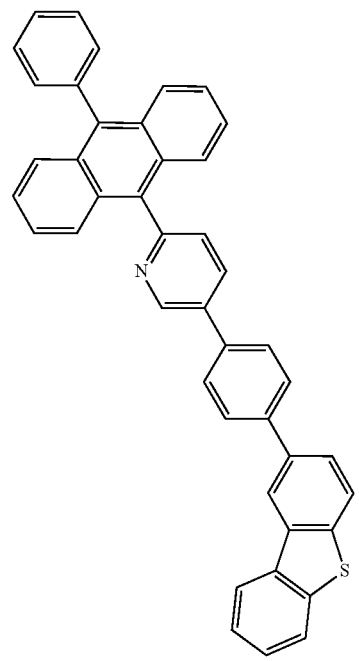
R108
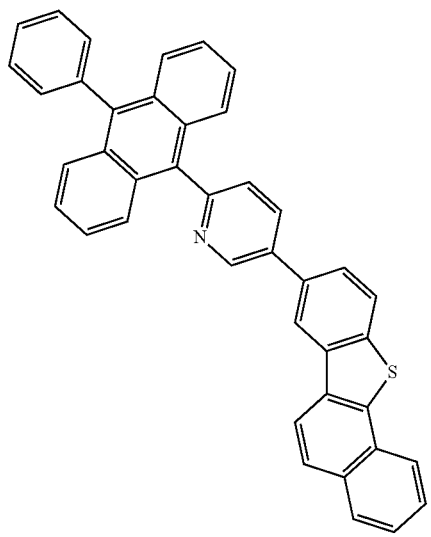
R106
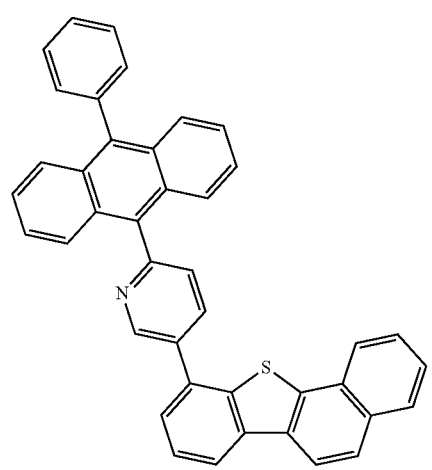
R107
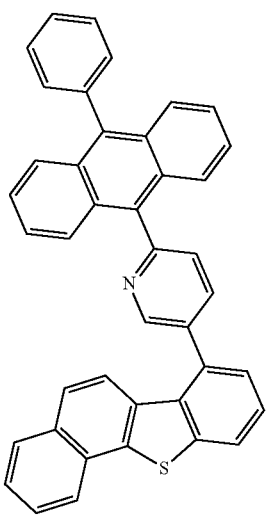
R109

R110
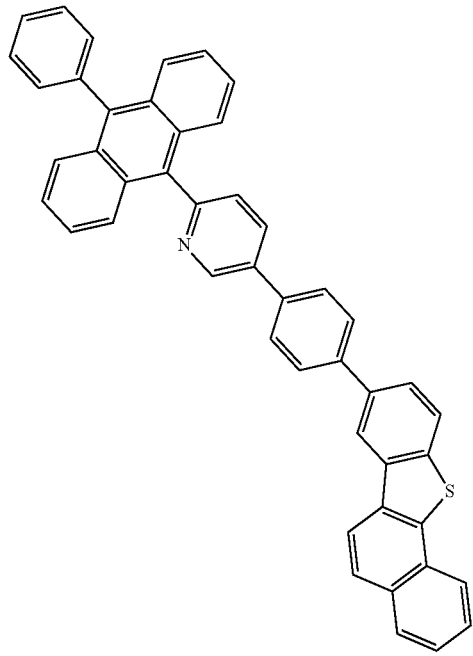
R111
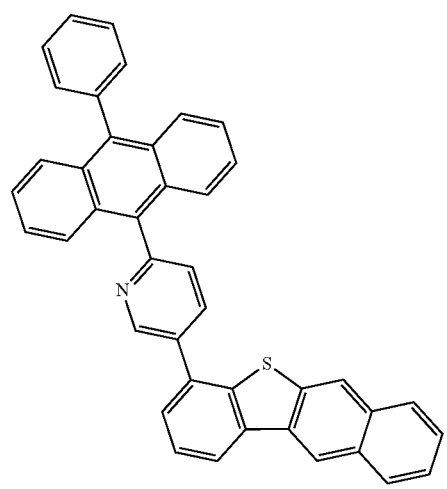
R112
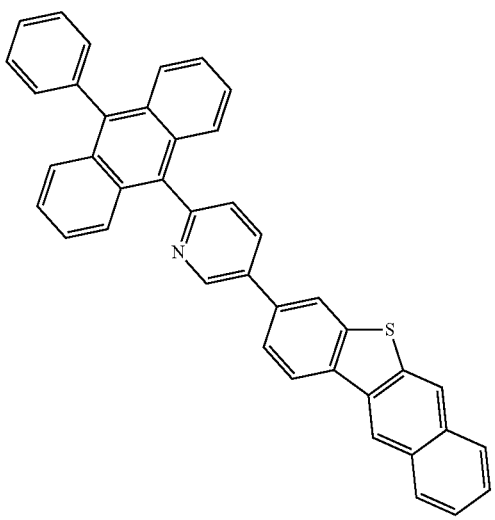
R113
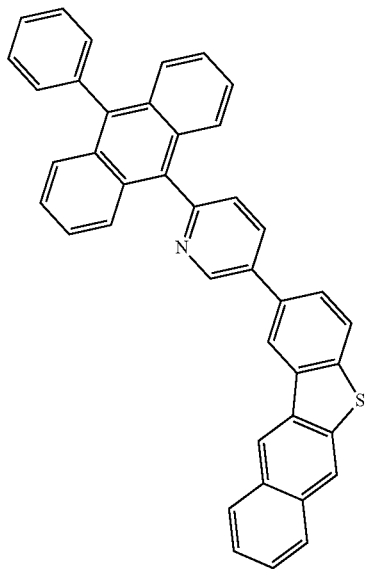
R114
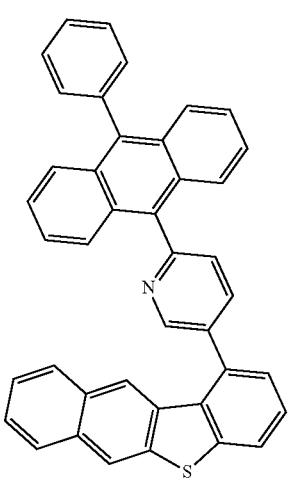
R115
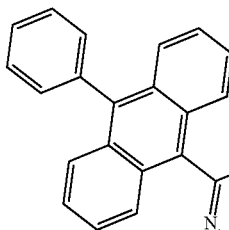

R116
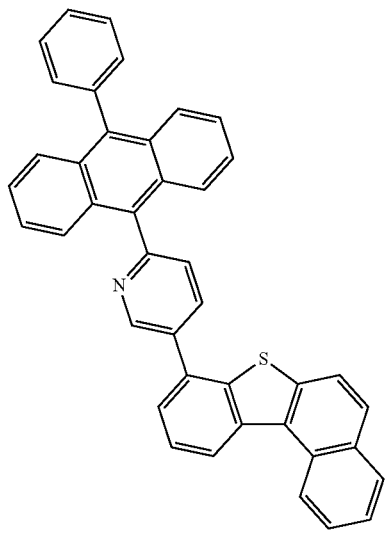
R117
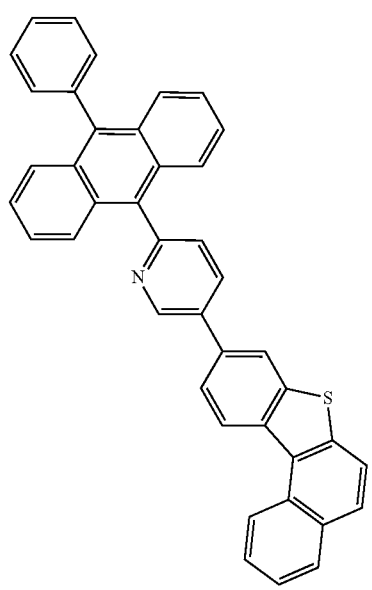
R118
R119
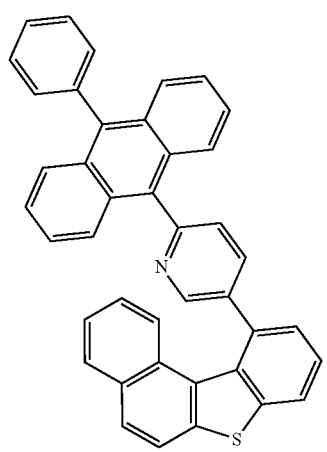
R120
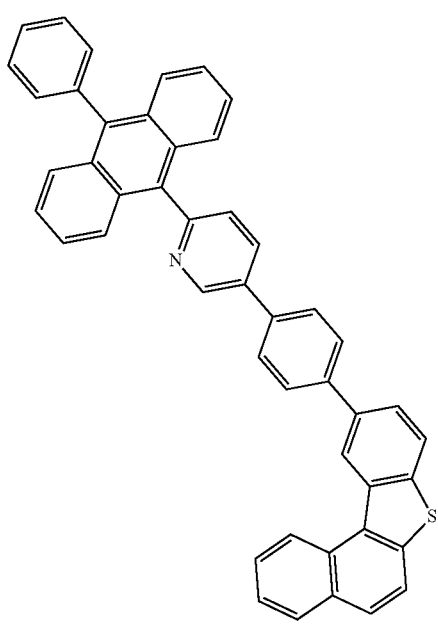
R121
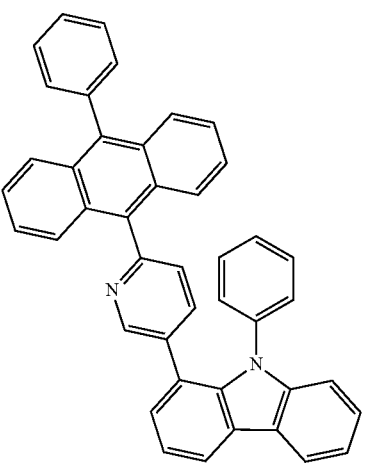

R122
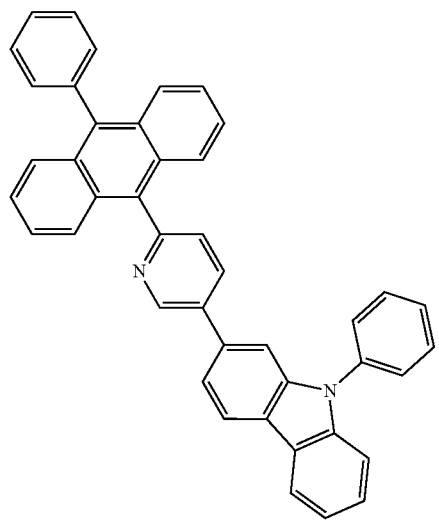
R123
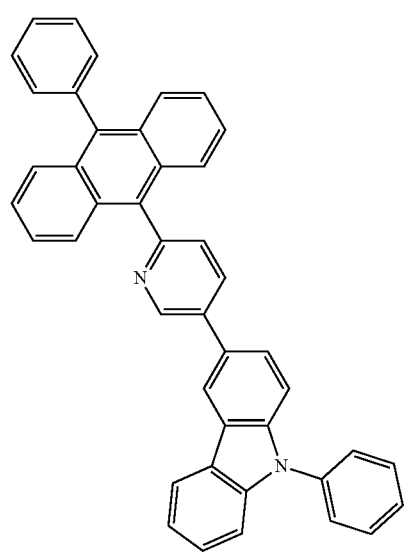
R124
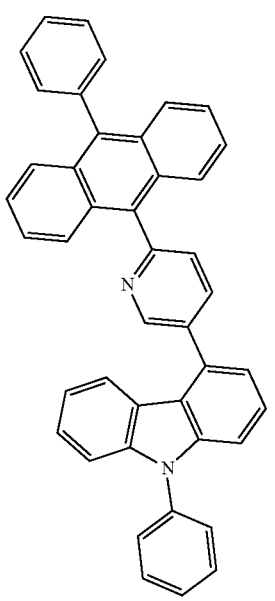
R125
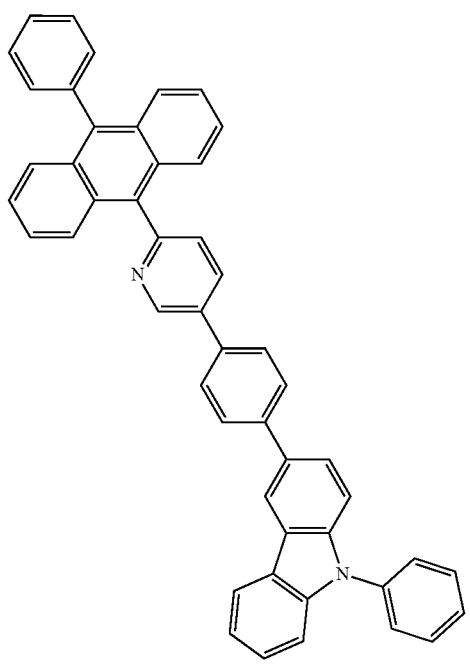
R126
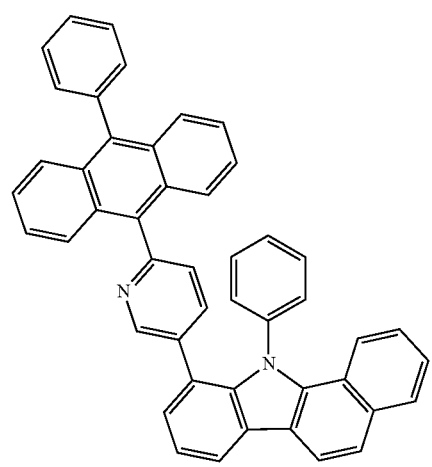
R127
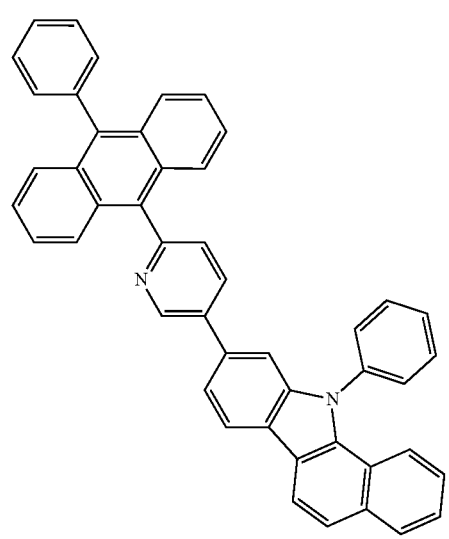

-continued
R128
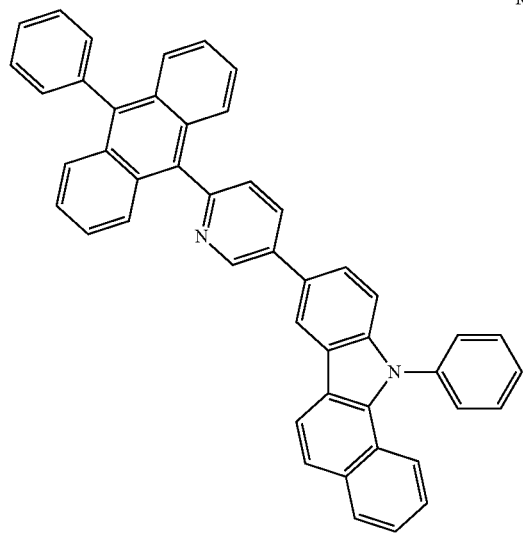
R129
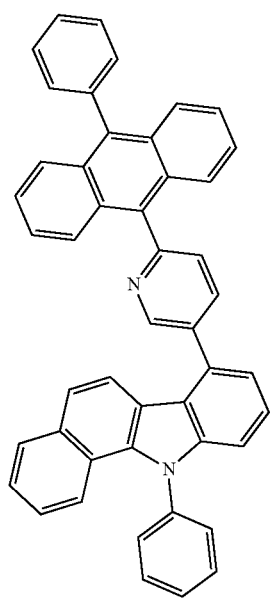
-continued
R130
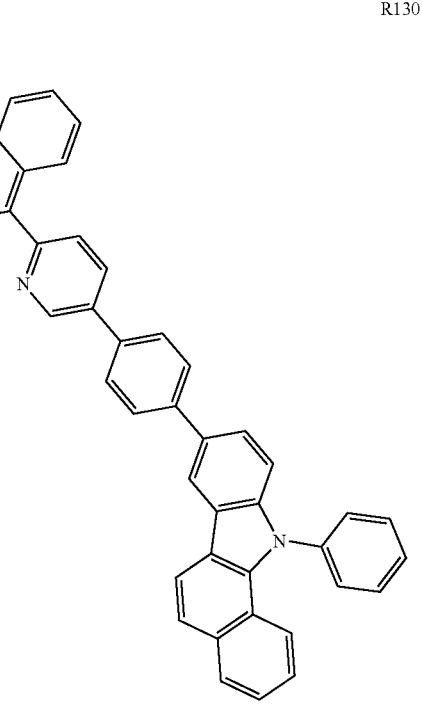
R131
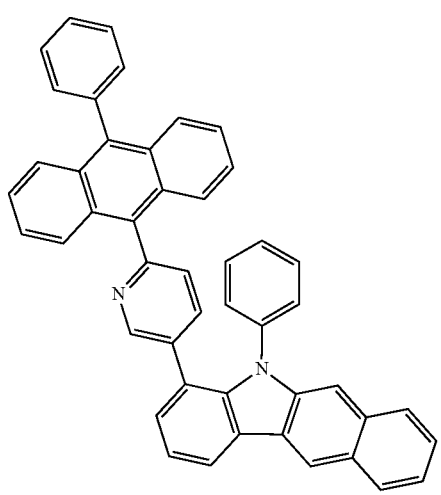

R132
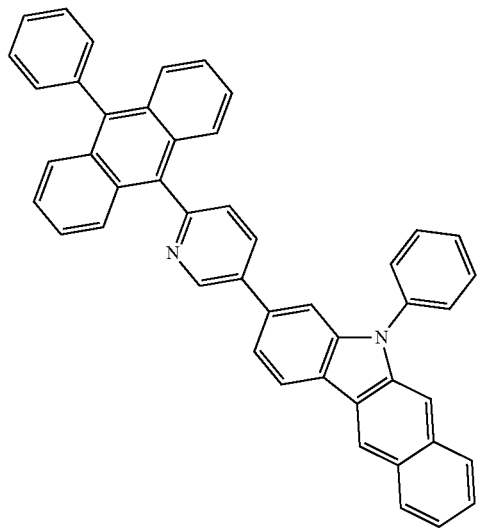
R133
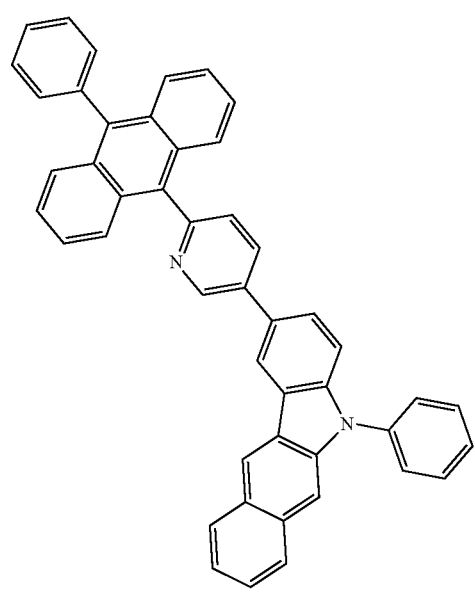
R134
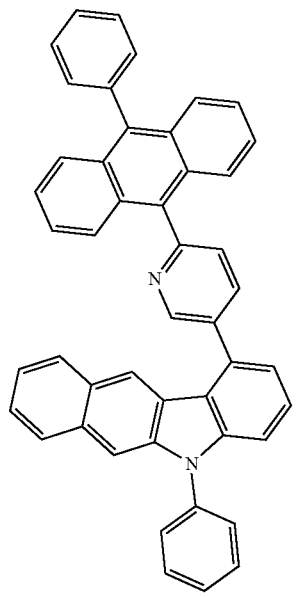
R135
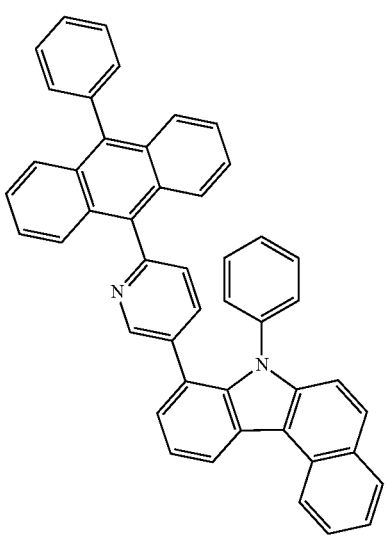
R136

R137
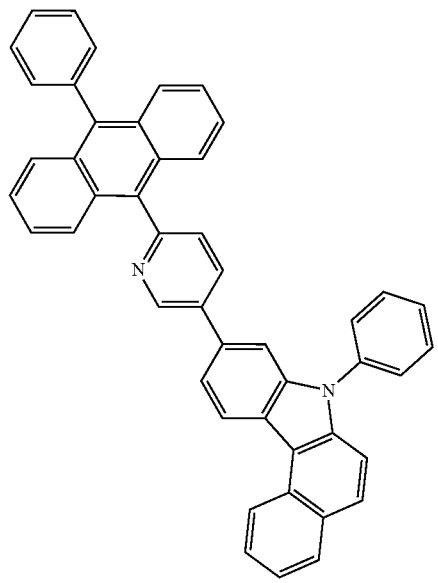
R138
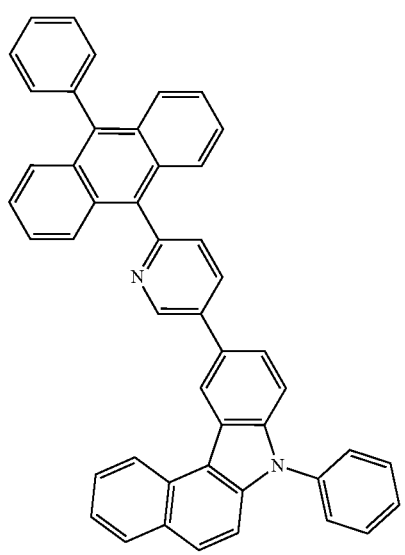
R139
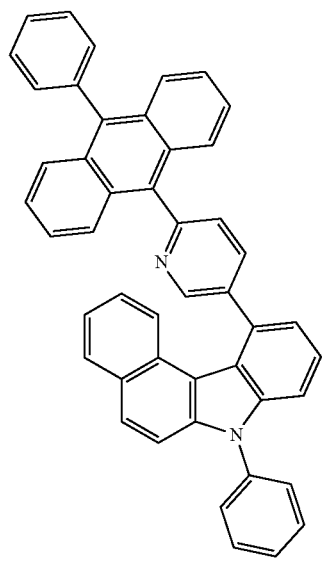
R140
R141
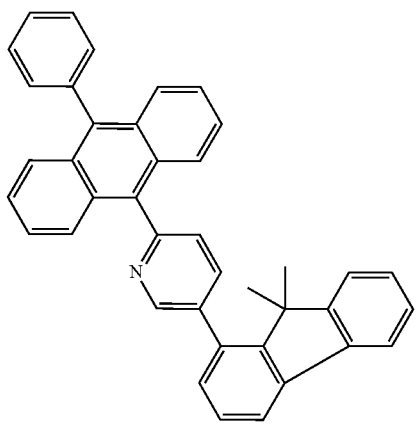

-continued
R142
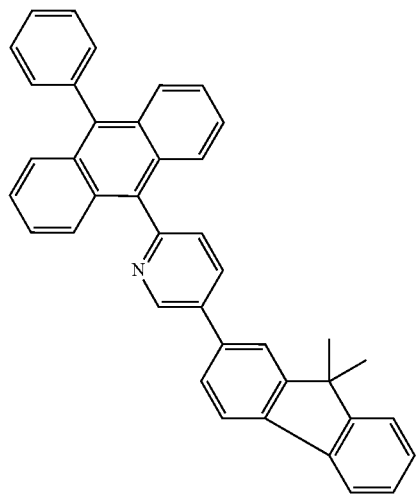
R143
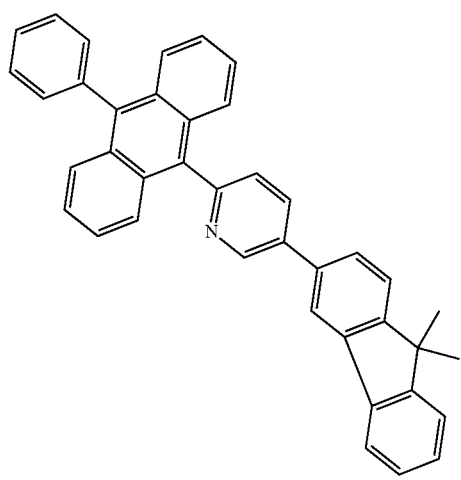
R144
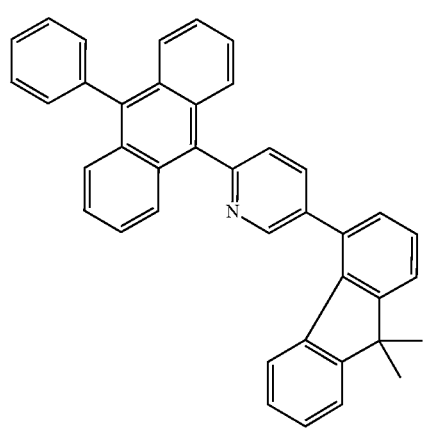
-continued
R145
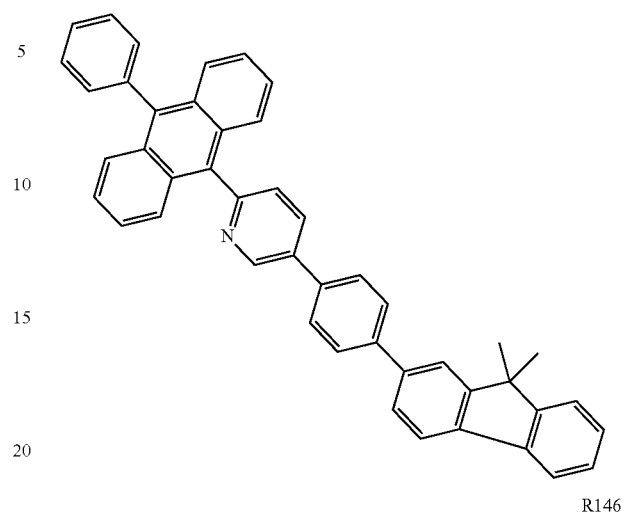
R146
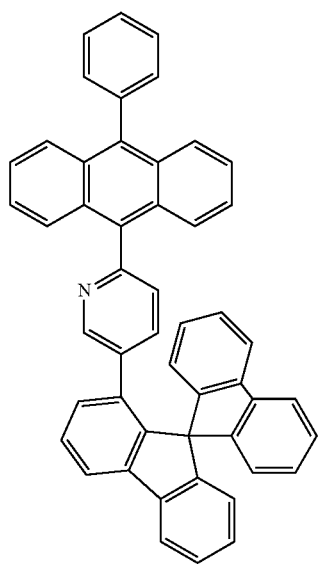
R147
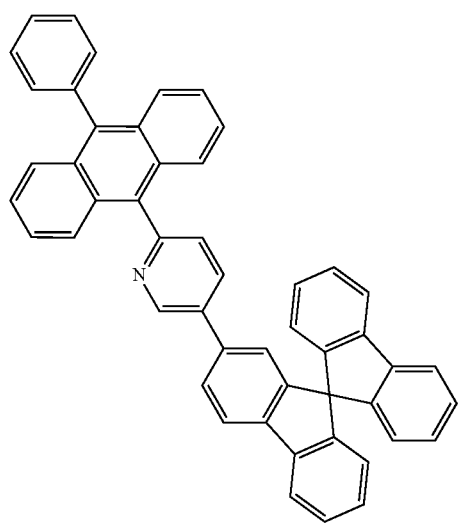

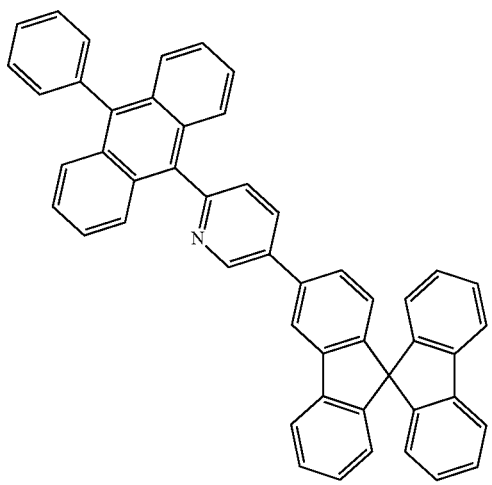
R148
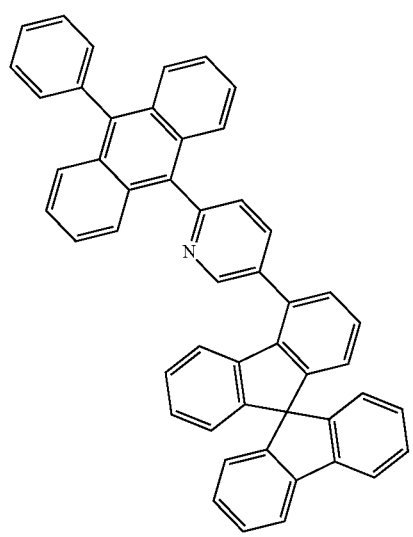
R149
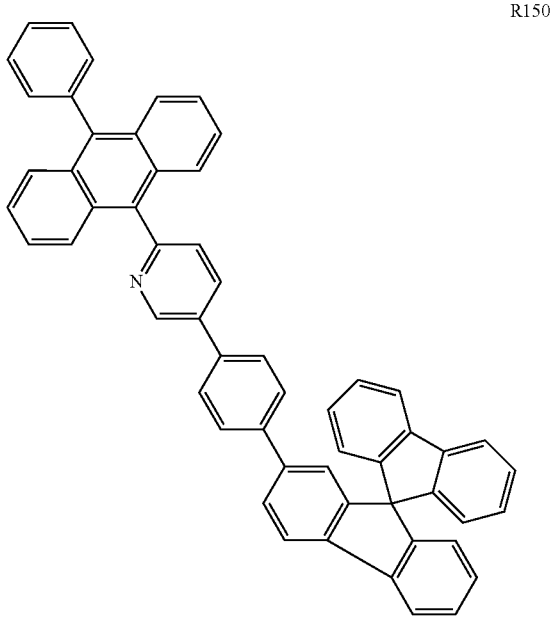
R150
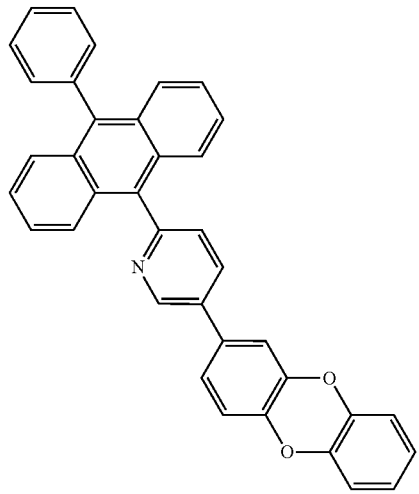
R151
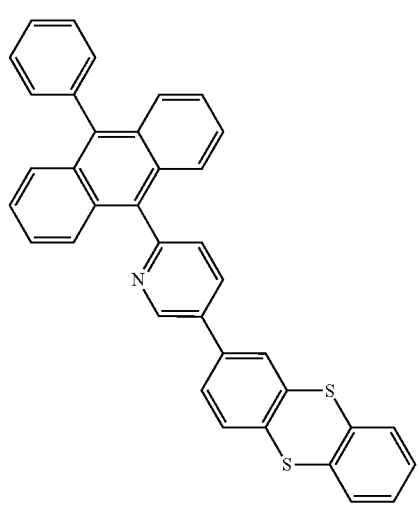
R152
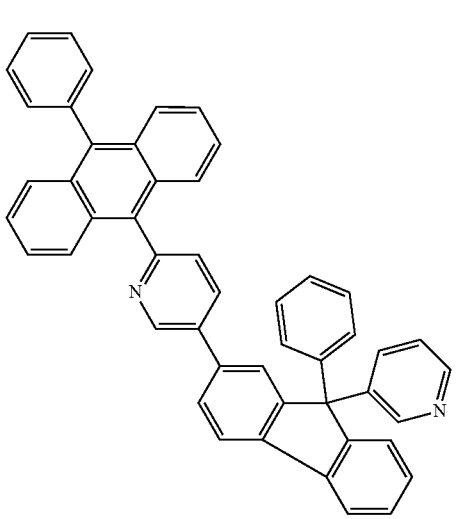
R153

R154
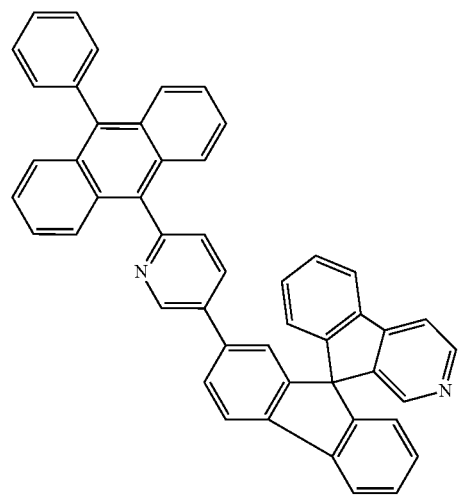
R155
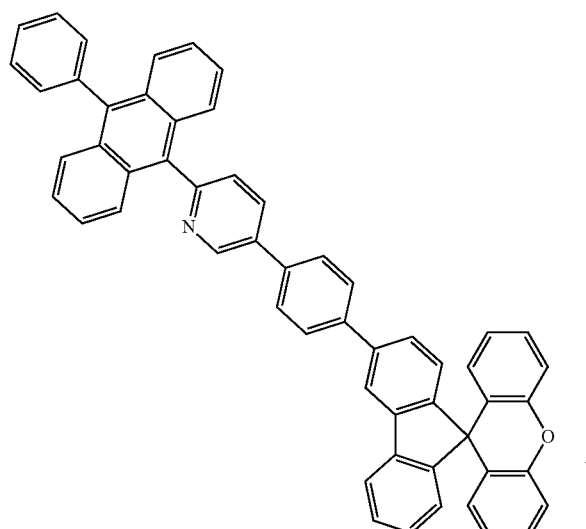
R156
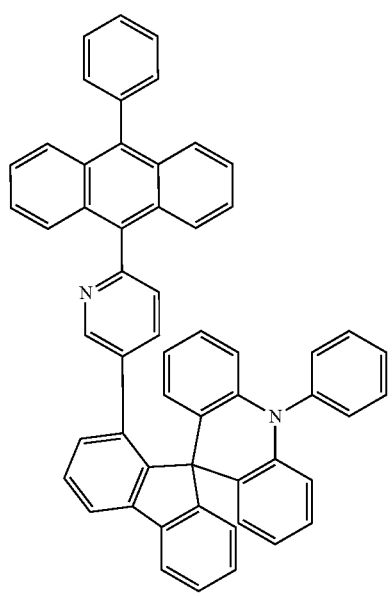
R157
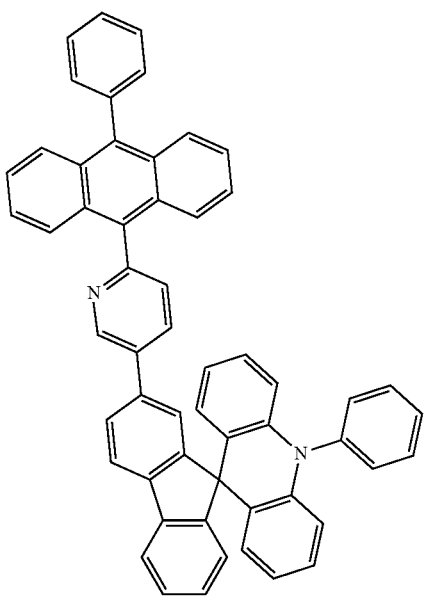
R158
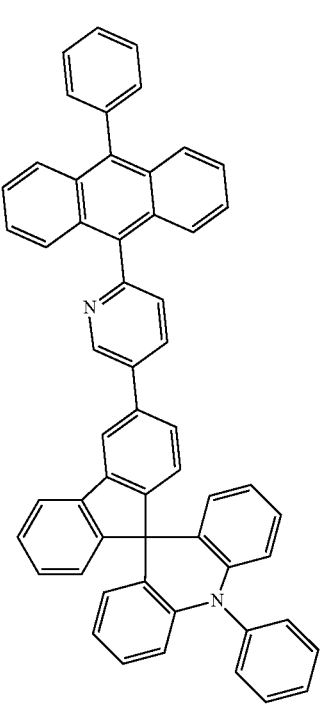

R159
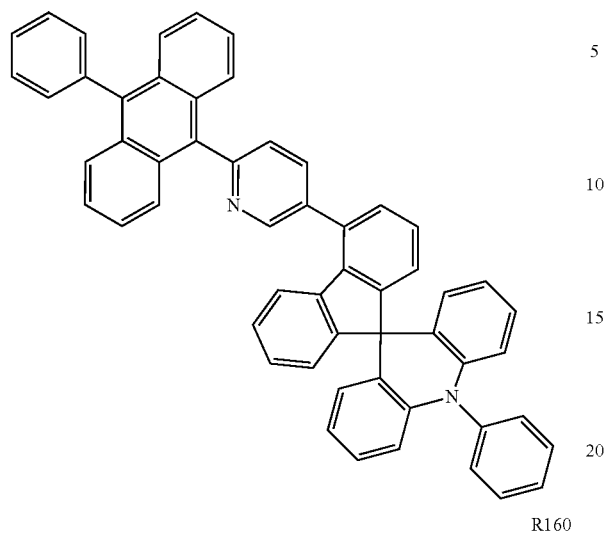
R160
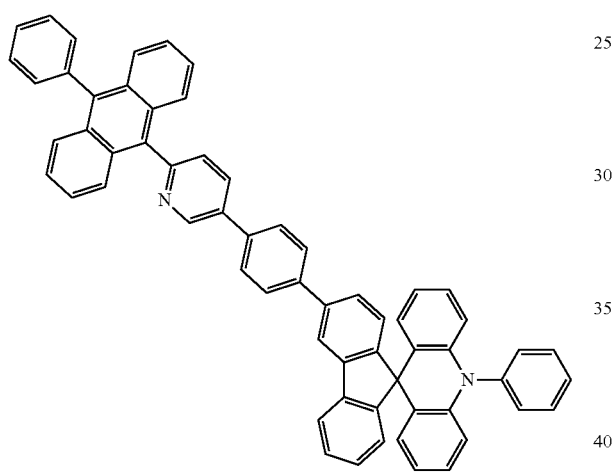
R161
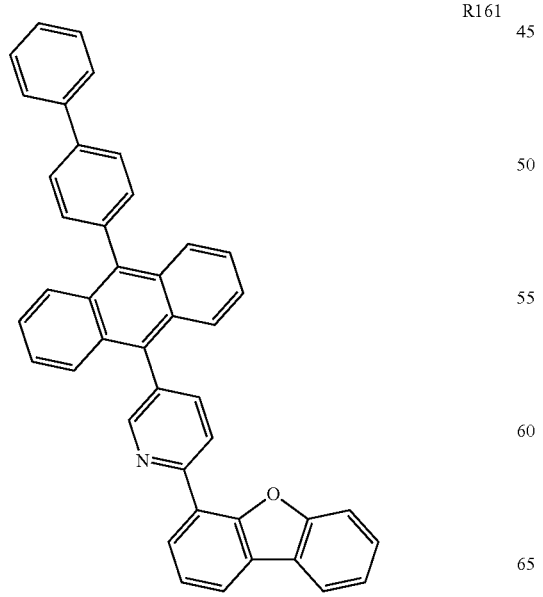
R162
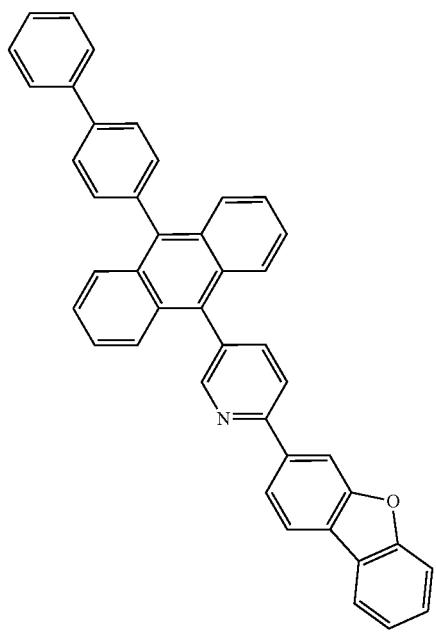
R163
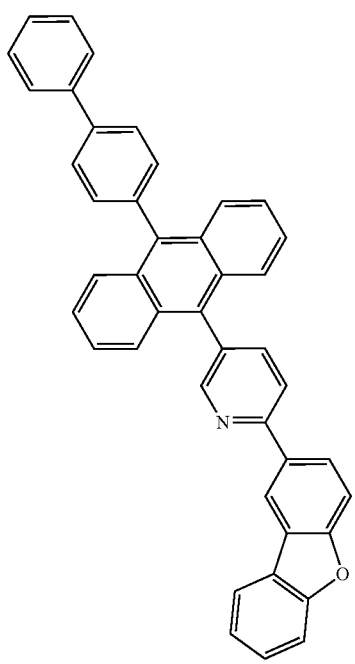

71
-continued
R164
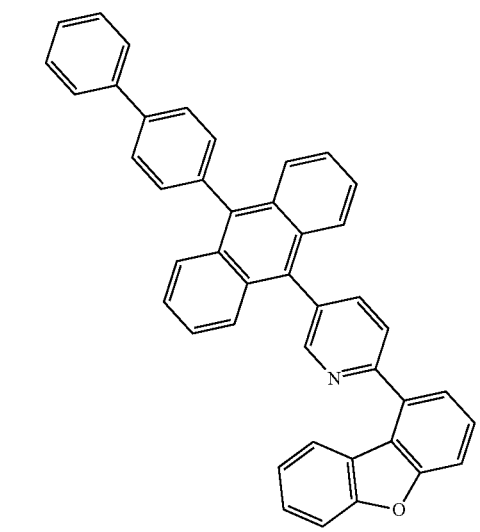
R165
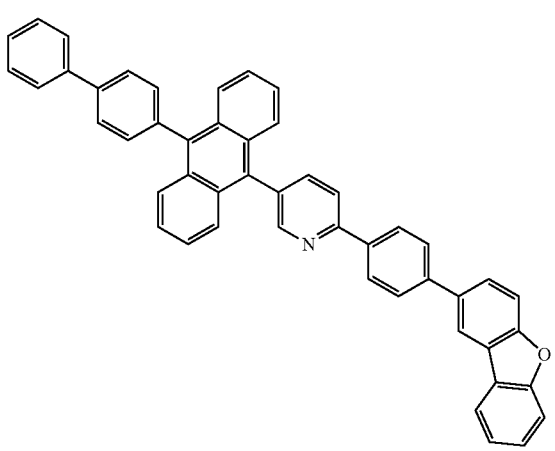
R166
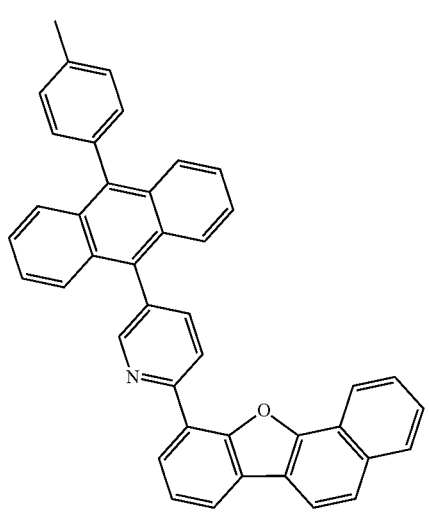
72
-continued
R167
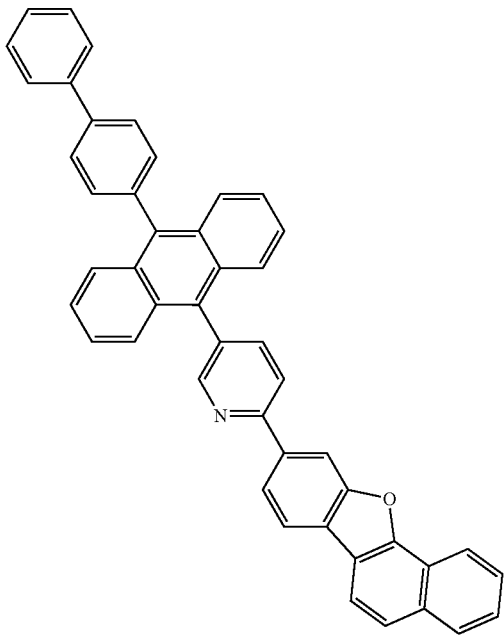
R168
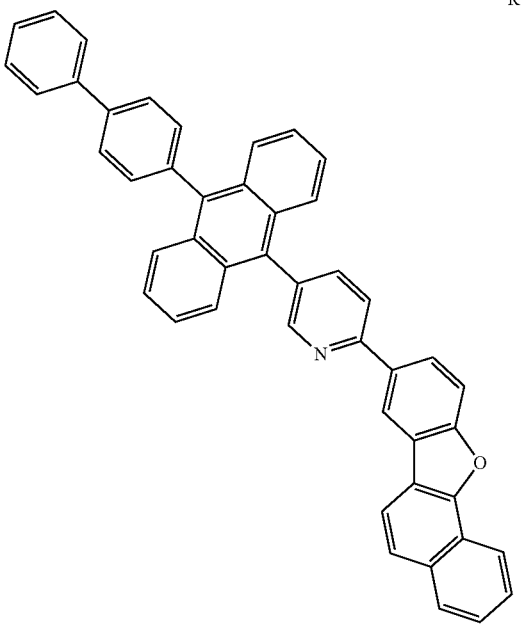

R169
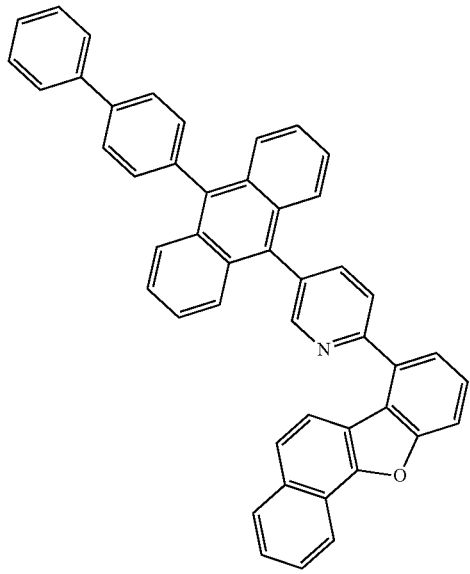
R170
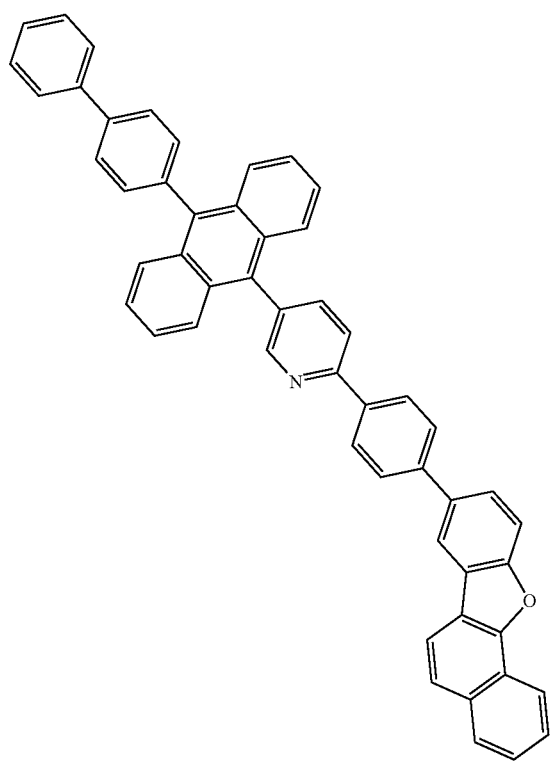
R171
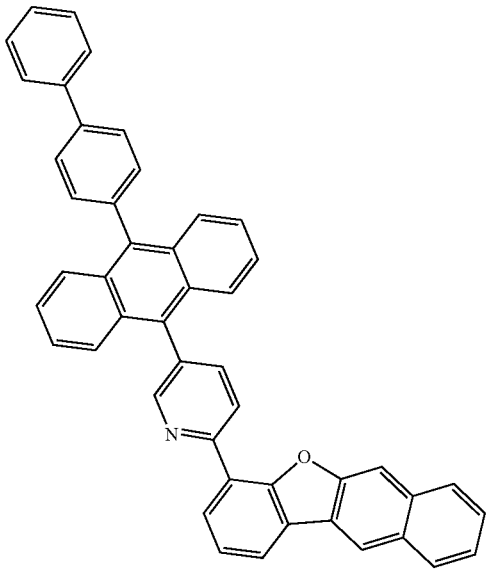
R172
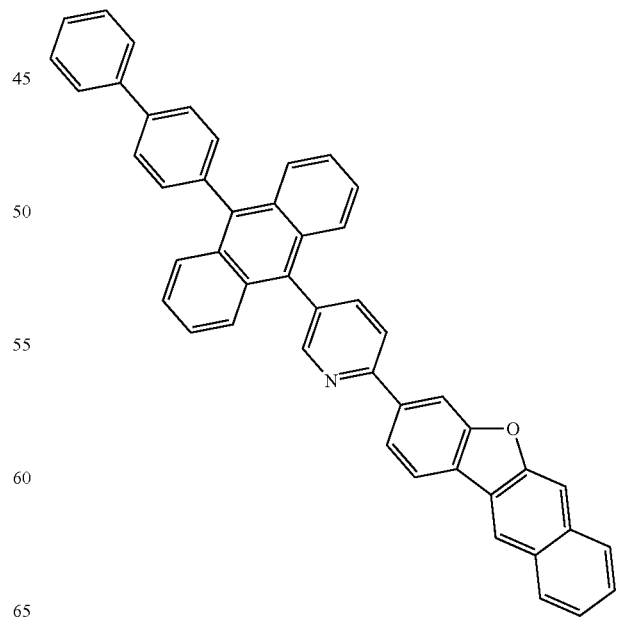

R173
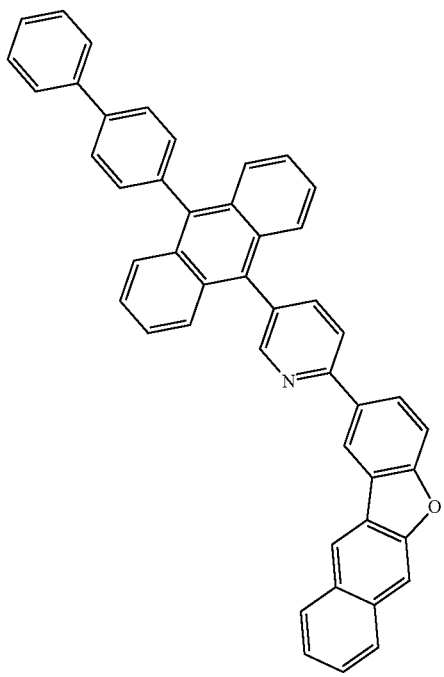
R174
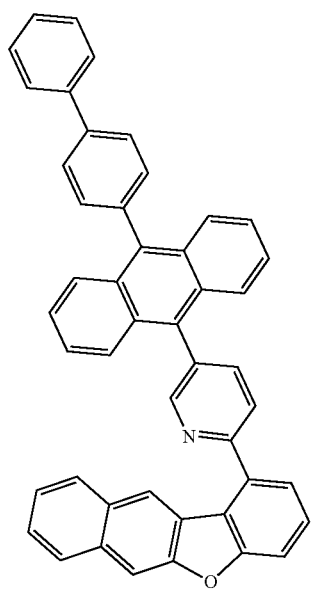
R175
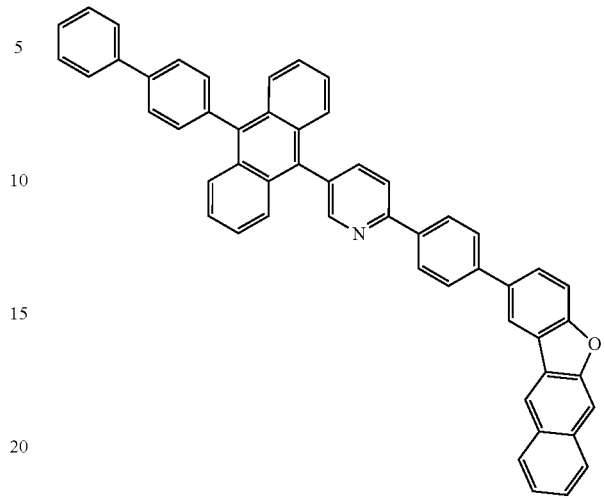
R176
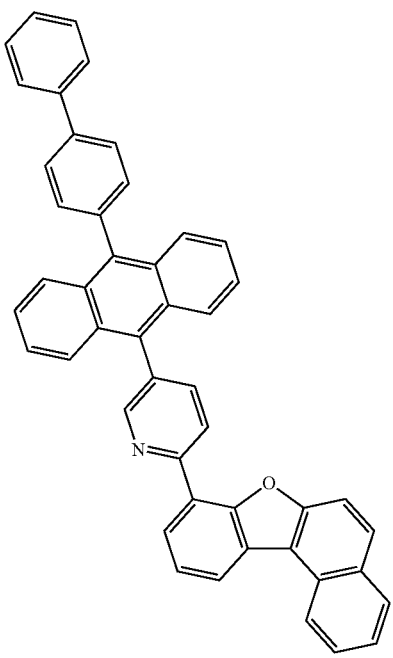

-continued
R177
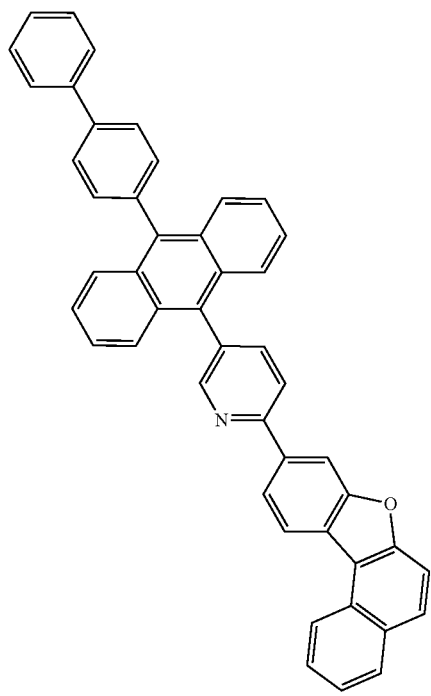
R178
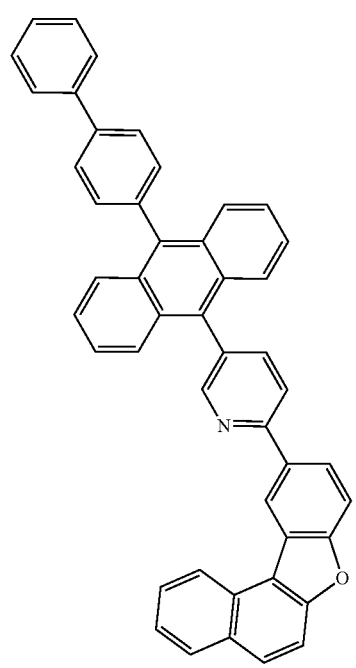
-continued
R179
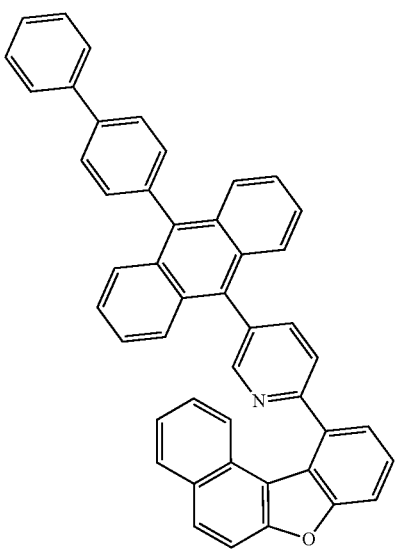
R180
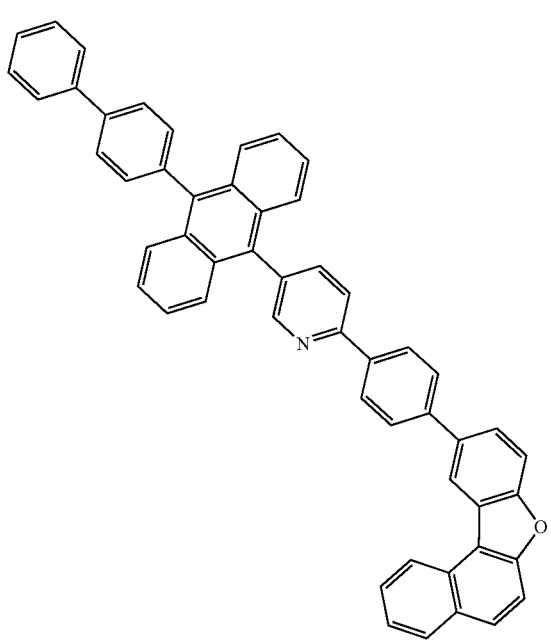

R181
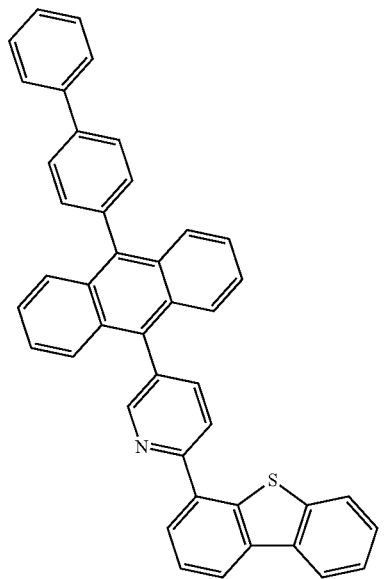
R182
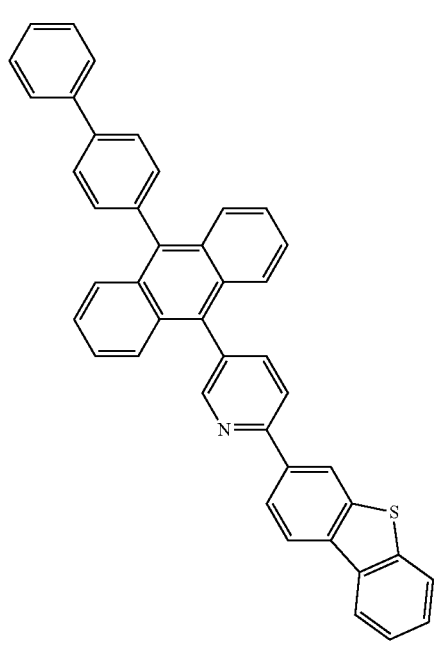
R183
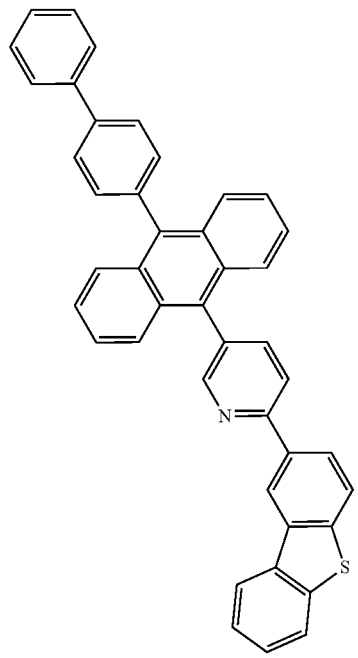
R184
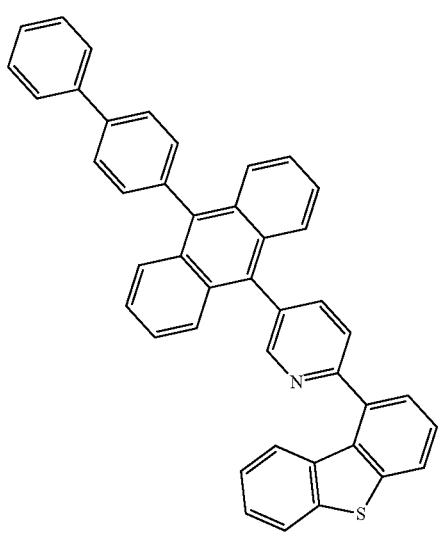
R185
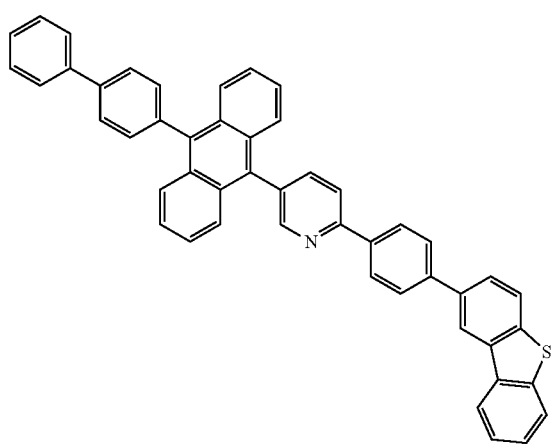

R186
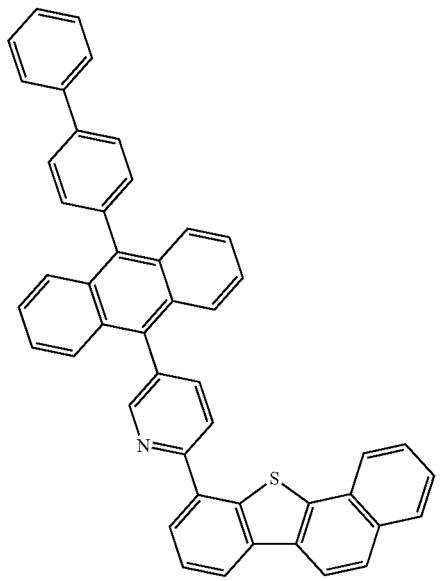
R187
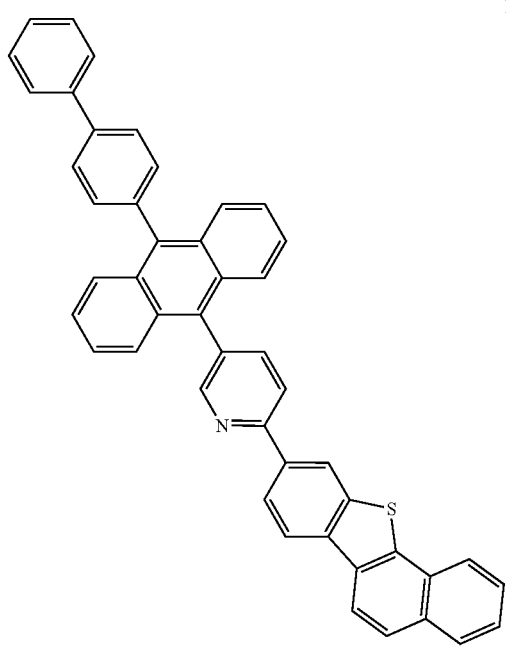
R188
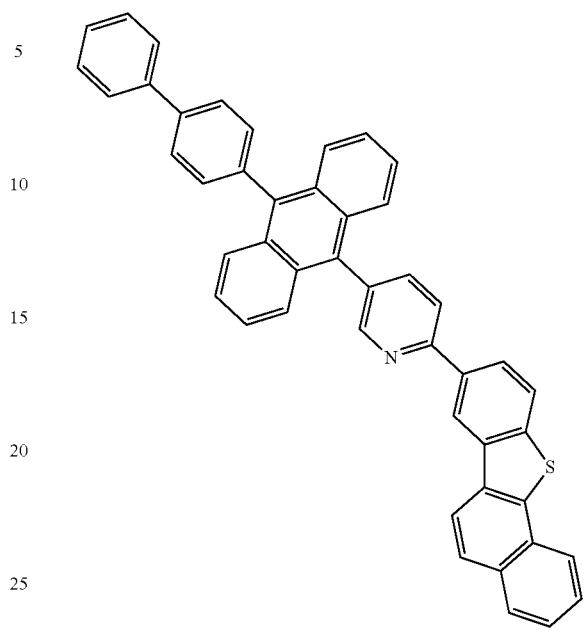
R189
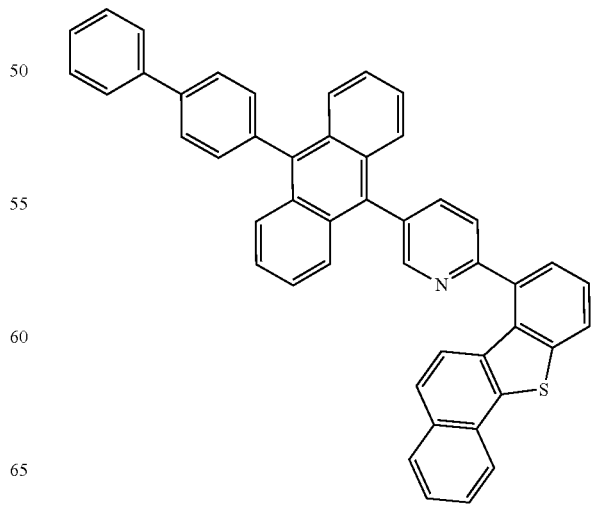

-continued
R190
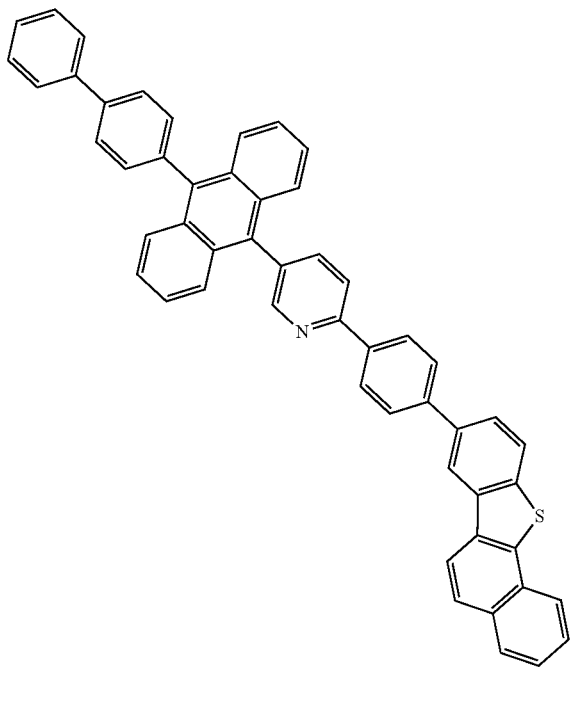
R192
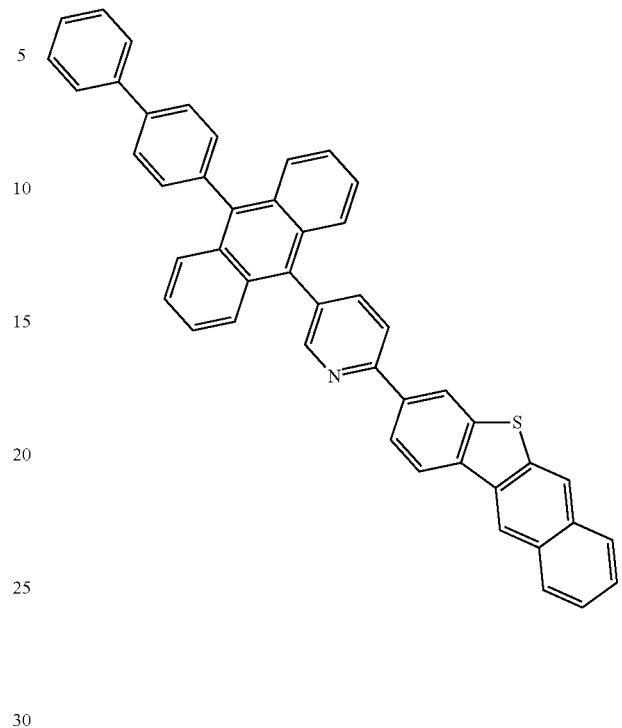
R191
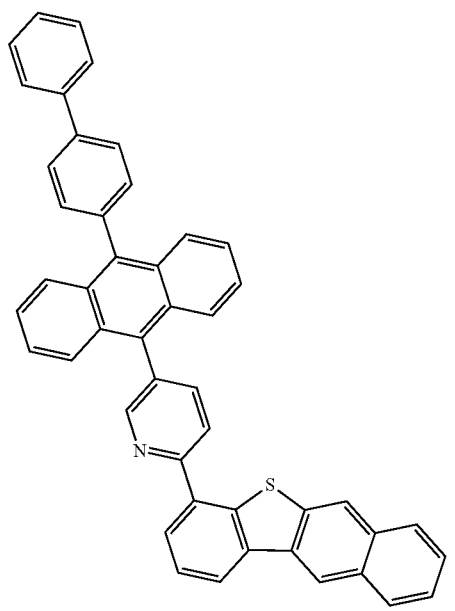
R193
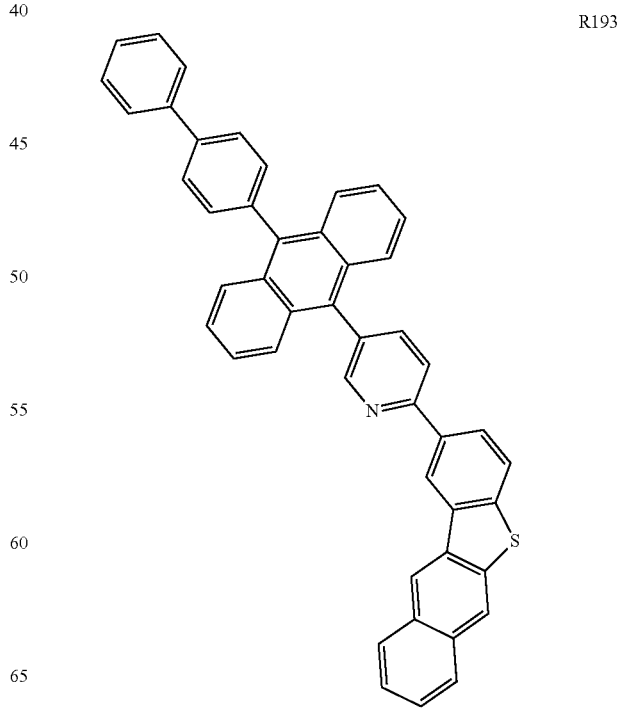

-continued
R194
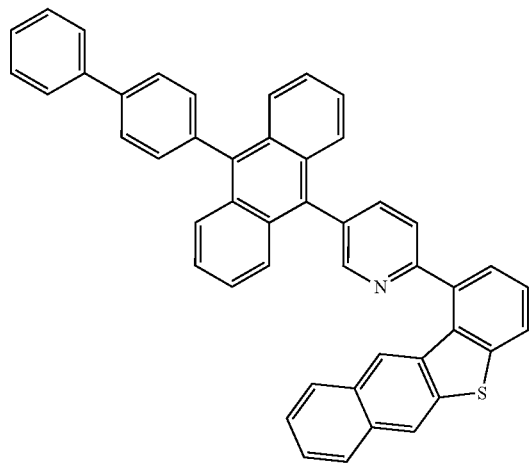
R195
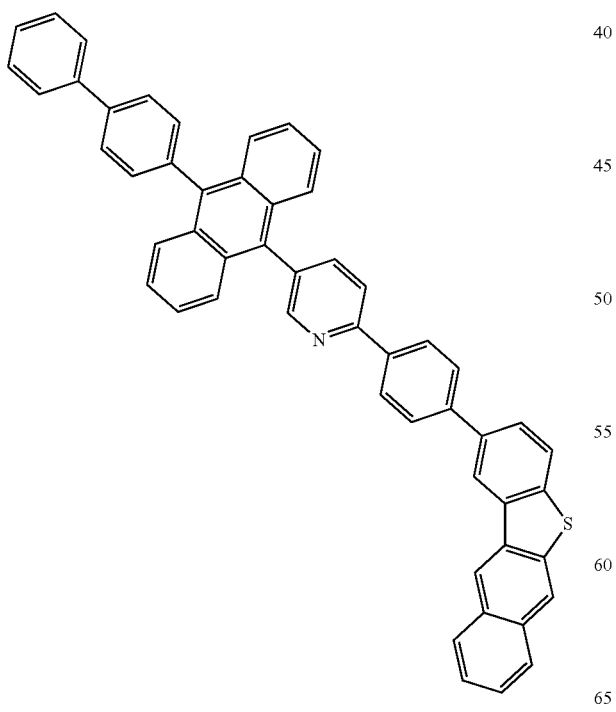
R196
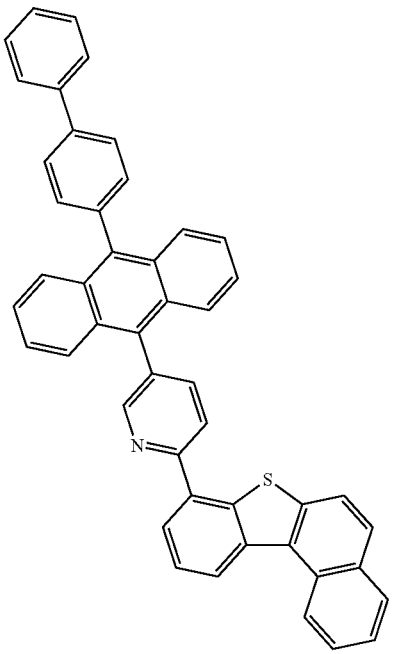
R197
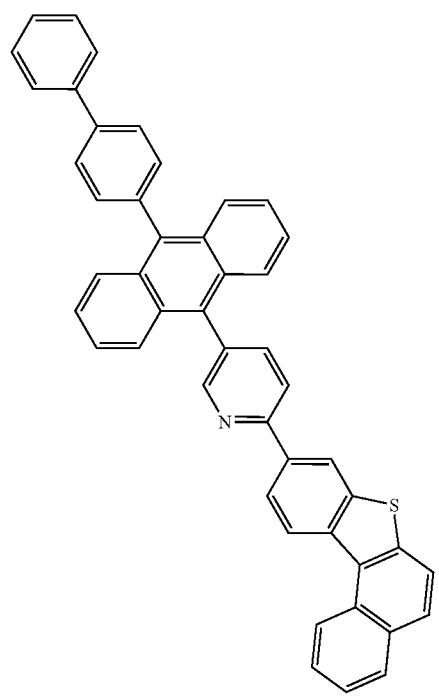

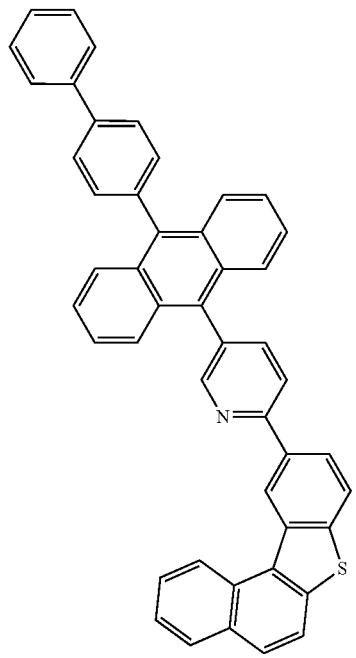
R198
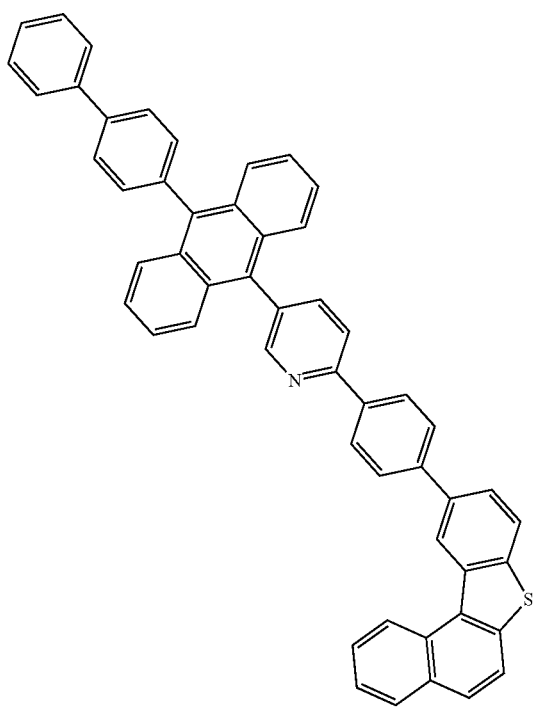
R200
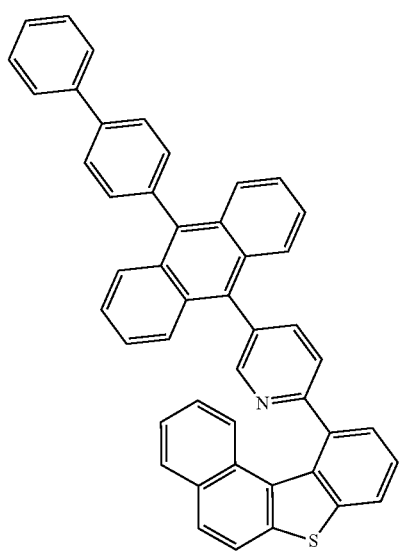
R199
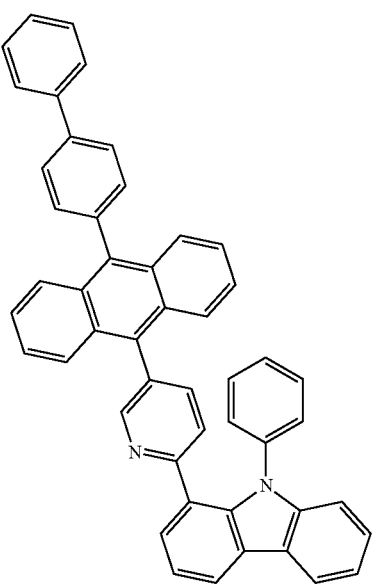
R201

R202
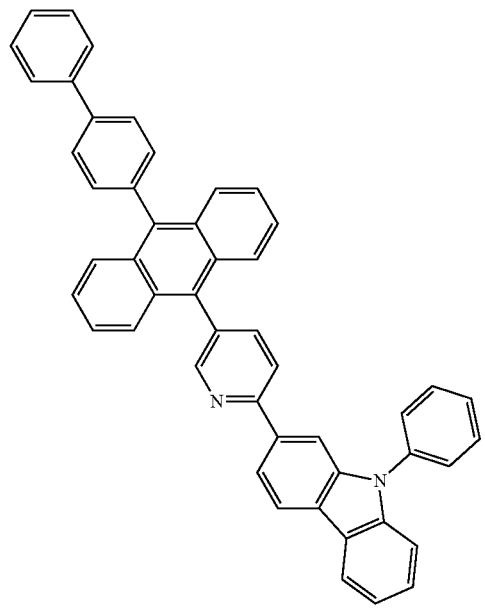
R203
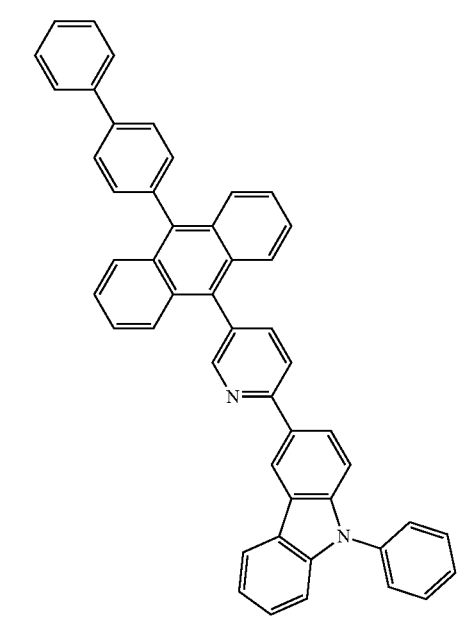
R204
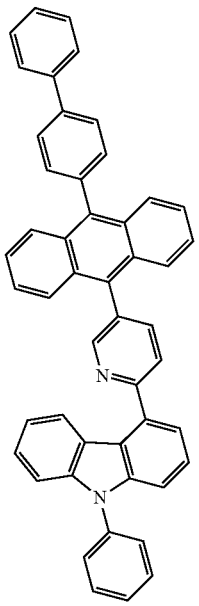
R205
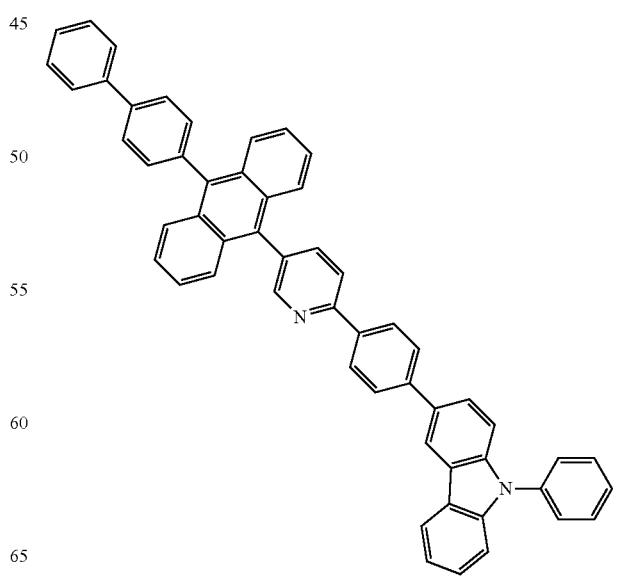

R206
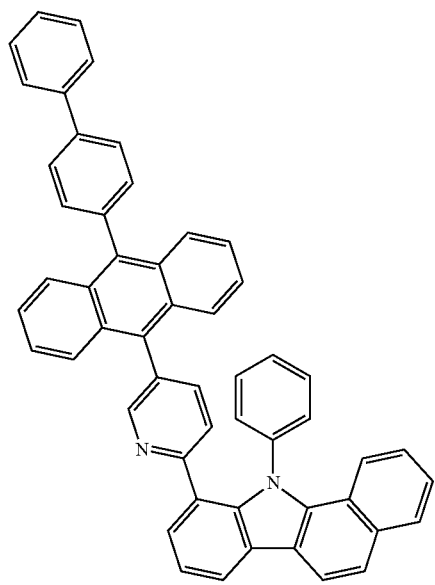
R207
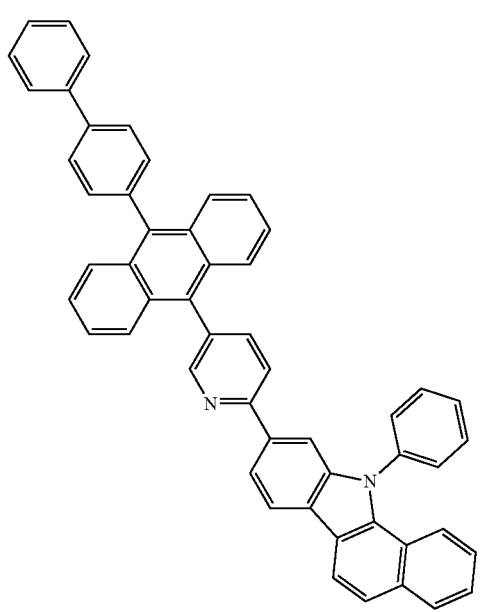
R208
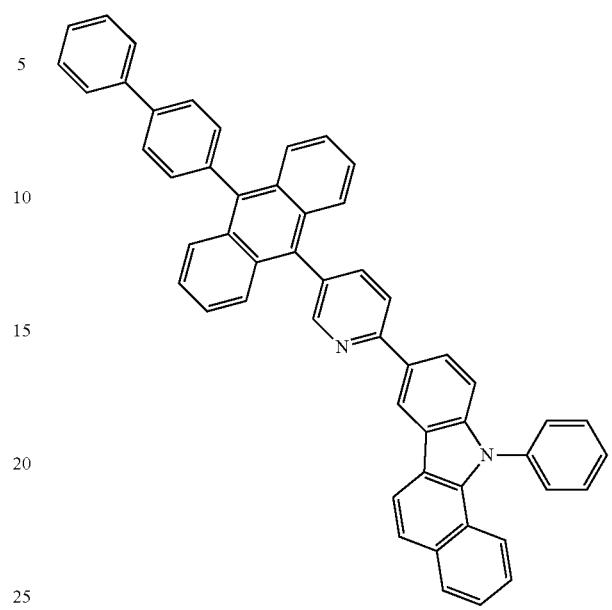
R209
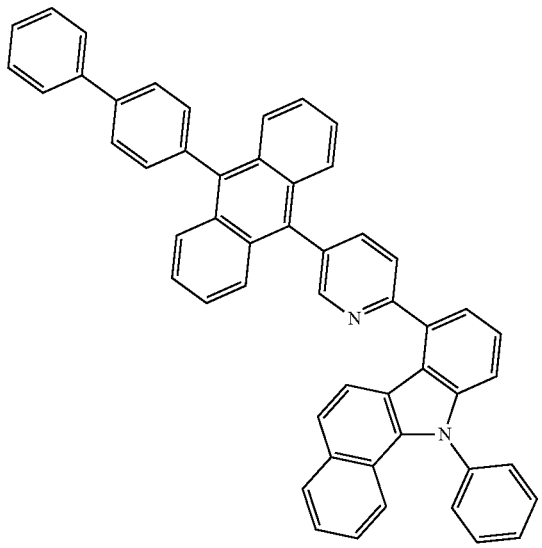

-continued
R210
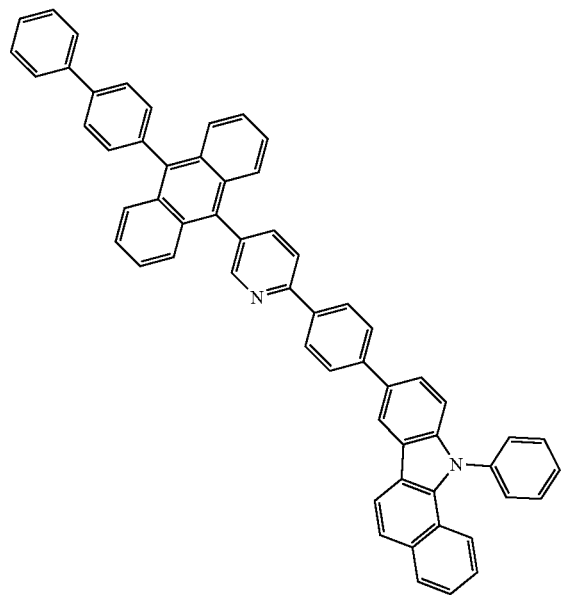
R212
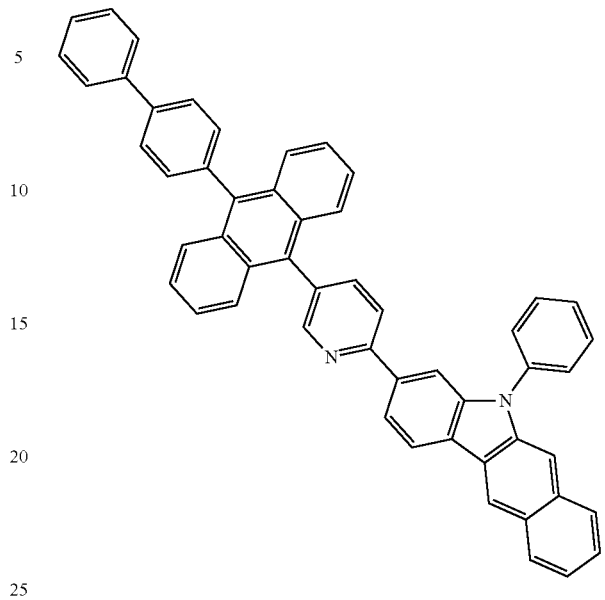
R211
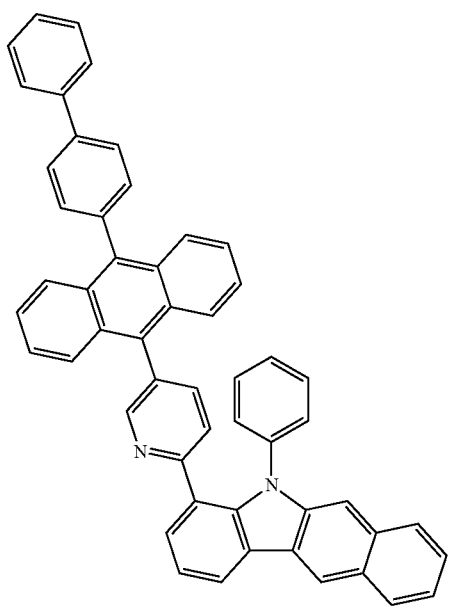
R213
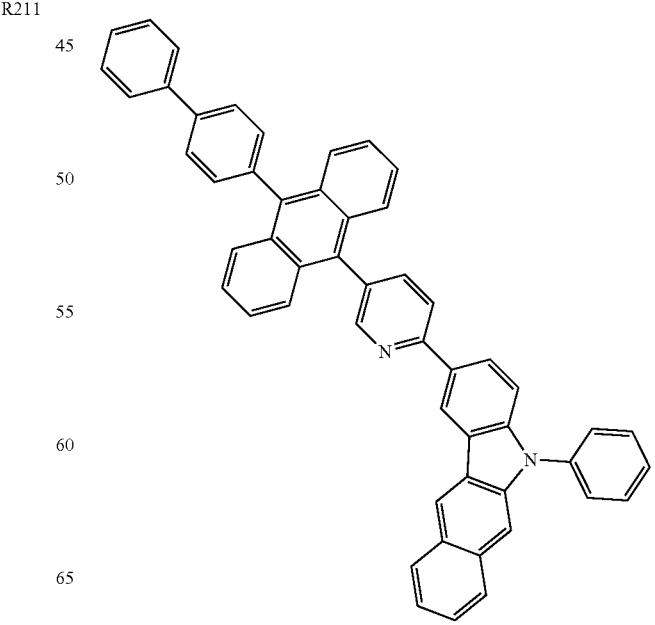

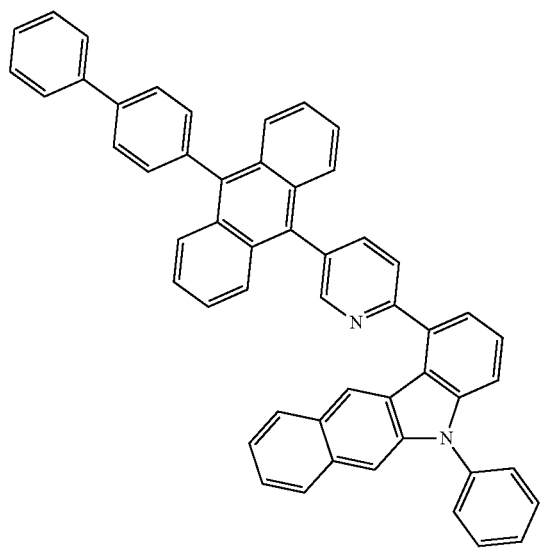
R214
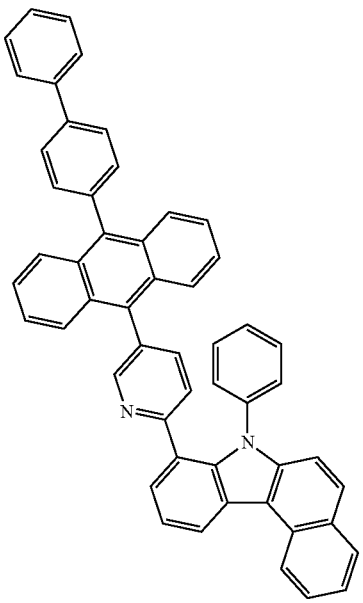
R216
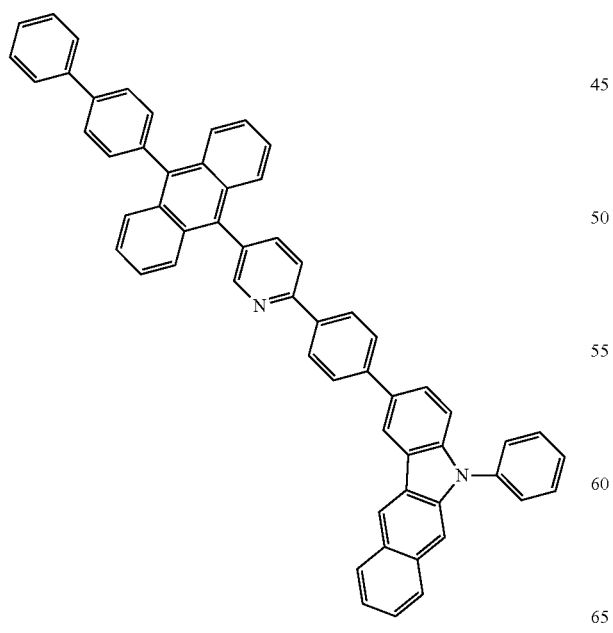
R215
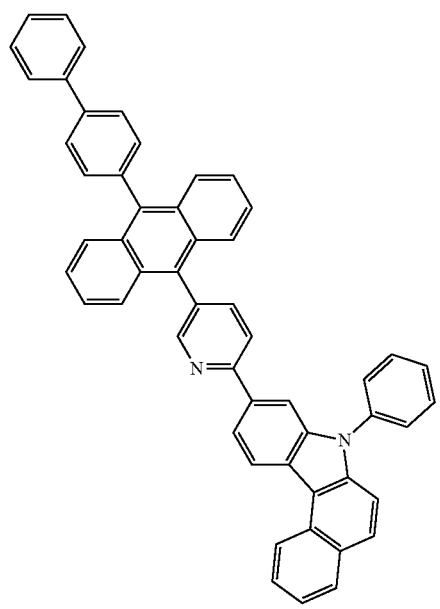
R217

-continued
R218
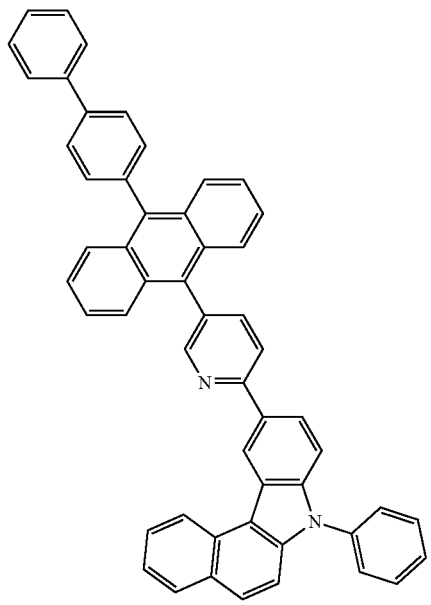
R219
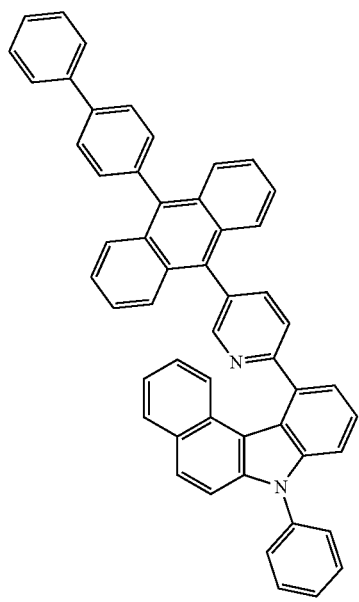
-continued
R220
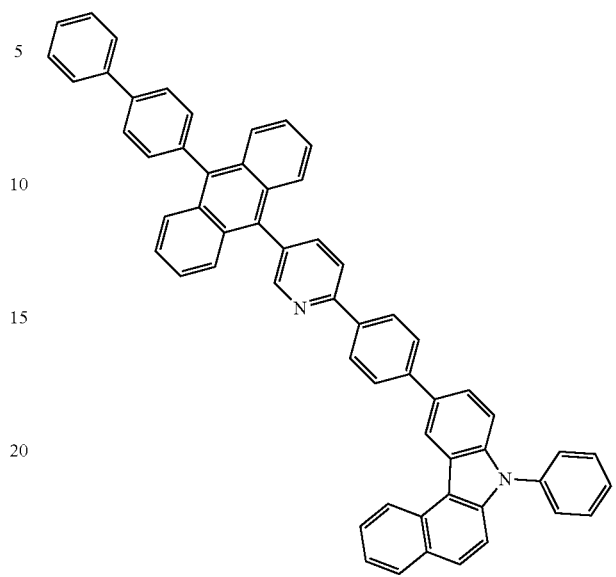
R221
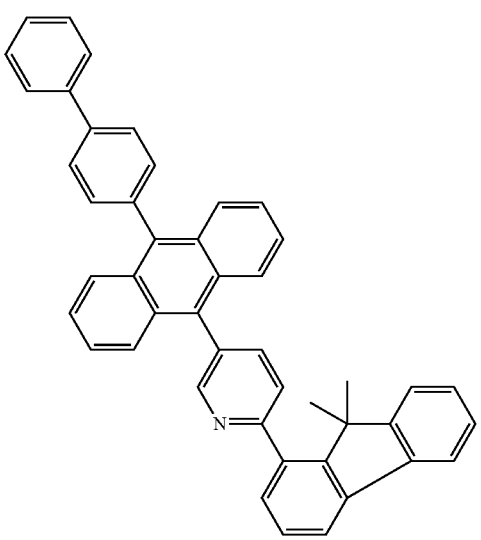

R222
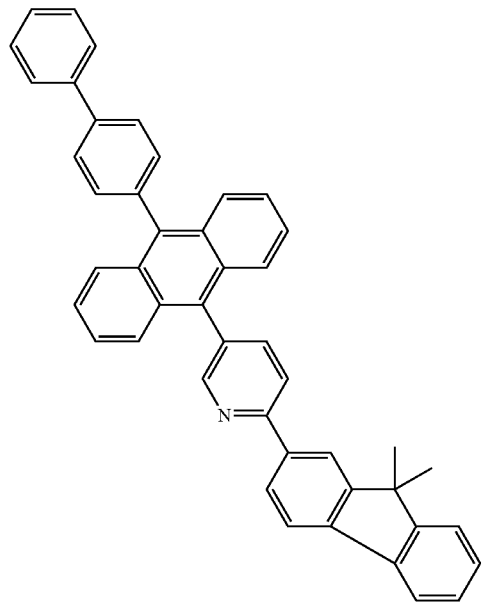
R223
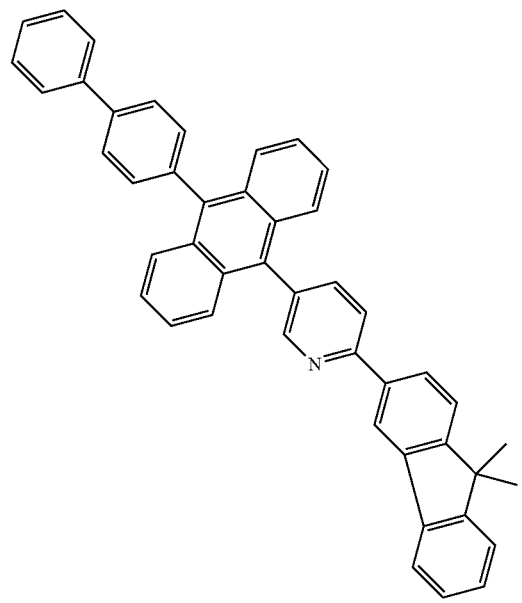
R224
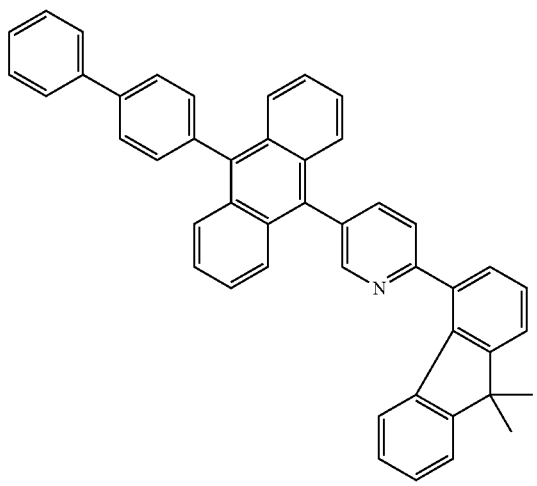
R225
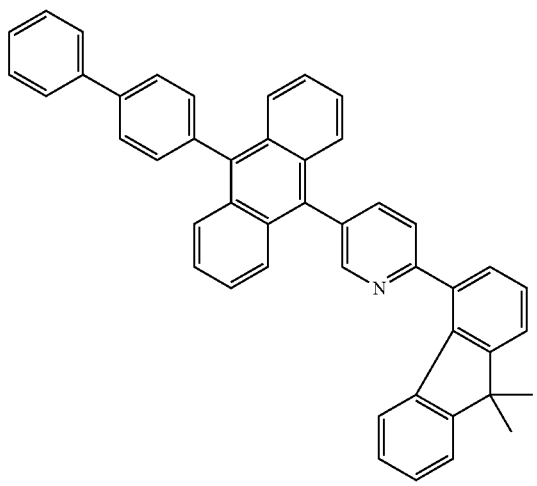
R226
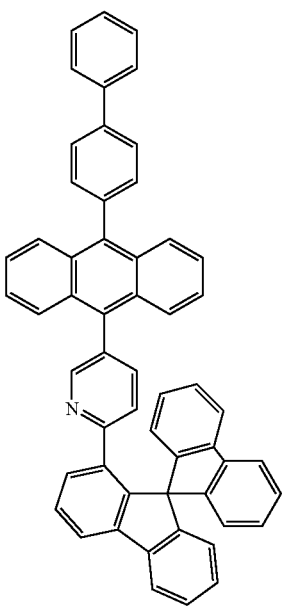

101
-continued
R227
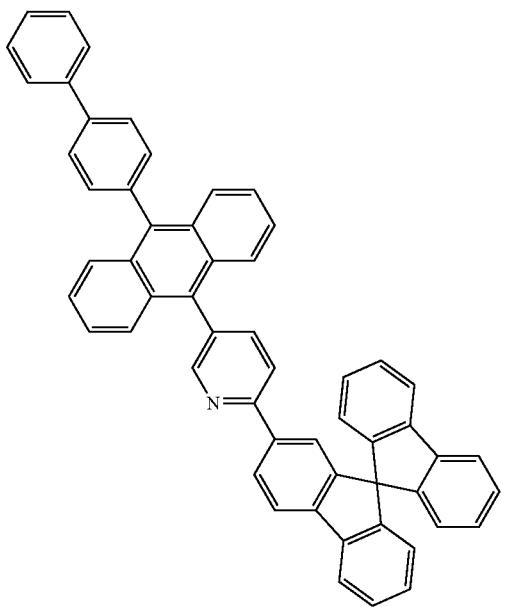
R228
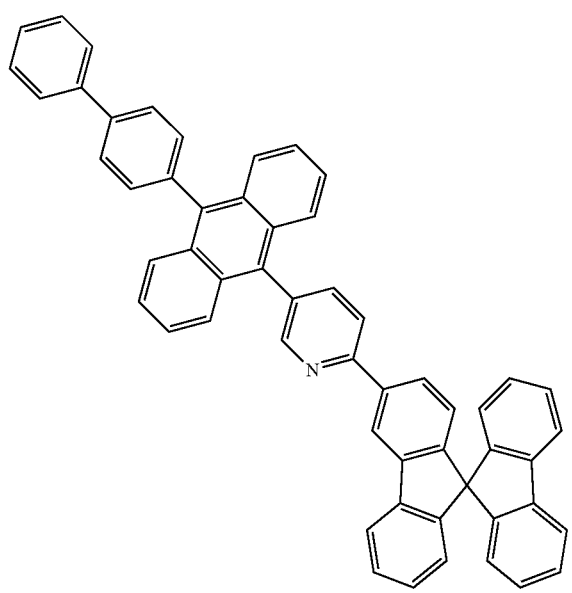
102
-continued
R229
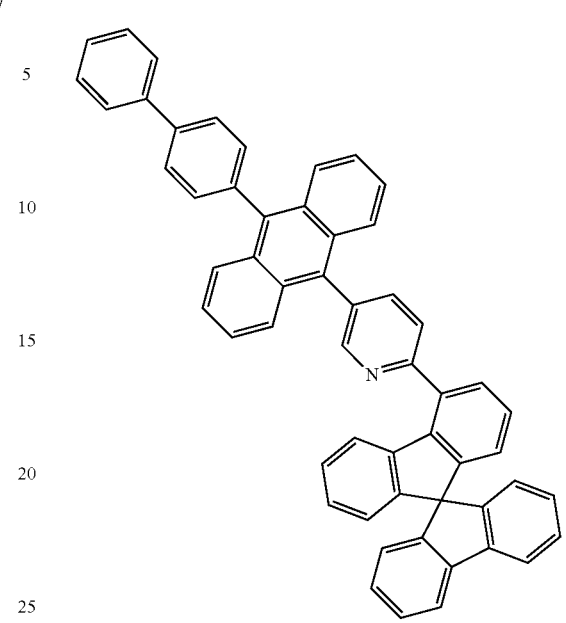
R230
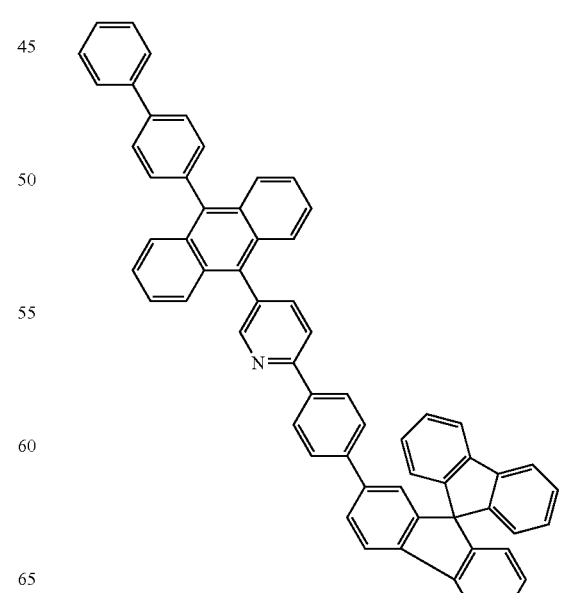

103
-continued
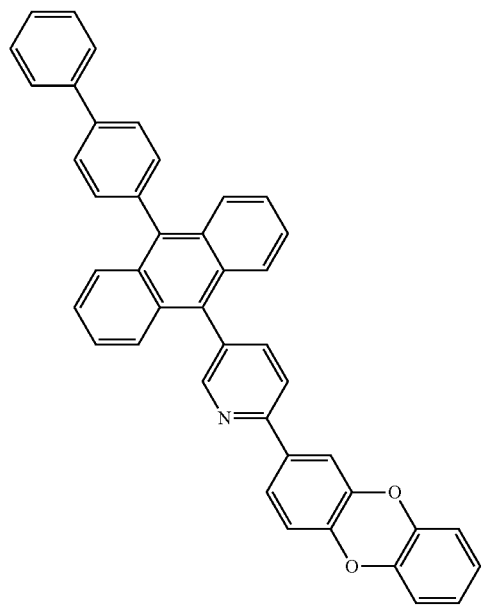
R231
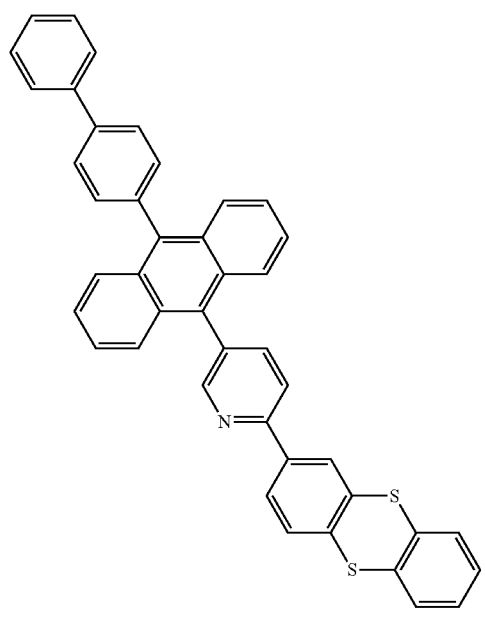
R232
104
-continued
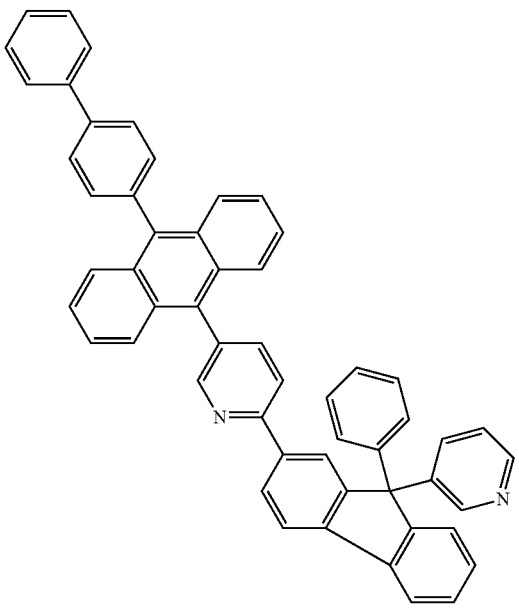
R233
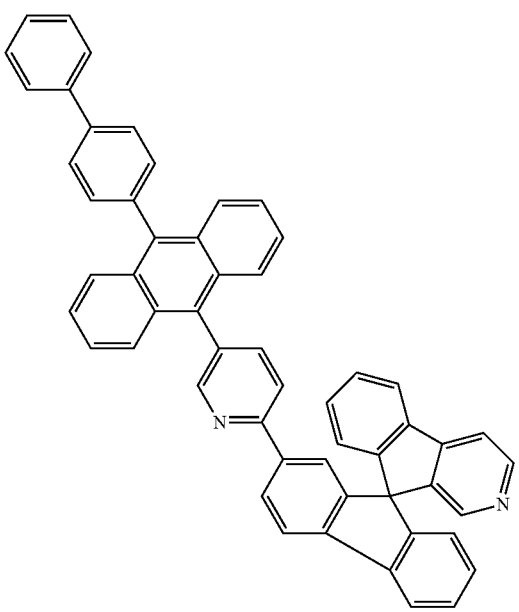
R234

105
-continued
R235
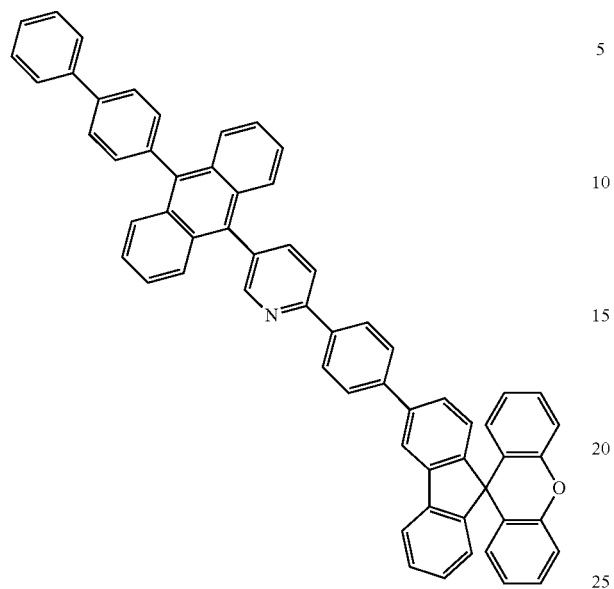
106
-continued
R237
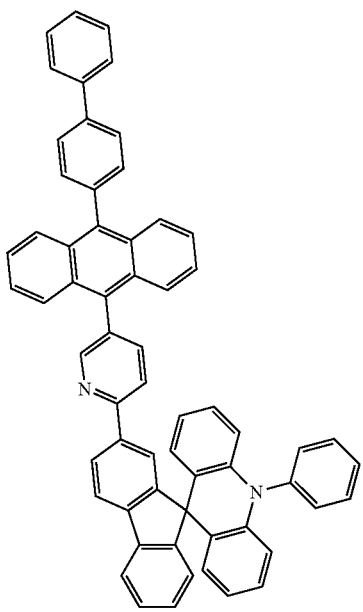
R236
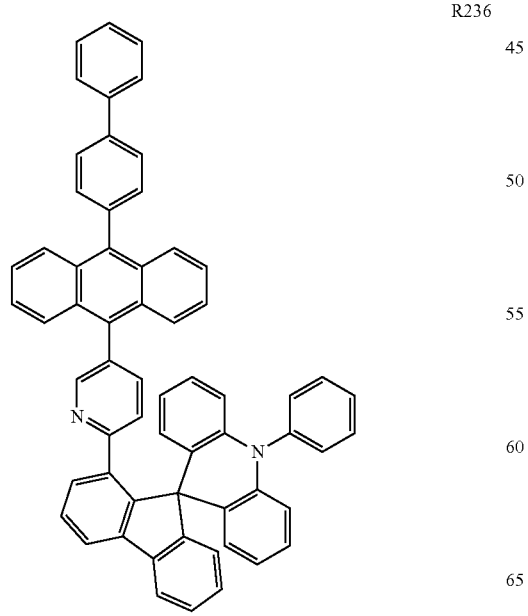
R238
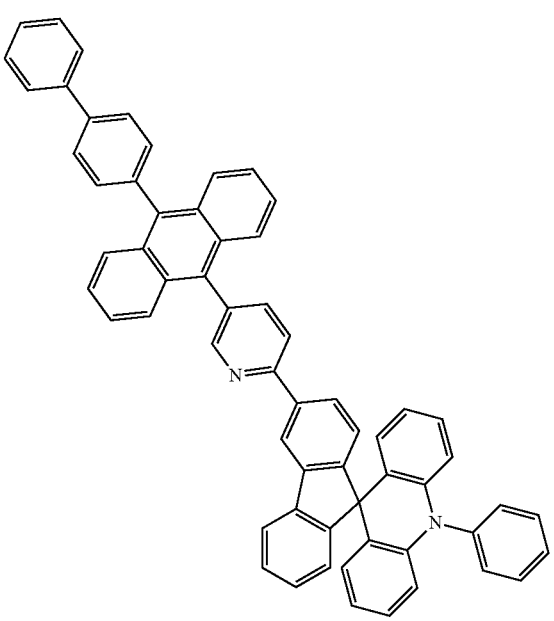

R239
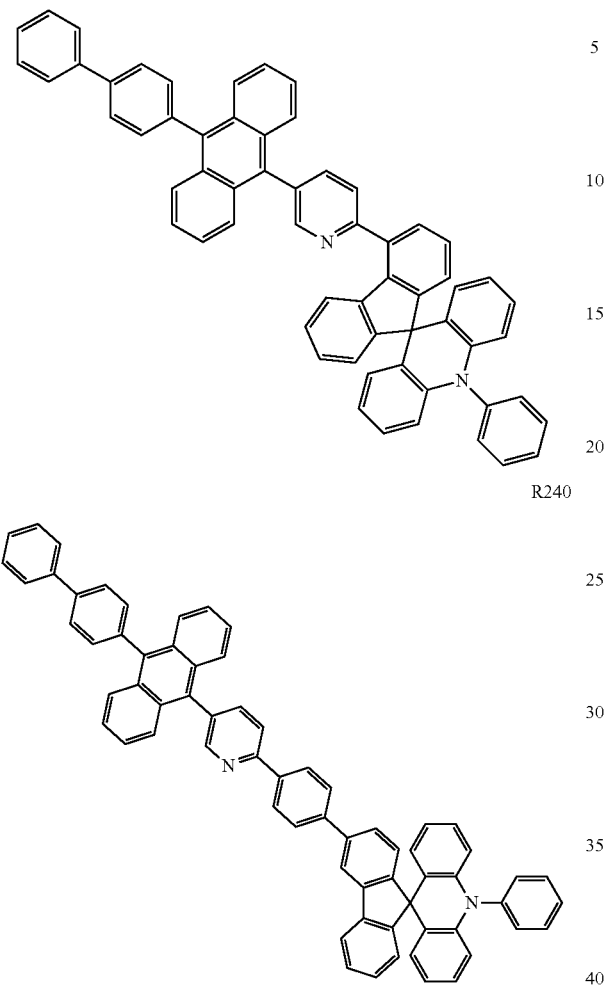
R240
R241
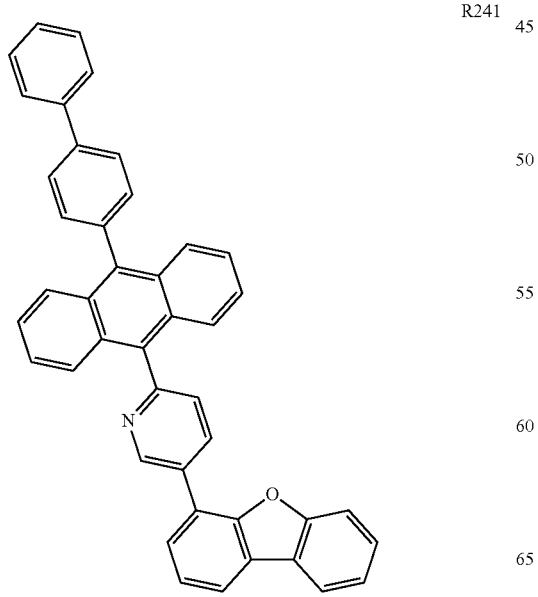
R242
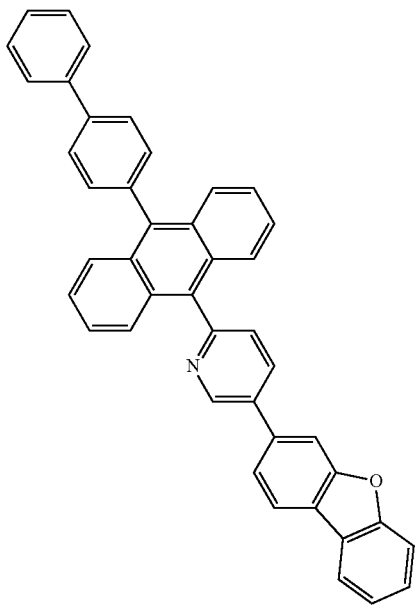
R243
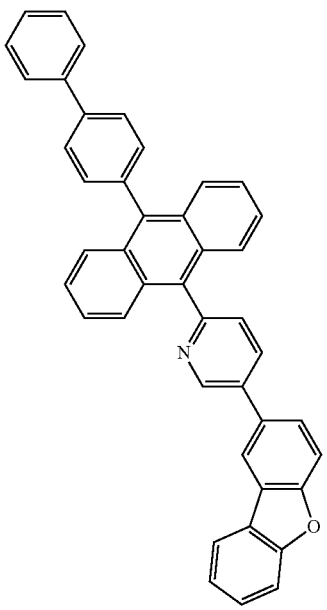

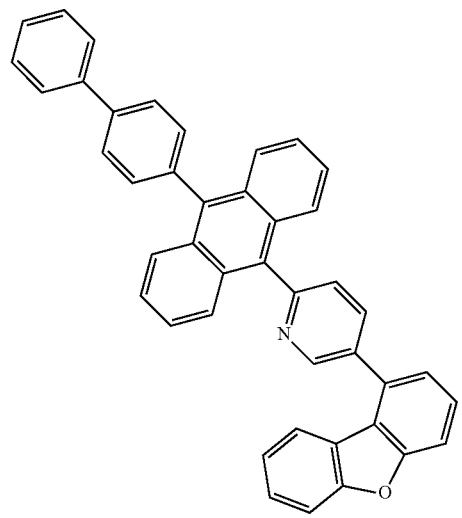
R244
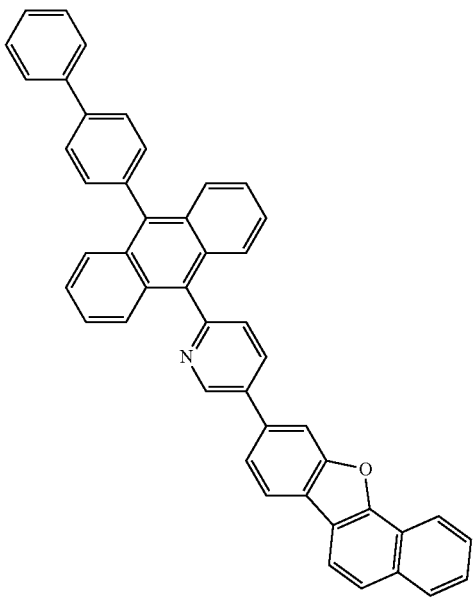
R247
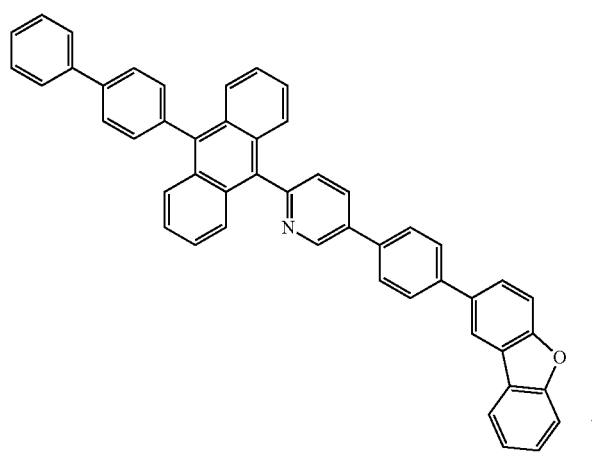
R245
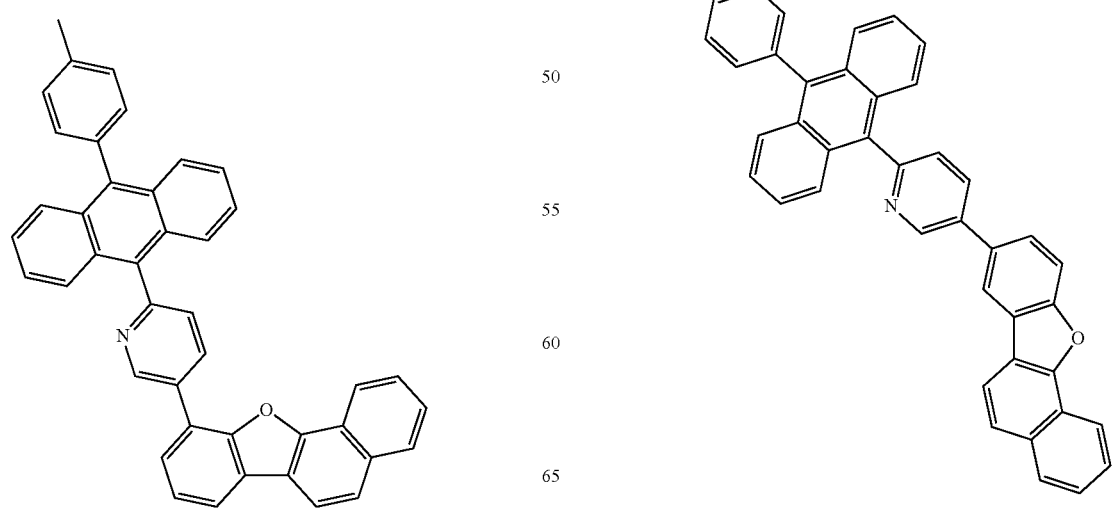
R246
R248

-continued
R249
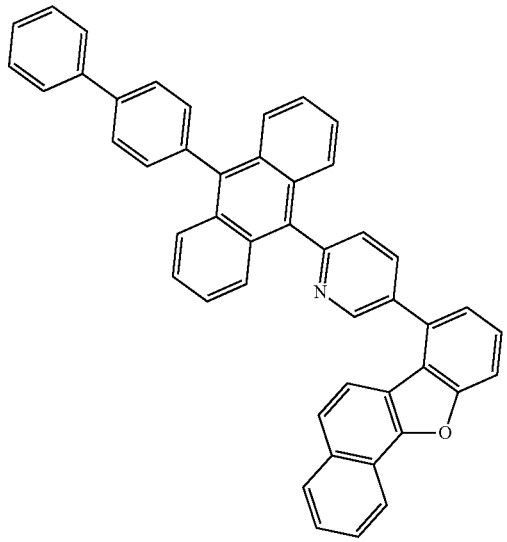
R250
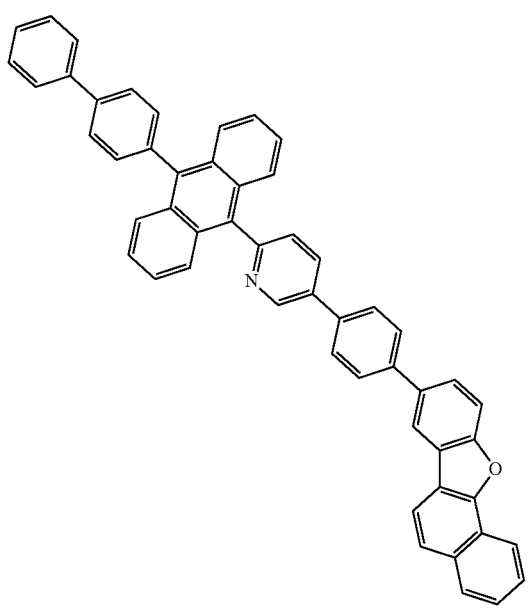
R251
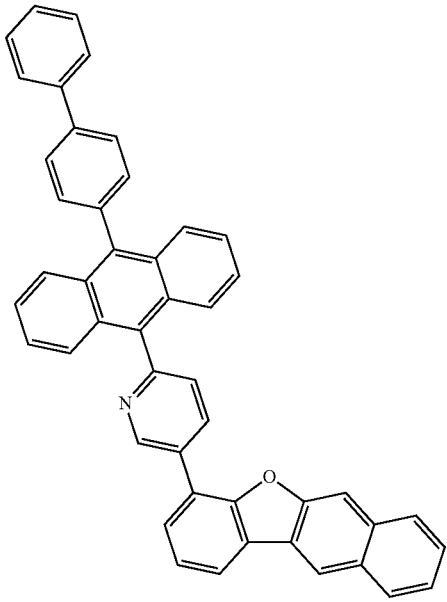
R252
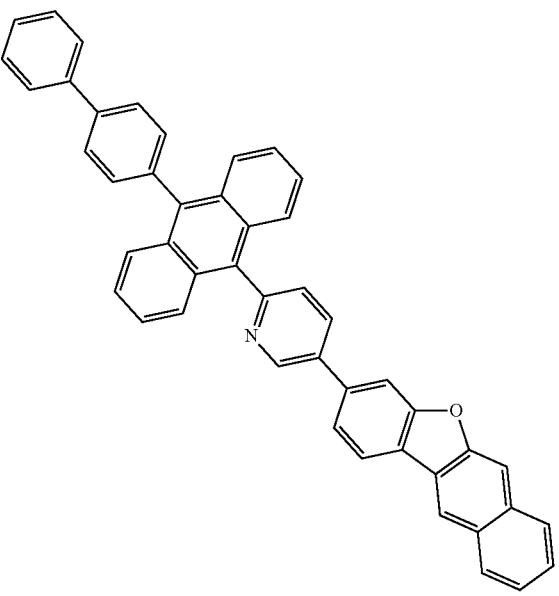

R253
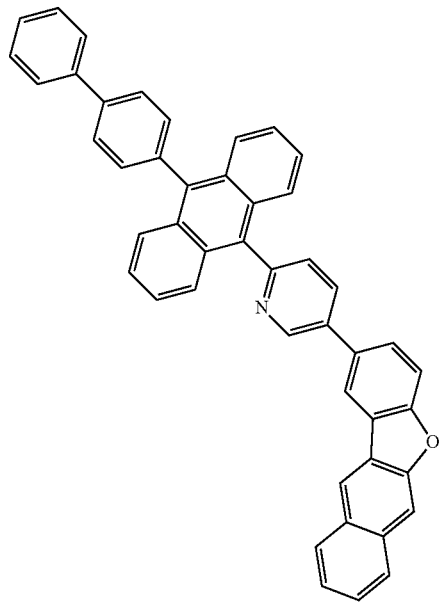
R254
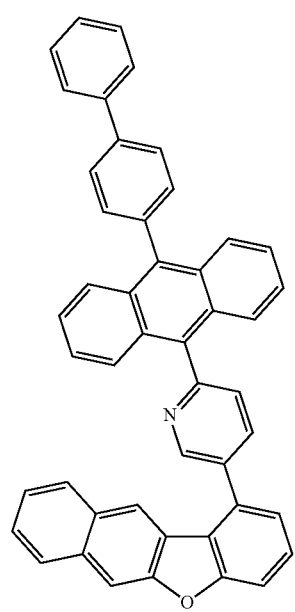
R255
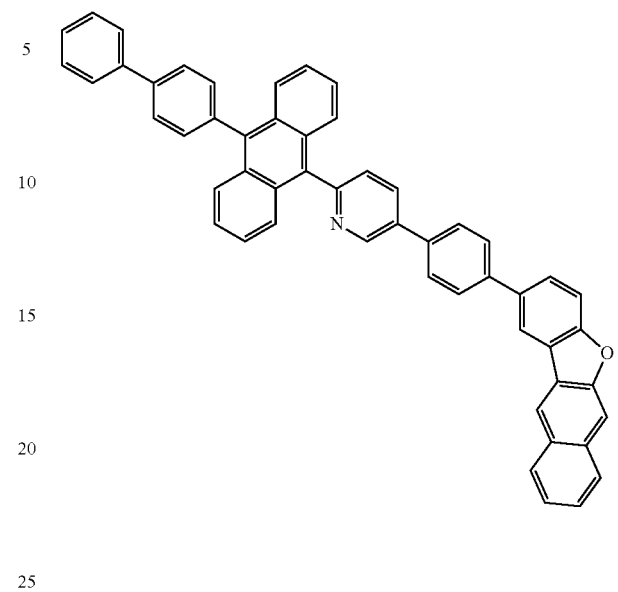
R256
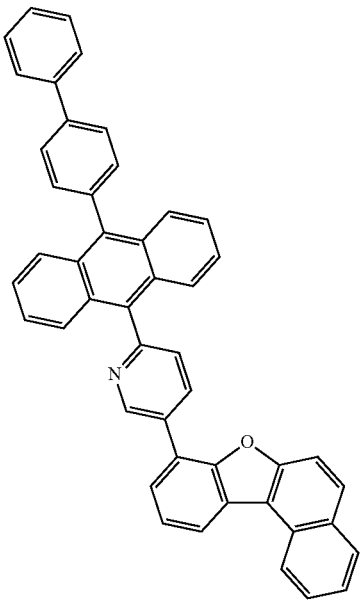

R257
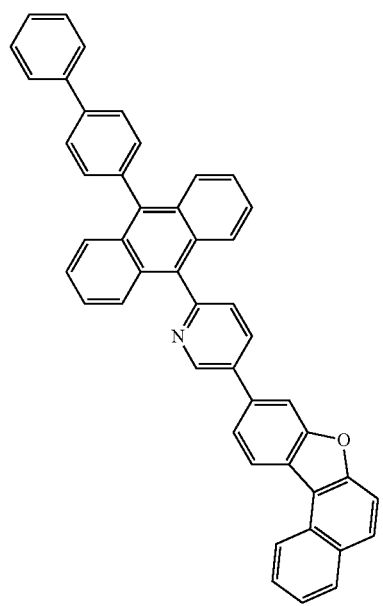
R259
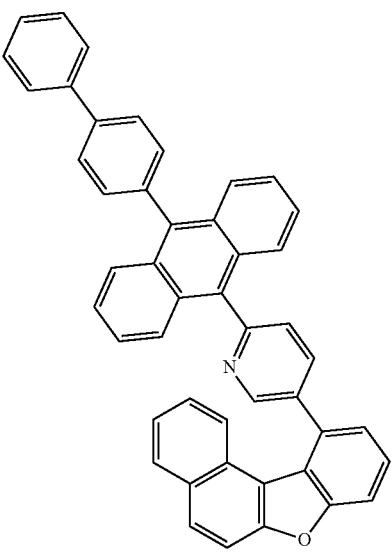
R258
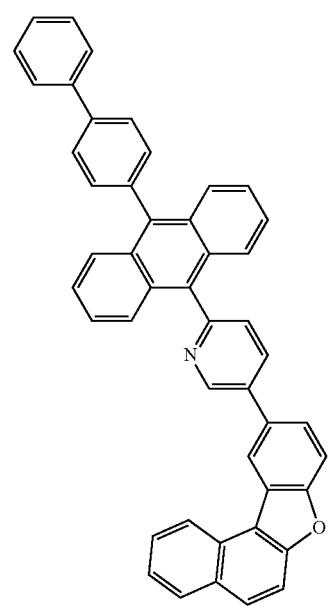
R260
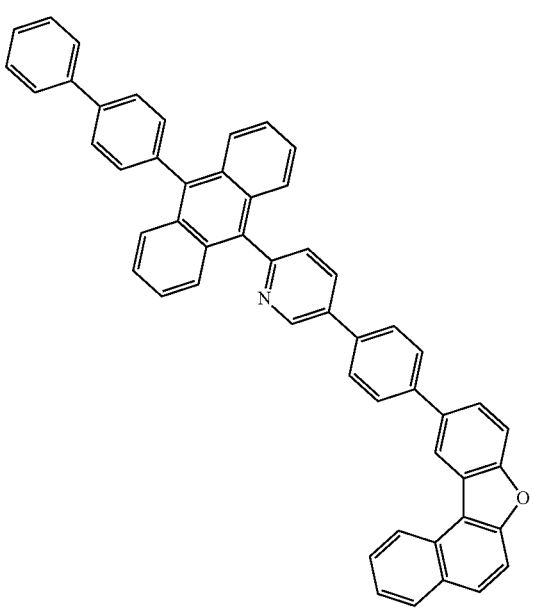

R261
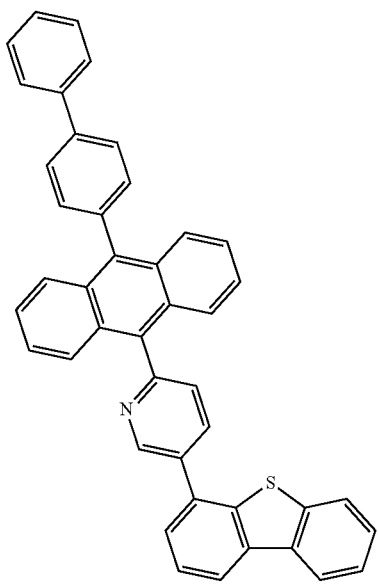
R262
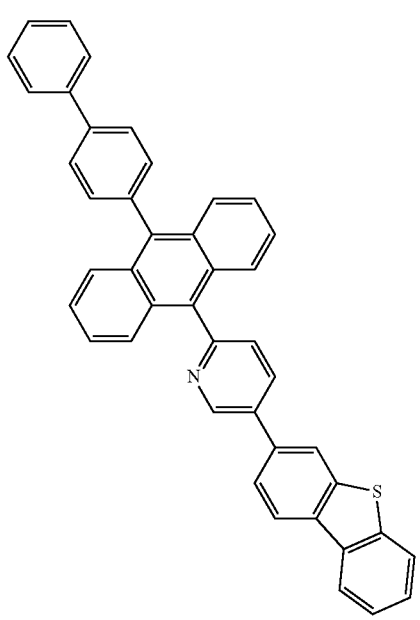
R263
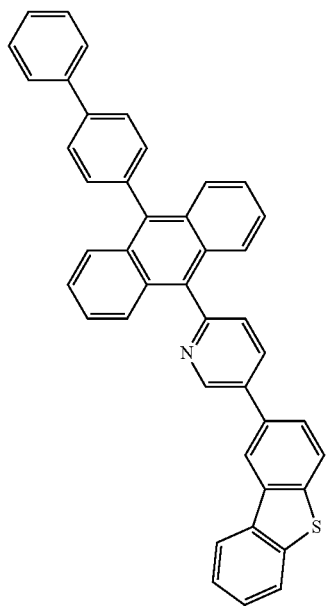
R264
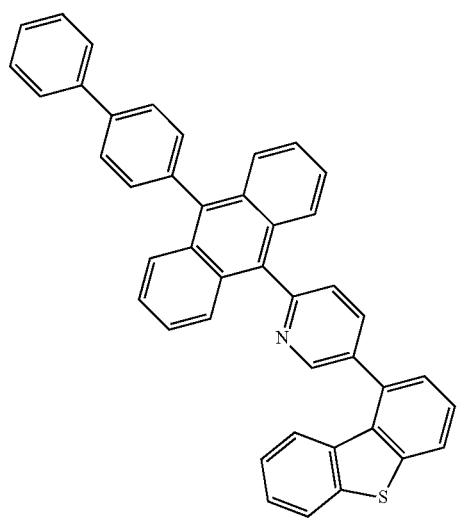
R265

R266
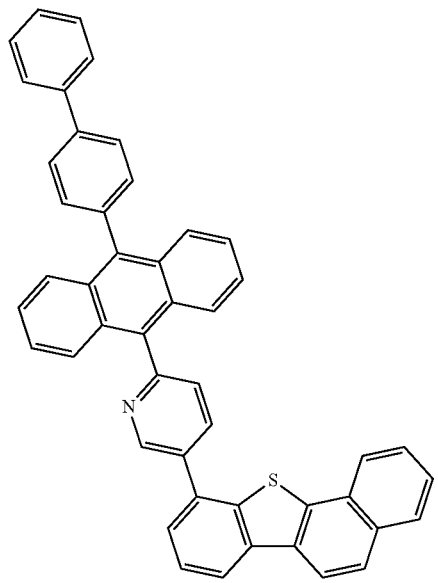
R268
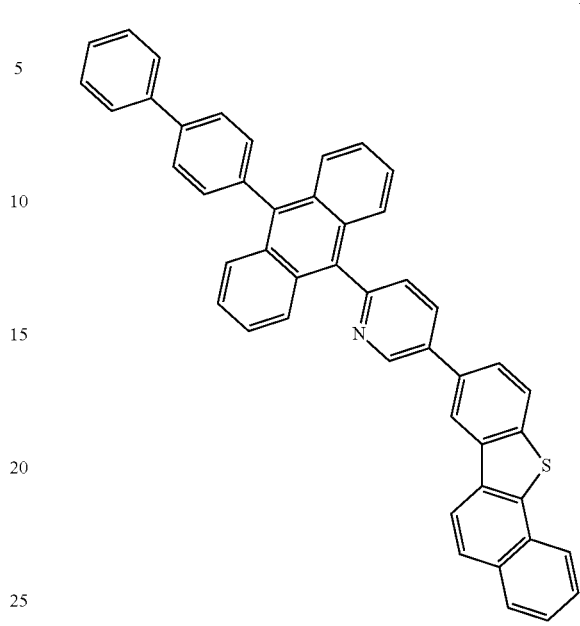
R267
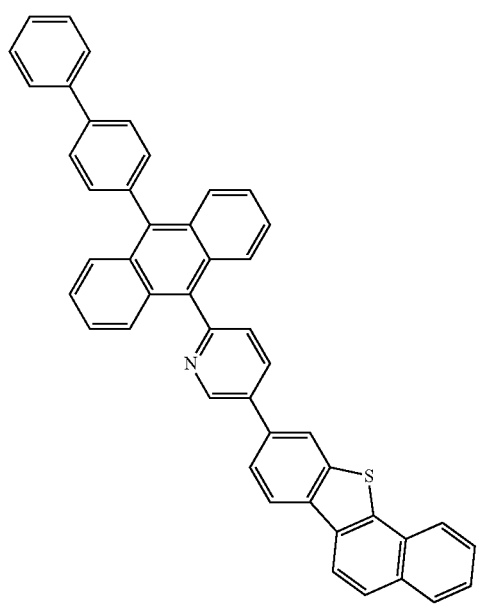
R269
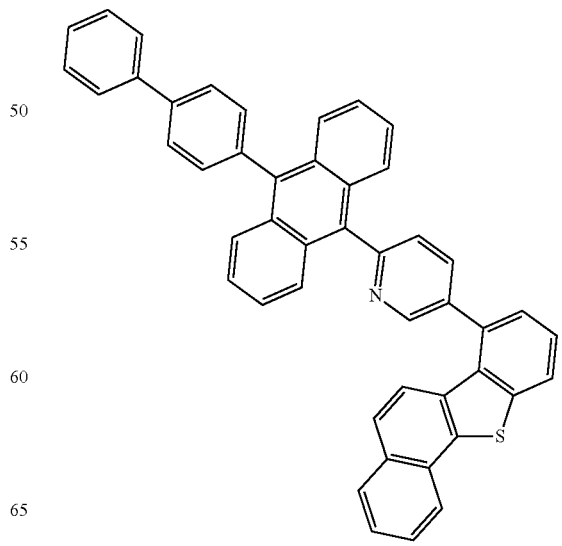

121
-continued
R270
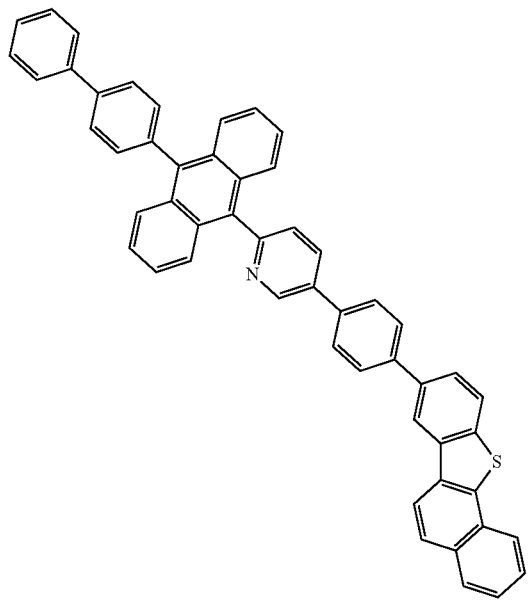
R271
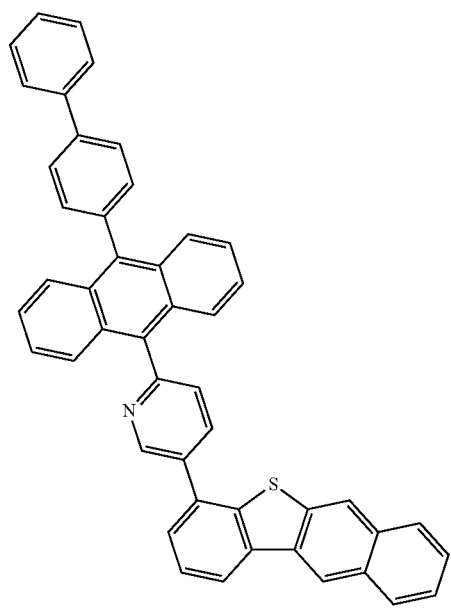
122
-continued
R272
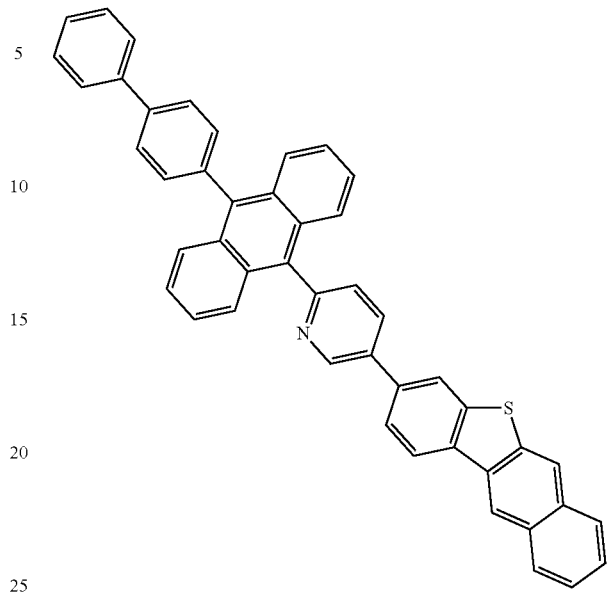
R273
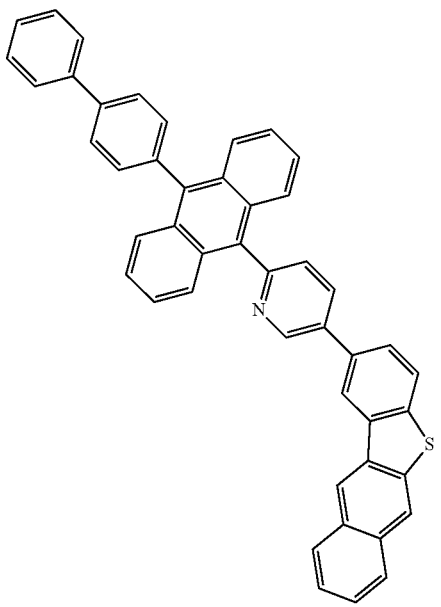

R274
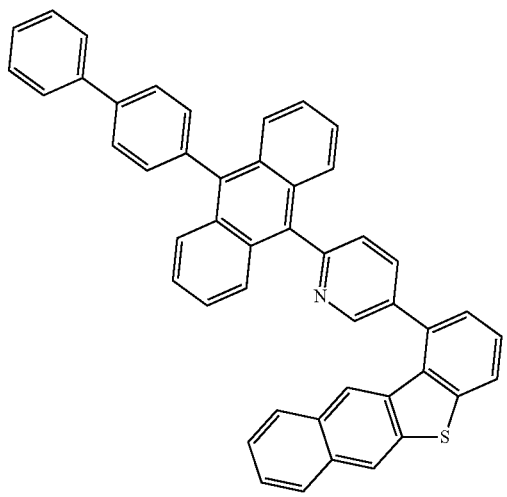
R275
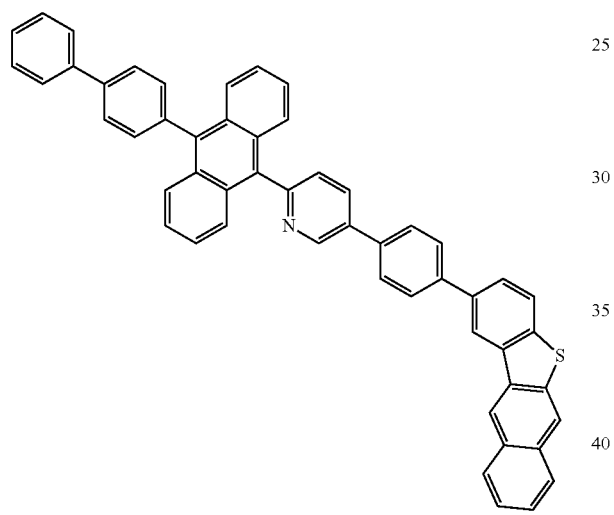
R276
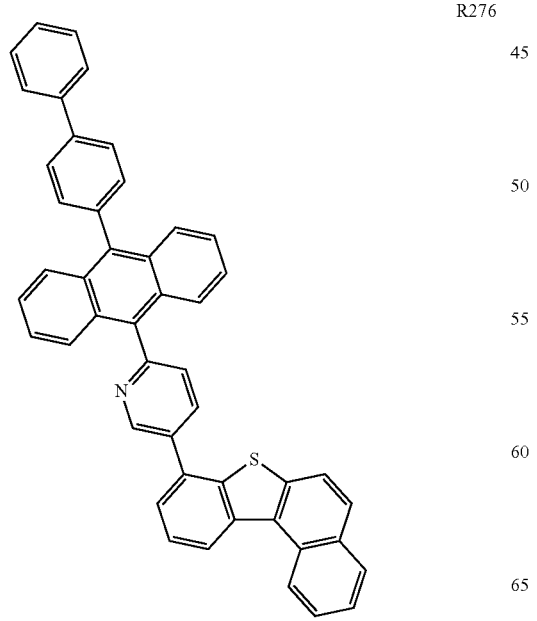
R277
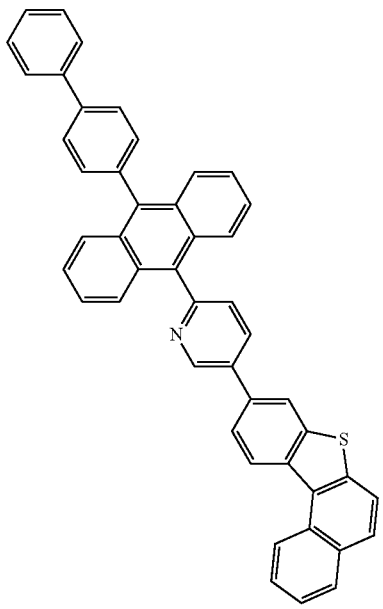
R278
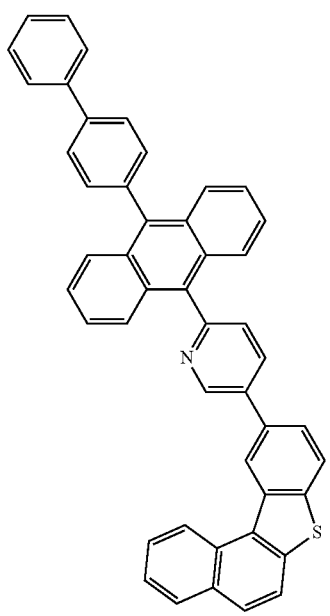

125
-continued
R279
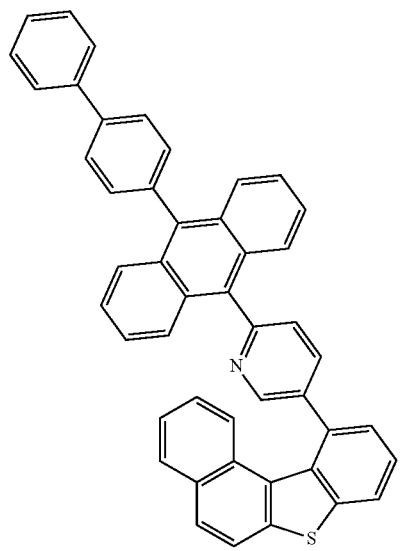
R280
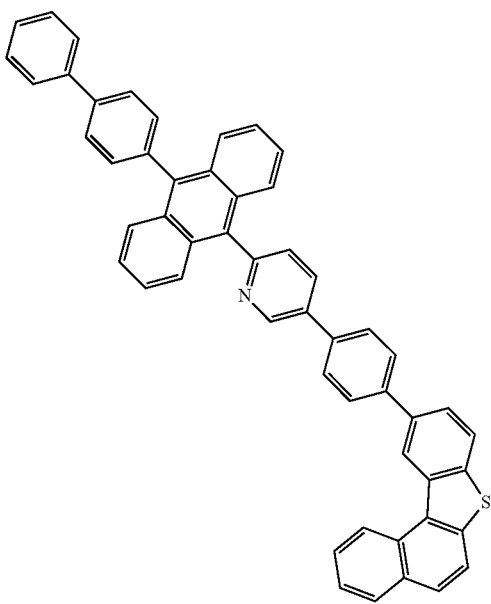
126
-continued
R281
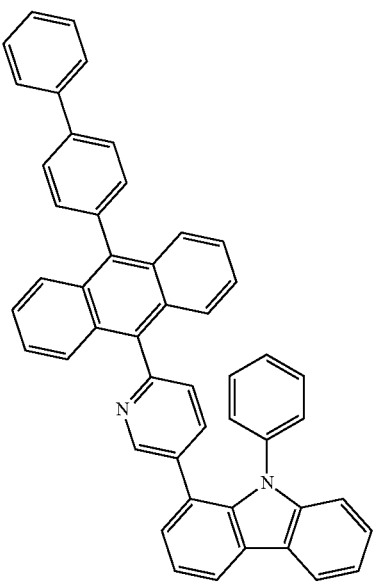
R282
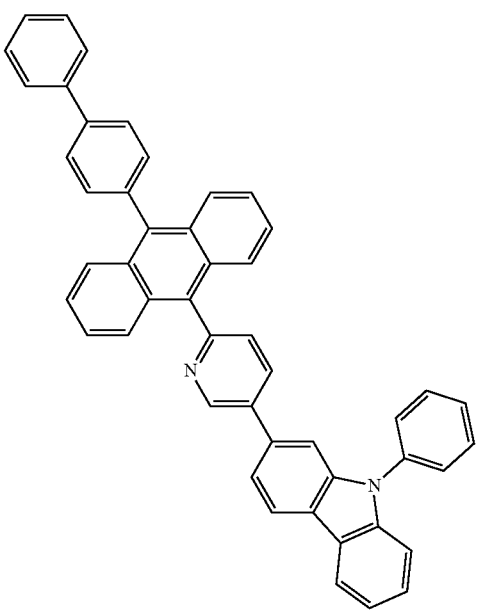

127
-continued
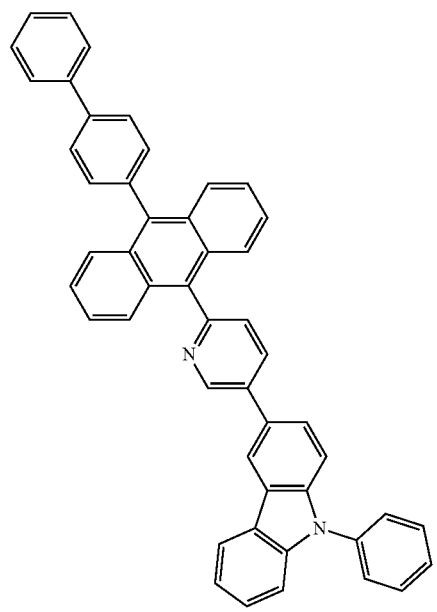
R283
128
-continued
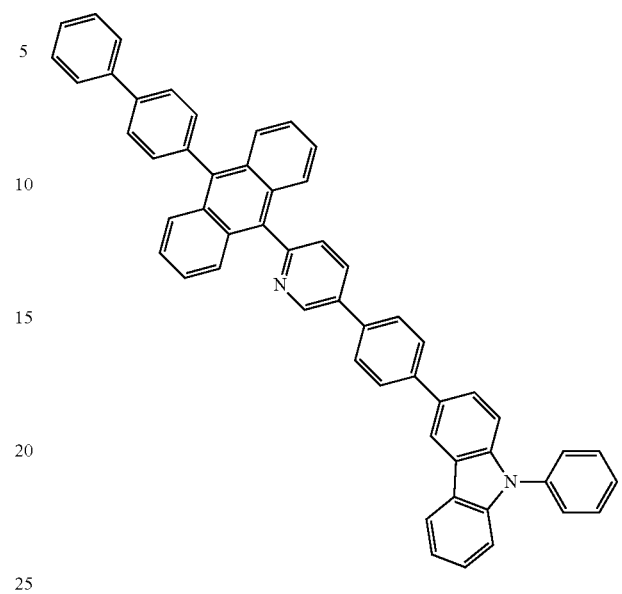
R285
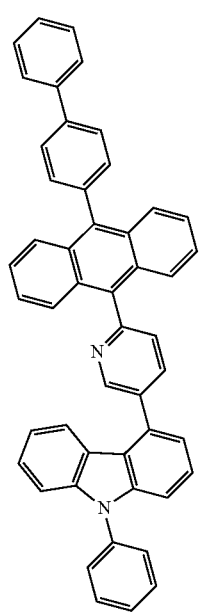
R284
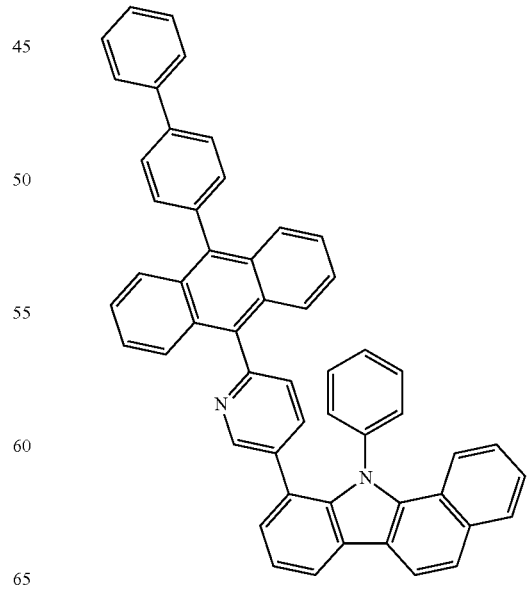
R286

R287
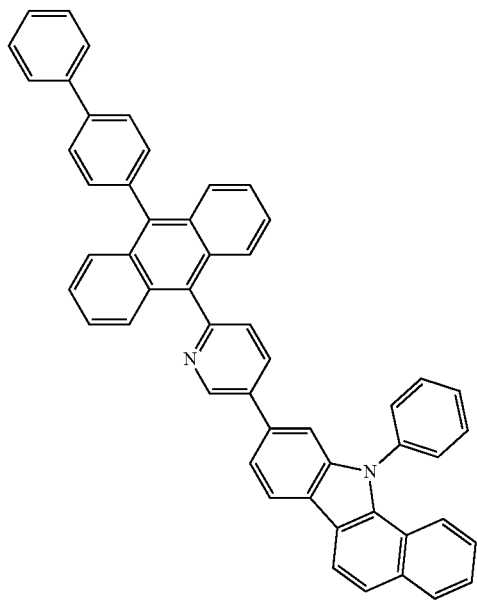
R289
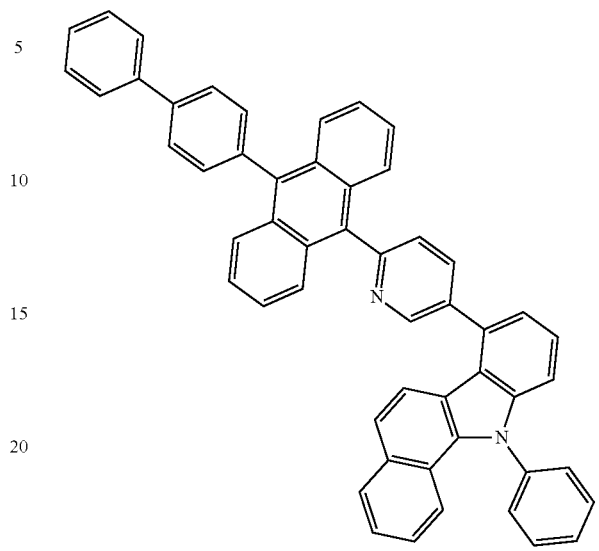
R288
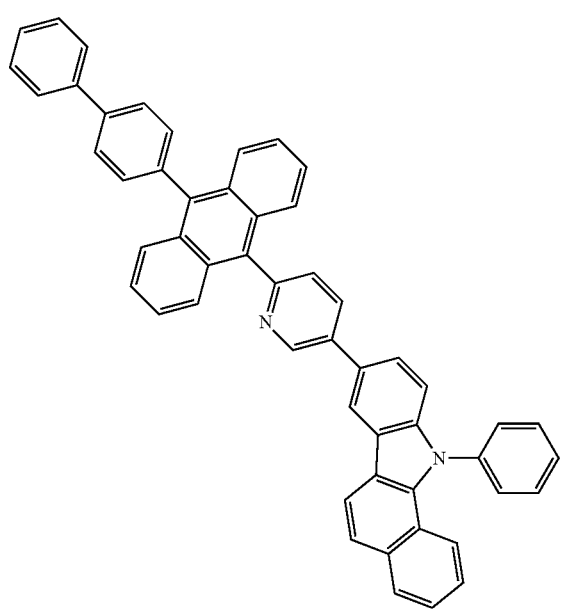
R290
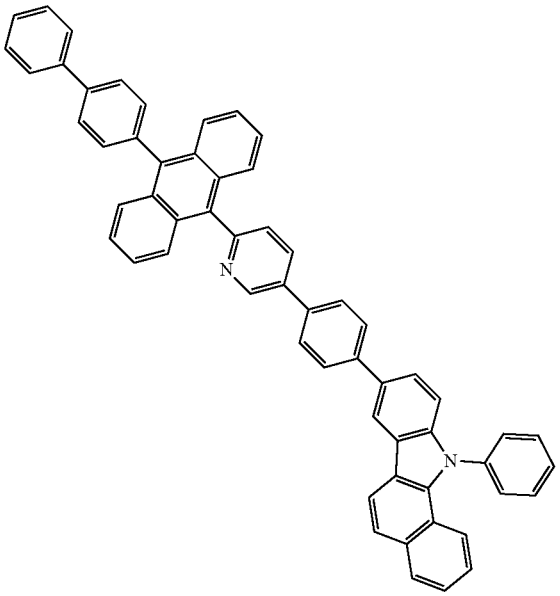

R291
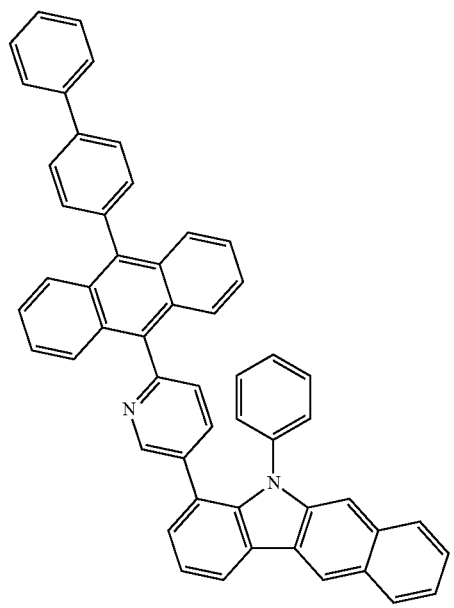
R292
R293
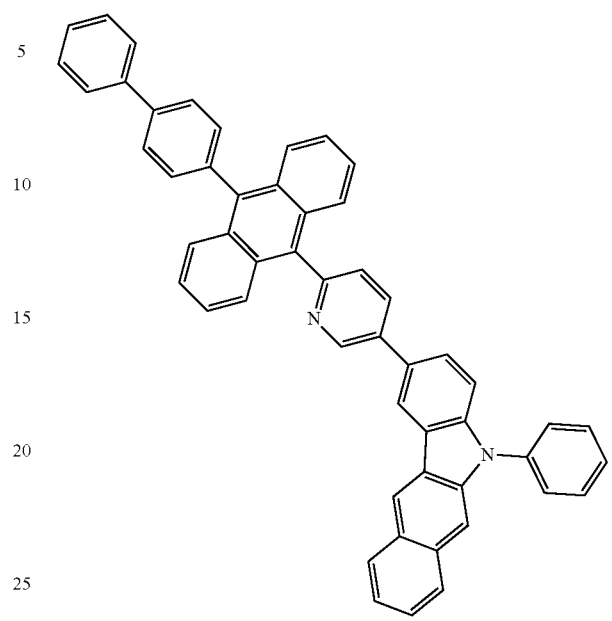
R294
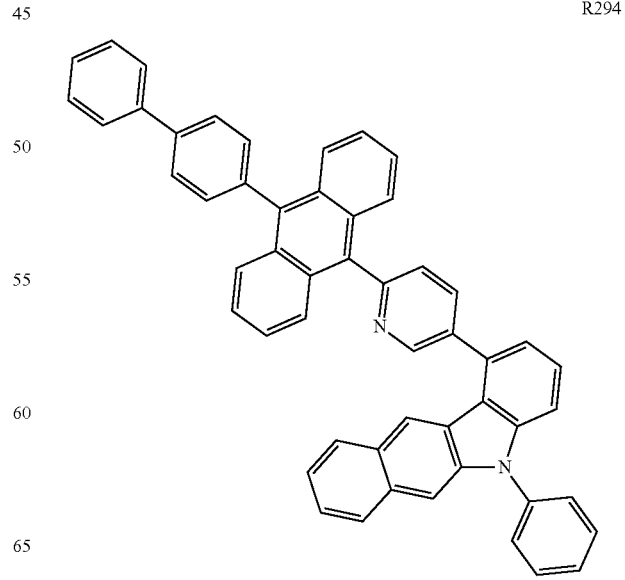

R295
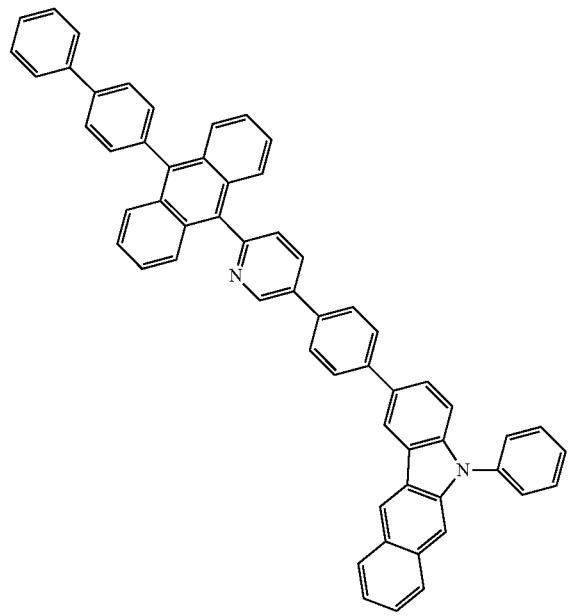
R296
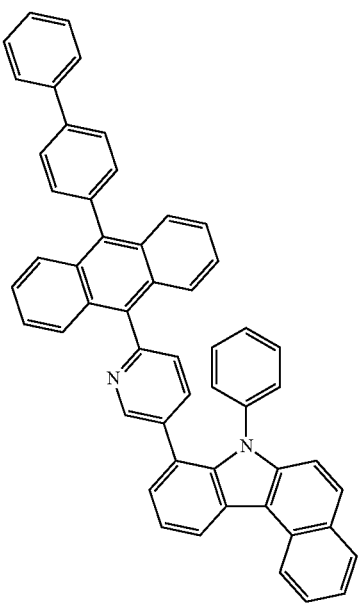
R297
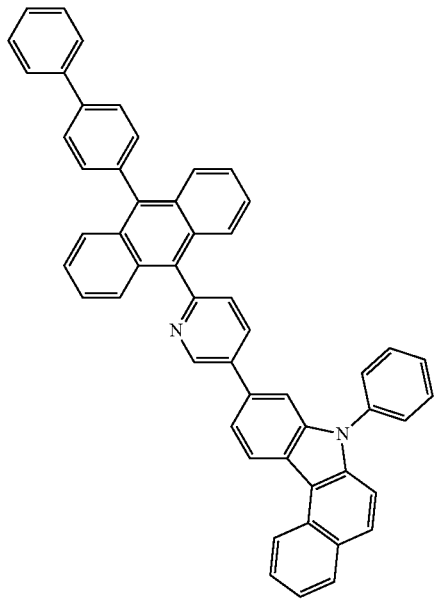
R298
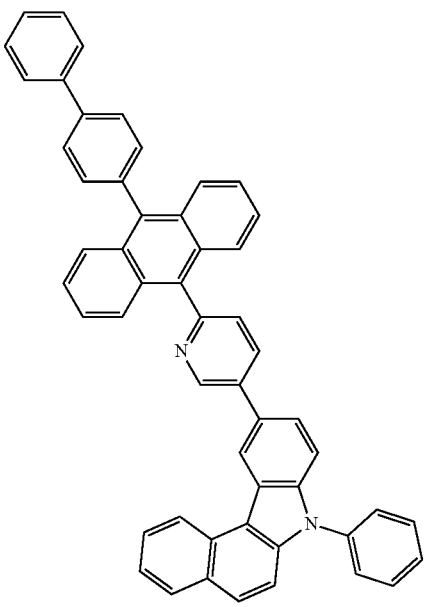

R299
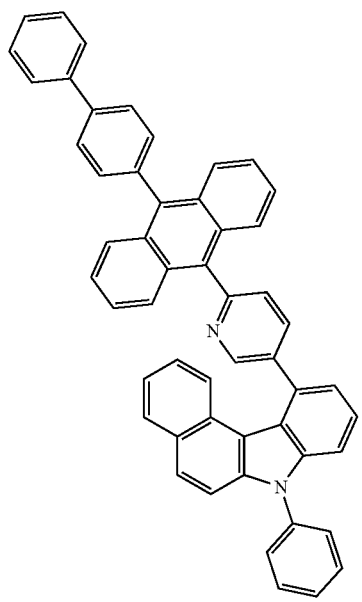
R300
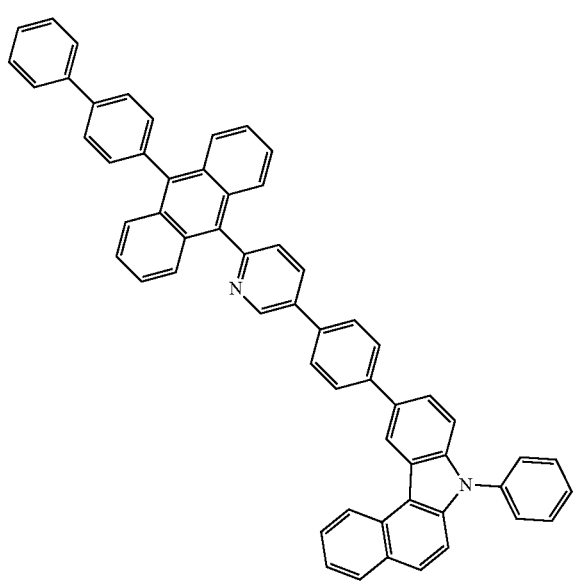
R301
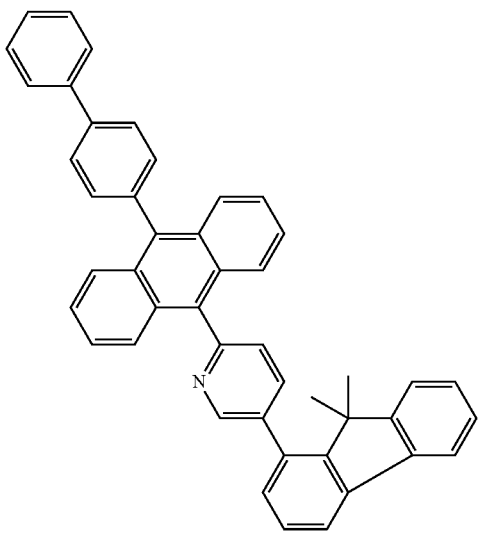
R302
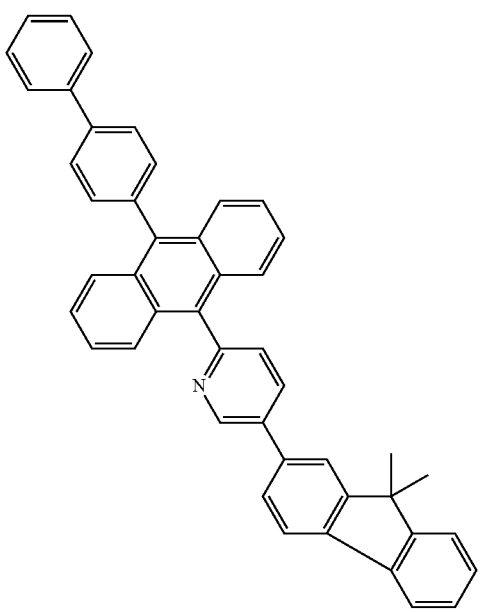

-continued
R303
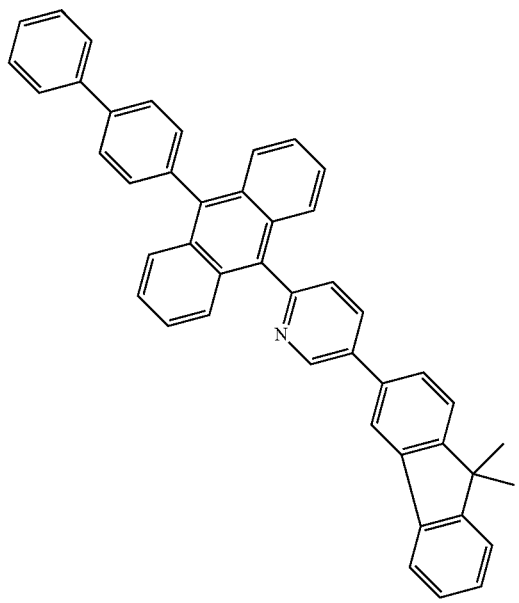
R304
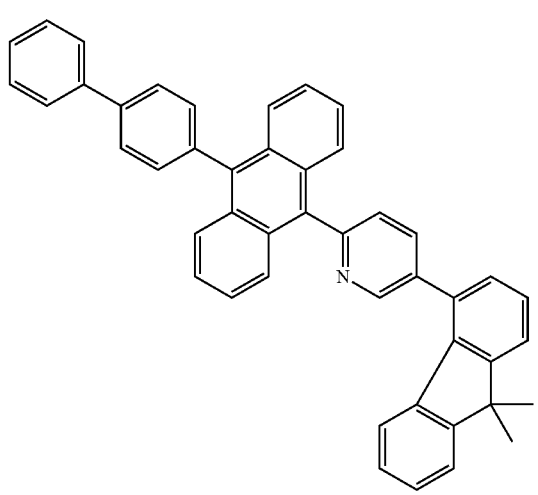
R305
-continued
R306
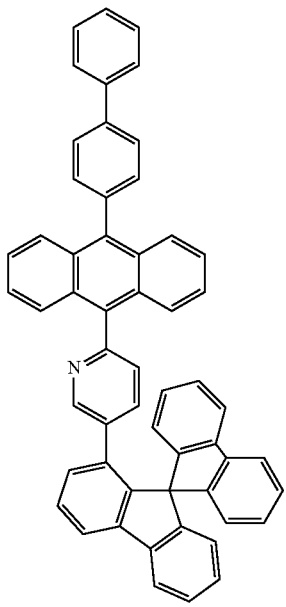
R307
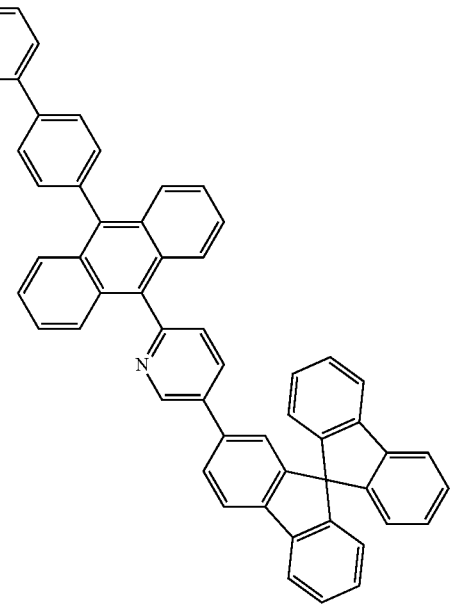

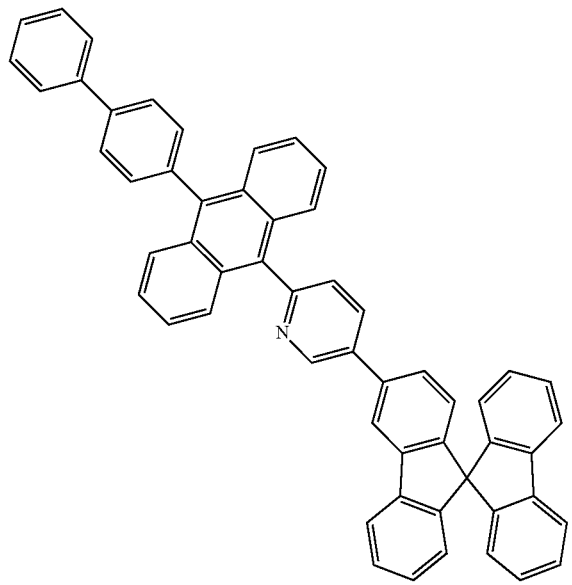 R308
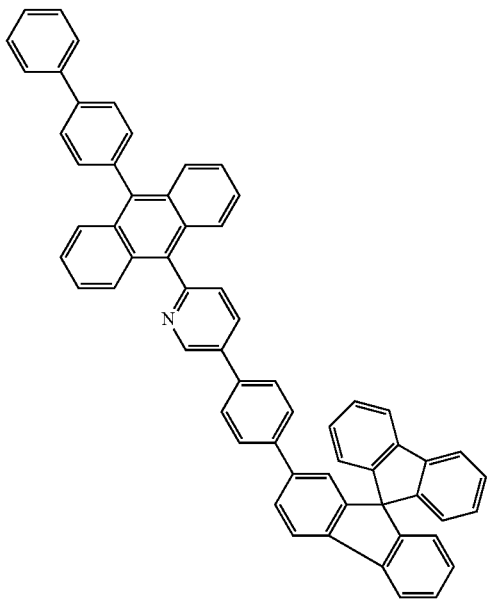 R310
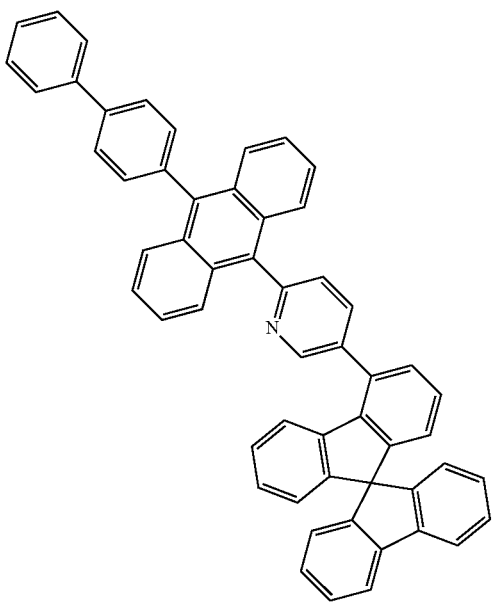 R309
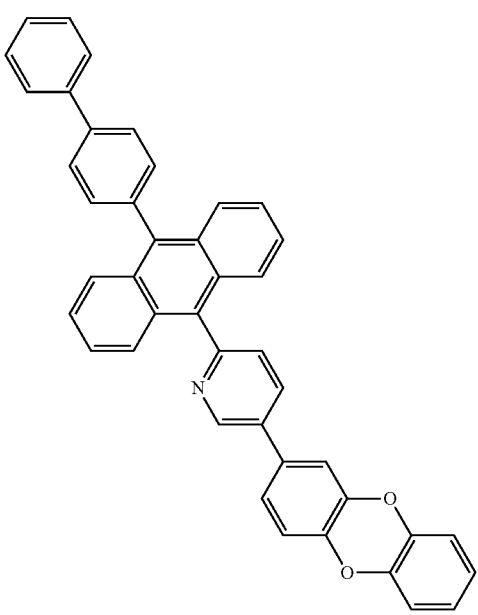 R311

R312
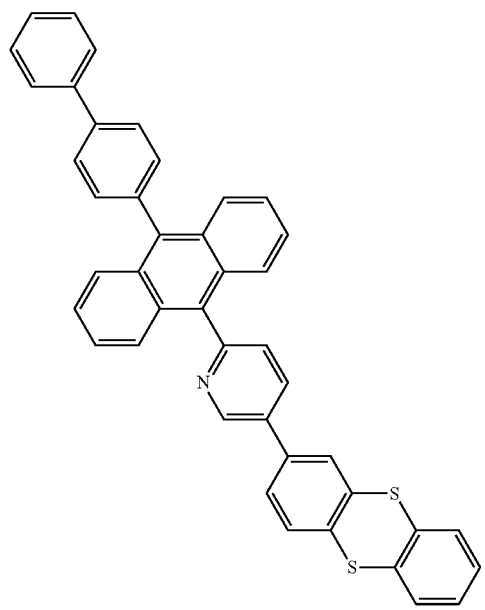
R314
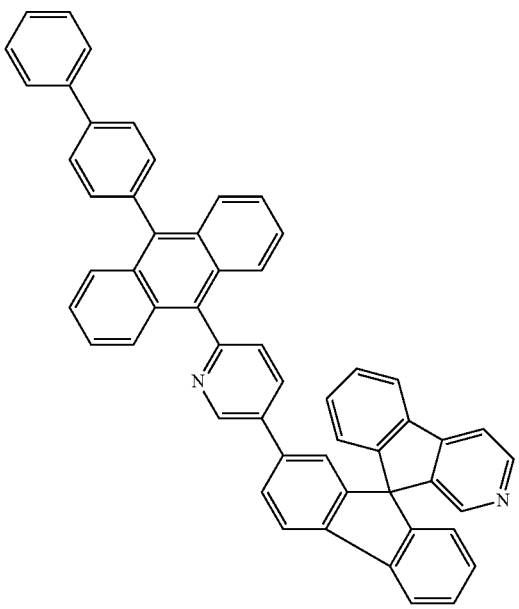
R313
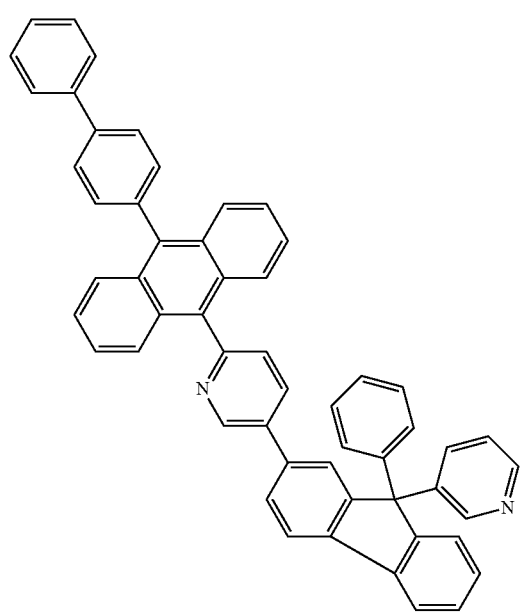
R315
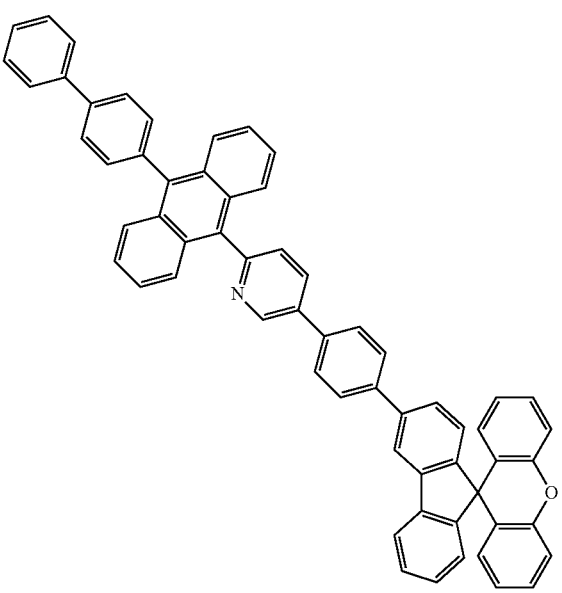

-continued
R316
R317
R318
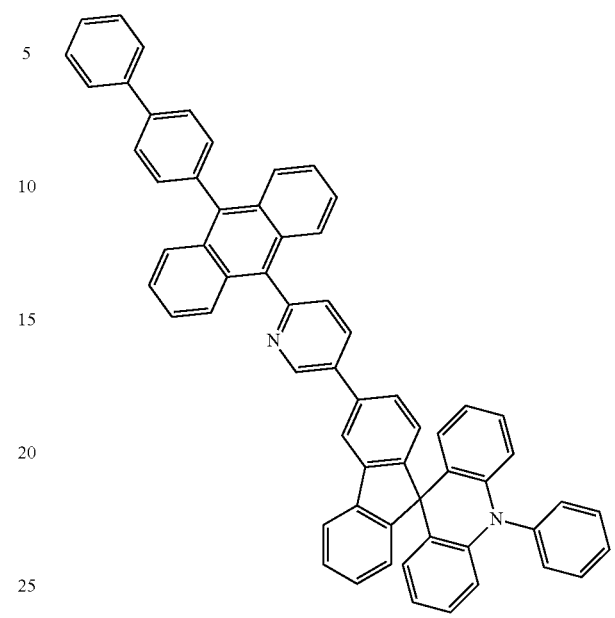
R319
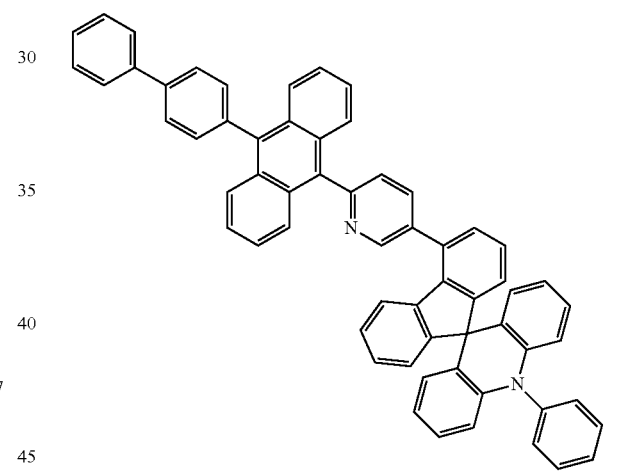
R320
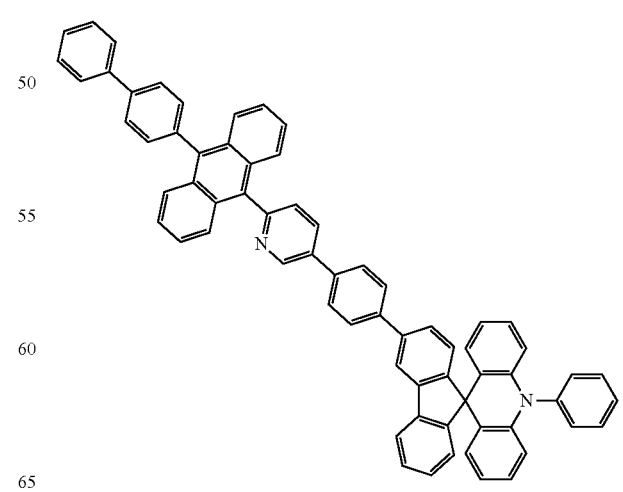

R321
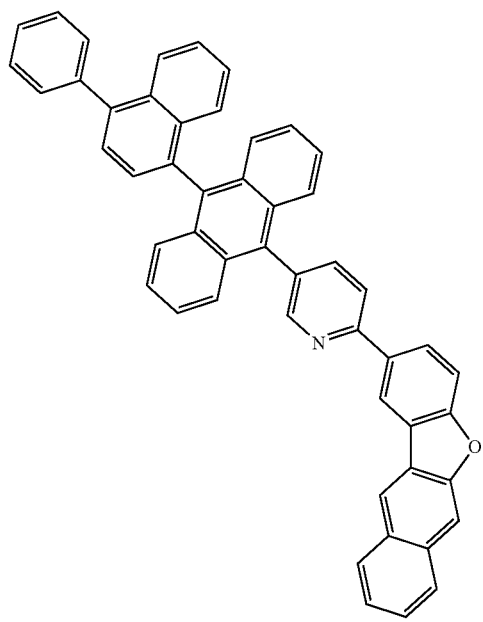
R322
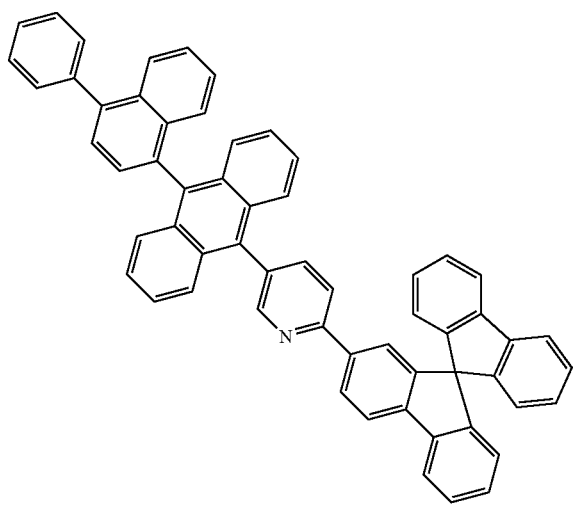
R323
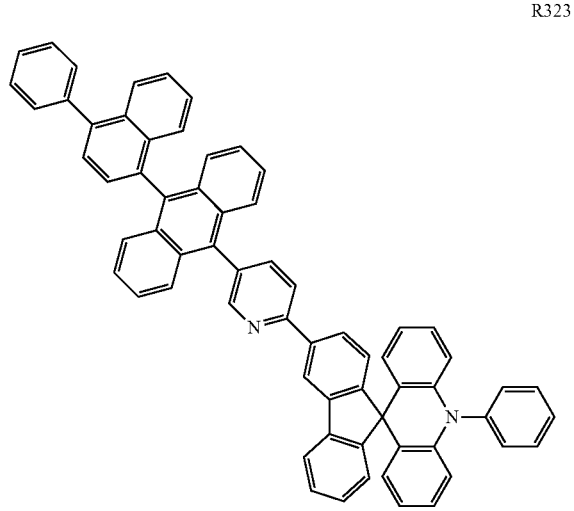
R324
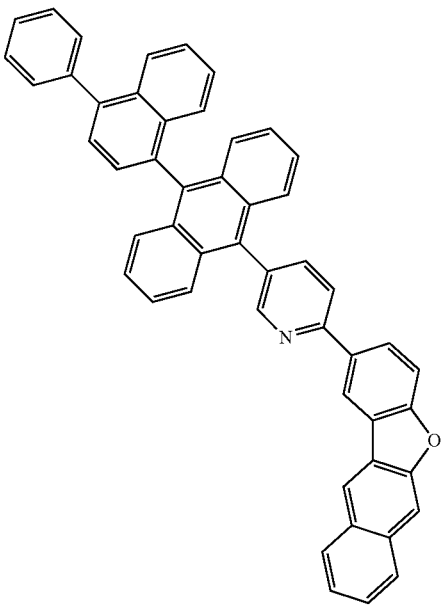
R325
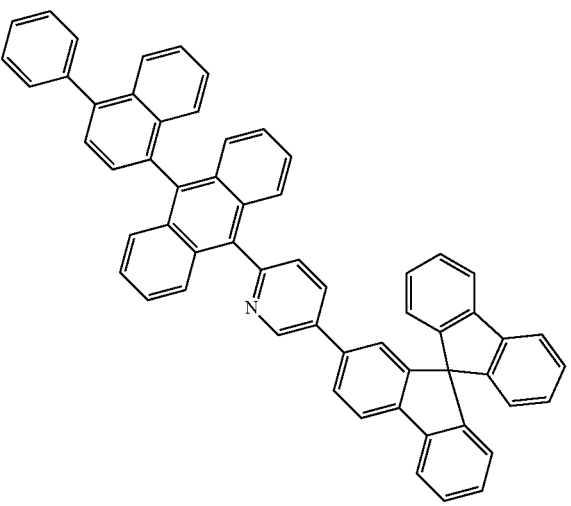

147
-continued
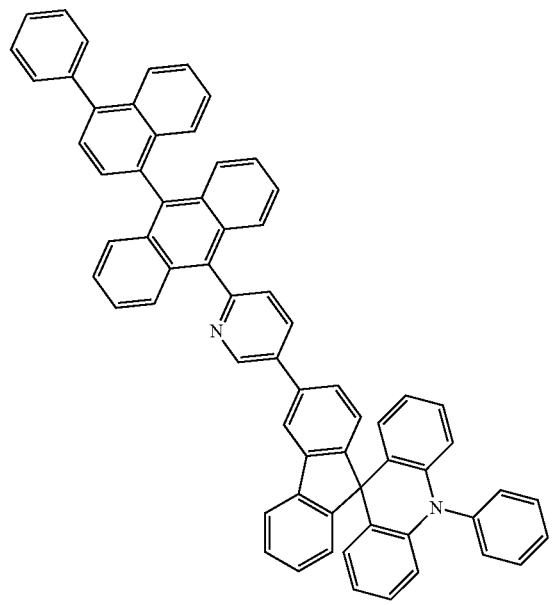
R326
148
-continued
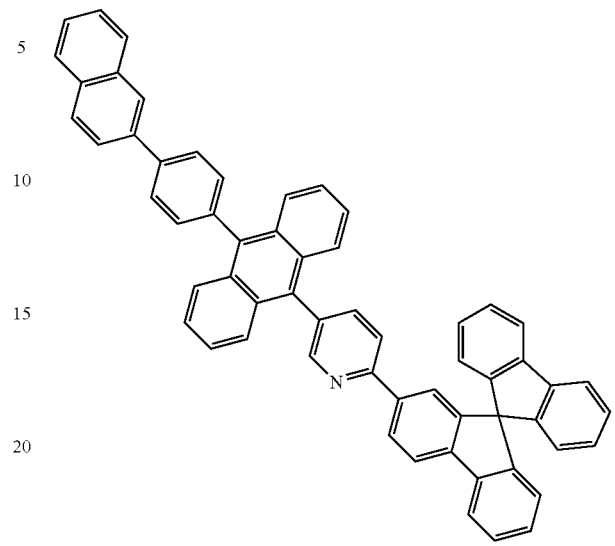
R328
R327
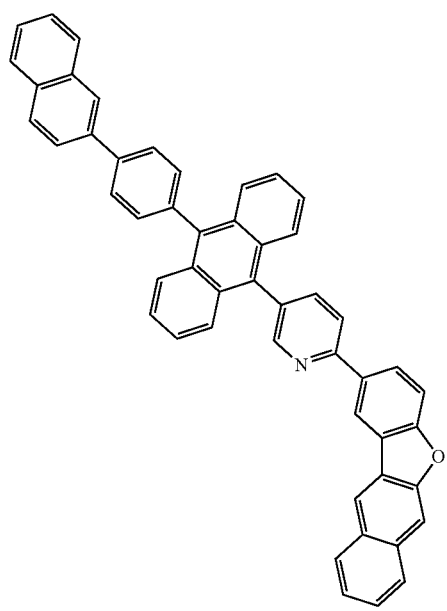
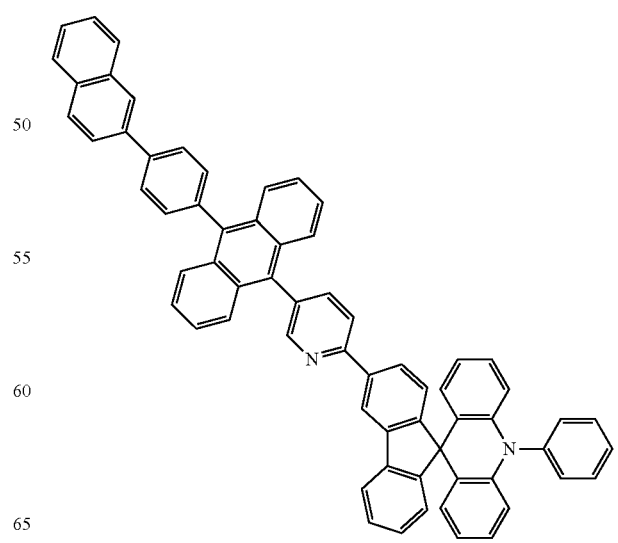
R329

149
-continued
R330
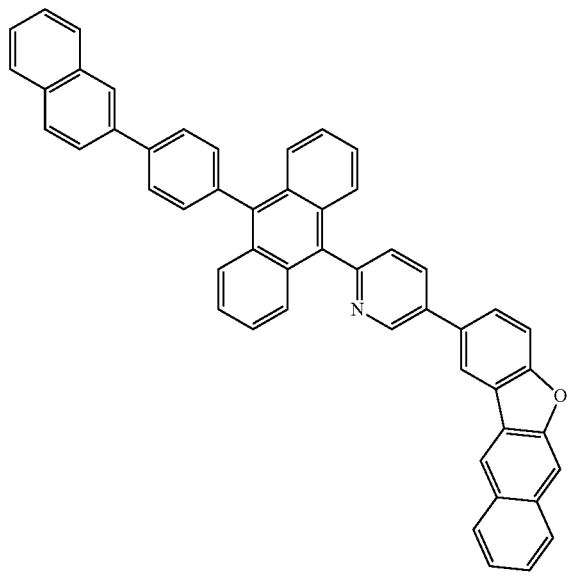
R331
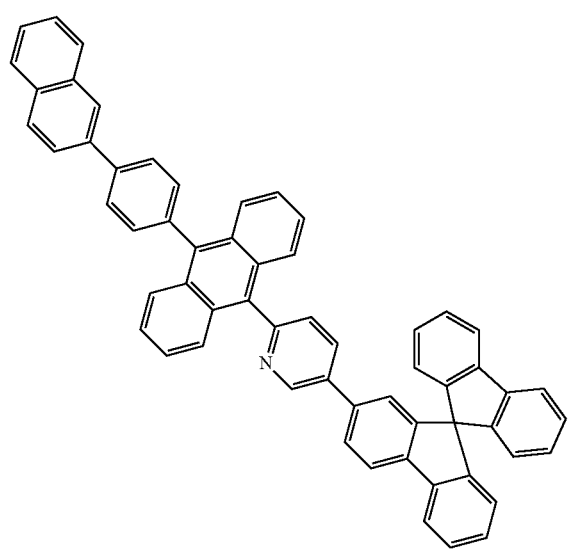
150
-continued
R332
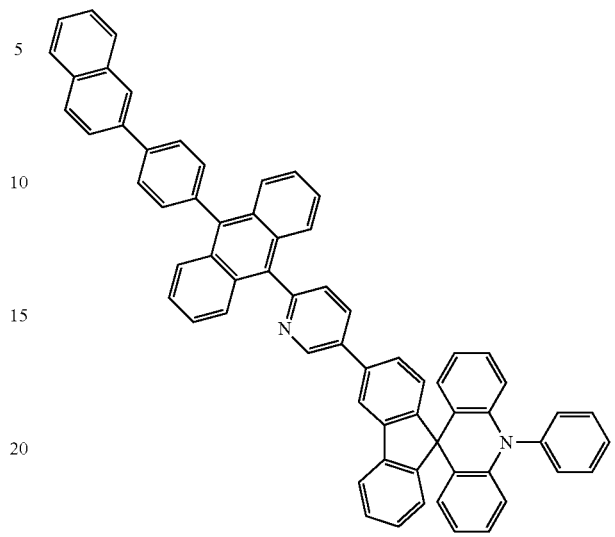
R333
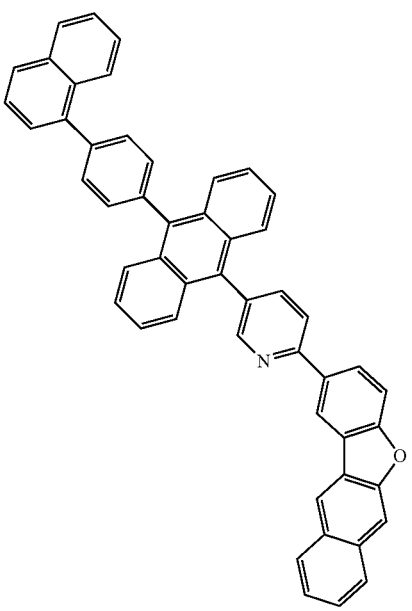

R334
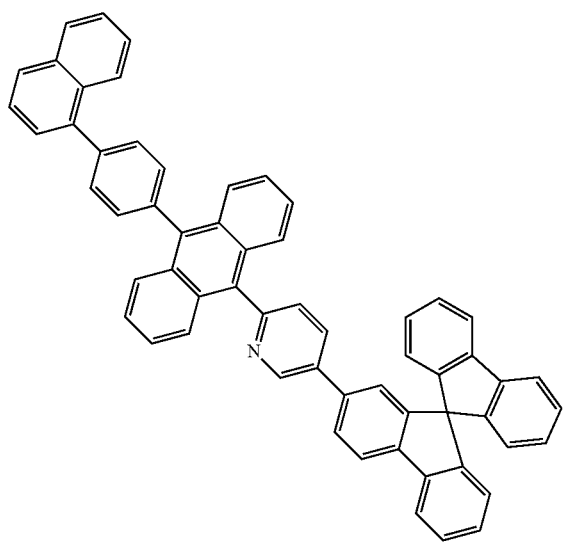
R335
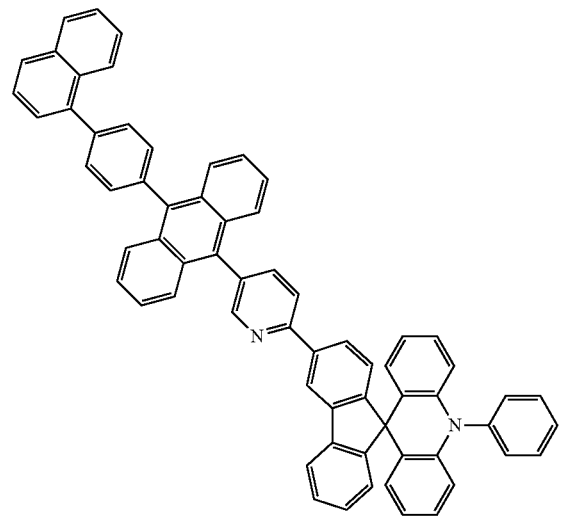
R336
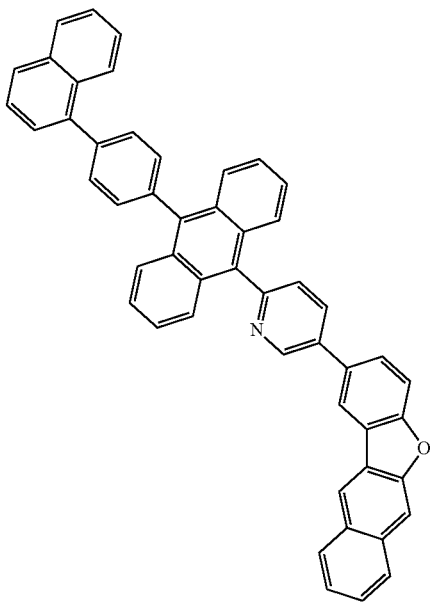
R337
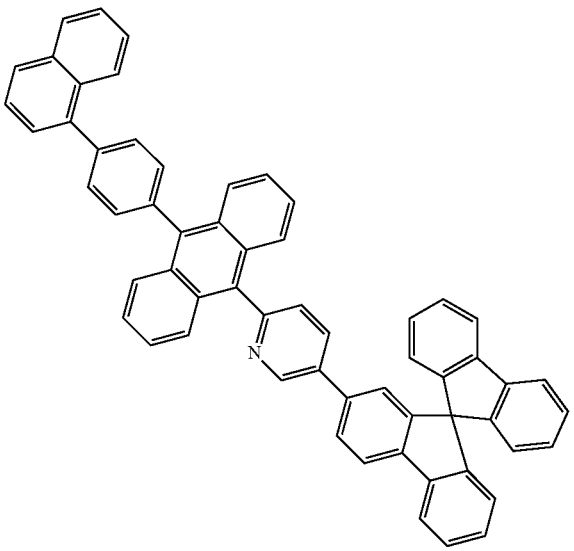

R338
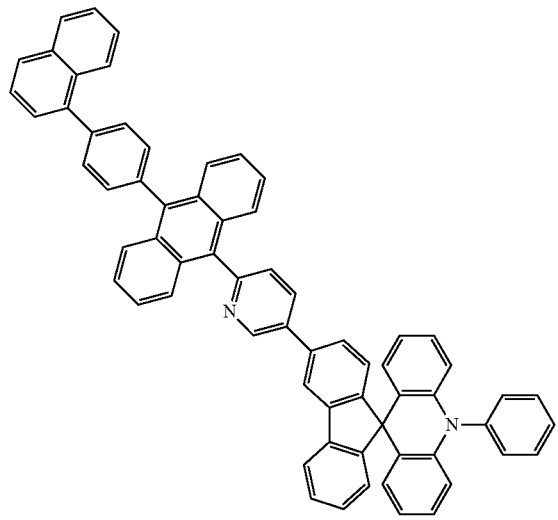
R341
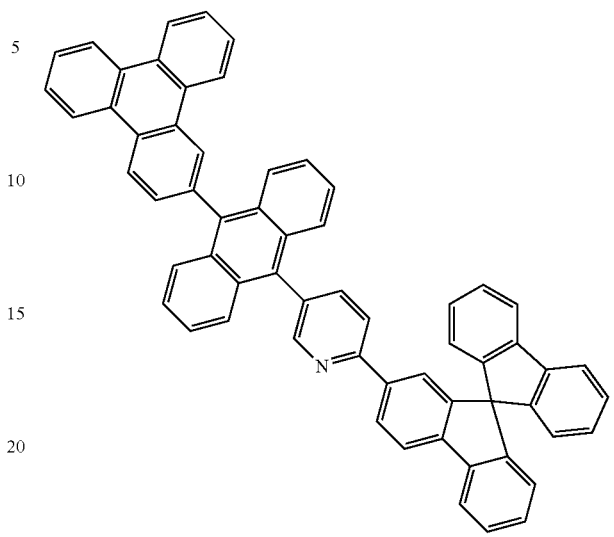
R339
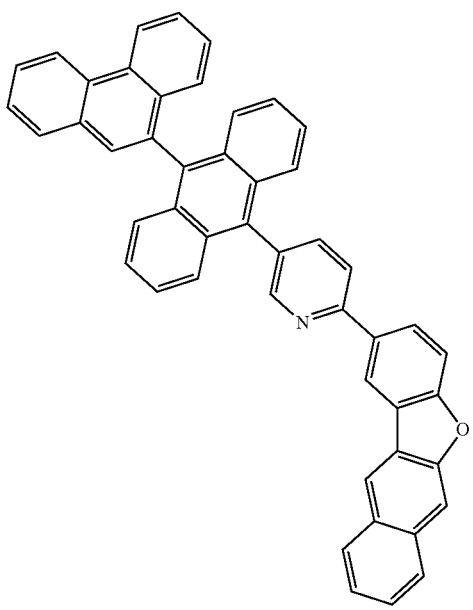
R342
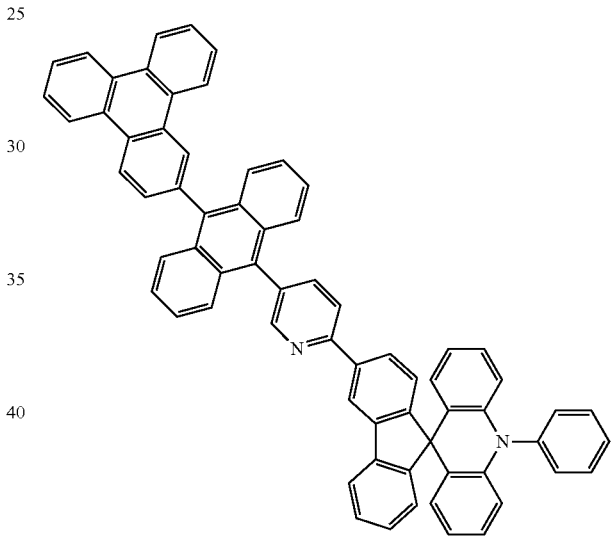
R340
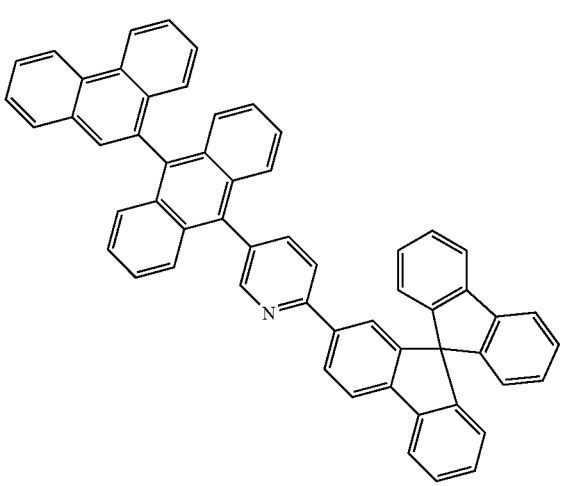
R343
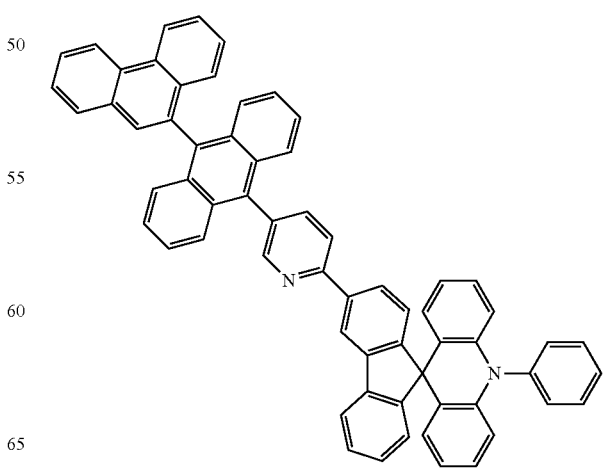

R344
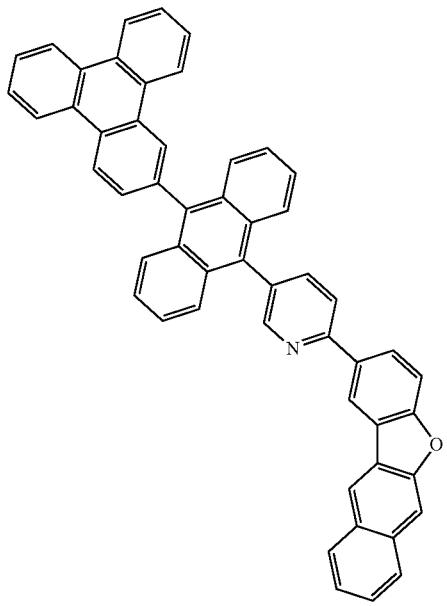
R345
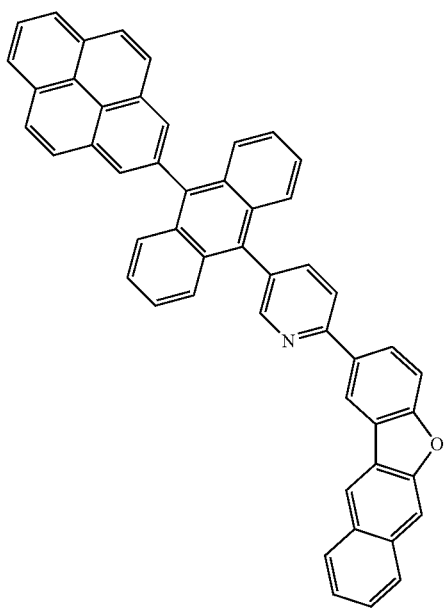
R346
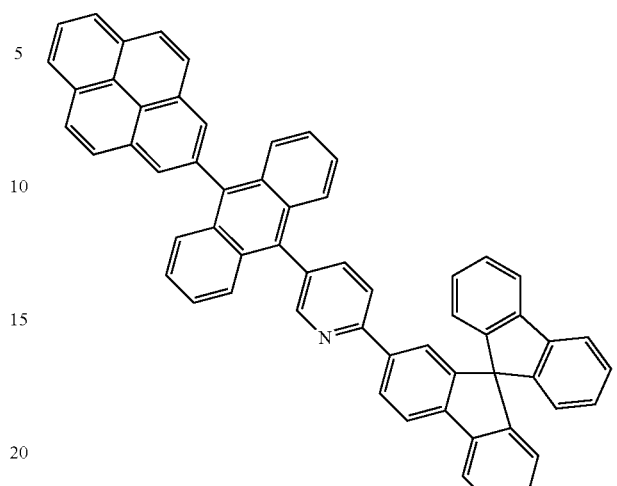
R347
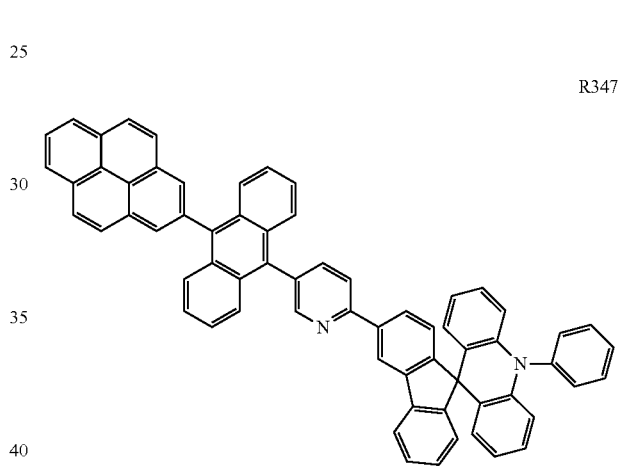
R348
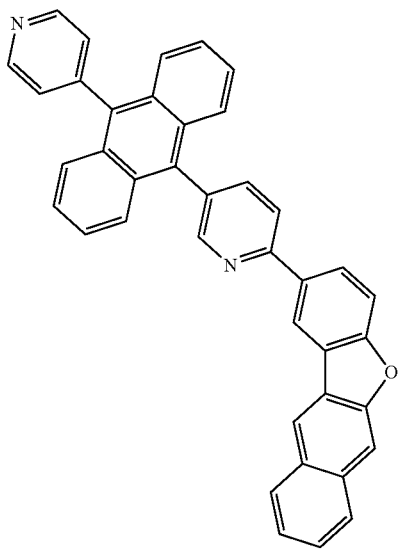

R349
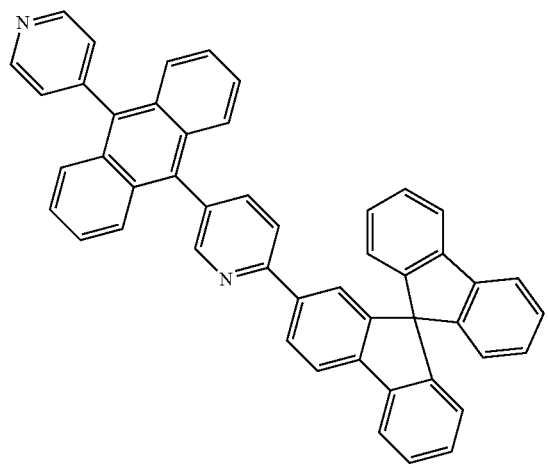
R350
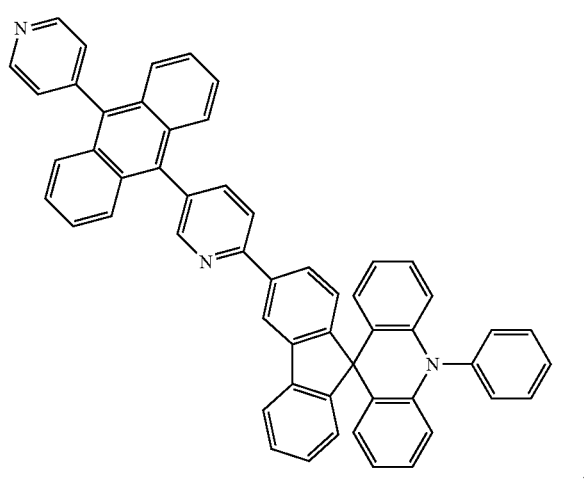
R351
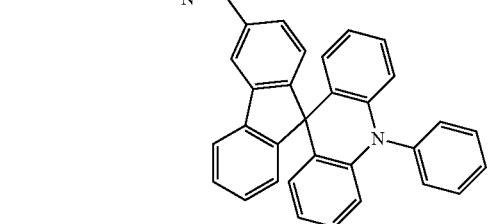
R352
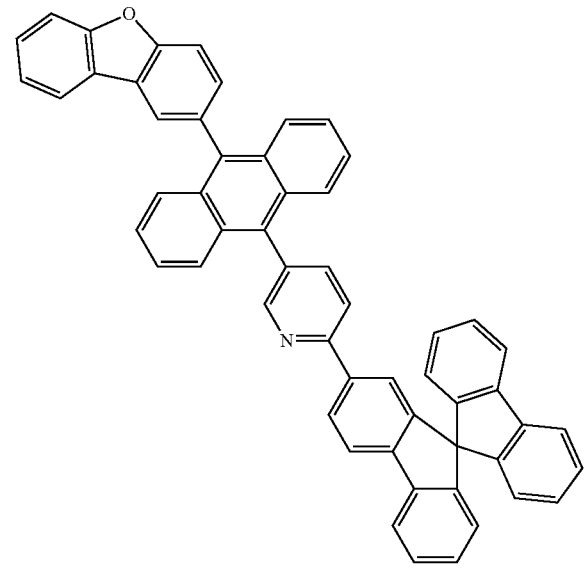
R353

R354
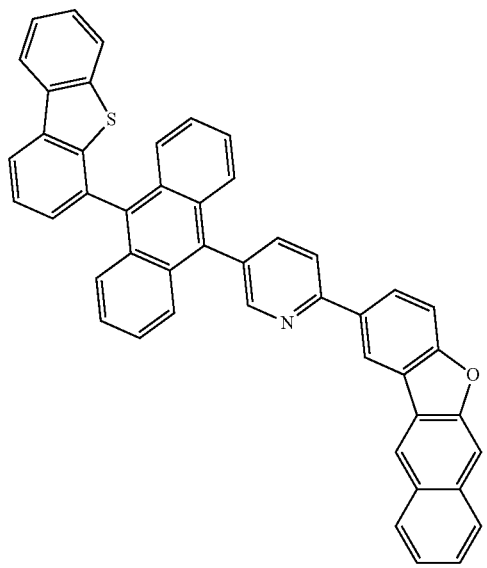
R355
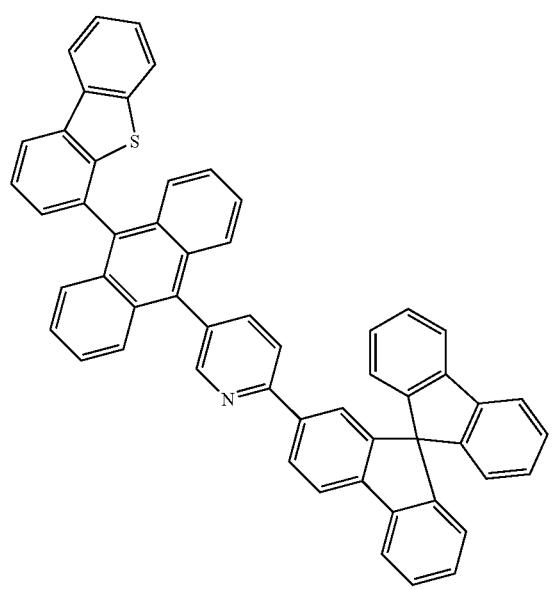
R356
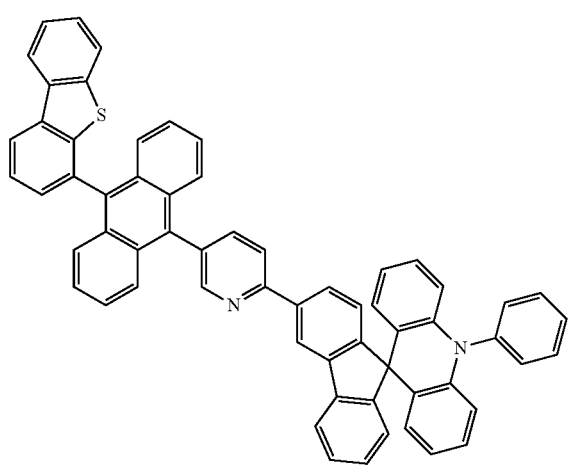
R357
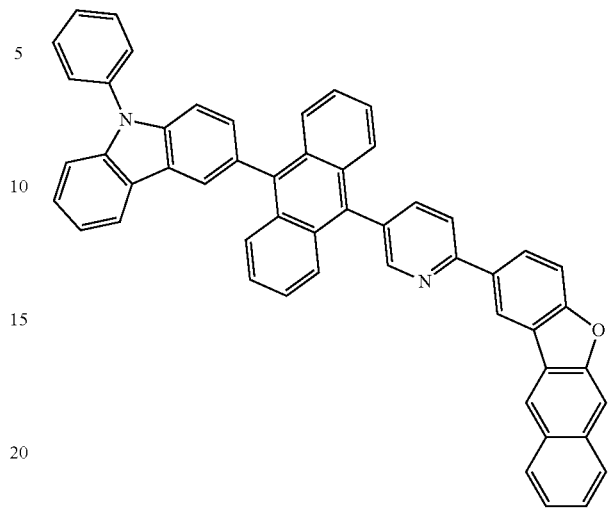
R358
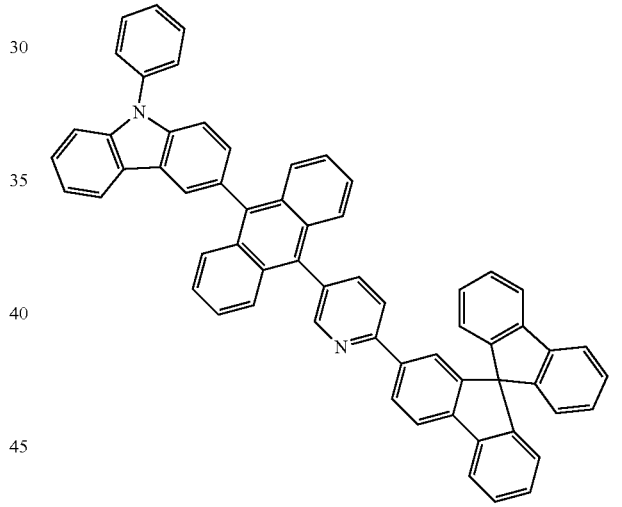
R359
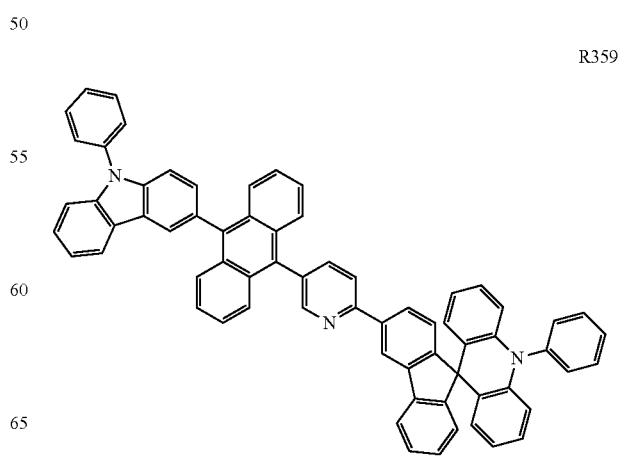

-continued
R360
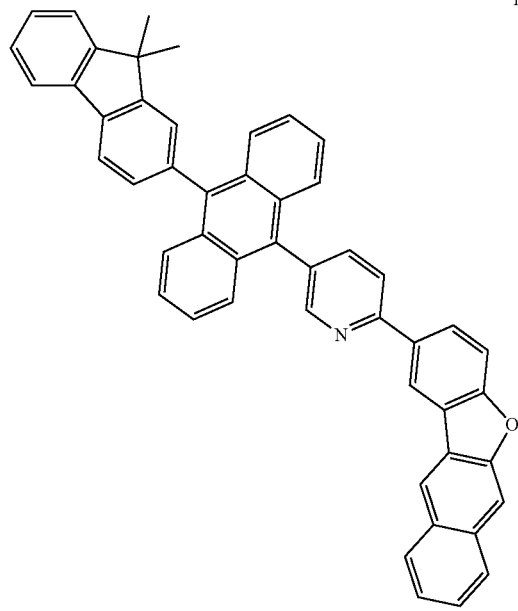
R361
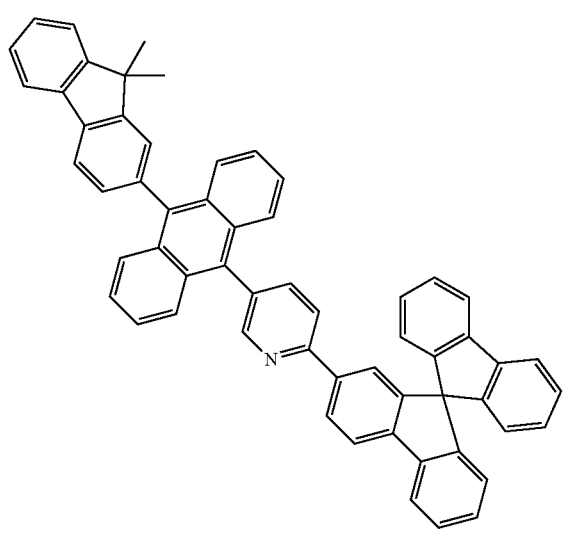
R362
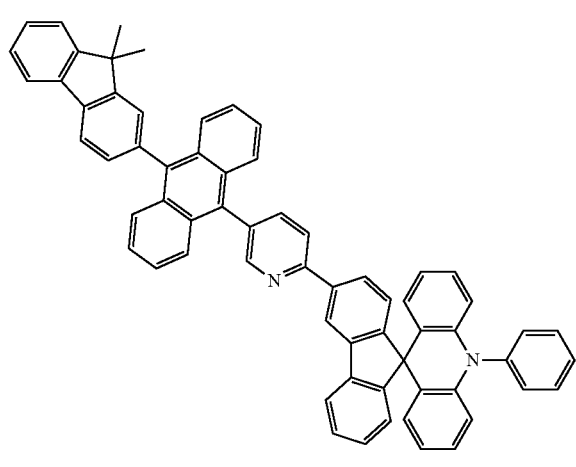
-continued
R363
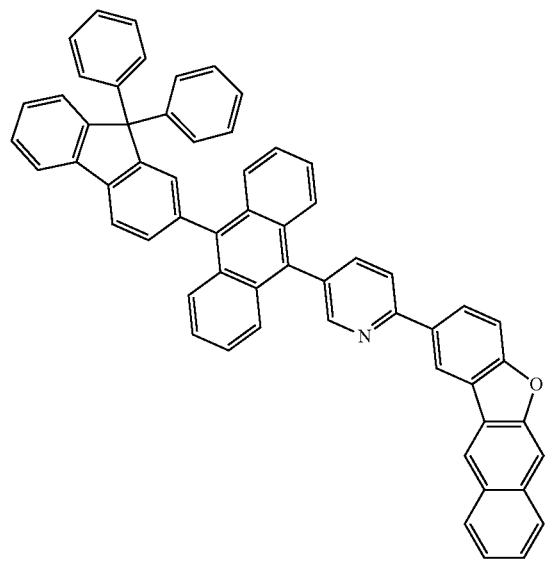
R364
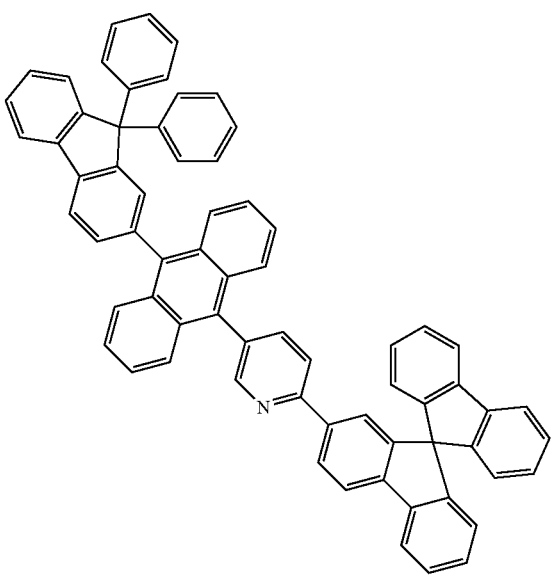
R365
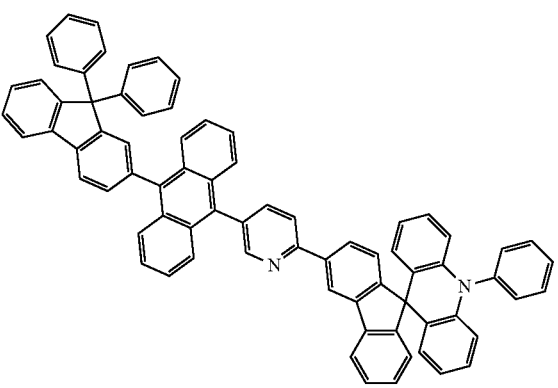

163
-continued
R366
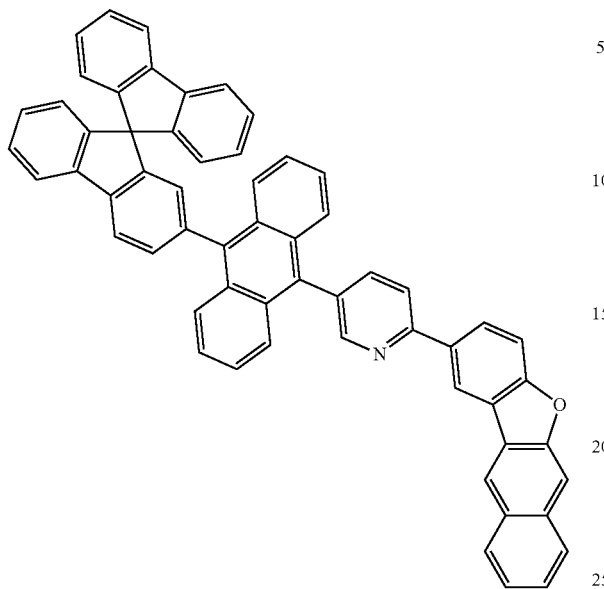
R367
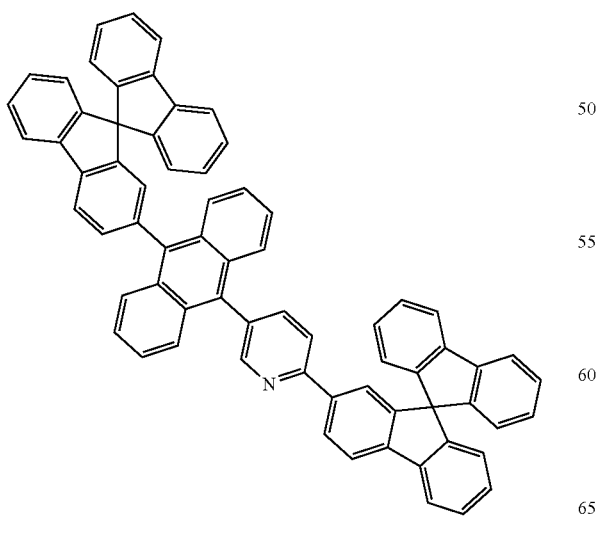
164
-continued
R368
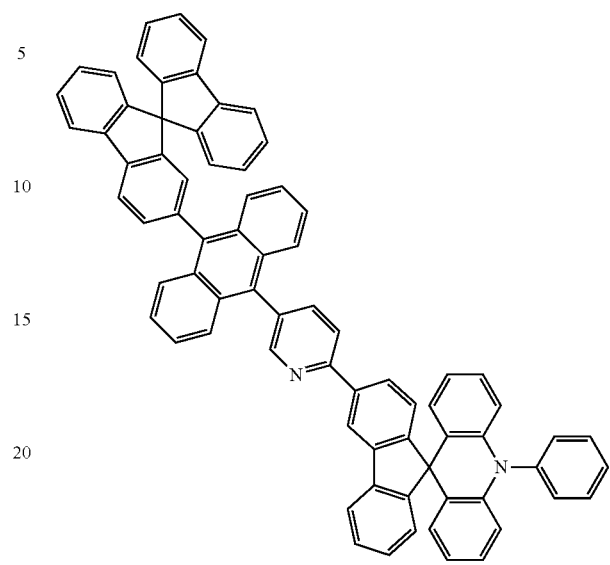
R369
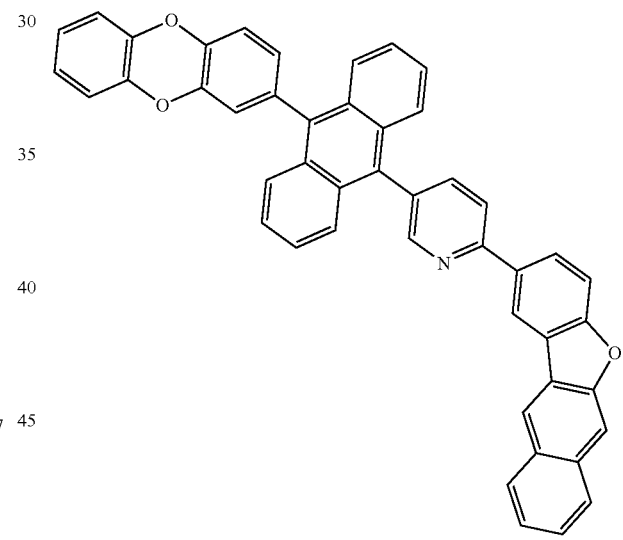
R370
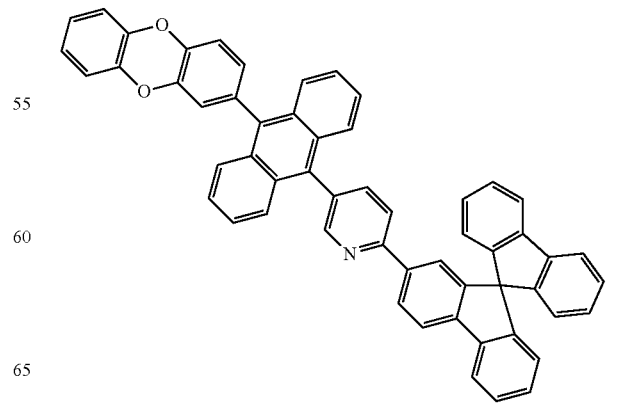

-continued
R371
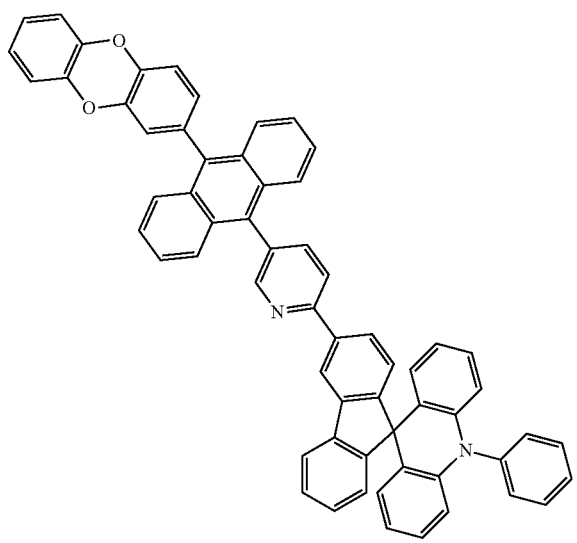
R372
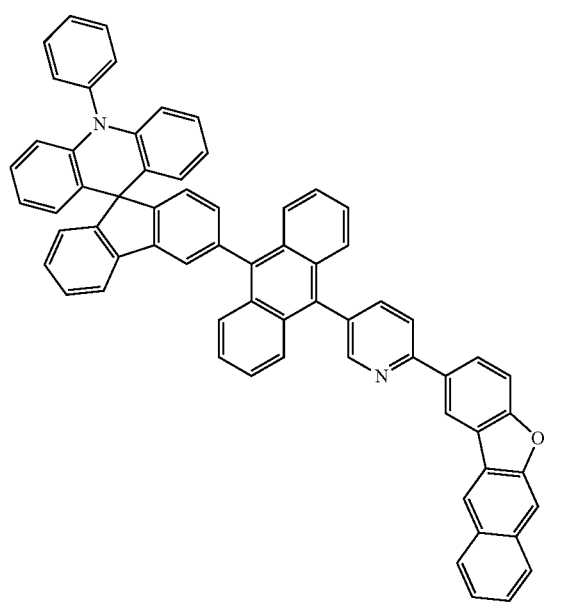
-continued
R373
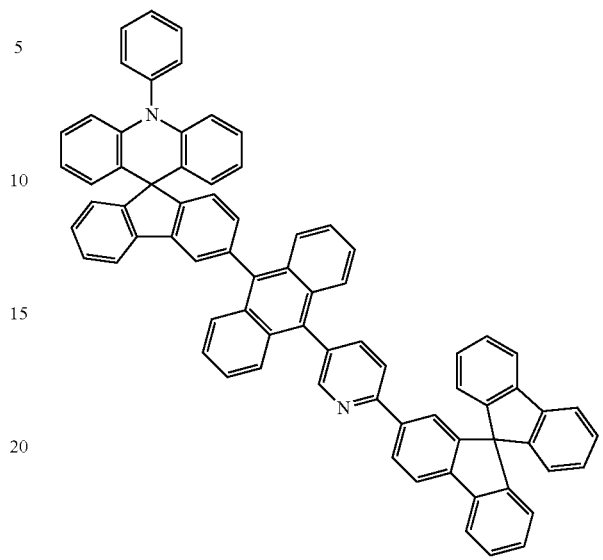
R374
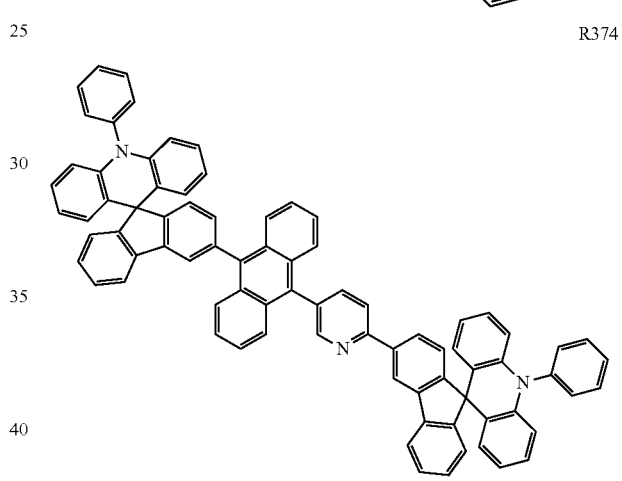
R375
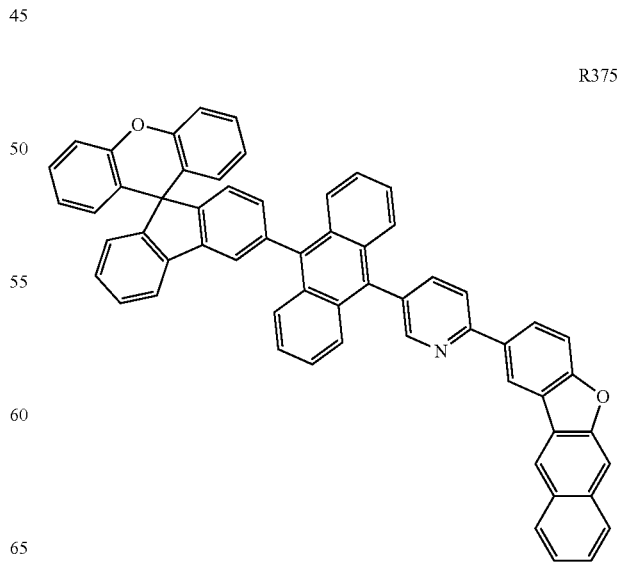

-continued
R376
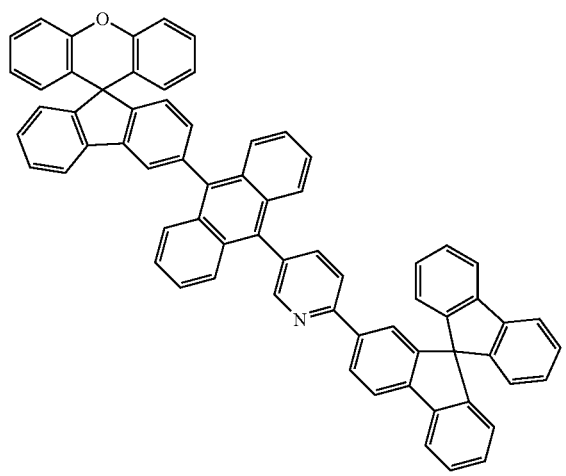
R377
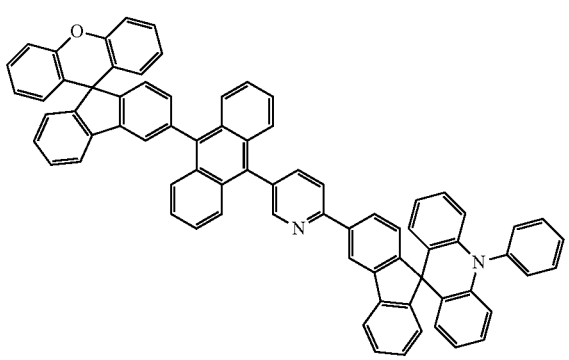
R378
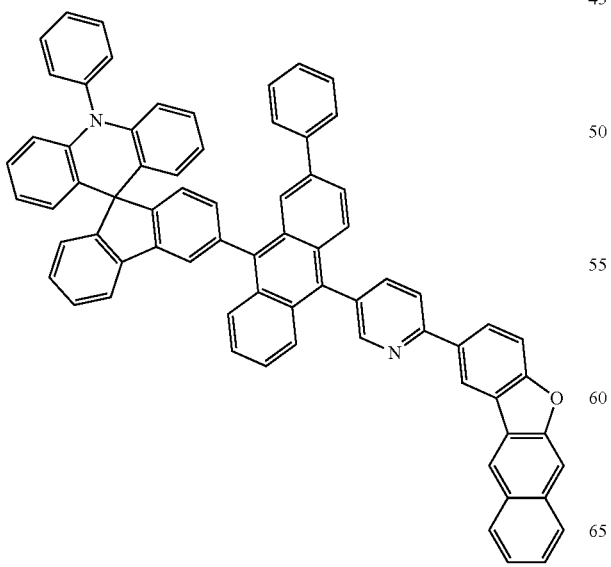
-continued
R379
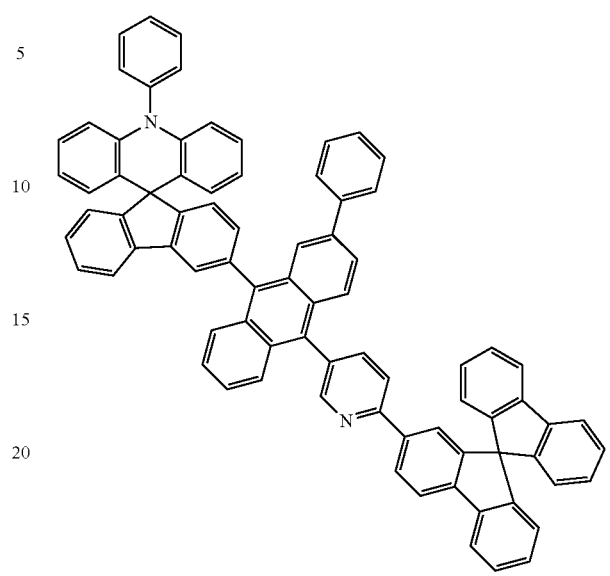
R380
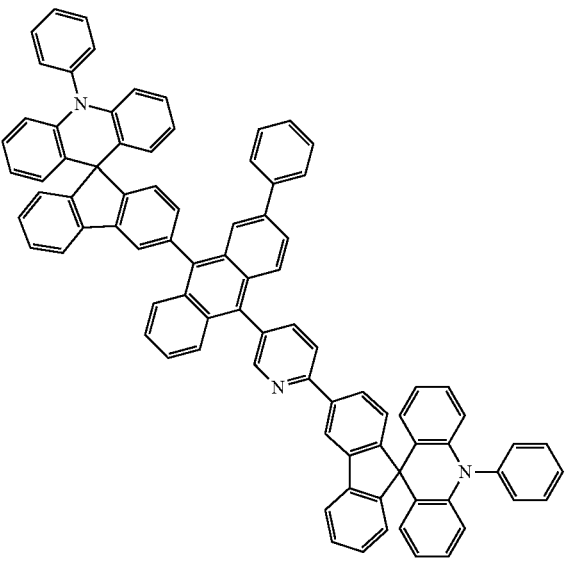

R381
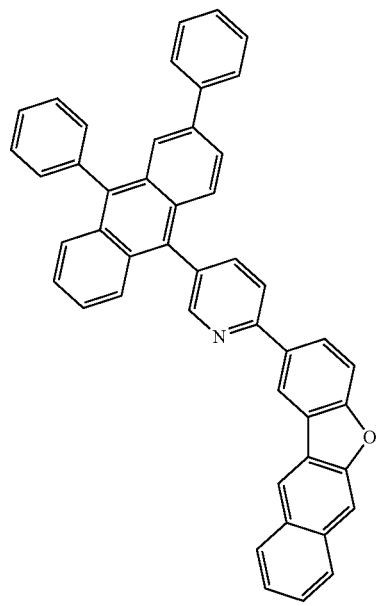
R383
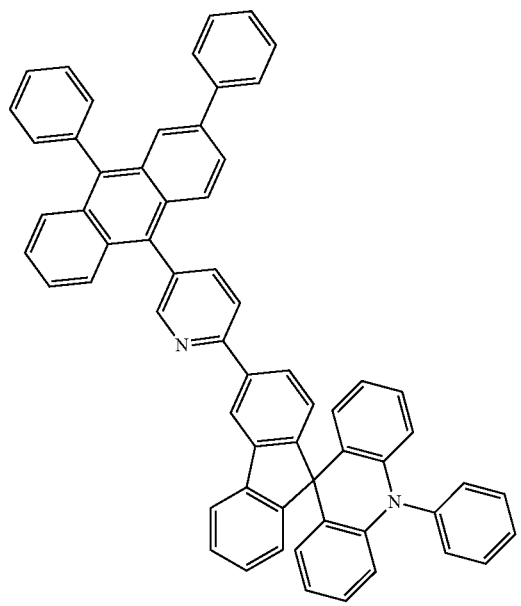
R382
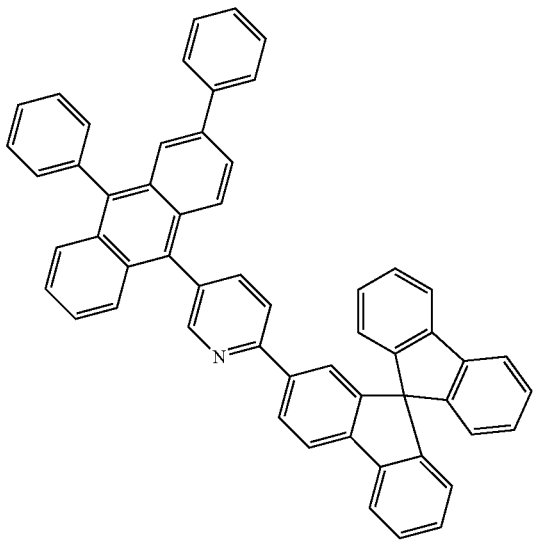
R384
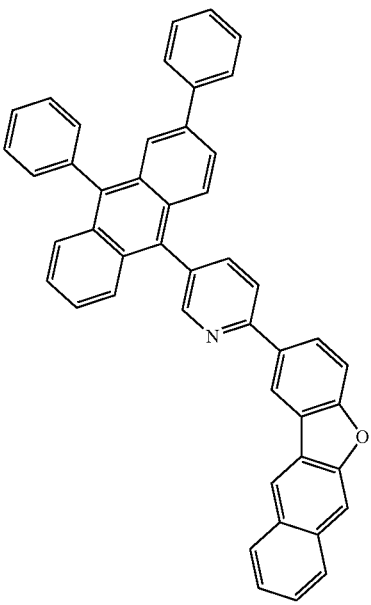

R385
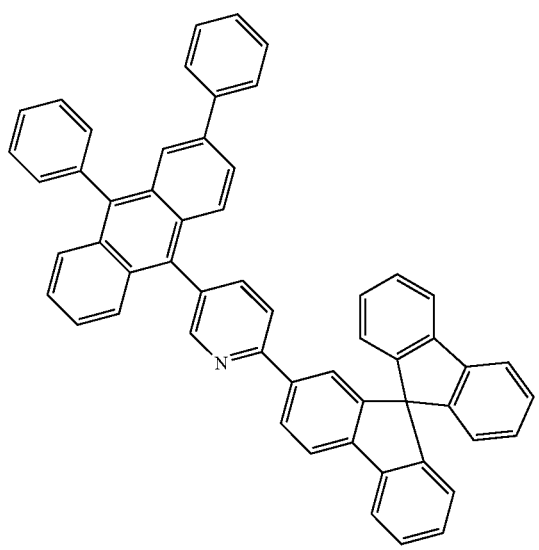
R386
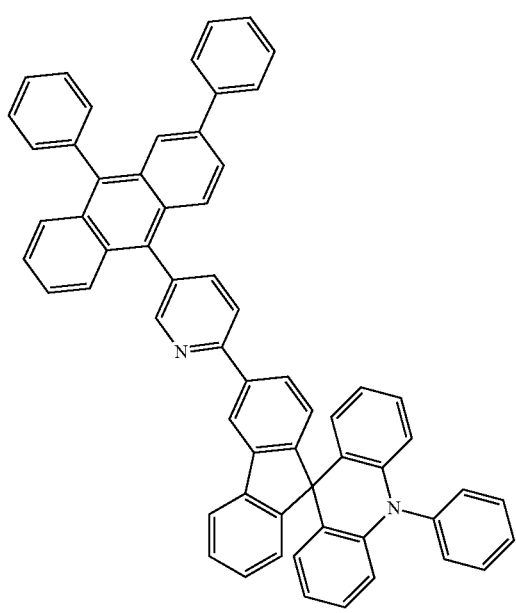
R387
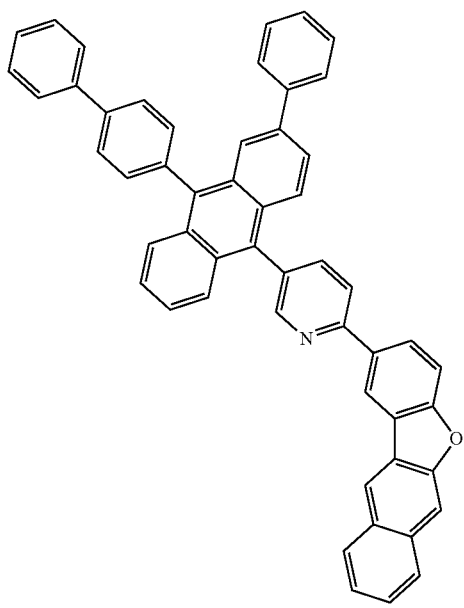
R388
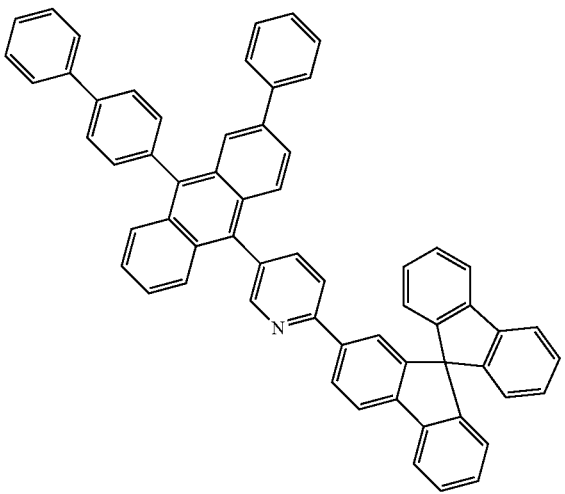

R389
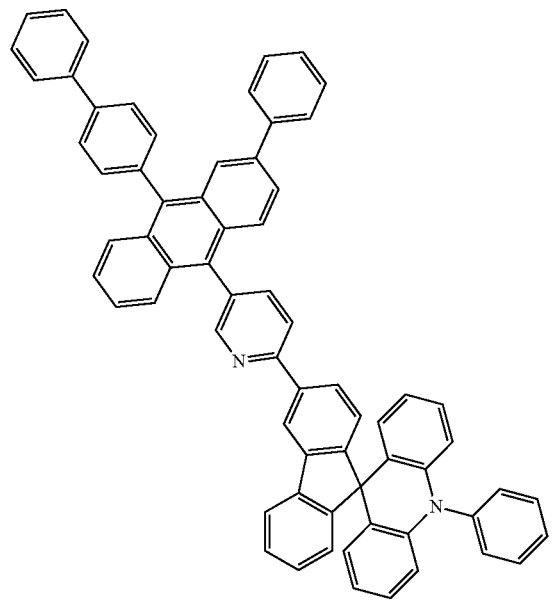
R391
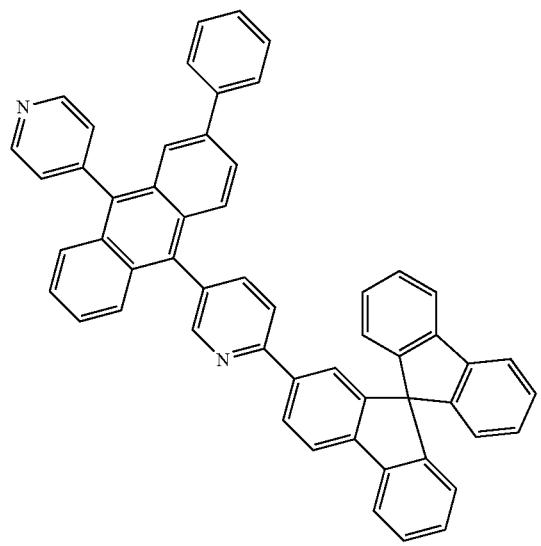
R390
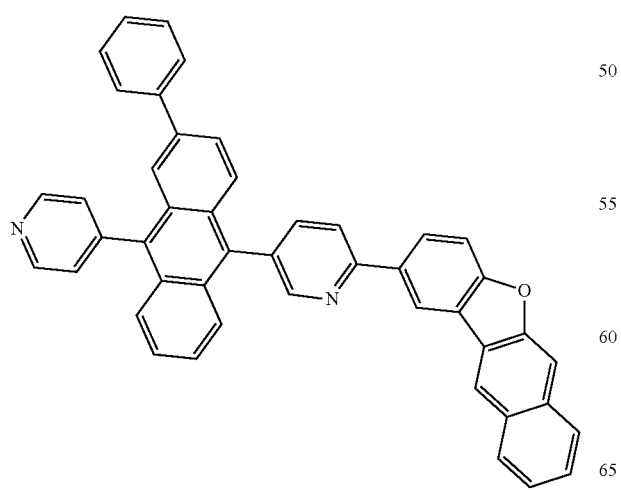
R392
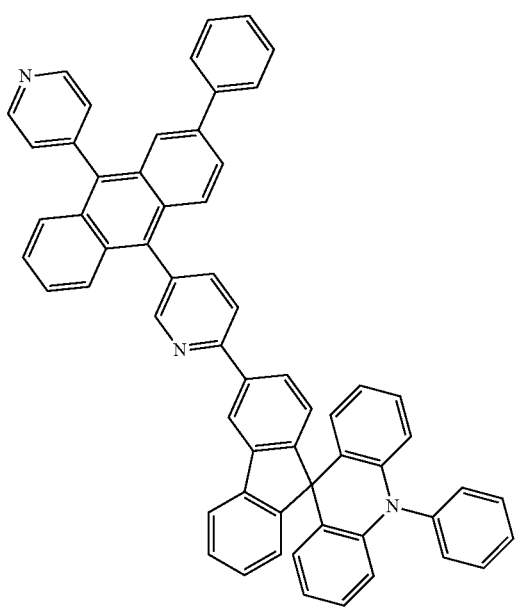

-continued
R393
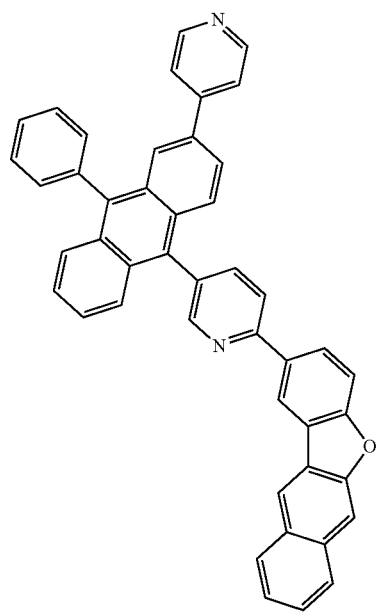
R394
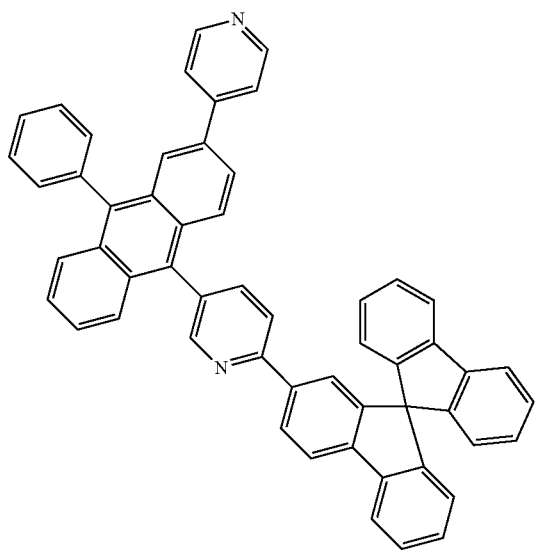
-continued
R395
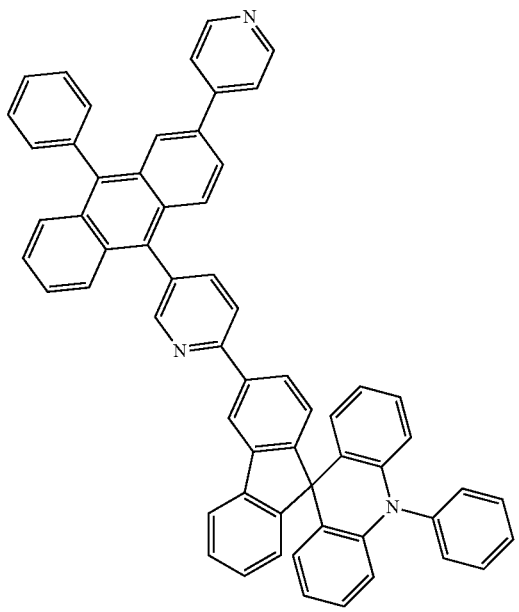
R396
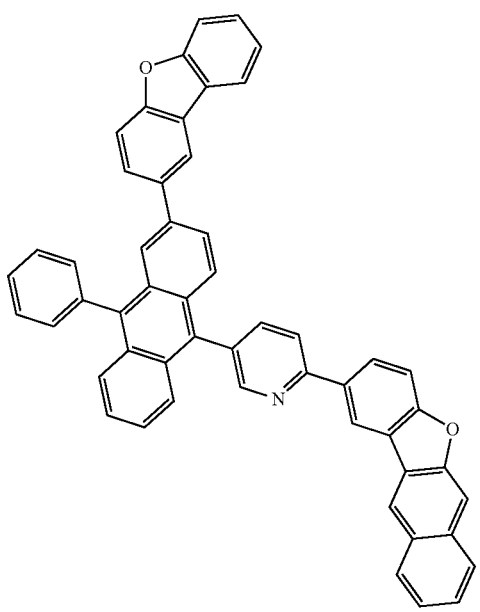

177
-continued
178
-continued
R397
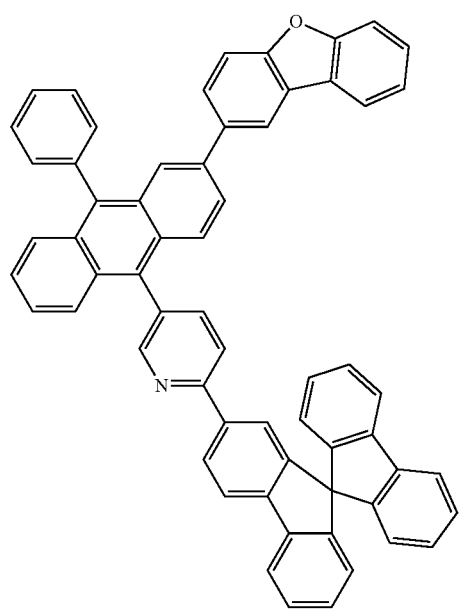
R399
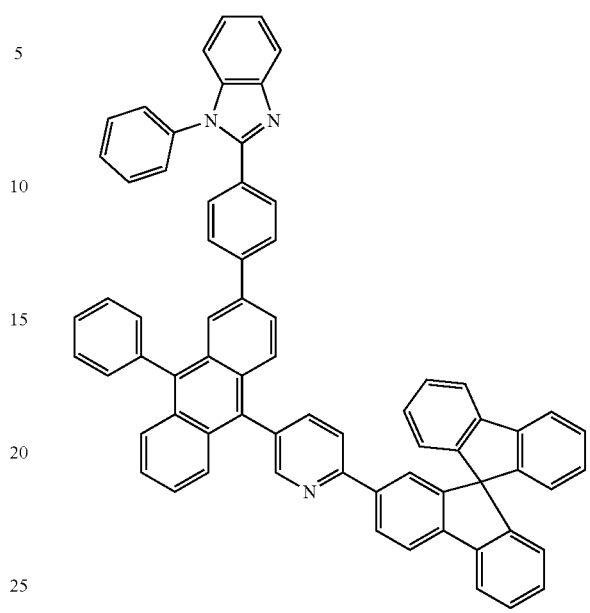
R398
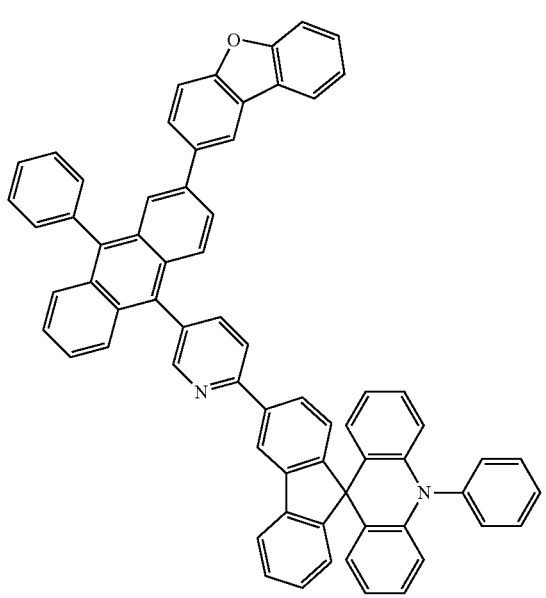
R400

-continued

R401

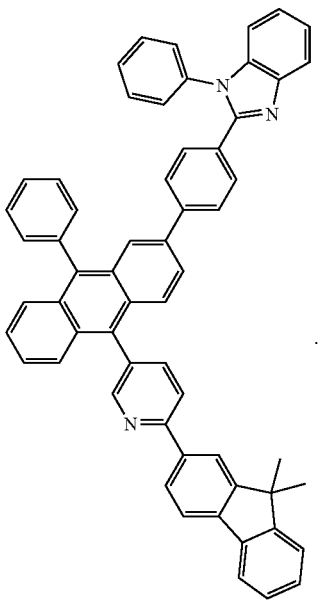

As used herein, the term "alkyl" refers to a monovalent substituent derived from a saturated linear or branched hydrocarbon having 1 to 40 carbon atoms. Examples thereof include methyl, ethyl, propyl, isopropyl, sec-butyl, pentyl, iso-amyl, and hexyl, but are not limited thereto.

As used herein, the term "alkenyl" refers to a monovalent substituent derived from an unsaturated linear or branched hydrocarbon having 2 to 40 carbon atoms with one or more carbon-carbon double bonds, as exemplified by, but not limited to, vinyl, allyl, isopropenyl, 2-butenyl, etc., but are not limited thereto.

As used herein, the term "alkynyl" refers to a monovalent substituent derived from an unsaturated linear or branched hydrocarbon having 2 to 40 carbon atoms with one or more carbon-carbon triple bonds, as exemplified by, but not limited to, ethynyl, 2-propynyl, etc.

As used herein, the term "aryl" refers to a monovalent substituent derived from an aromatic hydrocarbon having 6 to 60 carbon atoms with a single ring or a combination of two or more rings in which two or more rings may be simply pendant to each other or fused together. Examples of such aryl include, but are not limited to, phenyl, naphthyl, phenanthryl, anthryl, etc.

The term "heteroaryl", as used herein, is intended to mean a monovalent substituent derived from a mono- or polyheterocyclic aromatic hydrocarbon having 5 to 60 nucleus atoms in which at least one, but preferably one to three carbon atoms of the ring members are substituted by a heteroatom, such as N, O, S, or Se. Two or more rings of the heteroaryl, if present, may be simply pendant to each other or fused together or to an aryl group. Examples of such heteroaryl include 6-membered monocyclic rings such as pyridyl, pyrazinyl, pyrimidinyl, pyridazinyl, and triazinyl; polycyclic rings such as phenoxathienyl, indolizinyl, indolyl, purinyl, quinolyl, benzothiazole, and carbazolyl; 2-furanyl; N-imidazolyl; 2-ixosazolyl; 2-pyridinyl; and 2-pyrimidinyl, but are not limited thereto.

As used herein, the term "aryloxy" is intended to mean a monovalent substituent represented by RO— wherein R is an aryl having 5 to 60 carbon atoms, as exemplified by, but not limited to, phenyloxy, naphthyloxy, diphenyloxy, etc.

The term "alkyloxy", as used herein, refers to a monovalent substituent represented by R'O— wherein R' is an alkyl having 1 to 40 carbon atoms and is construed to include a linear, branched or cyclic structure and examples of which include, but are not limited to, methoxy, ethoxy, n-propoxy, 1-propoxy, t-butoxy, n-butoxy, pentoxy, etc.

As used herein, the term "cycloalkyl" refers to a monovalent substituent derived from a mono- or polycyclic non-aromatic hydrocarbon of 3 to 40 carbon atoms, examples of which include cyclopropyl, cyclopentyl, cyclohexyl, norbornyl, and adamantyl, but are not limited thereto.

As used herein, the term "heterocycloalkyl" refers to a monovalent substituent derived from a non-aromatic hydrocarbon having 3 to 40 nucleus atoms in which at least one, particularly one to three carbon atoms of the ring members are substituted by a heteroatom such as N, O, S or Se and examples of which include morpholinyl, piperazinyl, and the like, but are not limited thereto.

As used herein, the term "alkylsilyl" refers to a silyl group substituted with an alkyl having 1 to 40 carbon atoms, and the term "arylsilyl" refers to a silyl group substituted with an aryl having 5 to 60 carbon atoms.

As used herein, the term "alkylboron group" refers to a boron group substituted with an alkyl having 1 to 40 carbon atoms, the term "arylboron group" refers to a boron group substituted with an aryl having 6 to 60 carbon atoms, the term "alkylphosphinyl group" refers to a phosphine group substituted with an alkyl having 1 to 40 carbon atoms, and the term "mono- or diarylphosphinyl group" refers to a phosphine group substituted with a mono- or diaryl having 5 to 60 carbon atoms.

As used herein, the term "arylamine" refers to an amine group substituted with an aryl having 6 to 60 carbon atoms.

As used herein, the term "fused ring" refers to a fused aliphatic ring, a fused aromatic ring, a fused heteroaliphatic ring, a heteroaromatic ring, a spiro ring, or a combination thereof.

<Organic Electroluminescent Device>

Another aspect of the present disclosure provides an organic electroluminescent device (hereinafter referred to as "organic EL device") comprising the compound represented by Formula 1.

In detail, the organic EL device according to the present disclosure comprises an anode, a cathode, and one or more organic material layer interposed between the anode and the cathode, wherein at least one of the one or more organic material layer includes the compound represented by Formula 1. In this regard, the compounds may be used alone or in combination.

According to one embodiment, the one or more organic material layers comprise at least one of a hole injection layer, a hole transport layer, an emission auxiliary layer, a light-emitting layer, an electron transport layer, and an electron injection layer. Of them, the light-emitting layer may include the compound represented by Formula 1. In this regard, the compound represented by Formula 1 may be included as a light-emitting layer material, preferably as a fluorescent host in organic EL devices. In this regard, the organic EL device of the present invention is increased electron transport capabilities due to the compound of Formula 1 and thus exhibits high recombination capability between holes and electrons in the light-emitting layer, which the consequent improvement thereof in emission efficiency, power efficiency, lifespan, luminance, driving voltage, and thermal stability. In detail, the compound represented by Formula 1 is preferably included as a blue and/or green fluorescent host in an organic EL device.

According to another embodiment, the one or more organic material layer comprises a hole injection layer, a hole transport layer, a light-emitting layer, an electron transport auxiliary layer, an electron transport layer, and an electron injection layer, wherein the electron transport auxiliary layer may include the compound represented by Formula 1. The compound represented by Formula 1 may be included as a material for the electron transport auxiliary layer in the organic EL device. In this regard, the organic EL device of the present invention is increased in electron transport from the electron transport layer to the light-emitting layer by the compound of Formula 1 and thus exhibits high recombination capability between holes and electrons in the light-emitting layer, which the consequent improvement thereof in emission efficiency, power efficiency, and luminance.

Although particular structural limitations are not imparted thereto, the organic EL device of the present disclosure may have a structure in which, for example, an anode, one or more organic material layer, and a cathode are sequentially stacked on a substrate, optionally with the insertion of an insulation or an adhesive layer into the interface between the electrodes and the organic material layer.

According to one embodiment, the organic EL device may have a structure in which an anode, a hole injection layer, a hole transport layer, a light-emitting layer, an electron transport layer, and a cathode are sequentially stacked on a substrate. Optionally, an electron transport auxiliary layer may be interposed between the light-emitting layer and the electron transport layer or an electron injection layer may be interposed between the electron transport layer and the cathode. The organic EL device of the present disclosure may be fabricated using the materials and methods known in the art to form the organic material layer and electrodes, with the exception that at least one of the organic material layer (for example, the light-emitting layer or the electron transport auxiliary layer) includes the compound represented by Formula 1.

The organic material layer may be formed using a vacuum evaporation method or a solution coating method. Examples of the solution coating method include spin coating, dip coating, doctor blading, inkjet printing, and a thermal transfer method, but are not limited thereto.

A substrate available in the present disclosure is not particularly limited, non-limiting examples of which include a silicon wafer, quartz, a glass plate, a metal plate, a plastic film, and a sheet.

Examples of a material for the anode include a metal such as vanadium, chromium, copper, zinc, gold, etc.; an alloy thereof; a metal oxide such as zinc oxide, indium oxide, indium tin oxide (ITO), and indium zinc oxide (IZO); a combination of metal and oxide such as ZnO:Al or $SnO_2$:Sb; a conductive polymer such as polythiophene, poly(3-methylthiophene), poly[3,4-(ethylene-1,2-dioxy)thiophene] (PEDT), polypyrrole, polyaniline, etc.; and carbon black, but are not limited thereto.

Examples of a material for the cathode include magnesium, calcium, sodium, potassium, titanium, indium, yttrium, lithium, gadolinium, aluminum, silver, tin, lead, etc.; an alloy thereof; and multilayer materials such as LiF/Al, $LiO_2$/Al, etc. without particular limitations thereto.

In addition, for the hole injection layer, the hole transport layer, the light-emitting layer, the electron injection layer, and the electron transport layer, typical materials known in the art may be used without particular limitations thereto.

Hereinafter, the present invention will be described in detail with reference to examples. These examples are only for illustrating the present invention more specifically, and it will be apparent to those skilled in the art that the scope of the present invention is not limited by these examples.

[Preparation Example 1] Synthesis of Compound A1

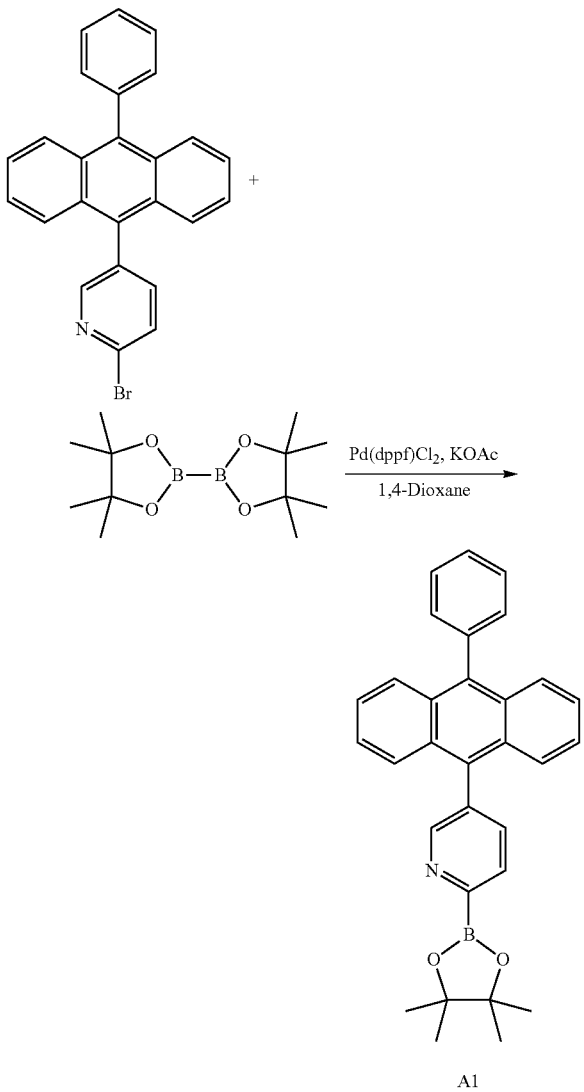

A1

In a nitrogen atmosphere, 2-bromo-5-(10-phenylanthracen-9-yl)pyridine (10.0 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A1 (7.8 g, 17.1 mmol, yield: 70%).

GC-Mass (Calcd.: 457.37 g/mol, Found: 457 g/mol).

1H-NMR: δ 1.25 (1S, 12H), 7.35~7.39 (m, 5H), 7.43~7.50 (m, 5H), 7.88~7.91 (m, 5H), 8.55 (s, 1H)

[Preparation Example 2] Synthesis of Compound A2

[Preparation Example 3] Synthesis of Compound A3

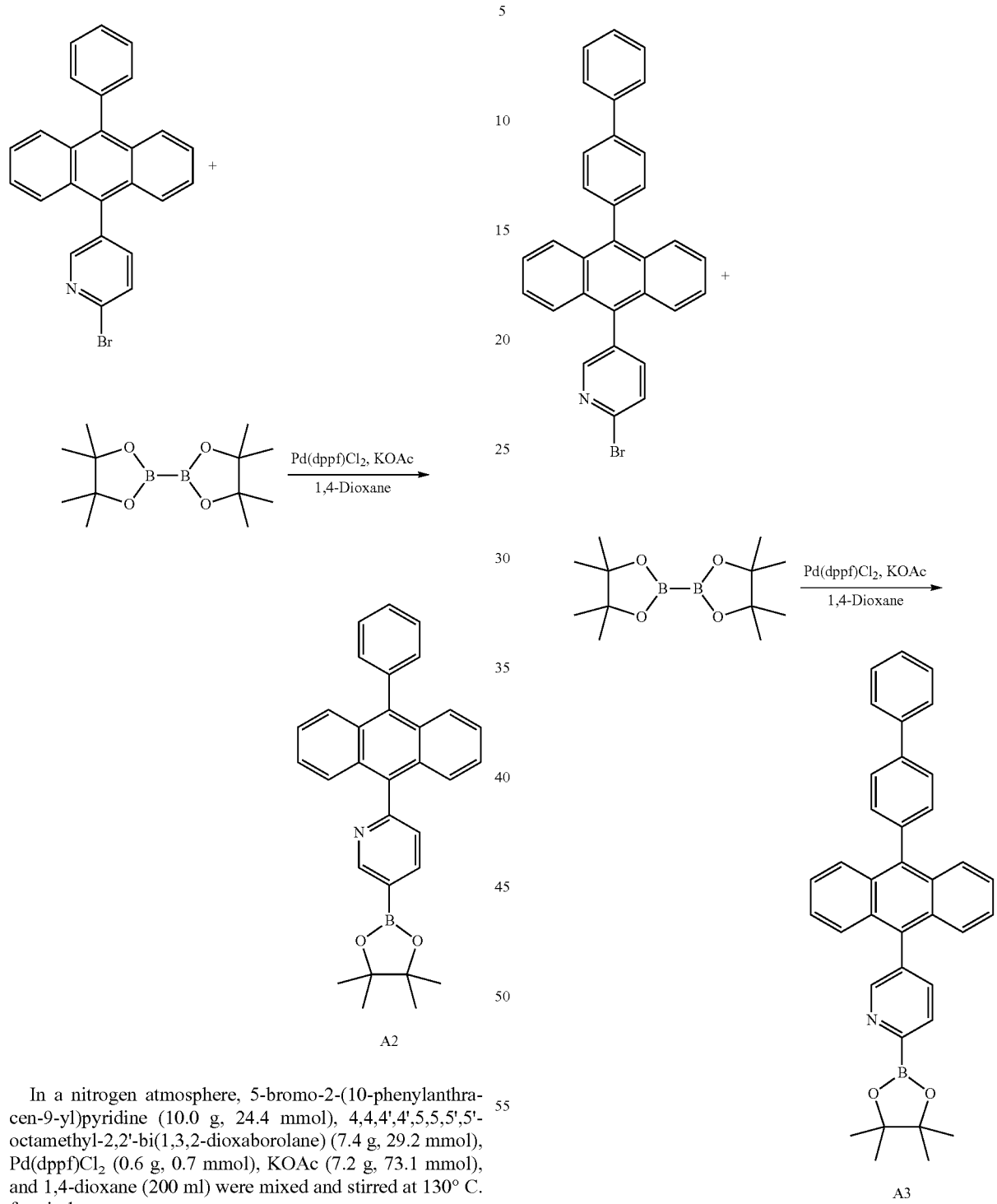

In a nitrogen atmosphere, 5-bromo-2-(10-phenylanthracen-9-yl)pyridine (10.0 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A2 (7.8 g, 17.1 mmol, yield: 70%).

GC-Mass (Calcd.: 457.37 g/mol, Found: 457 g/mol).

1H-NMR: δ 1.25 (1S, 12H), 7.35~7.39 (m, 5H), 7.43~7.50 (m, 5H), 7.88~7.91 (m, 5H), 8.39 (s, 1H)

In a nitrogen atmosphere, 5-(10-(biphenyl-4-yl)anthracen-9-yl)-2-bromopyridine (11.9 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A3 (9.7 g, 18.3 mmol, yield: 75%).

GC-Mass (Calcd.: 533.5 g/mol, Found: 533 g/mol).

1H-NMR: δ 1.25 (1S, 12H), 7.24~7.26 (m, 4H), 7.36~7.40 (m, 5H), 7.43~7.50 (m, 5H), 7.88~7.91 (m, 5H), 8.55 (s, 1H)

[Preparation Example 4] Synthesis of Compound A4

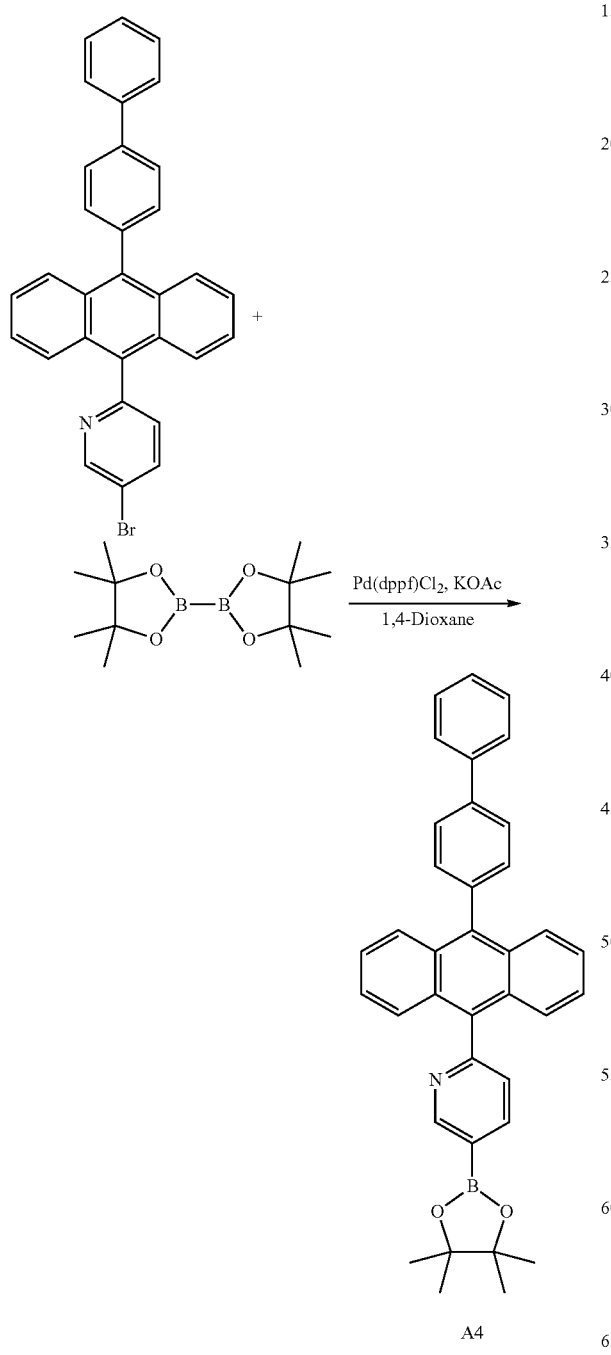

In a nitrogen atmosphere, 2-(10-(biphenyl-4-yl)anthracen-9-yl)-5-bromopyridine (11.9 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A4 (9.7 g, 18.3 mmol, yield: 75%).

GC-Mass (Calcd.: 533.5 g/mol, Found: 533 g/mol).

1H-NMR: δ 1.25 (1S, 12H), 7.24~7.26 (m, 4H), 7.36~7.40 (m, 5H), 7.43~7.50 (m, 5H), 7.88~7.91 (m, 5H), 8.36 (s, 1H)

[Preparation Example 5] Synthesis of Compound A5

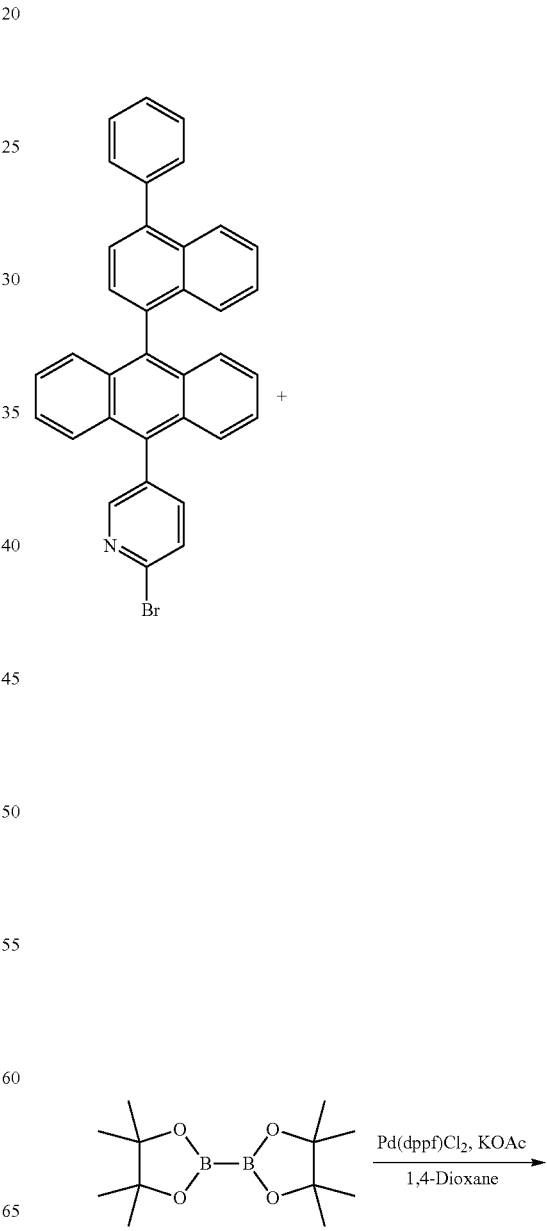

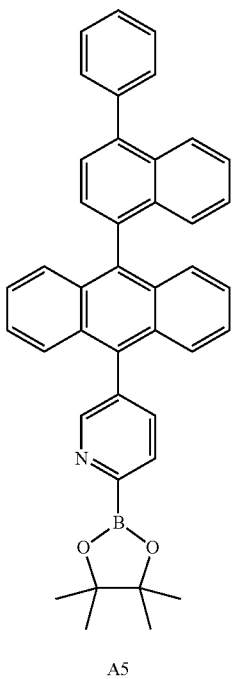

A5

In a nitrogen atmosphere, 2-bromo-5-(10-(4-phenylnaphthalen-1-yl)anthracen-9-yl)pyridine (13.1 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A5 (11.1 g, 19.0 mmol, yield: 78%).

GC-Mass (Calcd.: 583.53 g/mol, Found: 583 g/mol).

1H-NMR: δ 1.25 (1S, 12H), 7.35~7.39 (m, 5H), 7.43~7.50 (m, 5H), 7.88~7.93 (m, 7H), 8.02~8.03 (m, 2H), 8.54~8.55 (m, 2H), 8.59 (s, 1H)

[Preparation Example 6] Synthesis of Compound A6

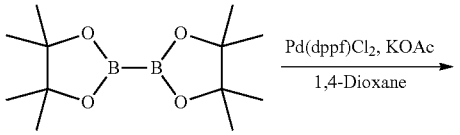

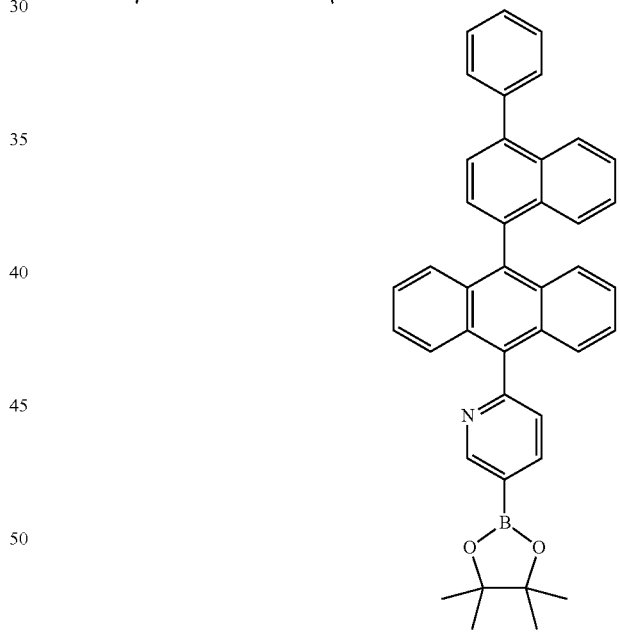

A6

In a nitrogen atmosphere, 5-bromo-2-(10-(4-phenylnaphthalen-1-yl)anthracen-9-yl)pyridine (13.1 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A6 (11.1 g, 19.0 mmol, yield: 78%).

GC-Mass (Calcd.: 583.53 g/mol, Found: 583 g/mol).

1H-NMR: δ 1.25 (1S, 12H), 7.35~7.39 (m, 5H), 7.43~7.50 (m, 5H), 7.88~7.93 (m, 7H), 8.02~8.03 (m, 2H), 8.32 (s, 1H), 8.54~8.55 (m, 2H)

[Preparation Example 7] Synthesis of Compound A7

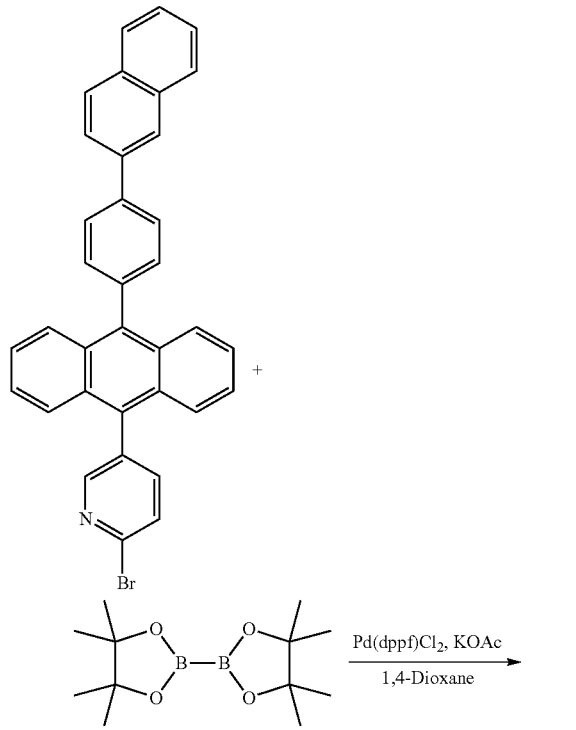

[Preparation Example 8] Synthesis of Compound A8

In a nitrogen atmosphere, 5-bromo-2-(10-(4-(naphthalen-2-yl)phenyl)anthracen-9-yl)pyridine (13.1 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A7 (10.5 g, 18.0 mmol, yield: 74%).

GC-Mass (Calcd.: 583.53 g/mol, Found: 583 g/mol).

1H-NMR: δ 1.25 (1S, 12H), 7.35~7.39 (m, 9H), 7.52~7.55 (m, 3H), 7.79~7.93 (m, 7H), 8.02~8.03 (m, 2H), 8.58 (s, 1H)

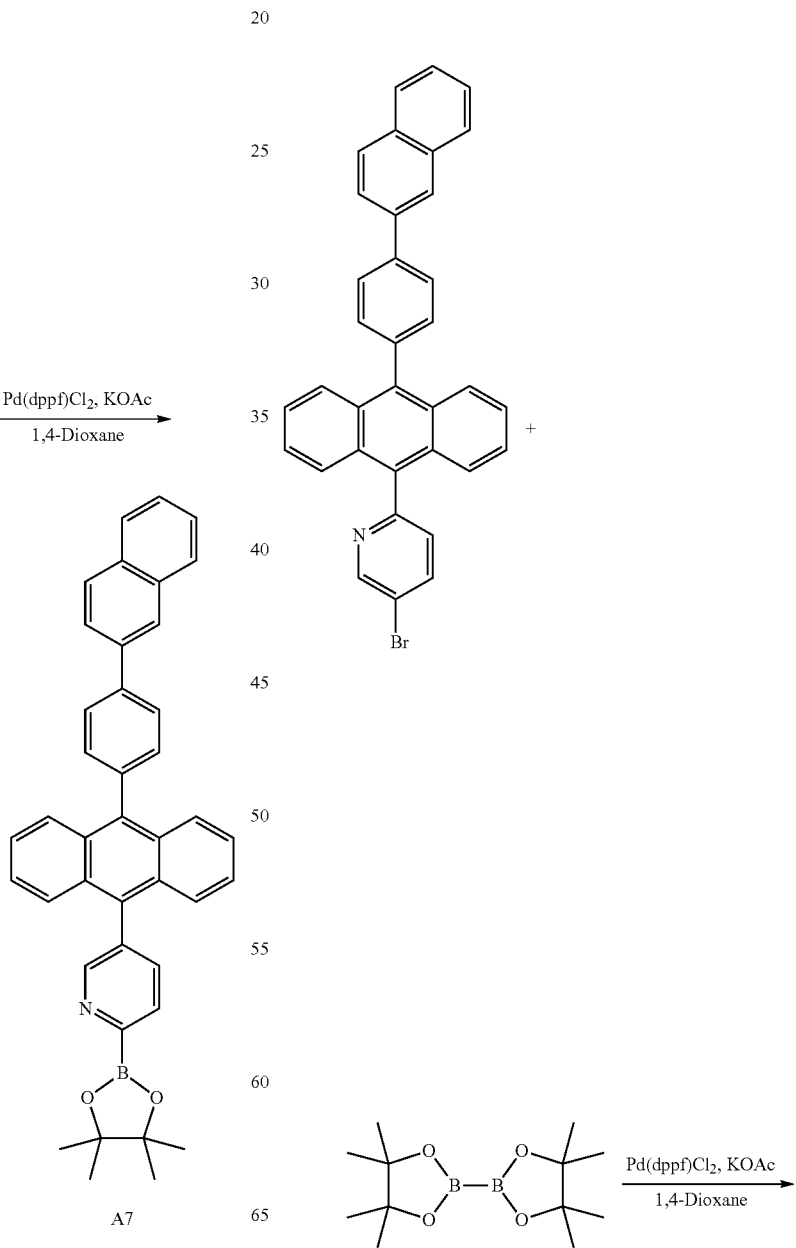

191
-continued

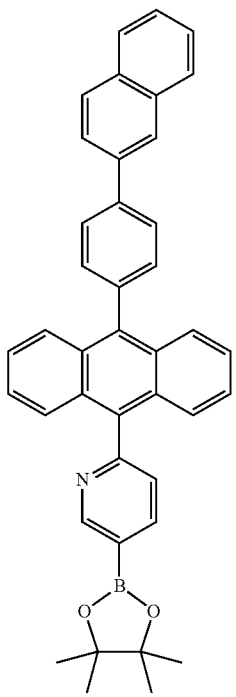

A8

In a nitrogen atmosphere, 5-bromo-2-(10-(4-(naphthalen-2-yl)phenyl)anthracen-9-yl)pyridine (13.1 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A8 (10.5 g, 18.0 mmol, yield: 74%).

GC-Mass (Calcd.: 583.53 g/mol, Found: 583 g/mol).

1H-NMR: δ 1.25 (1S, 12H), 7.35~7.39 (m, 9H), 7.52~7.55 (m, 3H), 7.79~7.93 (m, 7H), 8.02~8.03 (m, 2H), 8.34 (s, 1H)

192

[Preparation Example 9] Synthesis of Compound A9

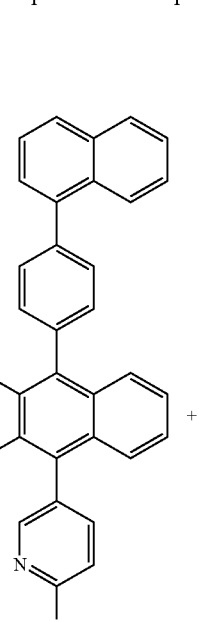

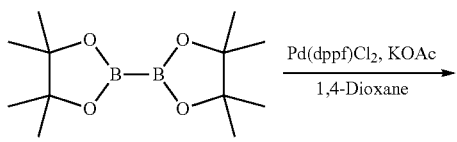

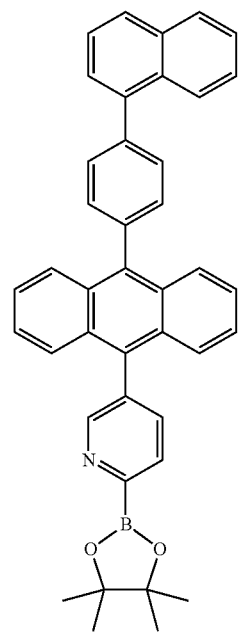

A9

In a nitrogen atmosphere, 2-bromo-5-(10-(4-(naphthalen-1-yl)phenyl)anthracen-9-yl)pyridine (13.1 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A9 (10.5 g, 18.0 mmol, yield: 74%).

GC-Mass (Calcd.: 583.53 g/mol, Found: 583 g/mol).

1H-NMR: δ 1.25 (1S, 12H), 7.23~7.25 (m, 4H), 7.35~7.39 (m, 5H), 7.55~7.59 (m, 3H), 7.88~7.91 (m, 5H), 8.04~8.06 (m, 2H), 8.42~8.50 (m, 2H), 8.58 (s, 1H)

[Preparation Example 10] Synthesis of Compound A10

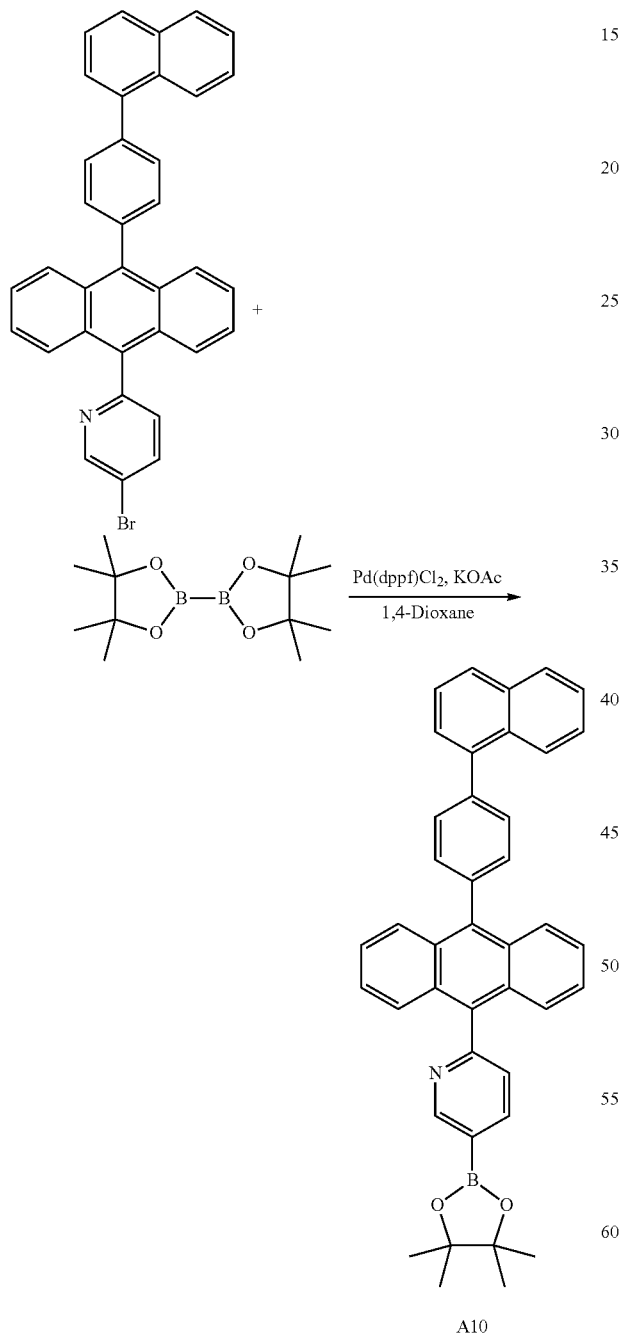

A10

In a nitrogen atmosphere, 5-bromo-2-(10-(4-(naphthalen-1-yl)phenyl)anthracen-9-yl)pyridine (13.1 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A10(10.5 g, 18.0 mmol, yield: 74%).

GC-Mass (Calcd.: 583.53 g/mol, Found: 583 g/mol).

1H-NMR: δ 1.25 (1S, 12H), 7.23~7.25 (m, 4H), 7.35~7.39 (m, 5H), 7.55~7.59 (m, 3H), 7.88~7.91 (m, 5H), 8.04~8.06 (m, 2H), 8.34 (s, 1H), 8.42~8.50 (m, 2H)

[Preparation Example 11] Synthesis of Compound A11

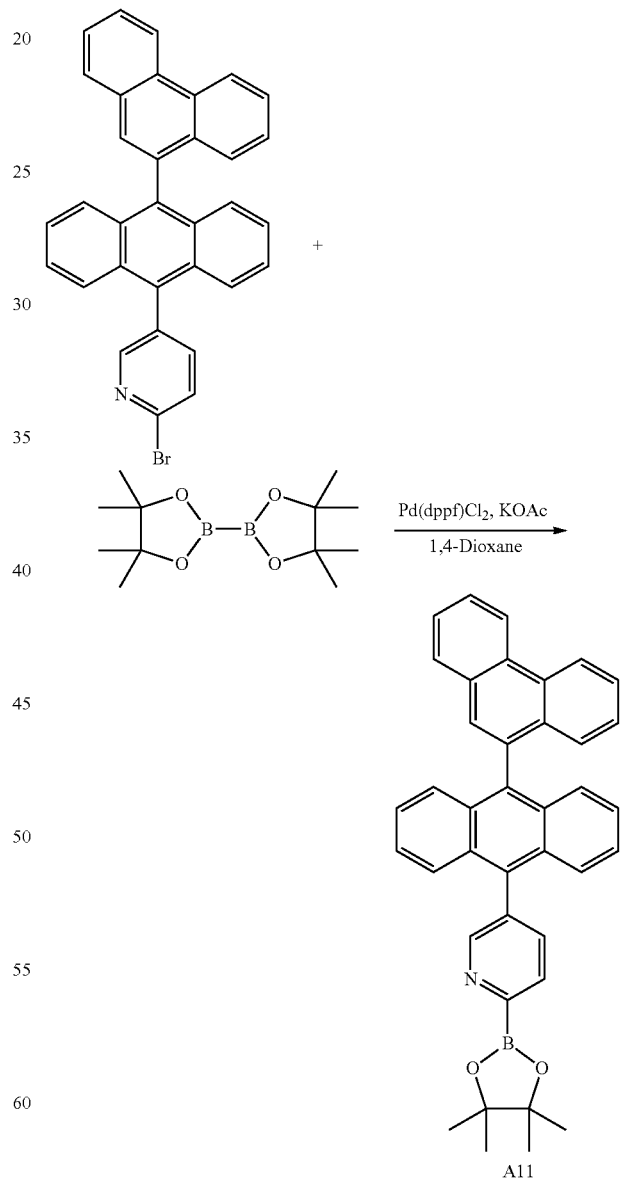

A11

In a nitrogen atmosphere, 2-bromo-5-(10-(phenanthren-9-yl)anthracen-9-yl)pyridine (12.4 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A11 (10.6 g, 19.0 mmol, yield: 78%).

GC-Mass (Calcd.: 510.42 g/mol, Found: 510 g/mol).

1H-NMR: δ 1.25 (1S, 12H), 7.35~7.39 (m, 5H), 7.85~7.92 (m, 10H), 8.10~8.11 (m, 2H), 8.58 (s, 1H), 8.88~8.90 (m, 2H)

[Preparation Example 12] Synthesis of Compound A12

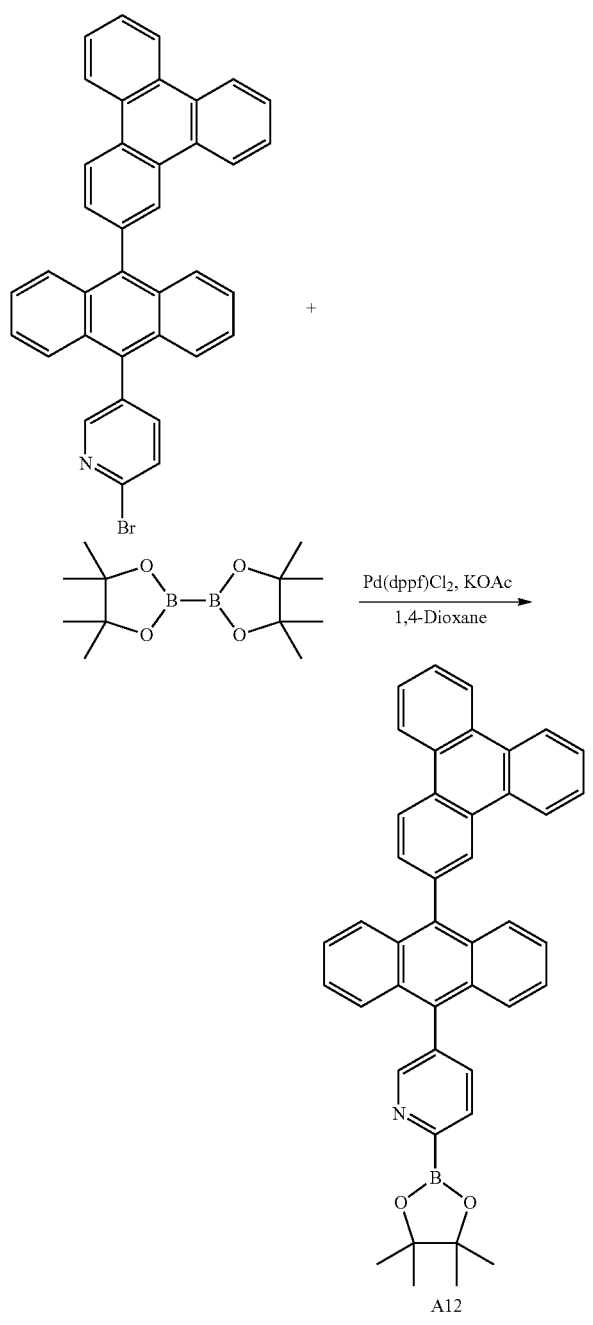

In a nitrogen atmosphere, 2-bromo-5-(10-(triphenylen-2-yl)anthracen-9-yl)pyridine (13.7 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A12(11.5 g, 19.0 mmol, yield: 78%).

GC-Mass (Calcd.: 607.55 g/mol, Found: 607 g/mol).

1H-NMR: δ 1.25 (1S, 12H), 7.35~7.39 (m, 5H), 7.88~7.92 (m, 9H), 8.07~8.14 (m, 4H), 8.58 (s, 1H), 8.87~8.90 (m, 2H), 9.11 (s, 1H)

[Preparation Example 13] Synthesis of Compound A13

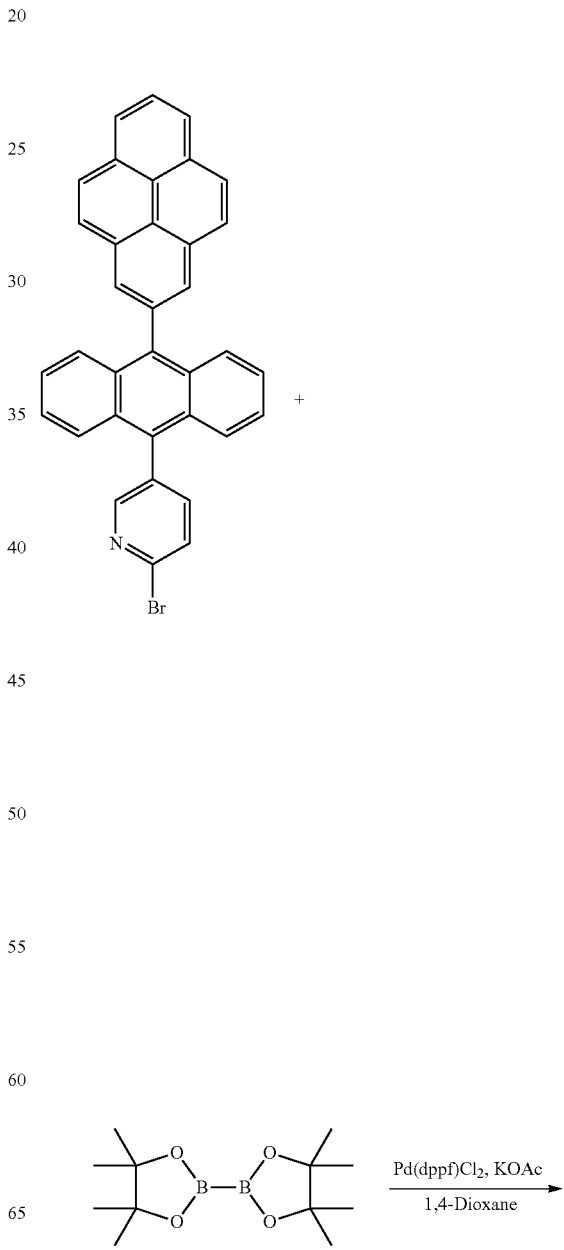

-continued

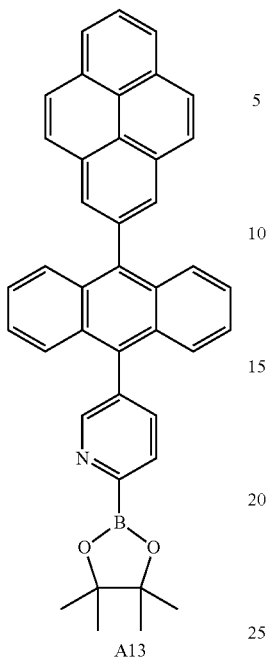

A13

In a nitrogen atmosphere, 2-bromo-5-(10-(pyren-2-yl) anthracen-9-yl)pyridine (13.0 g, 24.4 mmol), 4,4,4',4',5,5, 5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A13(10.5 g, 18.0 mmol, yield: 74%).

GC-Mass (Calcd.: 581.51 g/mol, Found: 581 g/mol).

1H-NMR: δ 1.25 (1S, 12H), 7.35~7.39 (m, 5H), 7.70~7.71 (m. 4H), 7.88~7.92 (m, 6H), 8.07~8.14 (m, 4H), 8.58 (s, 1H)

[Preparation Example 14] Synthesis of Compound A14

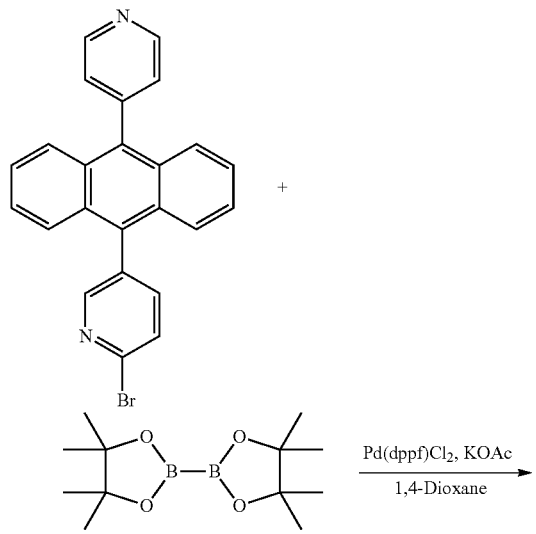

-continued

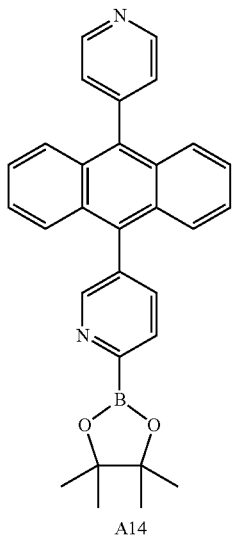

A14

In a nitrogen atmosphere, 2-bromo-5-(10-(pyridin-4-yl) anthracen-9-yl)pyridine (10.0 g, 24.4 mmol), 4,4,4',4',5,5, 5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A14 (8.3 g, 18.0 mmol, yield: 74%).

GC-Mass (Calcd.: 458.36 g/mol, Found: 458 g/mol).

1H-NMR: δ 1.25 (1S, 12H), 7.35~7.39 (m, 5H), 7.88~7.94 (m, 7H), 8.58 (s, 1H), 8.71~8.72 (m, 2H)

[Preparation Example 15] Synthesis of Compound A15

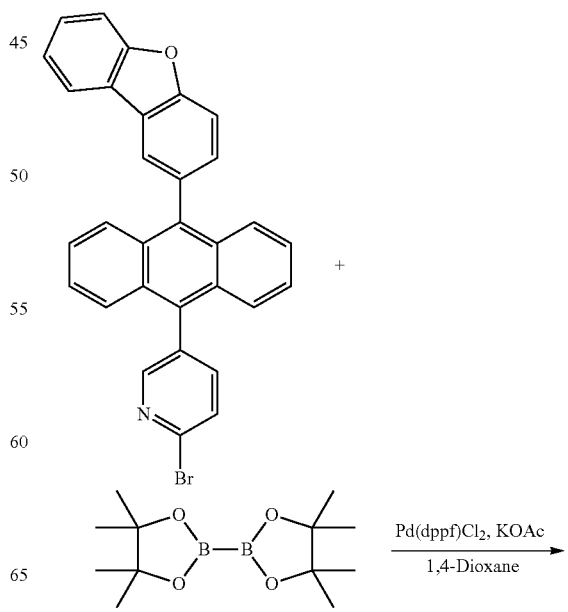

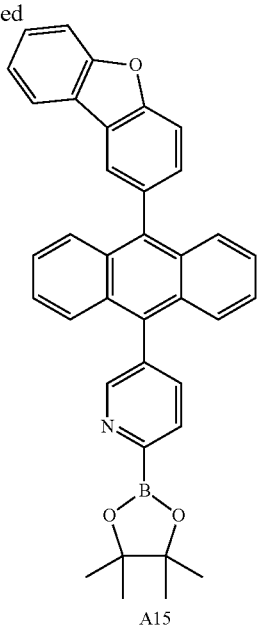

A15

In a nitrogen atmosphere, 2-bromo-5-(10-(dibenzo[b,d]furan-2-yl)anthracen-9-yl)pyridine (12.2 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A15 (10.1 g, 18.5 mmol, yield: 76%).

GC-Mass (Calcd.: 547.45 g/mol, Found: 547 g/mol).

1H-NMR: δ 1.25 (1S, 12H), 7.35~7.38 (m, 7H), 7.63~7.70 (m, 3H), 7.88~7.93 (m, 7H), 8.58 (s, 1H)

[Preparation Example 16] Synthesis of Compound A16

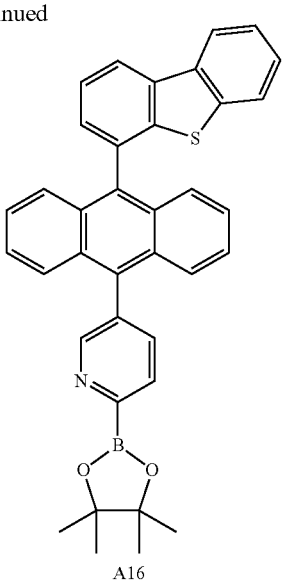

A16

In a nitrogen atmosphere, 2-bromo-5-(10-(dibenzo[b,d]thiophen-4-yl)anthracen-9-yl)pyridine (12.6 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A16 (10.8 g, 18.5 mmol, yield: 76%).

GC-Mass (Calcd.: 583.52 g/mol, Found: 583 g/mol).

1H-NMR: δ 1.25 (1S, 12H), 7.35~7.38 (m, 5H), 7.55~7.59 (m, 3H), 7.89~7.93 (m, 6H), 8.25~8.38 (m, 3H), 8.58 (s, 1H)

[Preparation Example 17] Synthesis of Compound A17

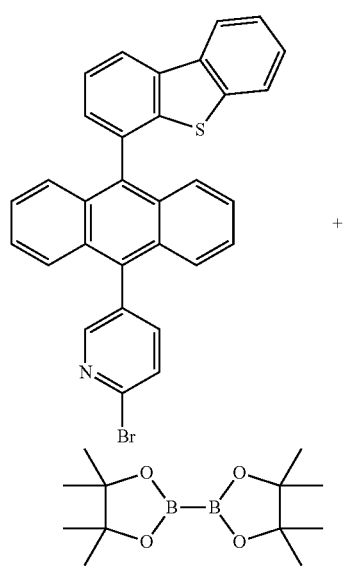 $\xrightarrow{\text{Pd(dppf)Cl}_2, \text{KOAc}}{\text{1,4-Dioxane}}$ 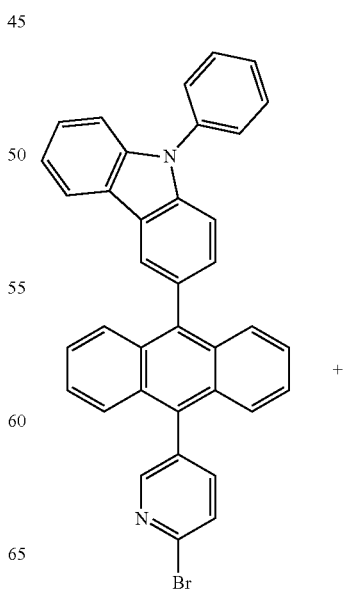 +

201

-continued

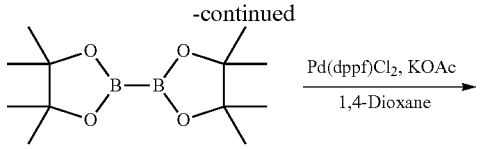

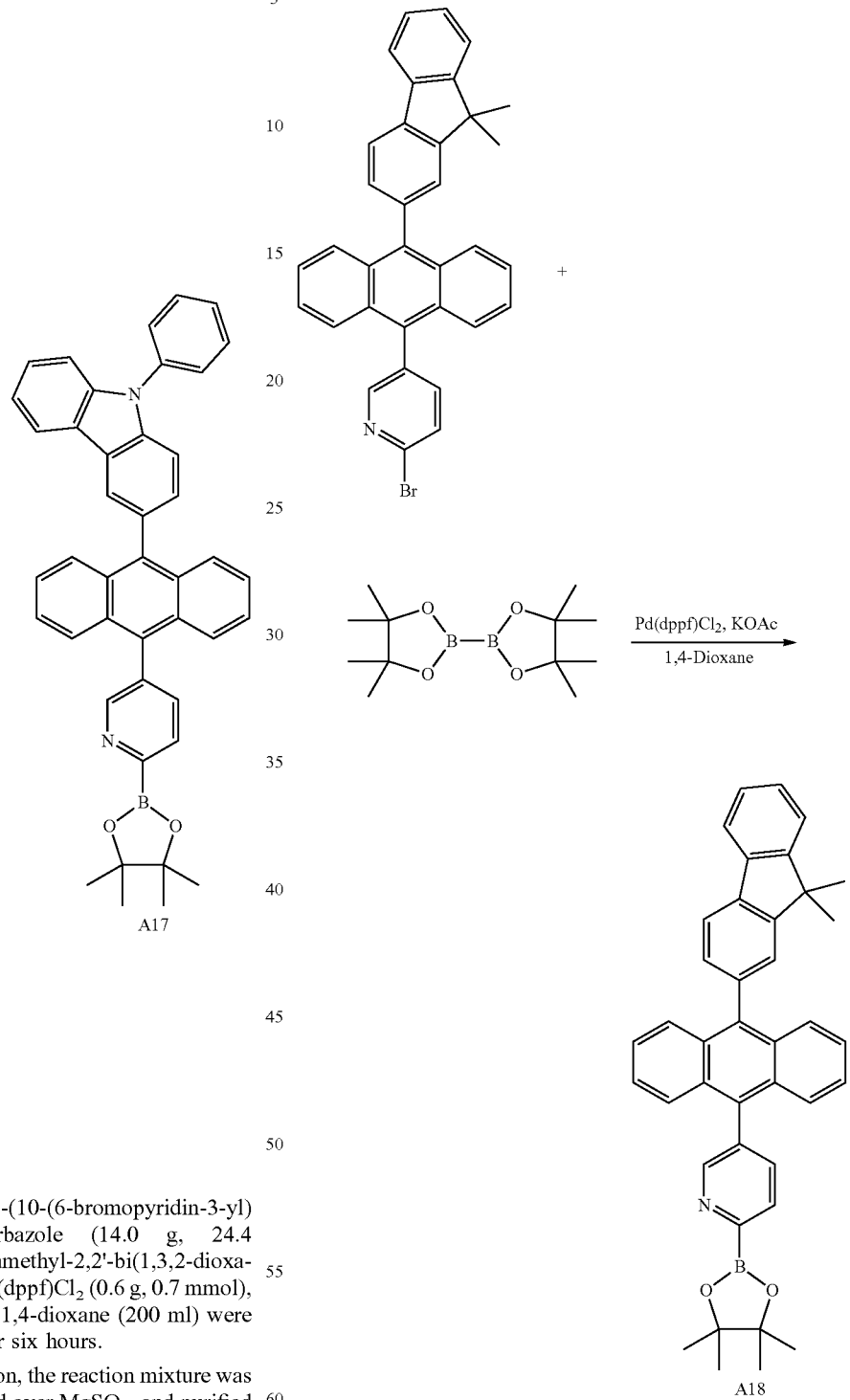

202

[Preparation Example 18] Synthesis of Compound A18

In a nitrogen atmosphere, 3-(10-(6-bromopyridin-3-yl)anthracen-9-yl)-9-phenyl-9H-carbazole (14.0 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A17 (11.5 g, 18.5 mmol, yield: 76%).

GC-Mass (Calcd.: 622.56 g/mol, Found: 622 g/mol).

1H-NMR: δ 1.25 (1S, 12H), 7.35~7.38 (m, 7H), 7.45~7.59 (m, 5H), 7.74~7.93 (m, 9H), 8.48 (d, 1H), 8.58 (s, 1H)

In a nitrogen atmosphere, 2-bromo-5-(10-(9,9-dimethyl-9H-fluoren-2-yl)anthracen-9-yl)pyridine (12.8 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A18 (10.6 g, 18.5 mmol, yield: 76%).

GC-Mass (Calcd.: 573.53 g/mol, Found: 573 g/mol).

1H-NMR: δ 1.25 (1S, 12H), 1.70 (s, 6H), 7.34~7.38 (m, 7H), 7.45~7.59 (m, 2H), 7.74~7.93 (m, 8H), 8.58 (s, 1H)

[Preparation Example 19] Synthesis of Compound A19

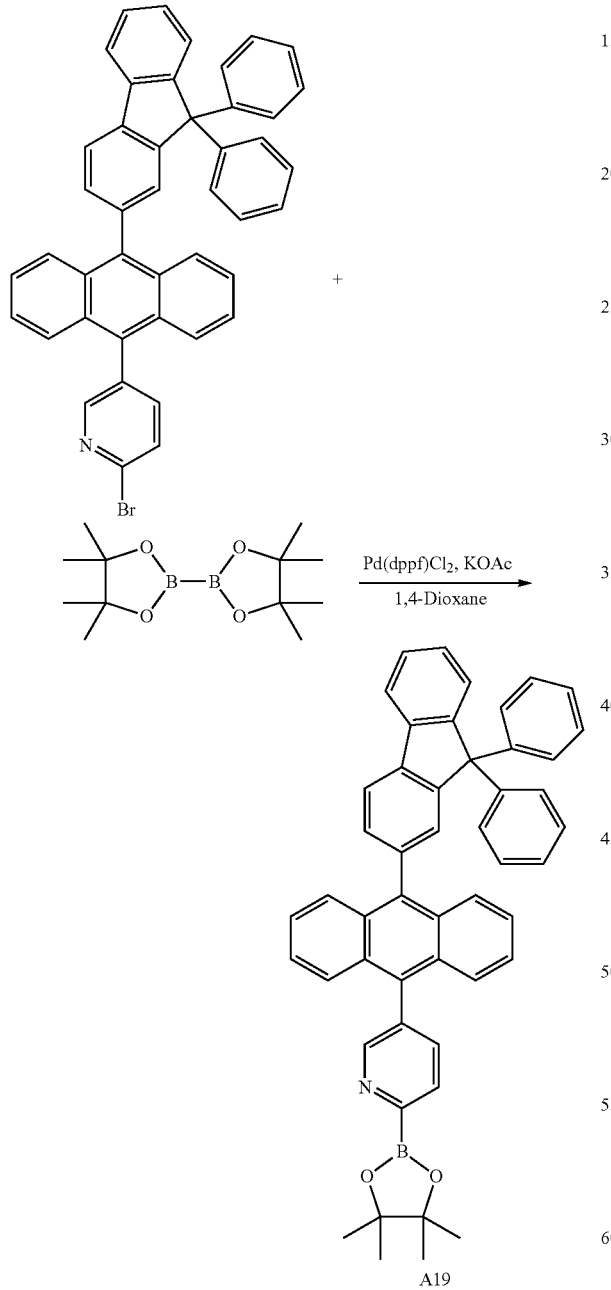

A19

In a nitrogen atmosphere, 2-bromo-5-(10-(9,9-diphenyl-9H-fluoren-2-yl)anthracen-9-yl)pyridine (15.9 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A19 (12.7 g, 18.3 mmol, yield: 75%).

GC-Mass (Calcd.: 697.67/mol, Found: 697 g/mol).

1H-NMR: δ 1.25 (1S, 12H), 7.12~7.22 (m, 5H), 7.34~7.38 (m, 12H), 7.51~7.65 (m, 2H), 7.74~7.93 (m, 8H), 8.58 (s, 1H)

[Preparation Example 20] Synthesis of Compound A20

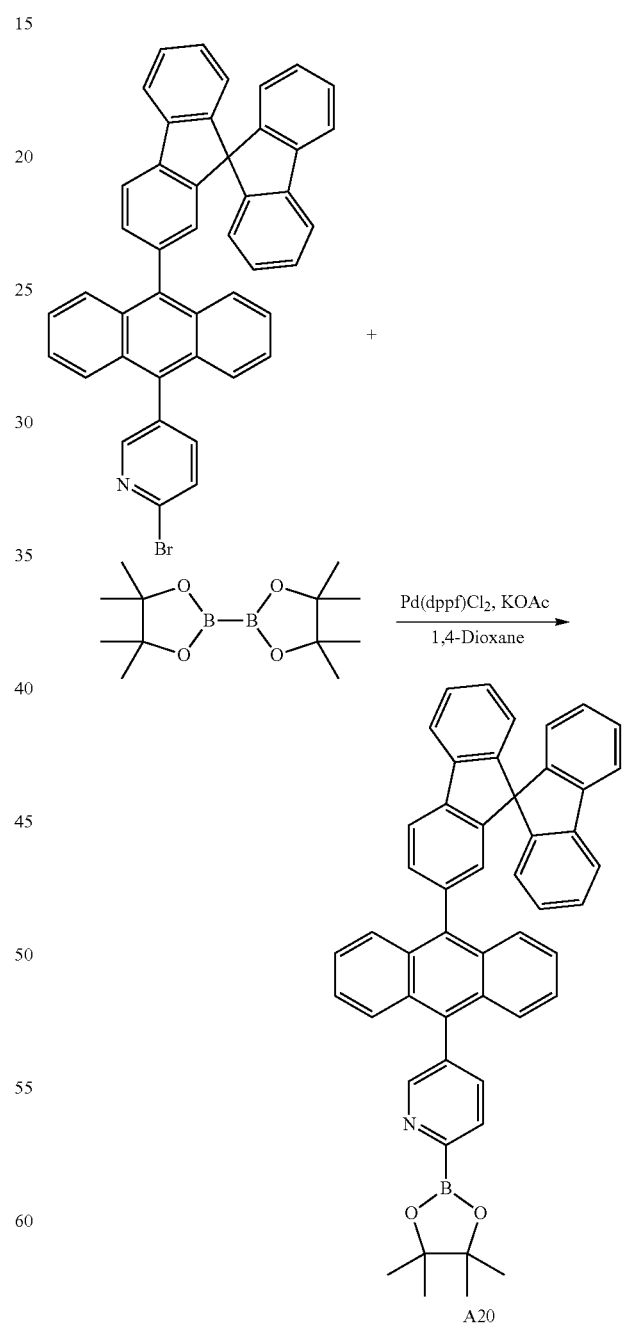

A20

In a nitrogen atmosphere, 5-(10-(9,9'-spirobi[fluorene]-2-yl)anthracen-9-yl)-2-bromopyridine (15.8 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A20 (12.7 g, 18.3 mmol, yield: 75%).

GC-Mass (Calcd.: 695.65/mol, Found: 695 g/mol).

1H-NMR: δ 1.25 (1S, 12H), 7.09~7.18 (m, 3H), 7.34~7.38 (m, 12H), 7.53~7.66 (m, 2H), 7.72~7.90 (m, 8H), 8.57 (s, 1H)

[Preparation Example 21] Synthesis of Compound A21

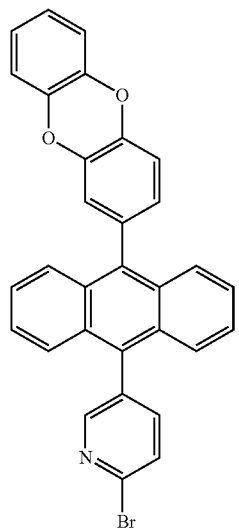

+

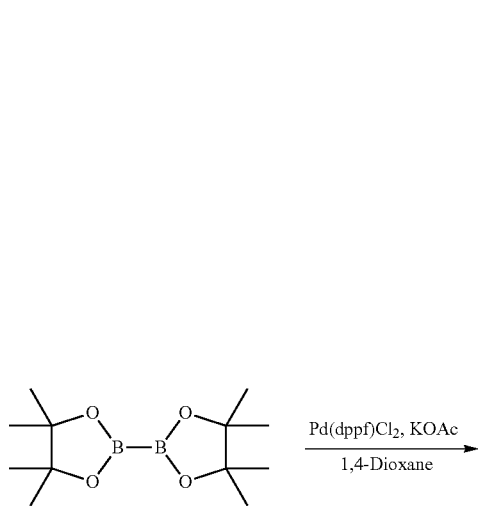

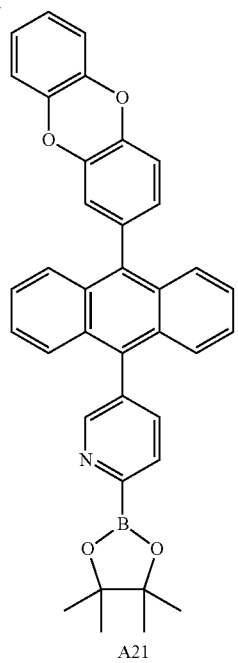

A21

In a nitrogen atmosphere, 2-bromo-5-(10-(dibenzo[b,e][1,4]dioxin-2-yl)anthracen-9-yl)pyridine (12.6 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A21 (10.3 g, 18.3 mmol, yield: 75%).

GC-Mass (Calcd.: 563.45/mol, Found: 563 g/mol).

1H-NMR: δ 1.25 (1S, 12H), 6.82~6.83 (m, 2H), 7.13~7.18 (m, 3H), 7.34~7.41 (m, 7H), 7.72~7.90 (m, 5H), 8.57 (s, 1H)

[Preparation Example 22] Synthesis of Compound A22

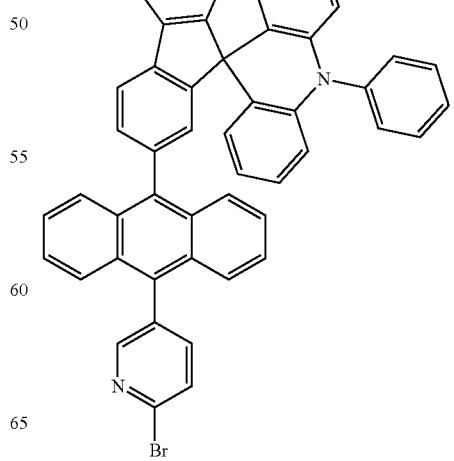

+

207
-continued

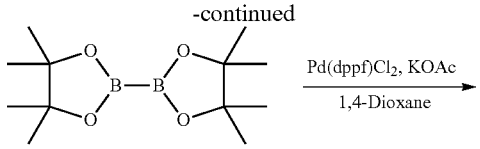

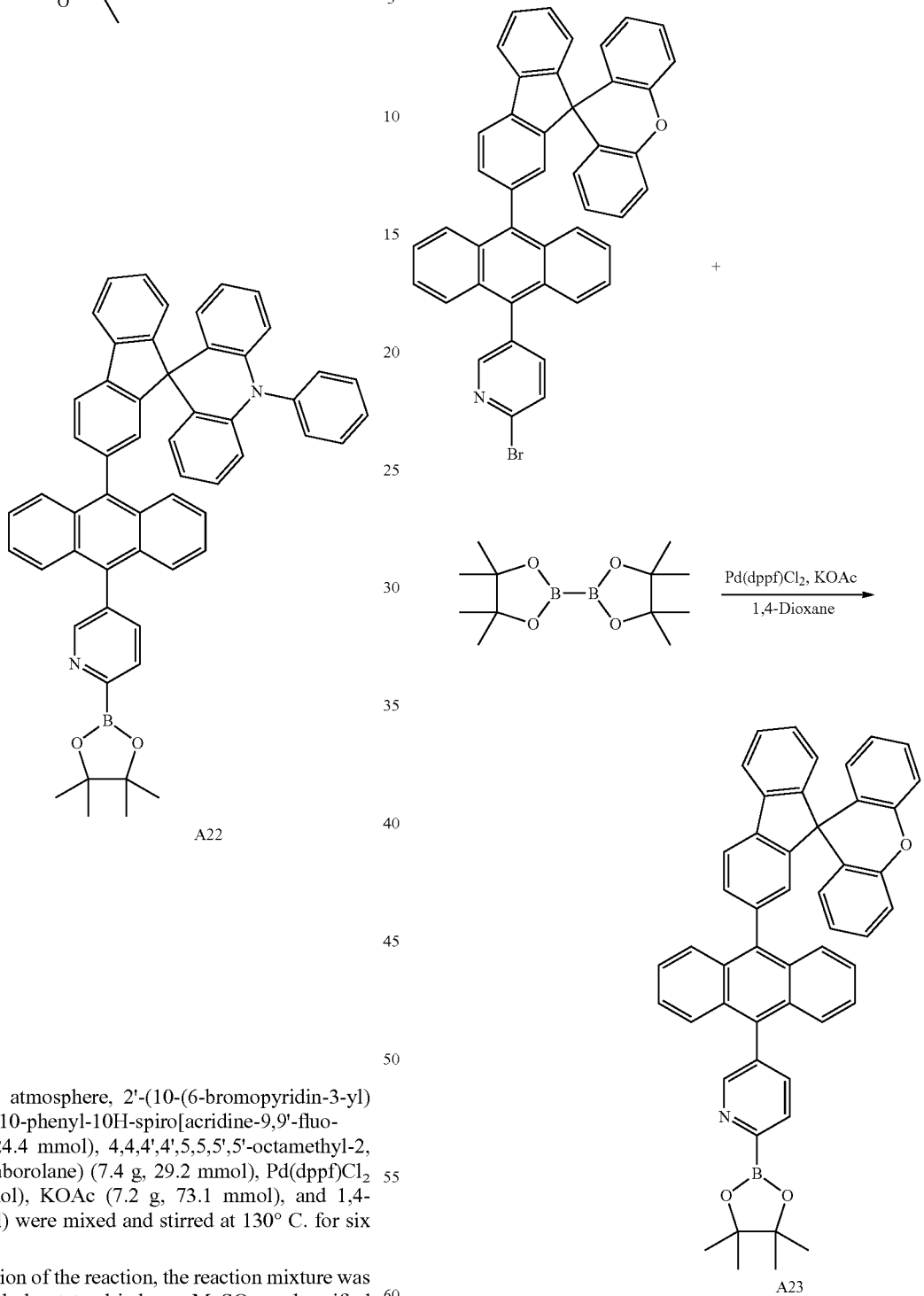

In a nitrogen atmosphere, 2'-(10-(6-bromopyridin-3-yl)anthracen-9-yl)-10-phenyl-10H-spiro[acridine-9,9'-fluorene] (18.0 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A22 (14.4 g, 18.3 mmol, yield: 75%).

GC-Mass (Calcd.: 786.76/mol, Found: 786 g/mol).

1H-NMR: δ 1.25 (1S, 12H), 6.52~6.83 (m, 9H), 7.11~7.18 (m, 5H), 7.34~7.48 (m, 7H), 7.72~7.90 (m, 8H), 8.57 (s, 1H)

208

[Preparation Example 23] Synthesis of Compound A23

In a nitrogen atmosphere, 2-bromo-5-(10-(spiro[fluorene-9,9'-xanthene]-2-yl)anthracen-9-yl)pyridine (18.0 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A23 (13.0 g, 18.3 mmol, yield: 75%).

GC-Mass (Calcd.: 711.65/mol, Found: 711 g/mol).

1H-NMR: δ 1.25 (1S, 12H), 7.08~7.18 (m, 9H), 7.34~7.48 (m, 7H), 7.72~7.90 (m, 9H), 8.57 (s, 1H)

[Preparation Example 24] Synthesis of Compound A24

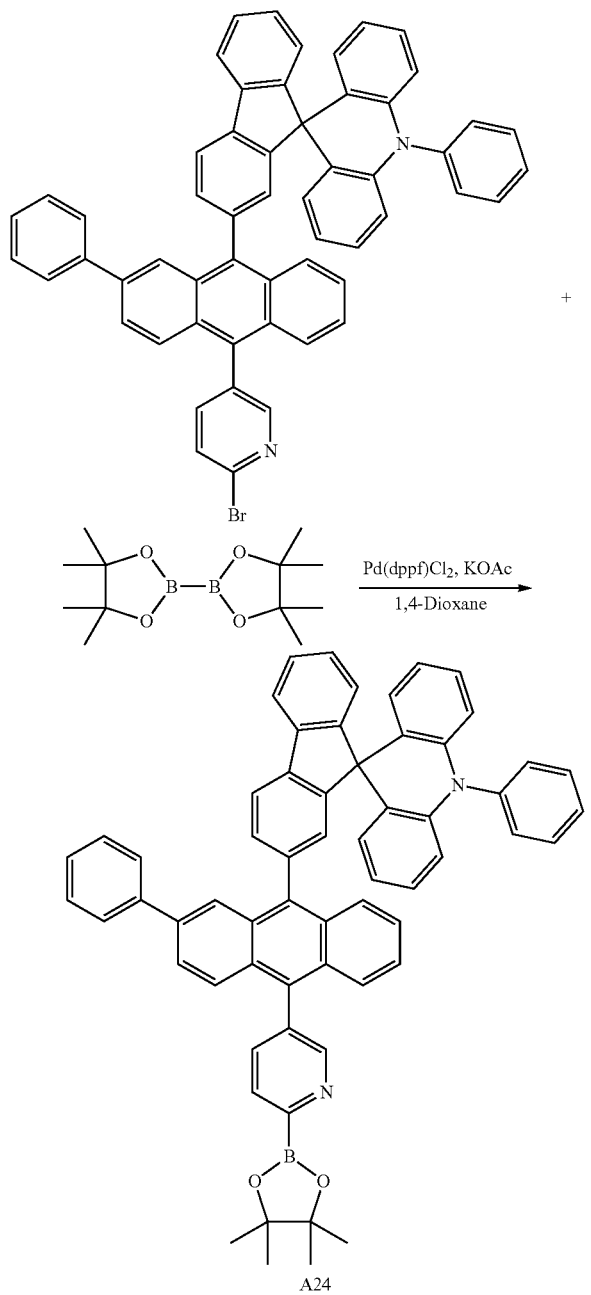

In a nitrogen atmosphere, 2'-(10-(6-bromopyridin-3-yl)-2-phenylanthracen-9-yl)-10-phenyl-10H-spiro[acridine-9,9'-fluorene] (19.9 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A24 (16.1 g, 18.3 mmol, yield: 75%).

GC-Mass (Calcd.: 882.86/mol, Found: 882 g/mol).

1H-NMR: δ 1.25 (1S, 12H), 6.53~6.83 (m, 9H), 7.11~7.19 (m, 5H), 7.34~7.52 (m, 12H), 7.72~7.91 (m, 7H), 8.10 (s, 1H), 8.57 (s, 1H)

[Preparation Example 25] Synthesis of Compound A25

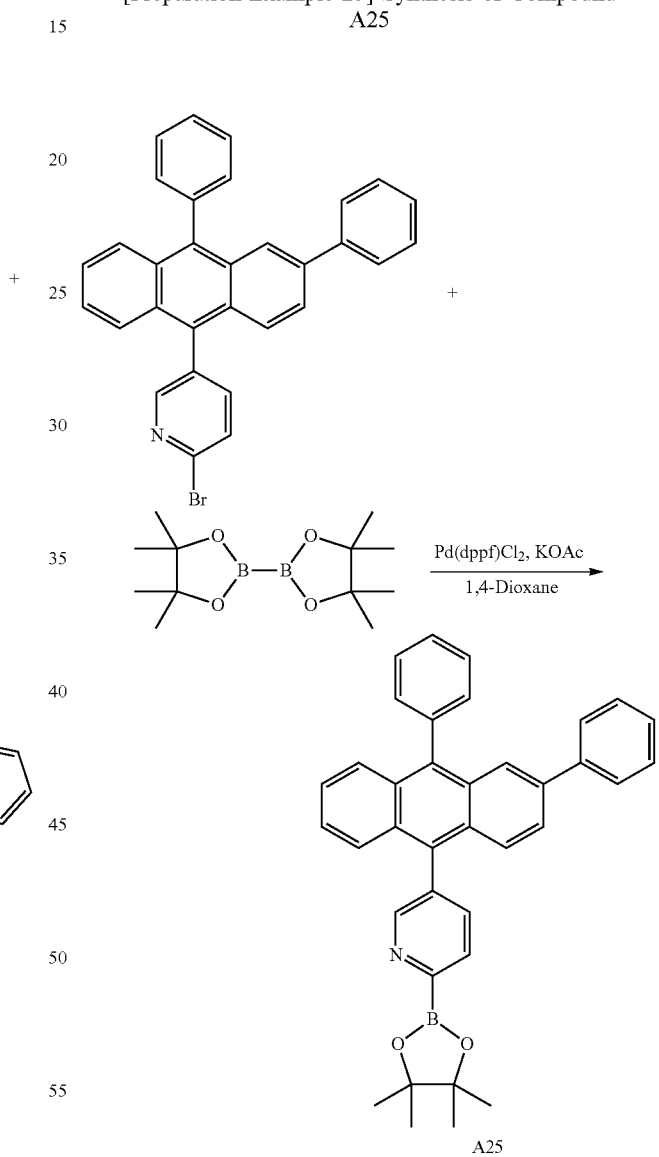

In a nitrogen atmosphere, 2-bromo-5-(3,10-diphenylanthracen-9-yl)pyridine (11.9 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol, and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A25 (9.4 g, 17.5 mmol, yield: 72%).

GC-Mass (Calcd.: 533.47 g/mol, Found: 533 g/mol).

1H-NMR: δ 1.25 (1S, 12H), 7.35~7.39 (m, 3H), 7.43~7.54 (m, 11H), 7.88~7.91 (m, 4H), 8.10 (s, 1H), 8.55 (s, 1H)

[Preparation Example 26] Synthesis of Compound A26

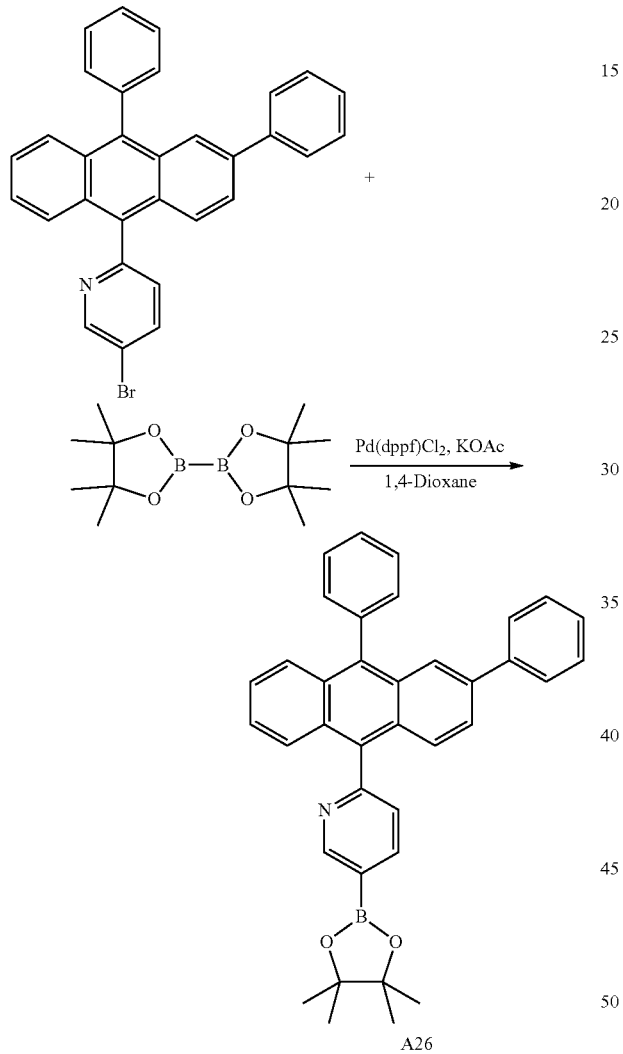

In a nitrogen atmosphere, 5-bromo-2-(3,10-diphenylanthracen-9-yl)pyridine (11.9 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol, and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A26 (9.4 g, 17.5 mmol, yield: 72%).

GC-Mass (Calcd.: 533.47 g/mol, Found: 533 g/mol).

1H-NMR: δ 1.25 (1S, 12H), 7.35~7.39 (m, 3H), 7.43~7.54 (m, 11H), 7.88~7.91 (m, 4H), 8.10 (s, 1H), 8.34 (s, 1H)

[Preparation Example 27] Synthesis of Compound A27

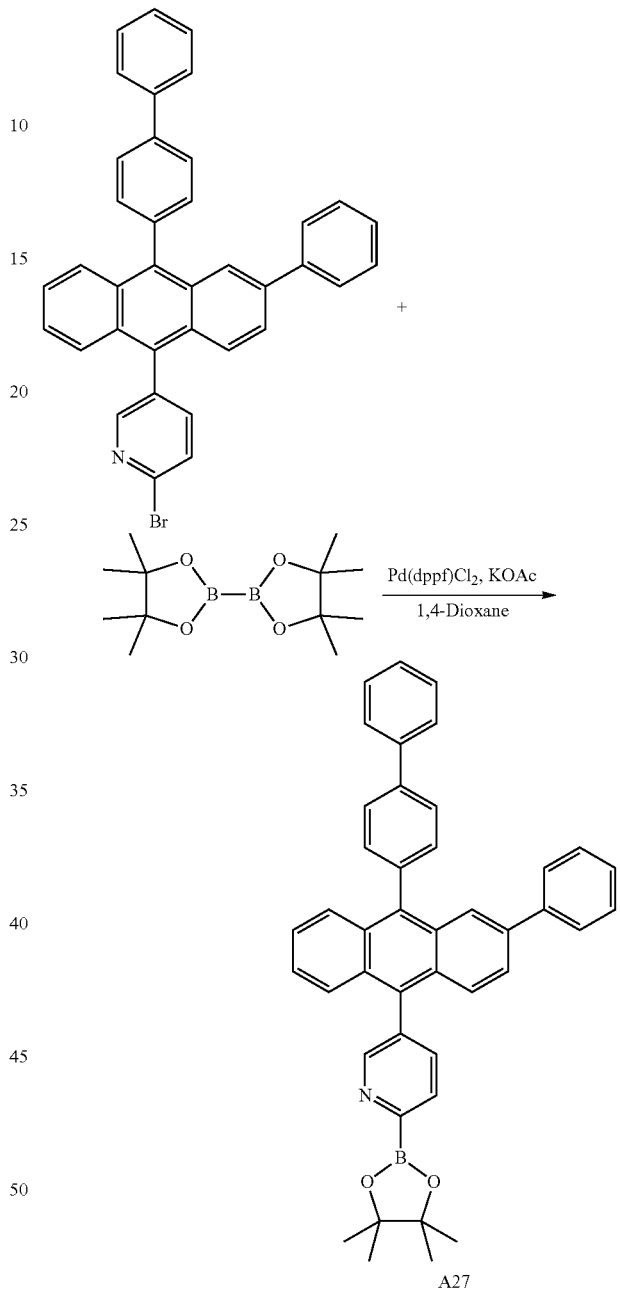

In a nitrogen atmosphere, 5-(10-(biphenyl-4-yl)-3-phenylanthracen-9-yl)-2-bromopyridine (13.7 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol, and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A27 (10.7 g, 17.5 mmol, yield: 72%).

GC-Mass (Calcd.: 609.56 g/mol, Found: 609 g/mol).

1H-NMR: δ 1.25 (1S, 12H), 7.35~7.39 (m, 3H), 7.43~7.54 (m, 15H), 7.88~7.91 (m, 4H), 8.10 (s, 1H), 8.34 (s, 1H)

[Preparation Example 28] Synthesis of Compound A28

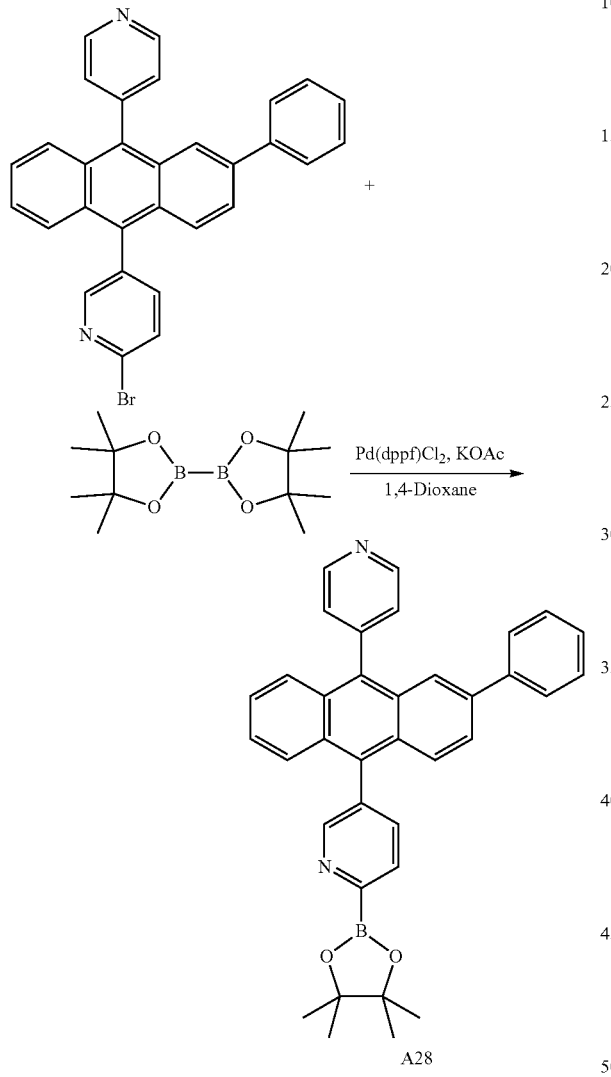

A28

In a nitrogen atmosphere, 2-bromo-5-(3-phenyl-10-(pyridin-4-yl)anthracen-9-yl)pyridine (11.9 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol, and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A28 (9.4 g, 17.5 mmol, yield: 72%).

GC-Mass (Calcd.: 534.45 g/mol, Found: 534 g/mol).

1H-NMR: δ 1.25 (1S, 12H), 7.35~7.36 (m, 3H), 7.43~7.54 (m, 6H), 7.88~7.91 (m, 6H), 8.10 (s, 1H), 8.55 (s, 1H), 8.86~8.87 (m, 2H)

[Preparation Example 29] Synthesis of Compound A29

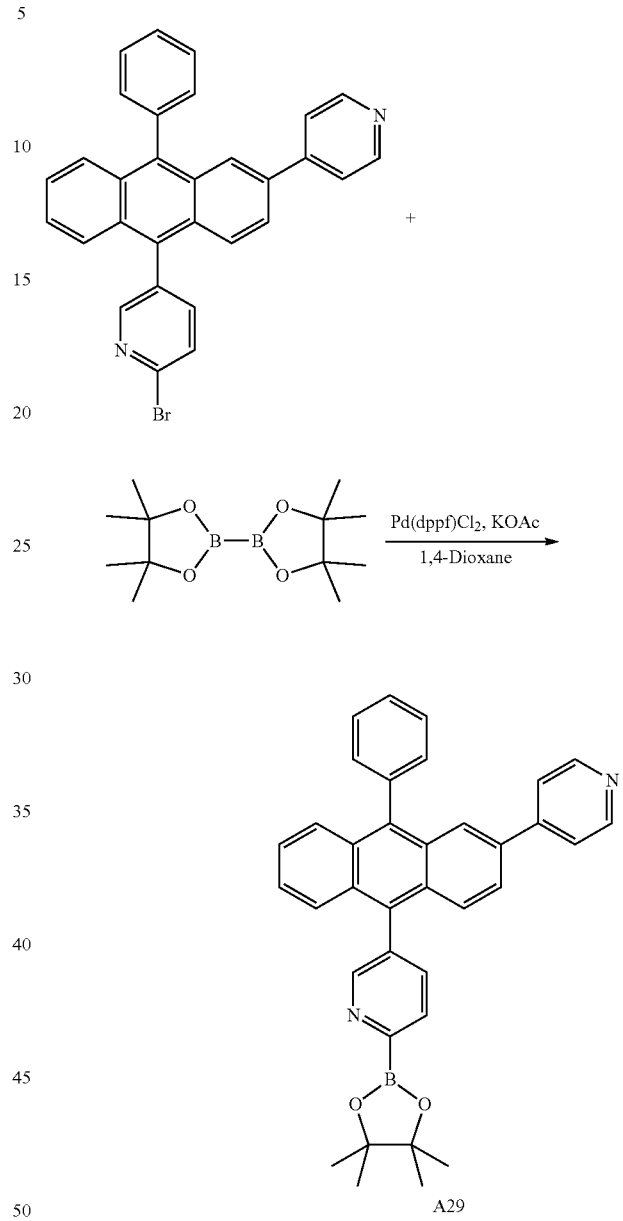

A29

In a nitrogen atmosphere, 2-bromo-5-(10-phenyl-3-(pyridin-4-yl)anthracen-9-yl)pyridine (11.9 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol, and 1,4-dioxane (200 ml) were mixed and stirred at 130° C. for six hours.

After completion of the reaction, the reaction mixture was extracted with ethylacetate, dried over MgSO₄, and purified by column chromatography to afford the object compound A29 (9.4 g, 17.5 mmol, yield: 72%).

GC-Mass (Calcd.: 534.45 g/mol, Found: 534 g/mol).

1H-NMR: δ 1.25 (1S, 12H), 7.35~7.36 (m, 3H), 7.45~7.54 (m, 6H), 7.88~7.92 (m, 6H), 8.10 (s, 1H), 8.55 (s, 1H), 8.86~8.87 (m, 2H)

[Preparation Example 30] Synthesis of Compound A30

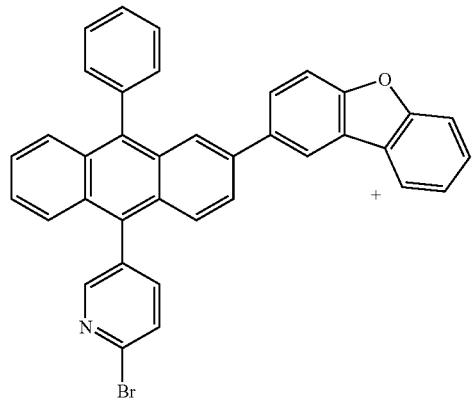

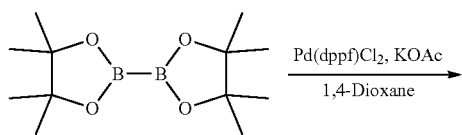

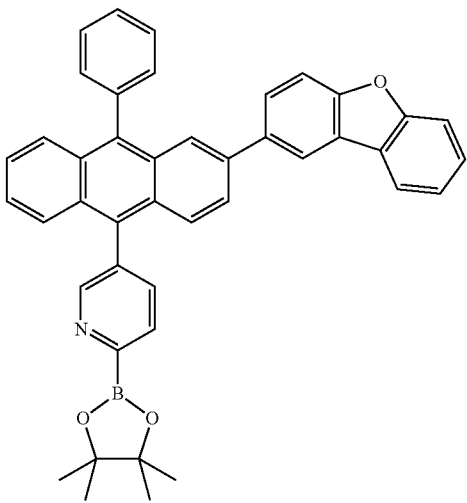

A30

In a nitrogen atmosphere, 2-bromo-5-(3-(dibenzo[b,d]furan-2-yl)-10-phenylanthracen-9-yl)pyridine (14.0 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A30 (10.9 g, 17.5 mmol, yield: 72%).

GC-Mass (Calcd.: 623.55 g/mol, Found: 623 g/mol).

1H-NMR: δ 1.25 (1S, 12H), 7.35~7.38 (m, 5H), 7.45~7.54 (m, 7H), 7.88~7.90 (m, 8H), 8.10 (s, 1H), 8.55 (s, 1H)

[Preparation Example 31] Synthesis of Compound A31

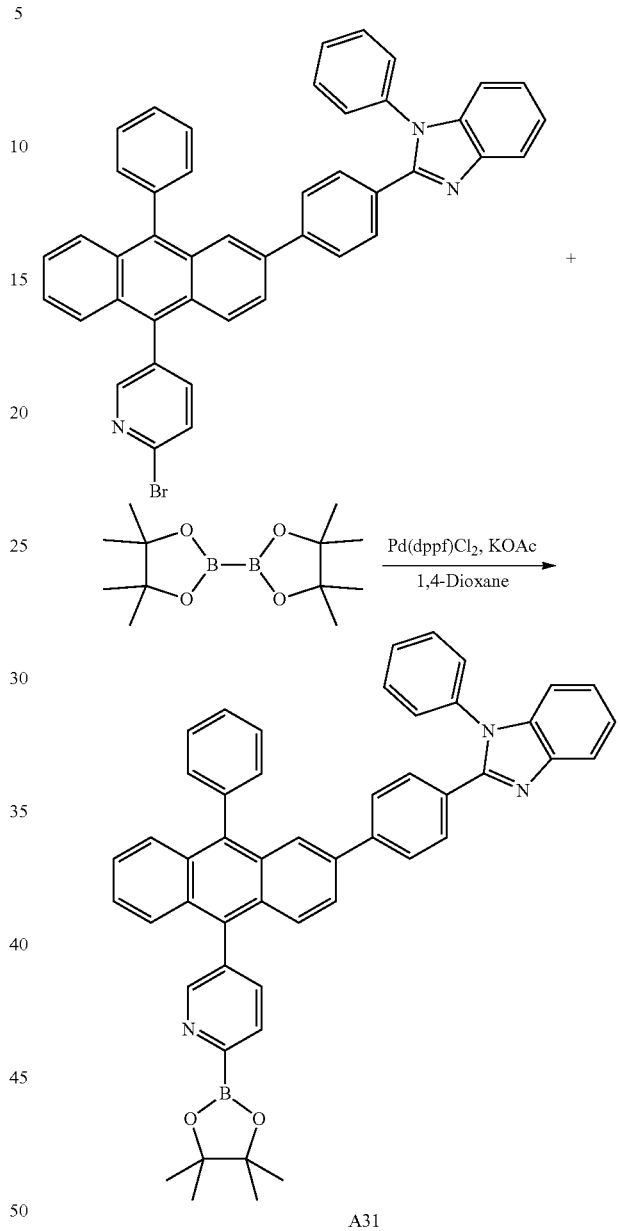

A31

In a nitrogen atmosphere, 2-(4-(10-(6-bromopyridin-3-yl)-9-phenylanthracen-2-yl)phenyl)-1-phenyl-1H-benzo[d]imidazole (16.5 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol), and 1,4-dioxane (200 ml) were mixed and stirred at 130° C. for six hours.

After completion of the reaction, the reaction mixture was extracted with ethylacetate, dried over MgSO$_4$, and purified by column chromatography to afford the object compound A31 (12.7 g, 17.5 mmol, yield: 72%).

GC-Mass (Calcd.: 725.68 g/mol, Found: 725 g/mol).

1H-NMR: δ 7.22~7.25 (m 4H), 7.42~7.63 (m, 15H), 7.85~7.92 (m, 5H), 8.12~8.14 (m, 2H), 8.52 (d, 1H), 8.80 (s, 1H)

[Synthesis Example 1] Synthesis of Compound R13

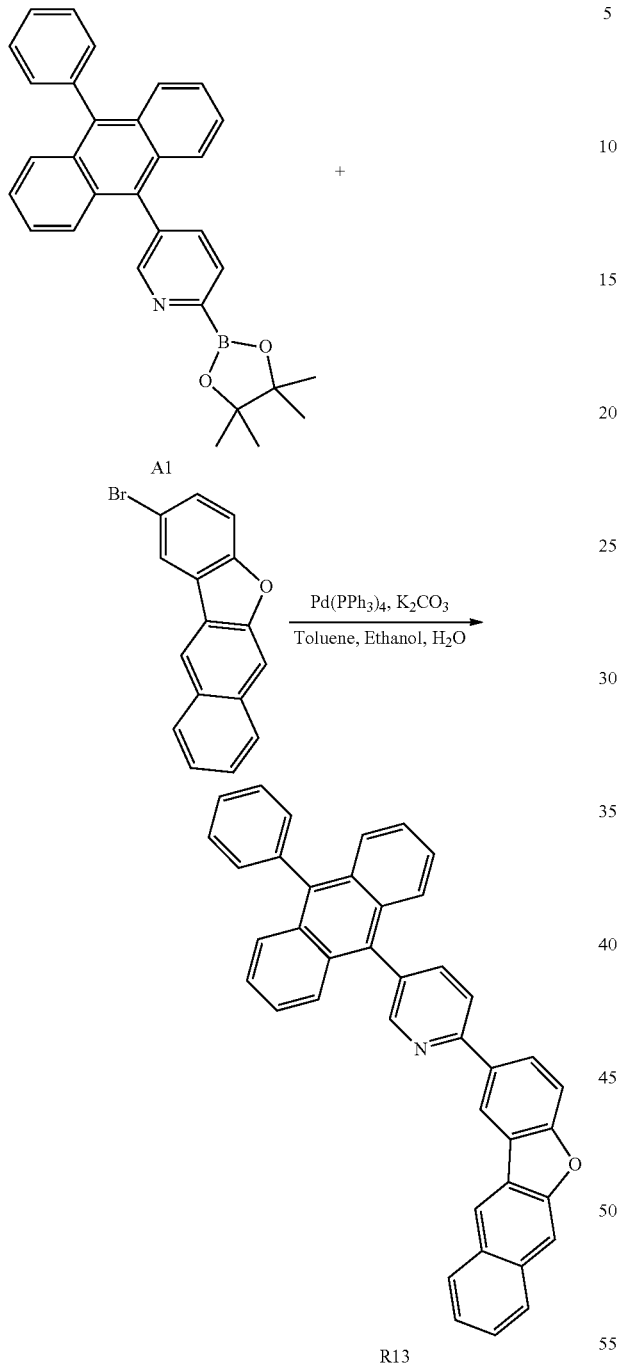

In a nitrogen atmosphere, Compound A1 (7.8 g, 17.1 mmol), 2-bromobenzo[b]naphtho[2,3-d]furan (7.0 g, 18.8 mmol), Pd(PPh$_3$)$_4$ (0.9 g, 5 mol %), and potassium carbonate (7.0 g, 51.2 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R13 (8.0 g, 12.8 mmol, yield: 75%).

GC-Mass (Calcd.: 623.74 g/mol, Found: 623 g/mol).

[Synthesis Example 2] Synthesis of Compound R15

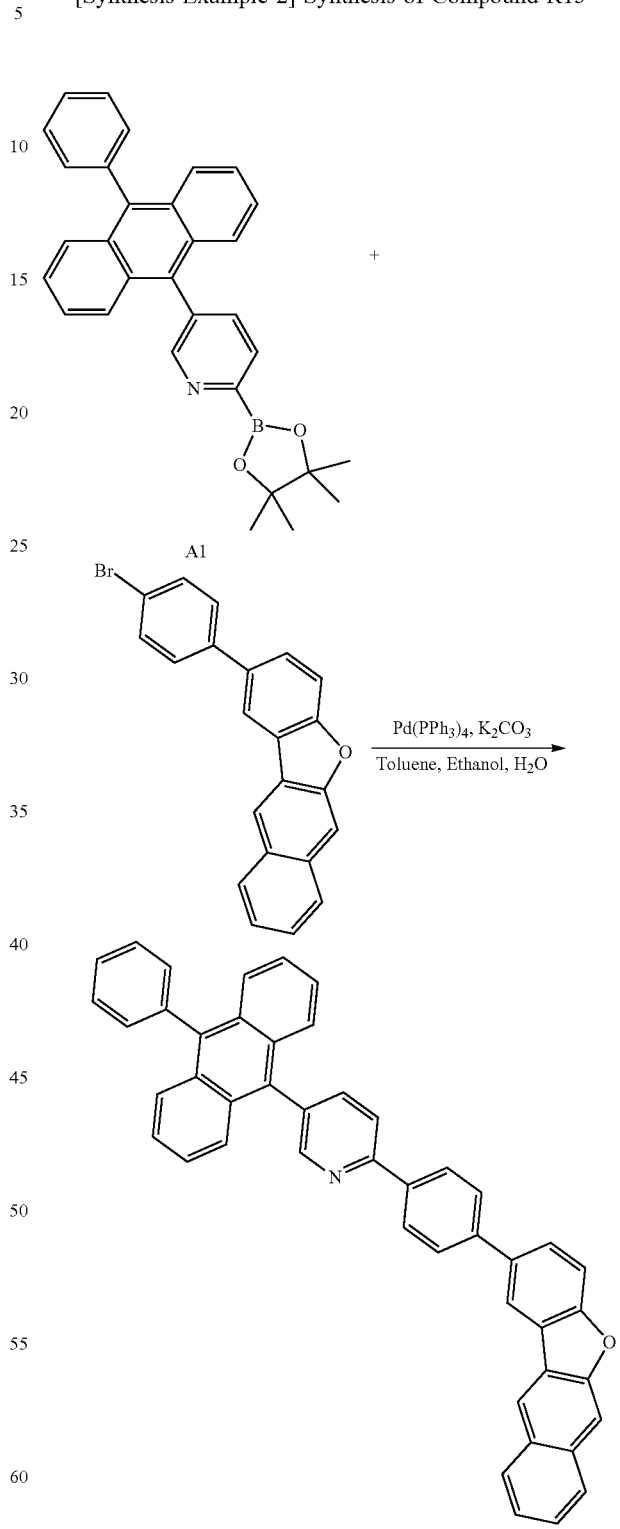

In a nitrogen atmosphere, Compound A1 (7.8 g, 17.1 mmol), 2-(4-bromophenyl)benzo[b]naphtho[2,3-d]furan (5.6 g, 18.8 mmol), Pd(PPh$_3$)$_4$ (0.9 g, 5 mol %), and potassium carbonate (7.0 g, 51.2 mmol) were added to toluene/H₂O/ethanol (80 ml/40 ml/40 ml) and stirred at 110° C. for three hours.

After completion of the reaction, the organic material layer was separated using methylene chloride and dried over MgSO₄. The solvent was removed from the organic material layer, followed by purification through column chromatography to afford the object compound R15 (7.0 g, 12.8 mmol, yield: 75%).

GC-Mass (Calcd.: 547.64 g/mol, Found: 547 g/mol).

[Synthesis Example 3] Synthesis of Compound R17

In a nitrogen atmosphere, Compound A1 (7.8 g, 17.1 mmol), 9-bromobenzo[b]naphtho[1,2-d]furan (5.6 g, 18.8 mmol), Pd(PPh₃)₄ (0.9 g, 5 mol %), and potassium carbonate (7.0 g, 51.2 mmol) were added to toluene/H₂O/ethanol (80 ml/40 ml/40 ml) and stirred at 110° C. for three hours.

After completion of the reaction, the organic material layer was separated using methylene chloride and dried over MgSO₄. The solvent was removed from the organic material layer, followed by purification through column chromatography to afford the object compound R17 (7.0 g, 12.8 mmol, yield: 75%).

GC-Mass (Calcd.: 547.64 g/mol, Found: 547 g/mol).

[Synthesis Example 4] Synthesis of Compound R33

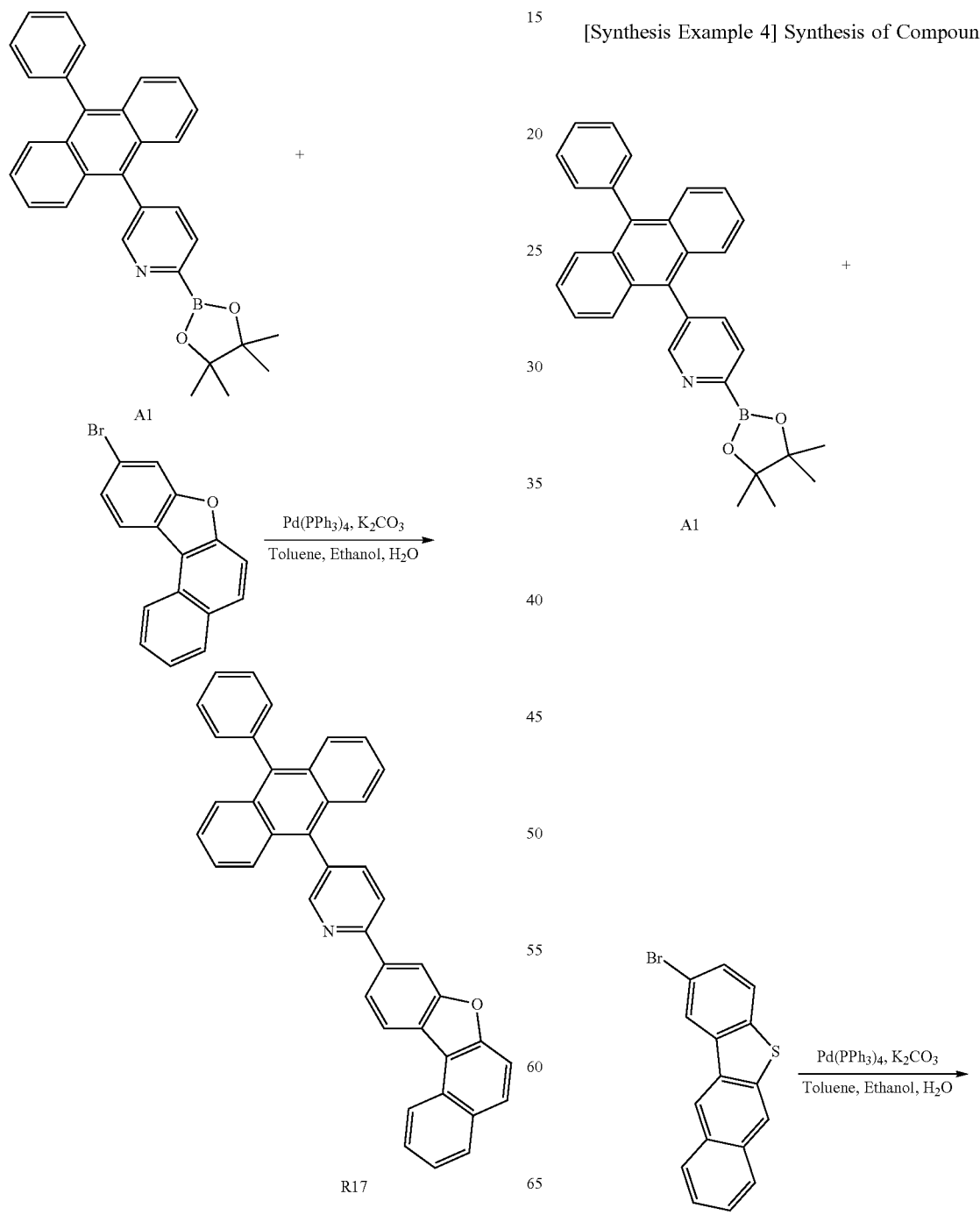

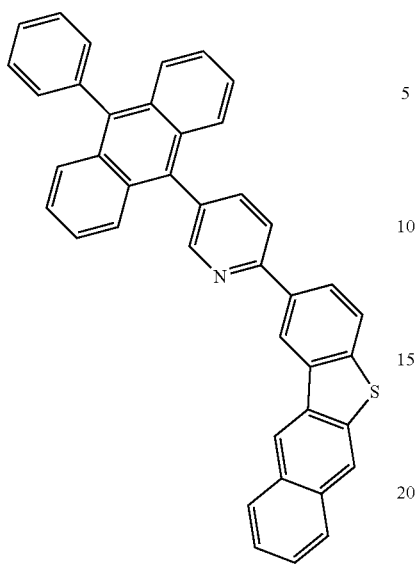

R33

In a nitrogen atmosphere, Compound A1 (7.8 g, 17.1 mmol), 2-bromobenzo[b]naphtho[2,3-d]thiophene (5.9 g, 18.8 mmol), Pd(PPh$_3$)$_4$ (0.9 g, 5 mol %), and potassium carbonate (7.0 g, 51.2 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R33 (6.9 g, 12.8 mmol, yield: 72%).

GC-Mass (Calcd.: 563.71 g/mol, Found: 563 g/mol).

[Synthesis Example 5] Synthesis of Compound R58

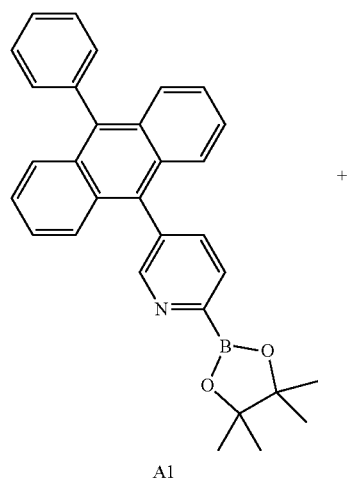

A1

+

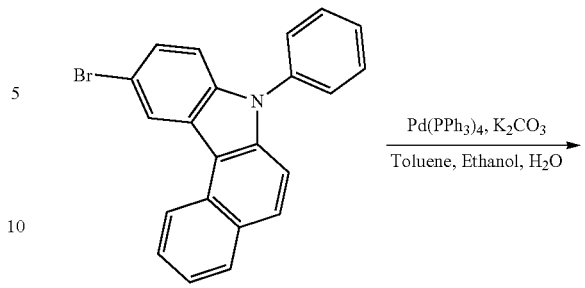

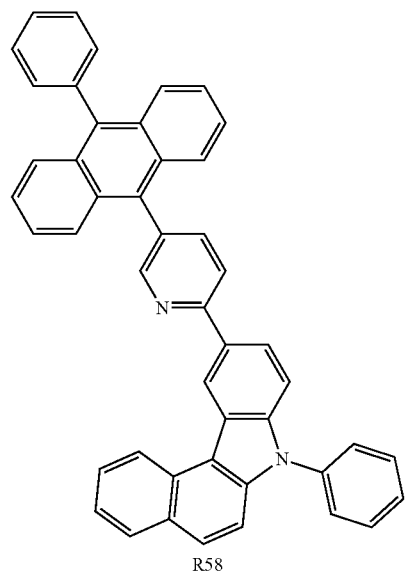

R58

In a nitrogen atmosphere, Compound A1 (7.8 g, 17.1 mmol), 10-bromo-7-phenyl-7H-benzo[c]carbazole (7.0 g, 18.8 mmol), Pd(PPh$_3$)$_4$ (0.9 g, 5 mol %), and potassium carbonate (7.0 g, 51.2 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R58 (7.6 g, 12.8 mmol, yield: 72%).

GC-Mass (Calcd.: 622.75 g/mol, Found: 622 g/mol).

[Synthesis Example 6] Synthesis of Compound R67

[Synthesis Example 7] Synthesis of Compound R75

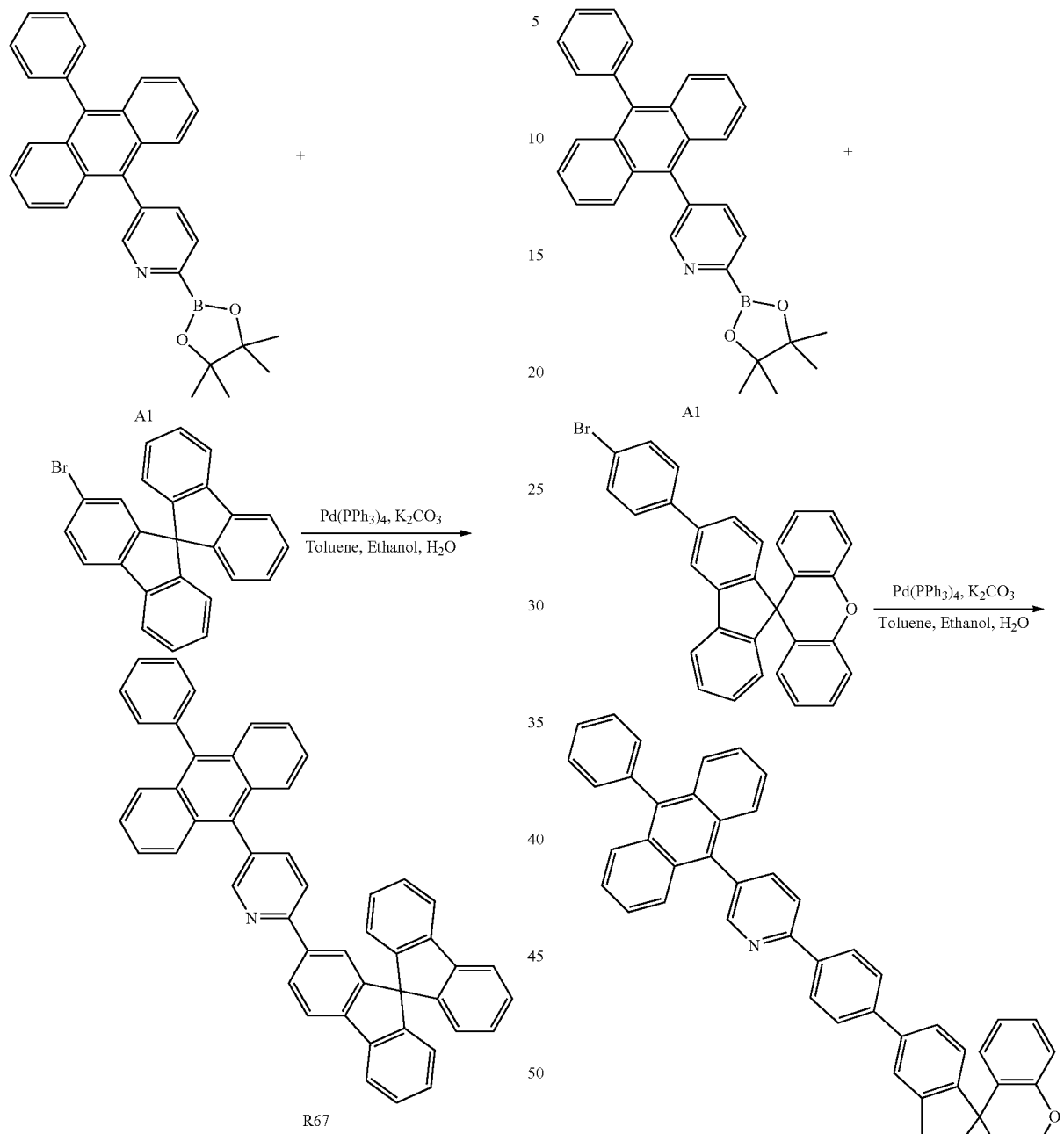

In a nitrogen atmosphere, Compound A1 (7.8 g, 17.1 mmol), 2-bromo-9,9'-spirobi[fluorene] (7.4 g, 18.8 mmol), Pd(PPh$_3$)$_4$ (0.9 g, 5 mol %), and potassium carbonate (7.0 g, 51.2 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R67 (7.9 g, 12.8 mmol, yield: 72%).

GC-Mass (Calcd.: 645.79 g/mol, Found: 645 g/mol).

In a nitrogen atmosphere, Compound A1 (7.8 g, 17.1 mmol), 3-(4-bromophenyl)spiro[fluorene-9,9'-xanthene] (9.1 g, 18.8 mmol), Pd(PPh$_3$)$_4$ (0.9 g, 5 mol %), and potassium carbonate (7.0 g, 51.2 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R75 (9.8 g, 13.3 mmol, yield: 78%).

GC-Mass (Calcd.: 737.88 g/mol, Found: 737 g/mol).

[Synthesis Example 8] Synthesis of Compound R78

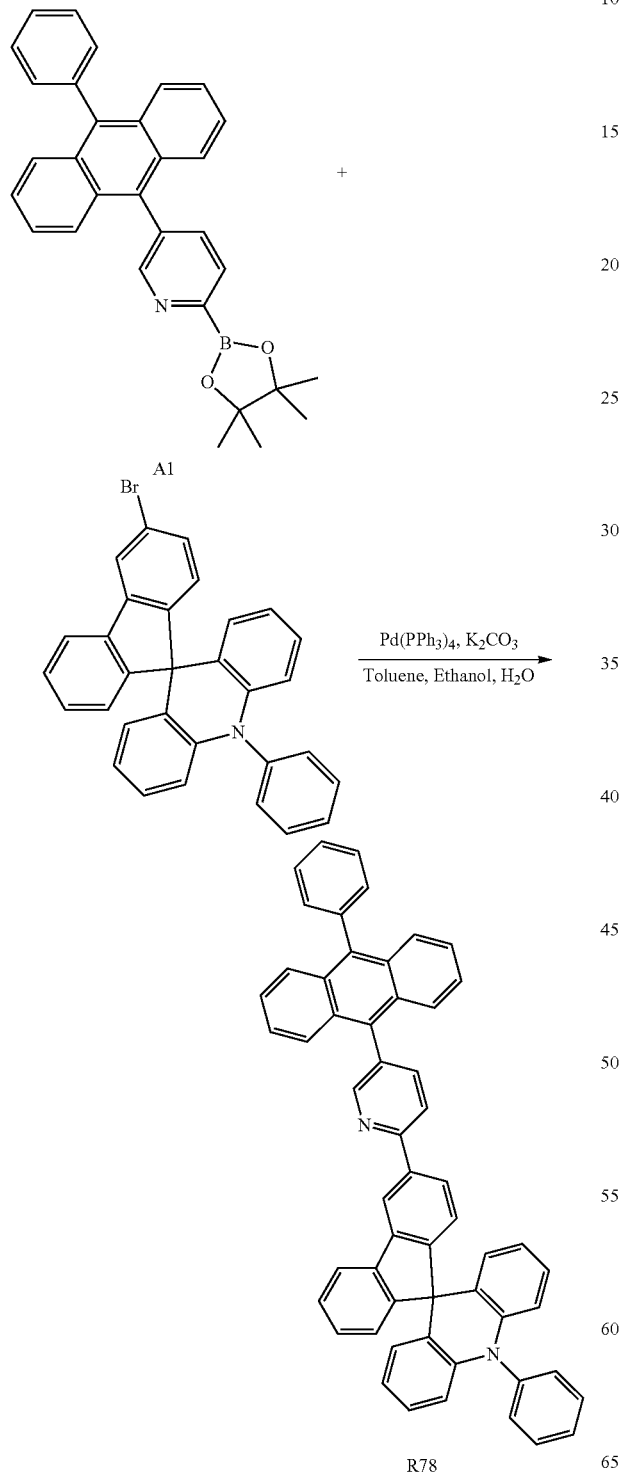

In a nitrogen atmosphere, Compound A1 (7.8 g, 17.1 mmol), 3'-bromo-10-phenyl-10H-spiro[acridine-9,9'-fluorene] (9.1 g, 18.8 mmol), Pd(PPh$_3$)$_4$ (0.9 g, 5 mol %), and potassium carbonate (7.0 g, 51.2 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R78 (9.8 g, 13.3 mmol, yield: 78%).

GC-Mass (Calcd.: 736.90 g/mol, Found: 736 g/mol).

[Synthesis Example 9] Synthesis of Compound R93

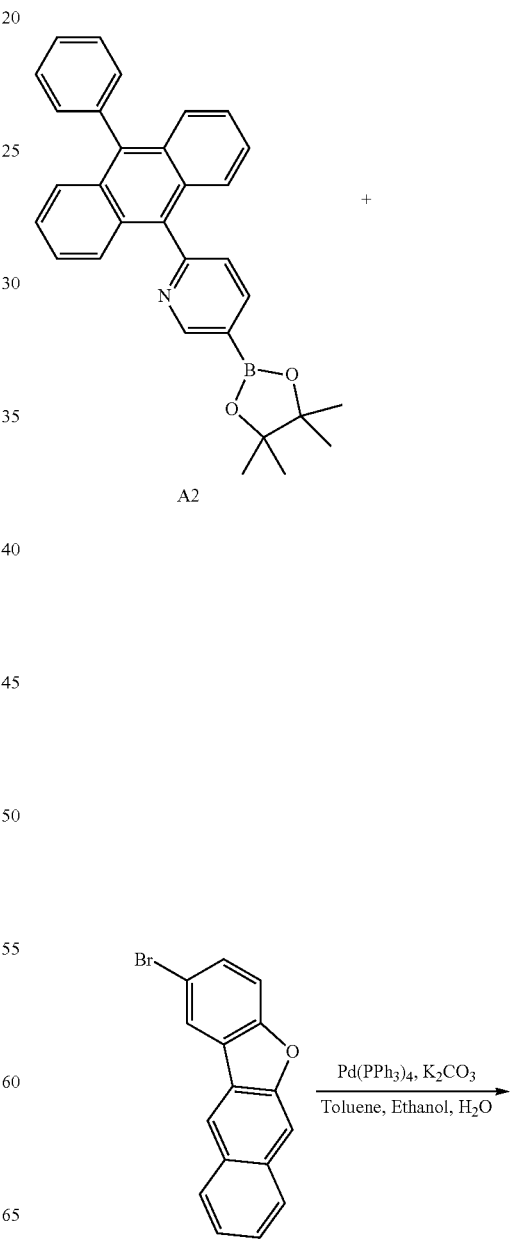

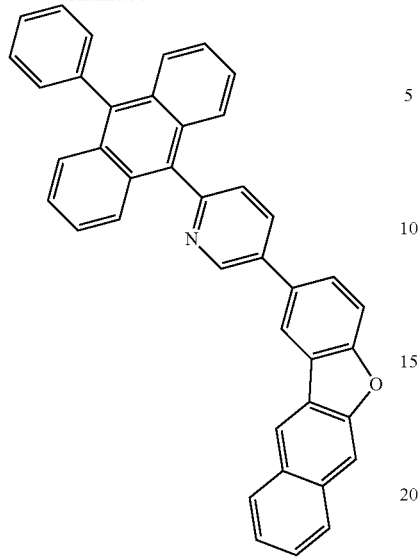

R93

In a nitrogen atmosphere, Compound A2 (7.8 g, 17.1 mmol), 2-bromobenzo[b]naphtho[2,3-d]furan (5.6 g, 18.8 mmol), Pd(PPh$_3$)$_4$ (1.0 g, 5 mol %), and potassium carbonate (7.1 g, 51.2 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R93 (7.2 g, 13.1 mmol, yield: 77%).

GC-Mass (Calcd.: 547.64 g/mol, Found: 547 g/mol).

[Synthesis Example 10] Synthesis of Compound R173

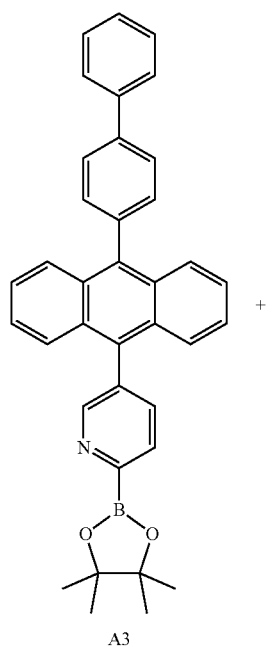

A3

+

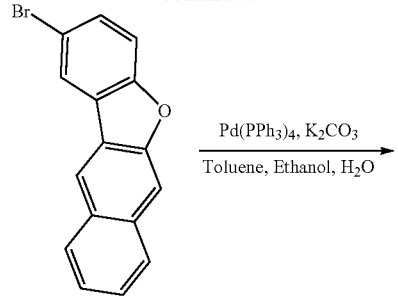

$\xrightarrow{\text{Pd(PPh}_3)_4, \text{K}_2\text{CO}_3}{\text{Toluene, Ethanol, H}_2\text{O}}$

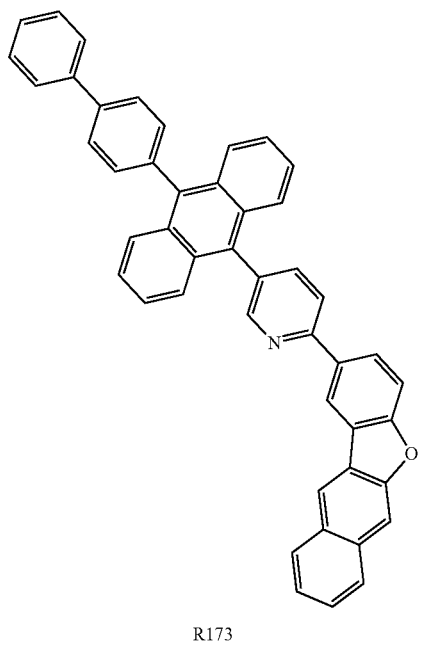

R173

In a nitrogen atmosphere, Compound A3 (9.7 g, 18.3 mmol), 2-bromobenzo[b]naphtho[2,3-d]furan (6.0 g, 20.1 mmol), Pd(PPh$_3$)$_4$ (1.0 g, 5 mol %), and potassium carbonate (7.6 g, 54.8 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R173 (8.7 g, 13.9 mmol, yield: 76%).

GC-Mass (Calcd.: 623.74 g/mol, Found: 623 g/mol).

[Synthesis Example 11] Synthesis of Compound R253

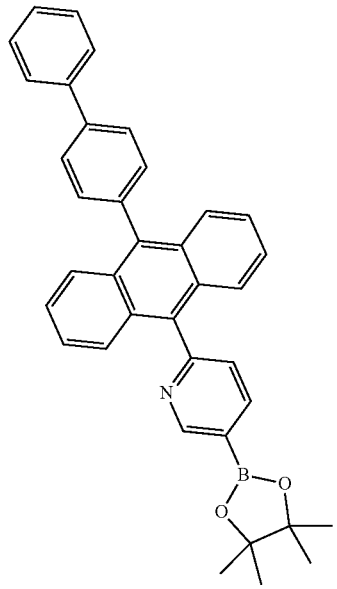

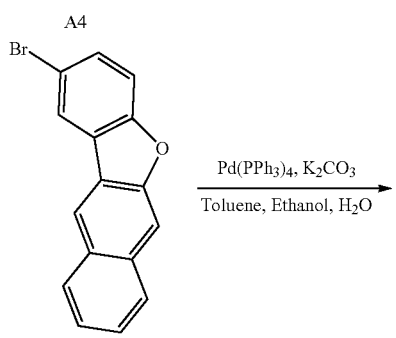

In a nitrogen atmosphere, Compound A4 (9.7 g, 18.3 mmol), 2-bromobenzo[b]naphtho[2,3-d]furan (6.0 g, 20.1 mmol), Pd(PPh₃)₄ (1.0 g, 5 mol %), and potassium carbonate (7.6 g, 54.8 mmol) were added to toluene/H₂O/ethanol (80 ml/40 ml/40 ml) and stirred at 110° C. for three hours.

After completion of the reaction, the organic material layer was separated using methylene chloride and dried over MgSO₄. The solvent was removed from the organic material layer, followed by purification through column chromatography to afford the object compound R253 (8.7 g, 13.9 mmol, yield: 76%).

GC-Mass (Calcd.: 623.74 g/mol, Found: 623 g/mol).

[Synthesis Example 12] Synthesis of Compound R321

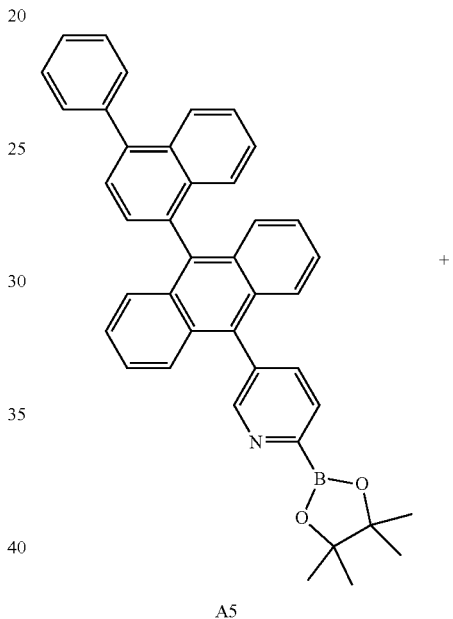

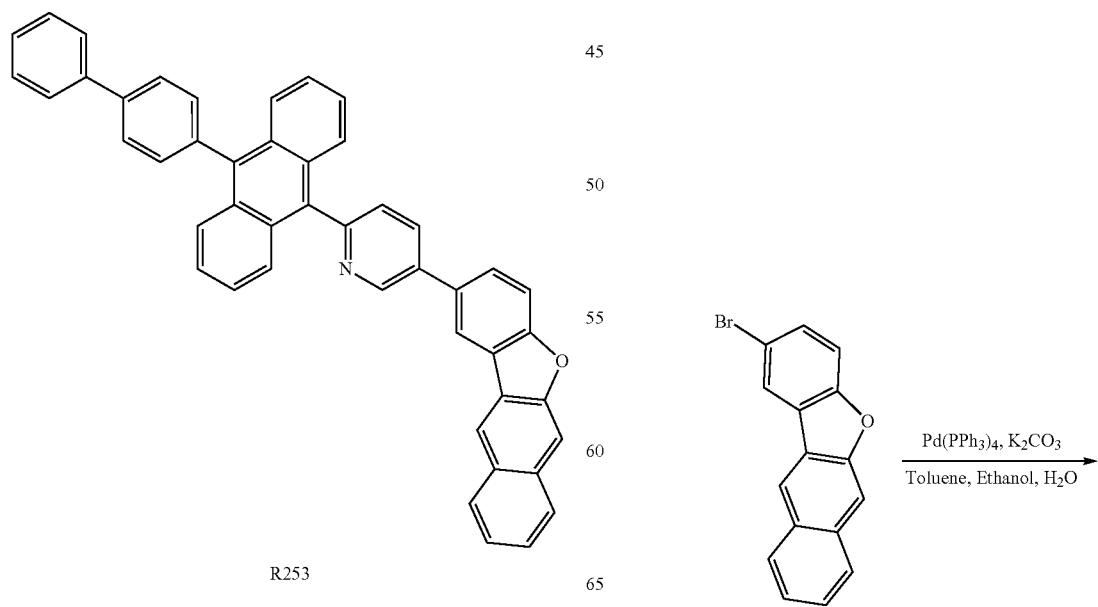

-continued

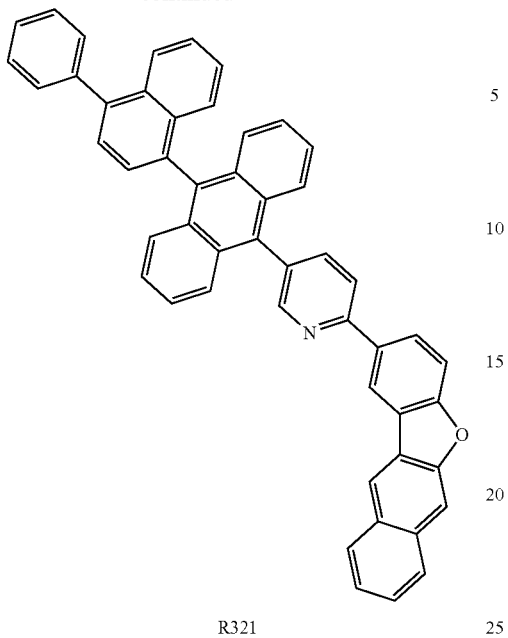

R321

In a nitrogen atmosphere, Compound A5 (11.1 g, 19.0 mmol), 2-bromobenzo[b]naphtho[2,3-d]furan (6.2 g, 20.9 mmol), Pd(PPh₃)₄ (1.1 g, 5 mol %), and potassium carbonate (7.9 g, 57.0 mmol) were added to toluene/H₂O/ethanol (80 ml/40 ml/40 ml) and stirred at 110° C. for three hours.

After completion of the reaction, the organic material layer was separated using methylene chloride and dried over MgSO₄. The solvent was removed from the organic material layer, followed by purification through column chromatography to afford the object compound R321 (9.3 g, 13.9 mmol, yield: 73%).

GC-Mass (Calcd.: 673.80 g/mol, Found: 673 g/mol).

[Synthesis Example 13] Synthesis of Compound R324

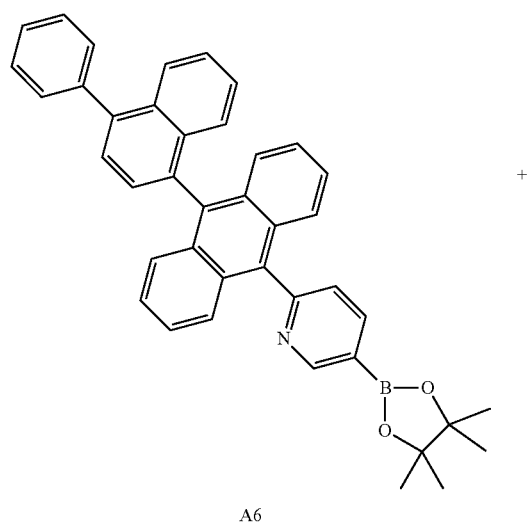

A6

+

-continued

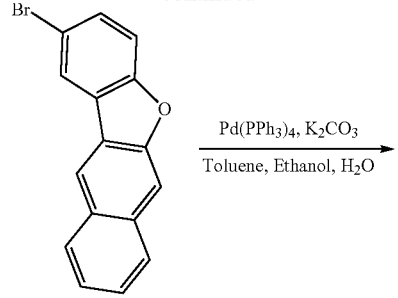

Pd(PPh₃)₄, K₂CO₃
Toluene, Ethanol, H₂O
→

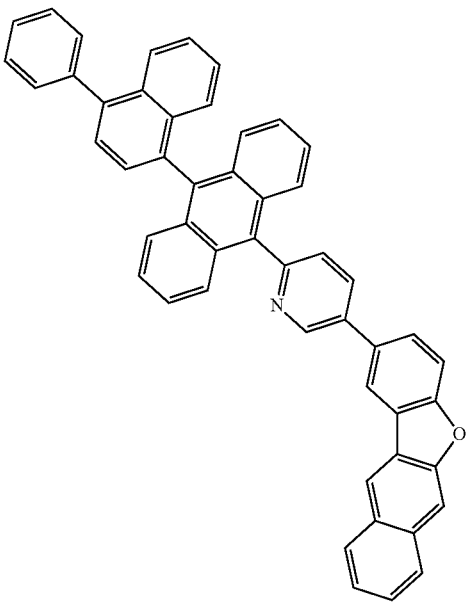

R324

In a nitrogen atmosphere, Compound A6 (11.1 g, 19.0 mmol), 2-bromobenzo[b]naphtho[2,3-d]furan (6.2 g, 20.9 mmol), Pd(PPh₃)₄ (1.1 g, 5 mol %), and potassium carbonate (7.9 g, 57.0 mmol) were added to toluene/H₂O/ethanol (80 ml/40 ml/40 ml) and stirred at 110° C. for three hours.

After completion of the reaction, the organic material layer was separated using methylene chloride and dried over MgSO₄. The solvent was removed from the organic material layer, followed by purification through column chromatography to afford the object compound R324(9.3 g, 13.9 mmol, yield: 73%).

GC-Mass (Calcd.: 673.80 g/mol, Found: 673 g/mol).

[Synthesis Example 14] Synthesis of Compound R327

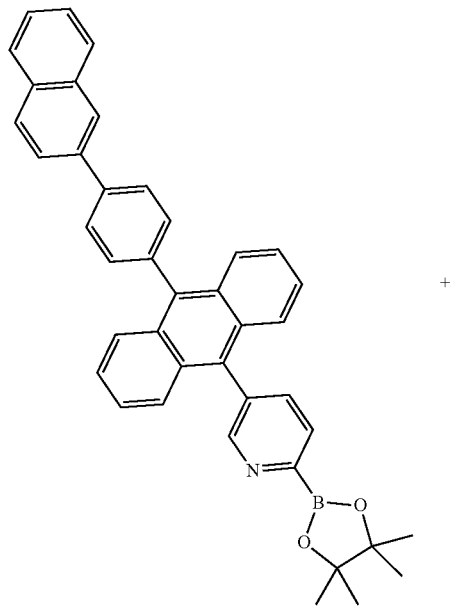

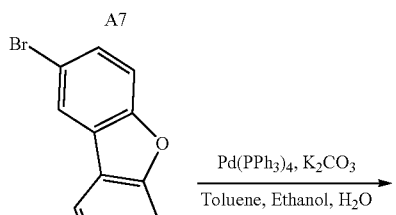

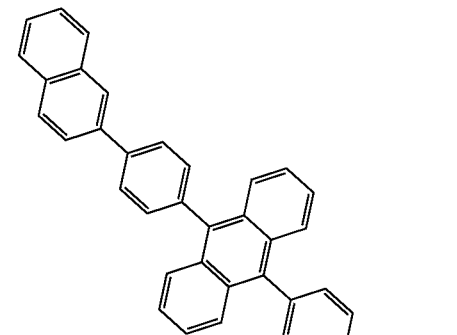

R327

In a nitrogen atmosphere, Compound A7 (10.5 g, 18.0 mmol), 2-bromobenzo[b]naphtho[2,3-d]furan (6.0 g, 19.8 mmol), Pd(PPh$_3$)$_4$ (1.0 g, 5 mol %), and potassium carbonate (7.5 g, 54.1 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R327 (8.9 g, 13.2 mmol, yield: 73%).

GC-Mass (Calcd.: 673.80 g/mol, Found: 673 g/mol).

[Synthesis Example 15] Synthesis of Compound R330

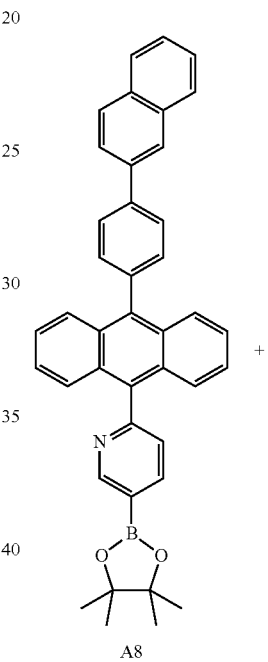

A8

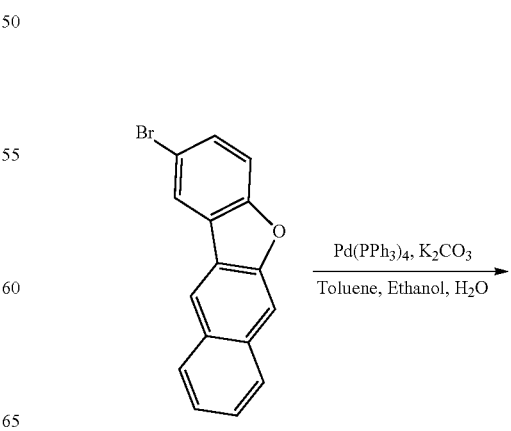

-continued

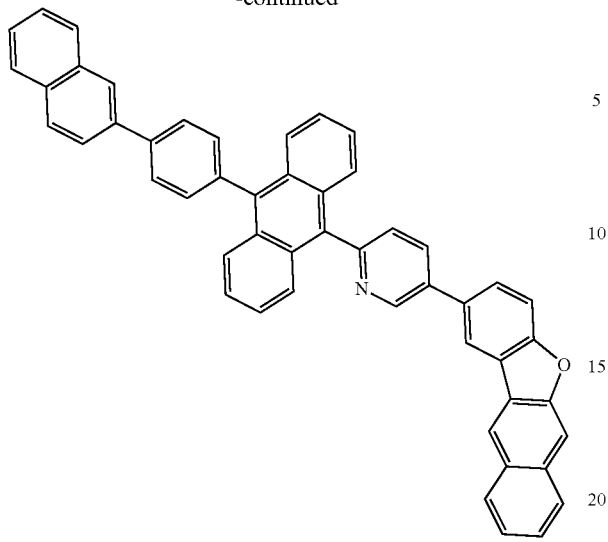

R330

In a nitrogen atmosphere, Compound A8 (10.5 g, 18.0 mmol), 2-bromobenzo[b]naphtho[2,3-d]furan (5.9 g, 19.8 mmol), Pd(PPh$_3$)$_4$ (1.0 g, 5 mol %), and potassium carbonate (7.5 g, 54.1 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R330 (9.1 g, 13.5 mmol, yield: 75%).

GC-Mass (Calcd.: 673.80 g/mol, Found: 673 g/mol).

[Synthesis Example 16] Synthesis of Compound R333

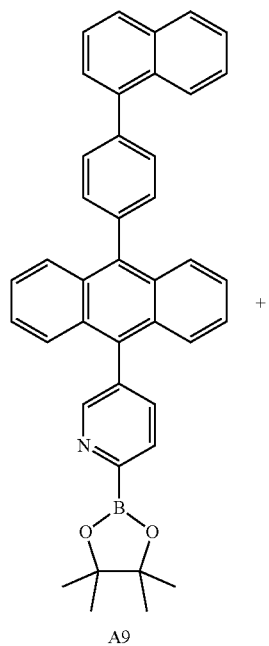

A9

+

-continued

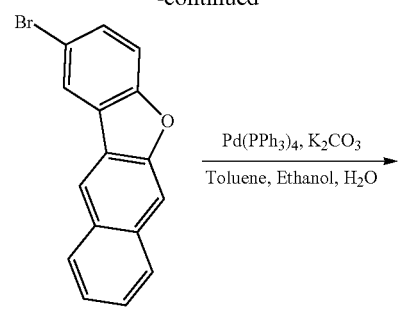

$\xrightarrow{\text{Pd(PPh}_3)_4, \text{K}_2\text{CO}_3}{\text{Toluene, Ethanol, H}_2\text{O}}$

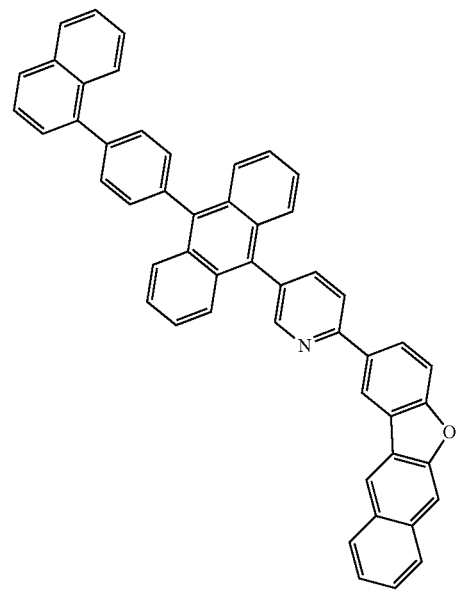

R333

In a nitrogen atmosphere, Compound A9 (10.5 g, 18.0 mmol), 2-bromobenzo[b]naphtho[2,3-d]furan (5.9 g, 19.8 mmol), Pd(PPh$_3$)$_4$ (1.0 g, 5 mol %), and potassium carbonate (7.5 g, 54.1 mmol) were added to toluene/H$_2$O/ethanol (80 ml/40 ml/40 ml) and stirred at 110° C. for three hours. After completion of the reaction, the organic material layer was separated using methylene chloride and dried over MgSO$_4$. The solvent was removed from the organic material layer, followed by purification through column chromatography to afford the object compound R333 (9.1 g, 13.5 mmol, yield: 75%).

GC-Mass (Calcd.: 673.80 g/mol, Found: 673 g/mol).

[Synthesis Example 17] Synthesis of Compound R336

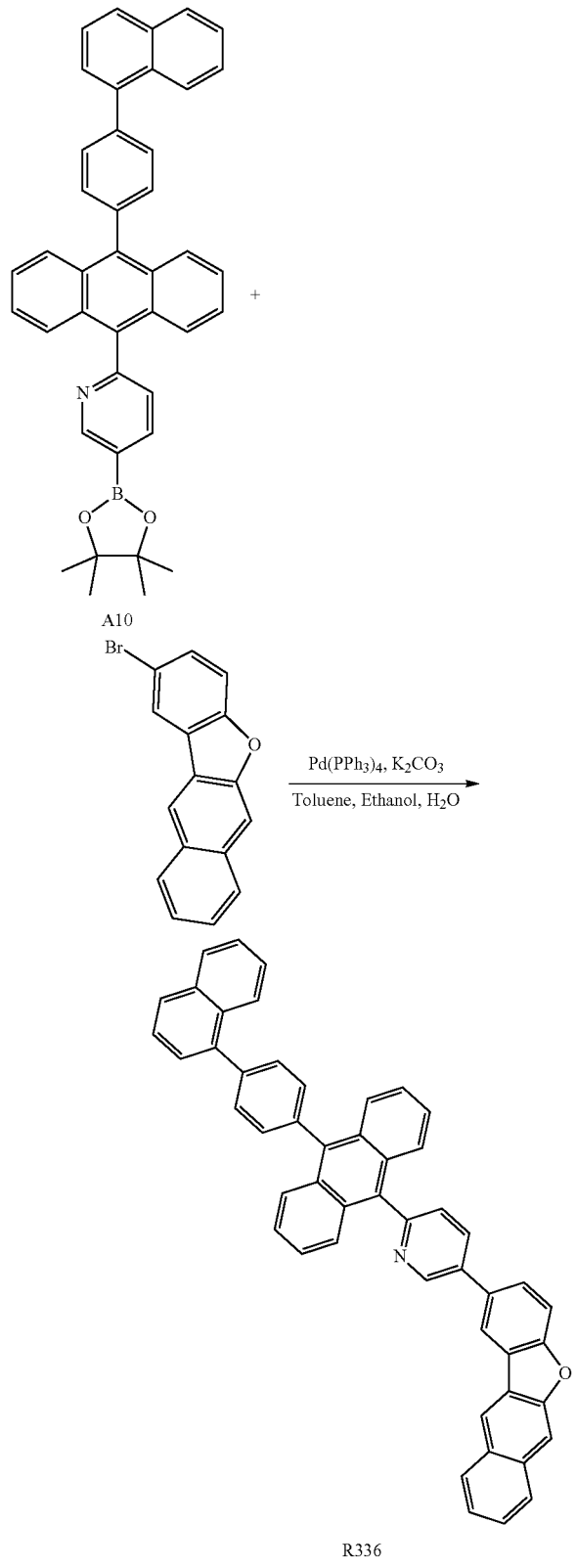

In a nitrogen atmosphere, Compound A10 (10.6 g, 19.0 mmol), 2-bromobenzo[b]naphtho[2,3-d]furan (6.2 g, 20.9 mmol), Pd(PPh$_3$)$_4$ (1.0 g, 5 mol %), and potassium carbonate (7.9 g, 57.0 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R336 (9.2 g, 14.3 mmol, yield: 75%).

GC-Mass (Calcd.: 647.76 g/mol, Found: 647 g/mol).

[Synthesis Example 18] Synthesis of Compound R339

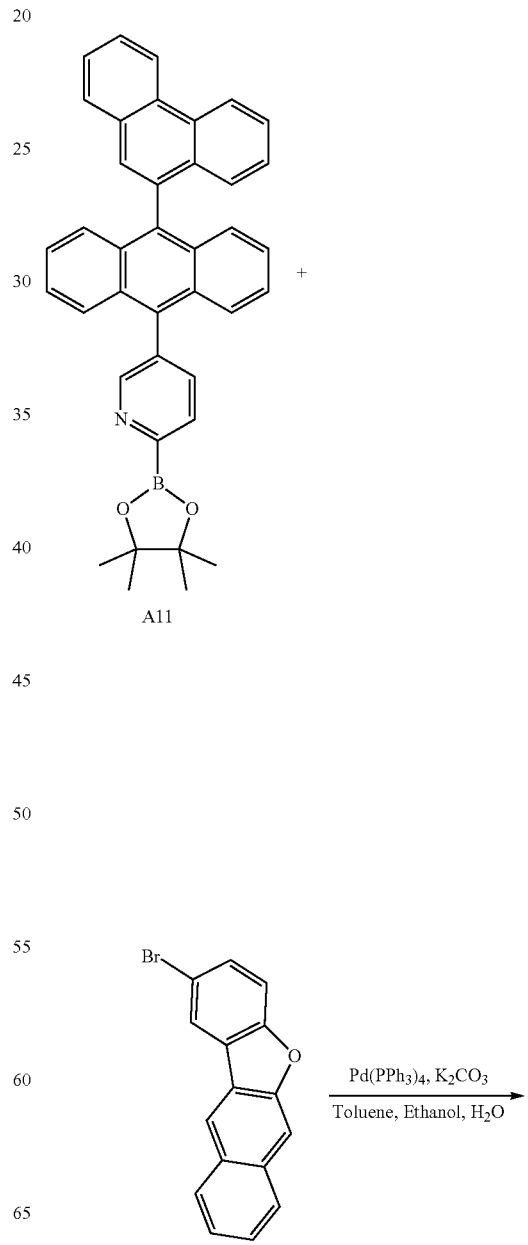

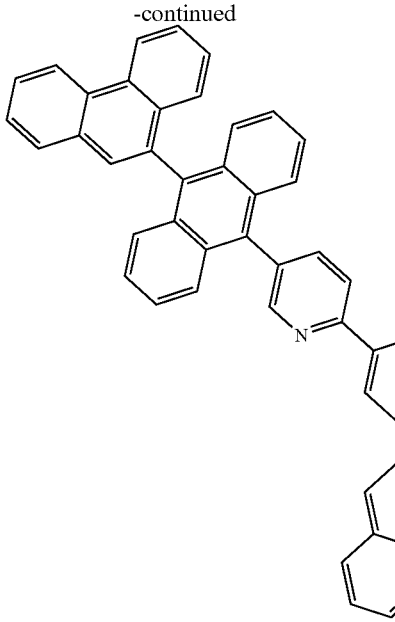

R339

[Synthesis Example 19] Synthesis of Compound R344

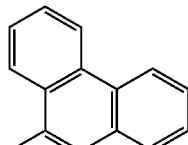

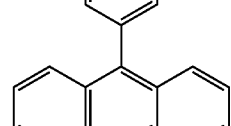

+

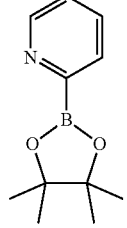

A12

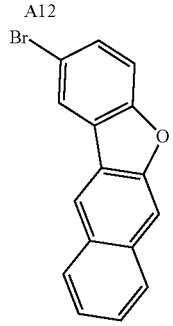

→ Pd(PPh$_3$)$_4$, K$_2$CO$_3$ / Toluene, Ethanol, H$_2$O

In a nitrogen atmosphere, Compound A11 (10.6 g, 19.0 mmol), 2-bromobenzo[b]naphtho[2,3-d]furan (6.2 g, 20.9 mmol), Pd(PPh$_3$)$_4$ (1.0 g, 5 mol %), and potassium carbonate (7.9 g, 57.0 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R339 (9.2 g, 14.3 mmol, yield: 75%).

GC-Mass (Calcd.: 647.76.g/mol, Found: 647 g/mol).

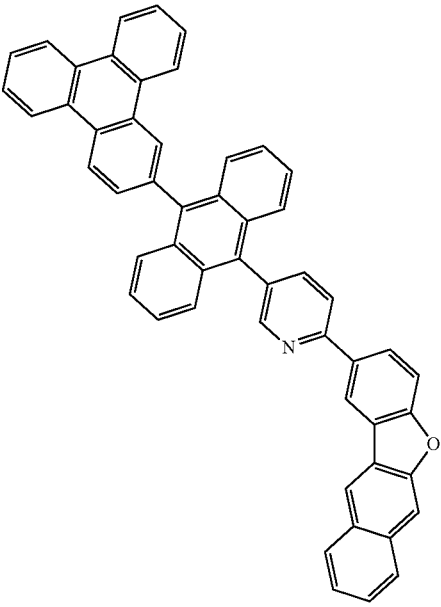

R344

In a nitrogen atmosphere, Compound A12 (11.5 g, 19.0 mmol), 2-bromobenzo[b]naphtho[2,3-d]furan (6.2 g, 20.9 mmol), Pd(PPh₃)₄ (1.1 g, 5 mol %), and potassium carbonate (7.9 g, 57.0 mmol) were added to toluene/H₂O/ethanol (80 ml/40 ml/40 ml) and stirred at 110° C. for three hours.

After completion of the reaction, the organic material layer was separated using methylene chloride and dried over MgSO₄. The solvent was removed from the organic material layer, followed by purification through column chromatography to afford the object compound R344 (9.9 g, 14.3 mmol, yield: 75%).

GC-Mass (Calcd.: 697.82 g/mol, Found: 697 g/mol).

[Synthesis Example 20] Synthesis of Compound R345

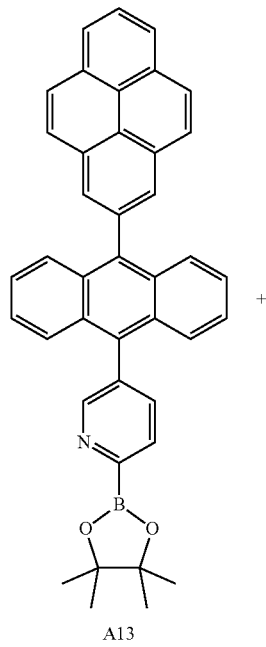

A13

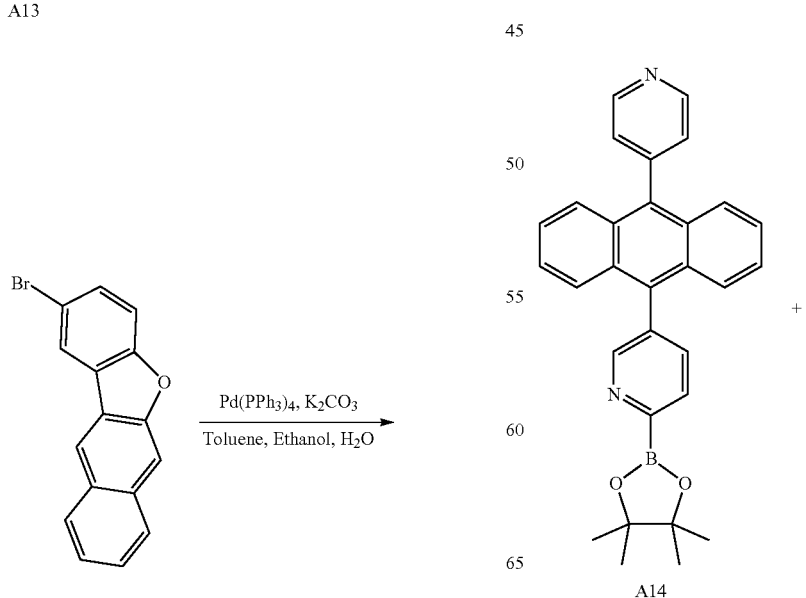

Pd(PPh₃)₄, K₂CO₃
Toluene, Ethanol, H₂O

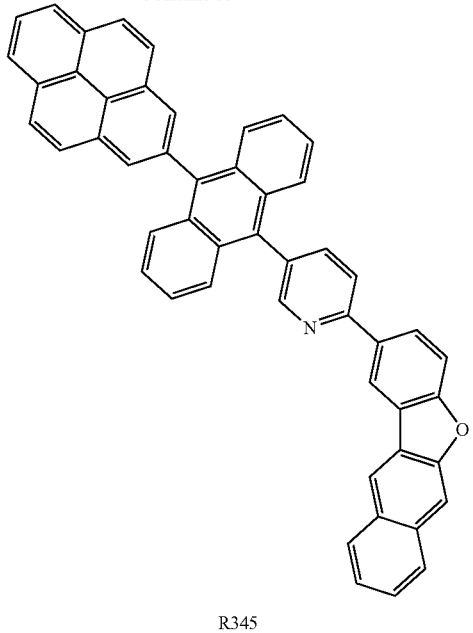

R345

In a nitrogen atmosphere, Compound A13 (10.5 g, 18.0 mmol), 2-bromobenzo[b]naphtho[2,3-d]furan (5.9 g, 19.8 mmol), Pd(PPh₃)₄ (1.0 g, 5 mol %), and potassium carbonate (7.5 g, 54.1 mmol) were added to toluene/H₂O/ethanol (80 ml/40 ml/40 ml) and stirred at 110° C. for three hours.

After completion of the reaction, the organic material layer was separated using methylene chloride and dried over MgSO₄. The solvent was removed from the organic material layer, followed by purification through column chromatography to afford the object compound R345 (9.1 g, 13.5 mmol, yield: 75%).

GC-Mass (Calcd.: 671.78 g/mol, Found: 671 g/mol).

[Synthesis Example 21] Synthesis of Compound R348

A14

243

-continued

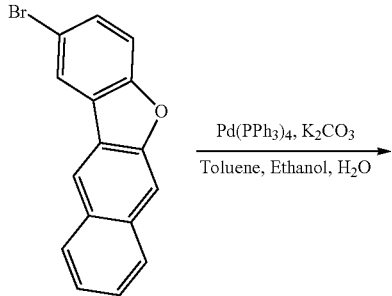

R348

In a nitrogen atmosphere, Compound A14 (8.3 g, 18.0 mmol), 2-bromobenzo[b]naphtho[2,3-d]furan (5.9 g, 19.8 mmol), Pd(PPh$_3$)$_4$ (1.0 g, 5 mol %), and potassium carbonate (7.5 g, 54.1 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R348 (9.9 g, 13.5 mmol, yield: 75%).

GC-Mass (Calcd.: 548.63 g/mol, Found: 548 g/mol).

244

[Synthesis Example 22] Synthesis of Compound R351

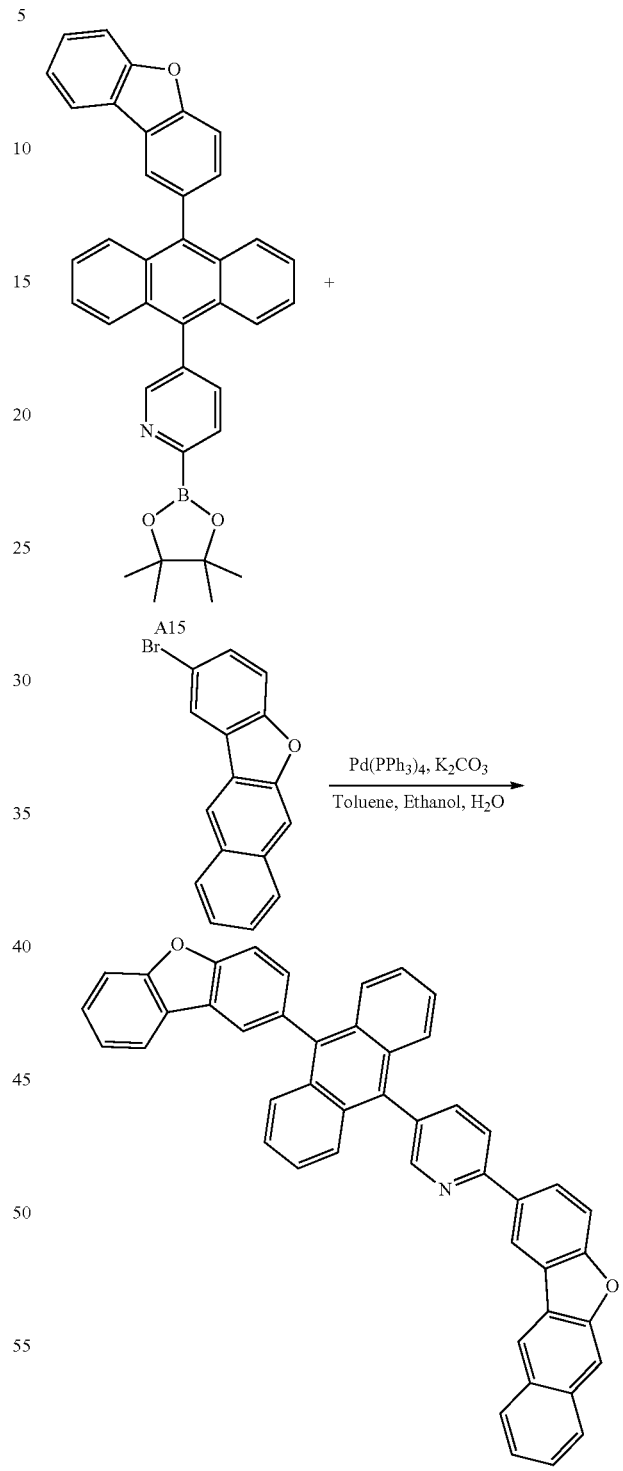

In a nitrogen atmosphere, Compound A15 (10.1 g, 18.5 mmol), 2-bromobenzo[b]naphtho[2,3-d]furan (5.9 g, 20.4 mmol), Pd(PPh$_3$)$_4$ (1.1 g, 5 mol %), and potassium carbonate (7.5 g, 55.5 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R351 (8.9 g, 13.9 mmol, yield: 75%).

GC-Mass (Calcd.: 637.72 g/mol, Found: 637 g/mol).

[Synthesis Example 23] Synthesis of Compound R354

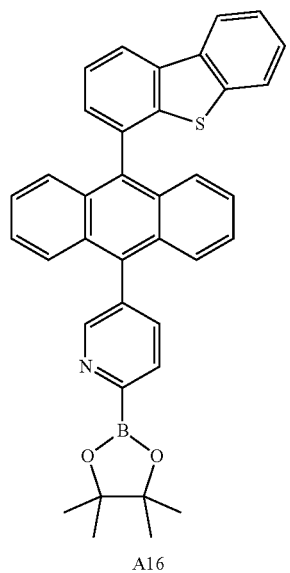

A16

+

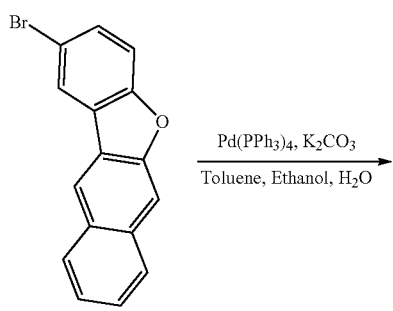

Pd(PPh$_3$)$_4$, K$_2$CO$_3$
Toluene, Ethanol, H$_2$O
→

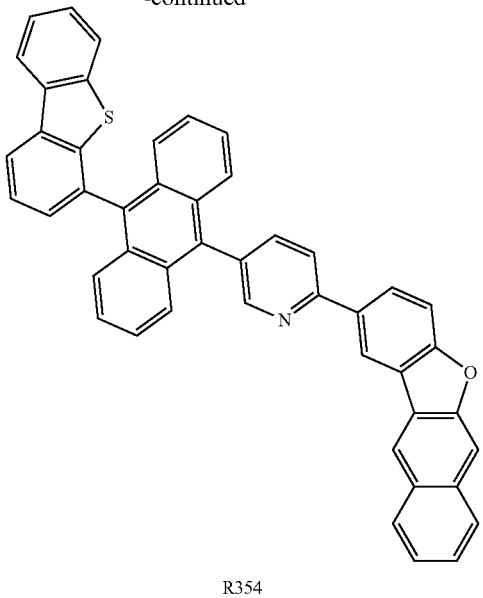

R354

In a nitrogen atmosphere, Compound A16 (10.8 g, 18.5 mmol), 2-bromobenzo[b]naphtho[2,3-d]furan (6.1 g, 20.4 mmol), Pd(PPh$_3$)$_4$ (1.1 g, 5 mol %), and potassium carbonate (7.5 g, 55.5 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R354 (9.1 g, 13.9 mmol, yield: 75%).

GC-Mass (Calcd.: 653.79 g/mol, Found: 653 g/mol).

[Synthesis Example 24] Synthesis of Compound R357

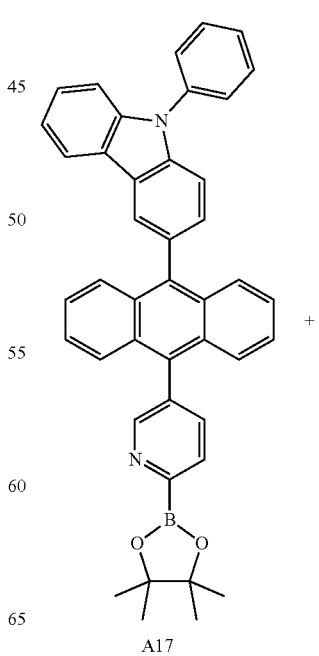

A17

+

247
-continued

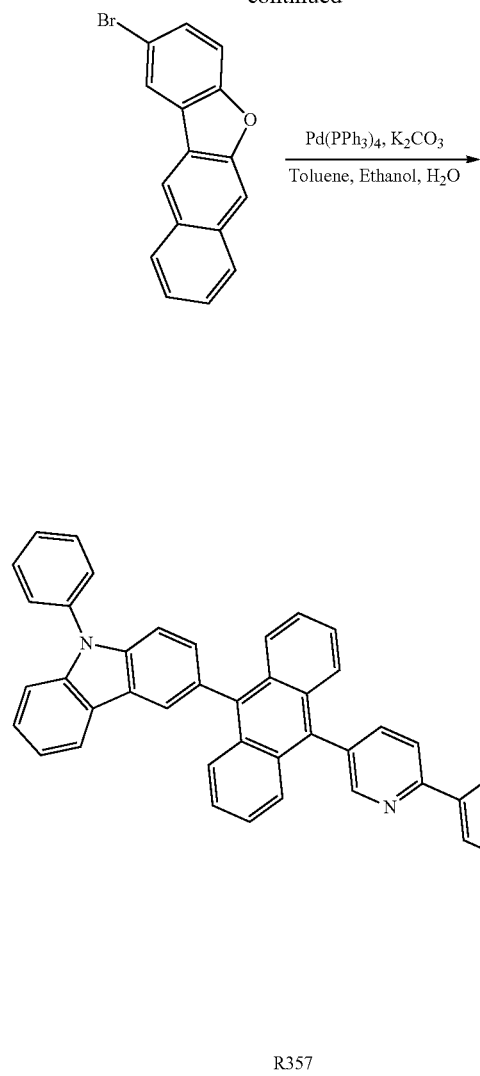

R357

248

[Synthesis Example 25] Synthesis of Compound R360

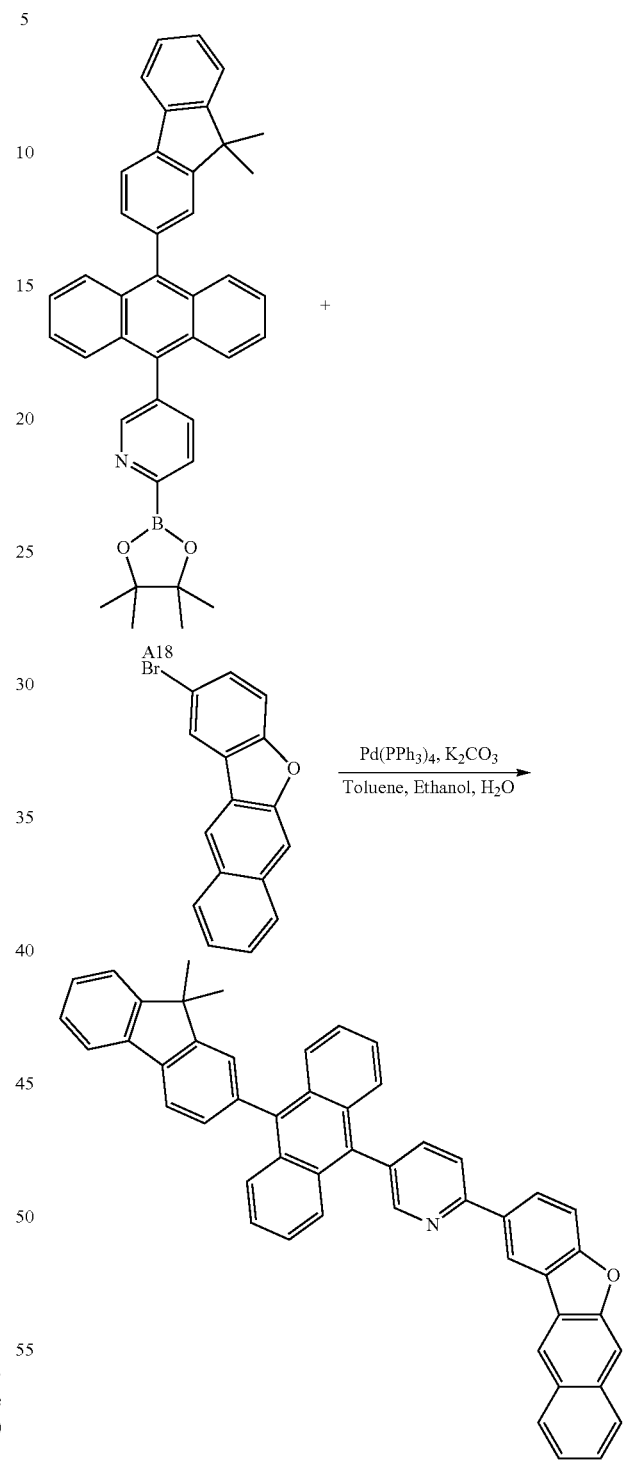

In a nitrogen atmosphere, Compound A17 (11.5 g, 18.5 mmol), 2-bromobenzo[b]naphtho[2,3-d]furan (6.1 g, 20.4 mmol), Pd(PPh₃)₄ (1.1 g, 5 mol %), and potassium carbonate (7.5 g, 55.5 mmol) were added to toluene/H₂O/ethanol (80 ml/40 ml/40 ml) and stirred at 110° C. for three hours.

After completion of the reaction, the organic material layer was separated using methylene chloride and dried over MgSO₄. The solvent was removed from the organic material layer, followed by purification through column chromatography to afford the object compound R357 (9.9 g, 13.2 mmol, yield: 75%).

GC-Mass (Calcd.: 712.83 g/mol, Found: 712 g/mol).

In a nitrogen atmosphere, Compound A18 (10.6 g, 18.5 mmol), 2-bromobenzo[b]naphtho[2,3-d]furan (6.1 g, 20.4 mmol), Pd(PPh₃)₄ (1.1 g, 5 mol %), and potassium carbonate (7.5 g, 55.5 mmol) were added to toluene/H₂O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R360(9.2 g, 12.3 mmol, yield: 75%).

GC-Mass (Calcd.: 663.80 g/mol, Found: 663 g/mol).

[Synthesis Example 26] Synthesis of Compound R363

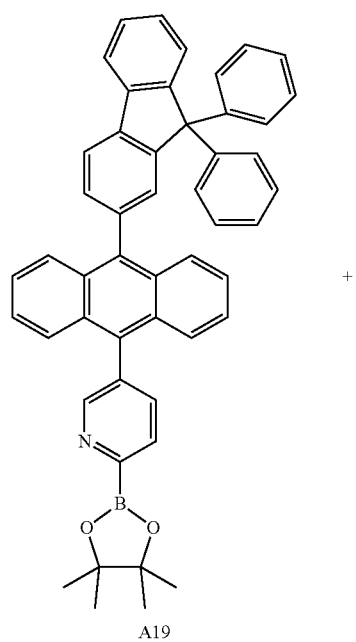

A19

+

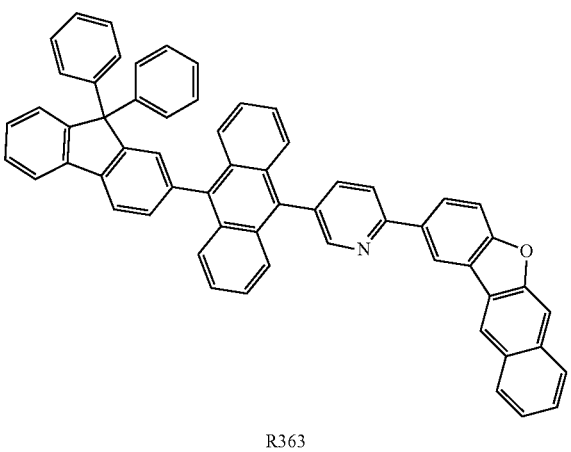

R363

In a nitrogen atmosphere, Compound A19 (12.8 g, 18.3 mmol), 2-bromobenzo[b]naphtho[2,3-d]furan (6.0 g, 20.1 mmol), Pd(PPh$_3$)$_4$ (1.0 g, 5 mol %), and potassium carbonate (7.6 g, 54.8 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R363 (10.8 g, 13.7 mmol, yield: 75%).

GC-Mass (Calcd.: 787.94 g/mol, Found: 787 g/mol).

[Synthesis Example 27] Synthesis of Compound R366

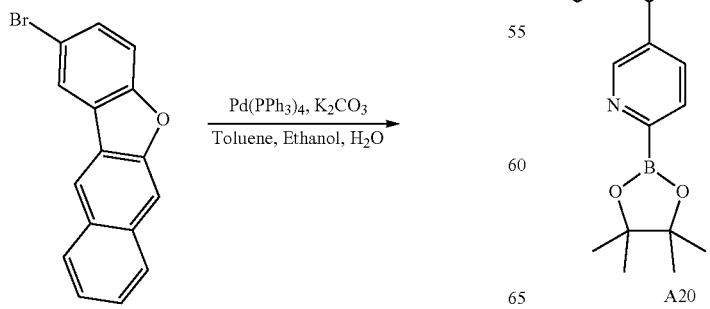

A20

251

-continued

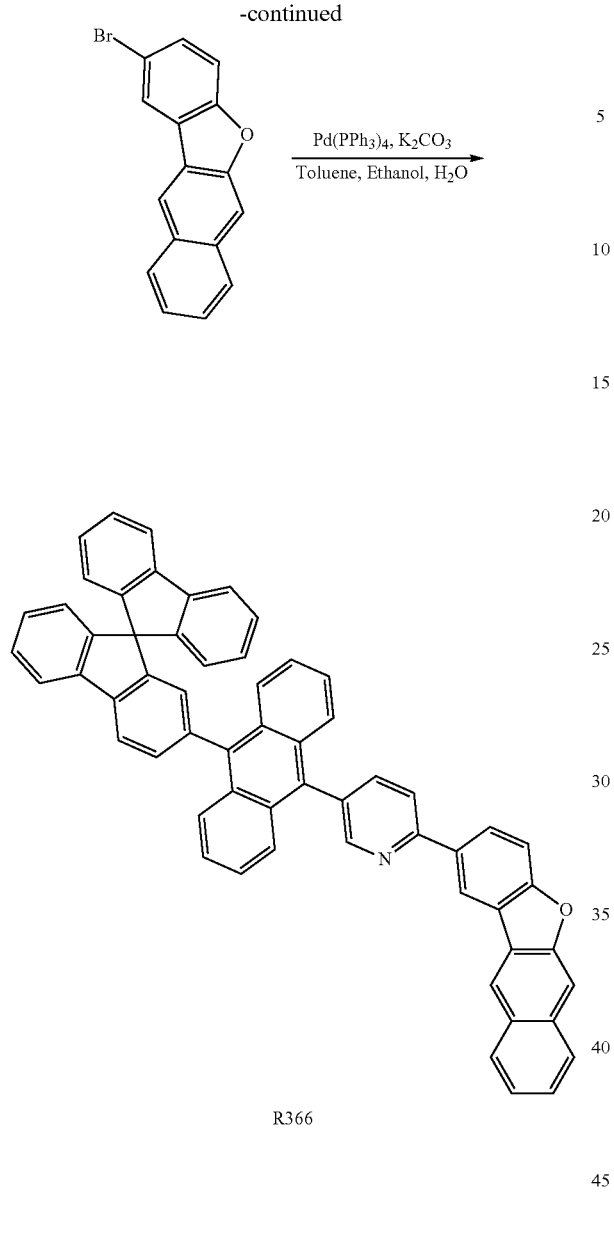

R366

In a nitrogen atmosphere, Compound A20 (12.7 g, 18.3 mmol), 2-bromobenzo[b]naphtho[2,3-d]furan (6.0 g, 20.1 mmol), Pd(PPh$_3$)$_4$ (1.0 g, 5 mol %), and potassium carbonate (7.6 g, 54.8 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R366 (10.8 g, 13.7 mmol, yield: 75%).

GC-Mass (Calcd.: 785.93 g/mol, Found: 785 g/mol).

252

[Synthesis Example 28] Synthesis of Compound R369

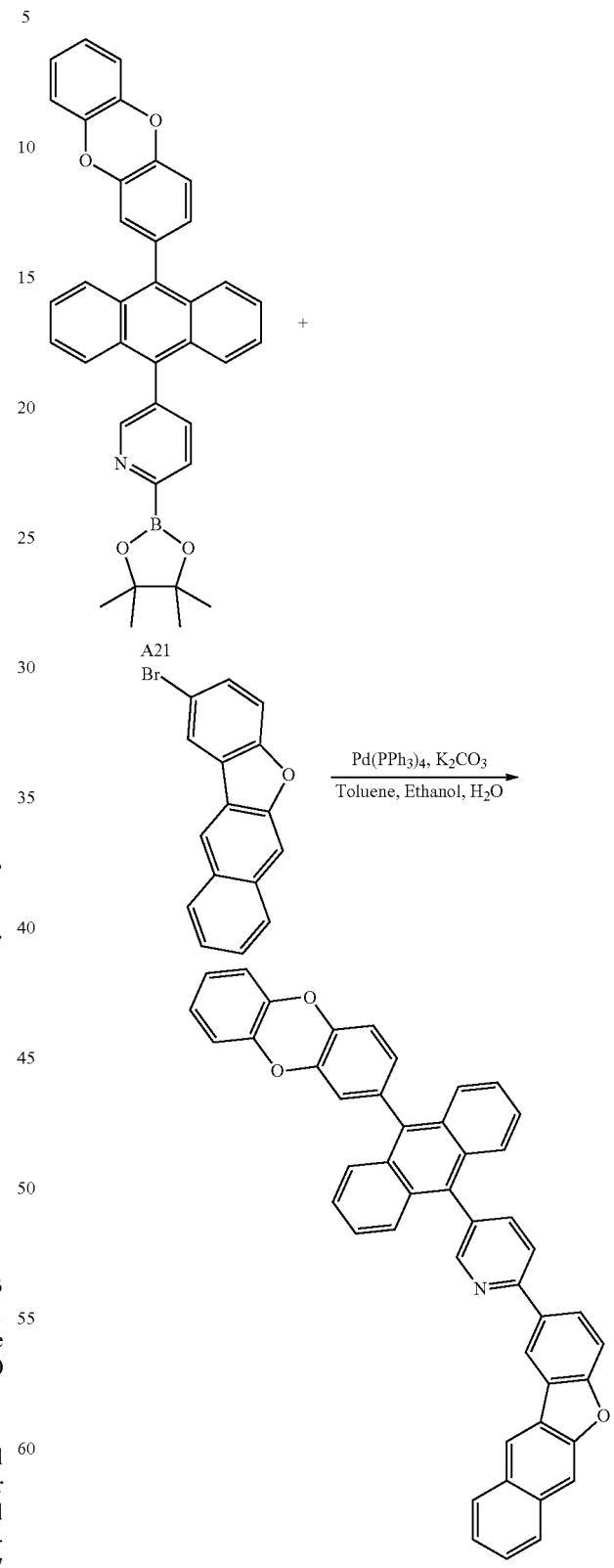

R369

In a nitrogen atmosphere, Compound A21 (10.3 g, 18.3 mmol), 2-bromobenzo[b]naphtho[2,3-d]furan (6.0 g, 20.1 mmol), Pd(PPh$_3$)$_4$ (1.0 g, 5 mol %), and potassium carbonate (7.6 g, 54.8 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R369 (9.0 g, 13.7 mmol, yield: 75%).

GC-Mass (Calcd.: 653.72 g/mol, Found: 653 g/mol).

[Synthesis Example 29] Synthesis of Compound R372

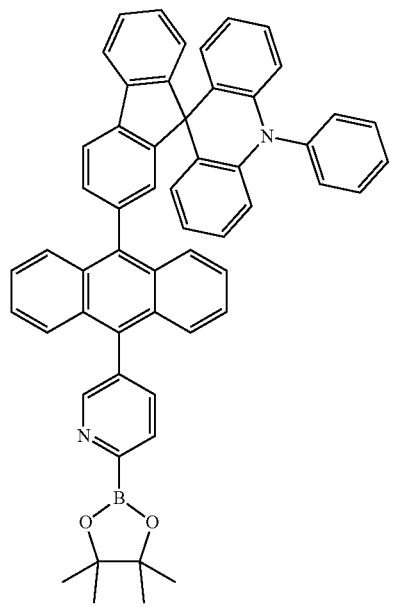

A22

+

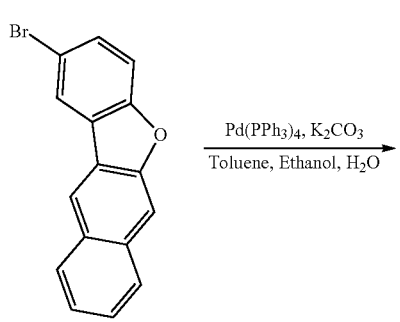

Pd(PPh$_3$)$_4$, K$_2$CO$_3$
Toluene, Ethanol, H$_2$O

-continued

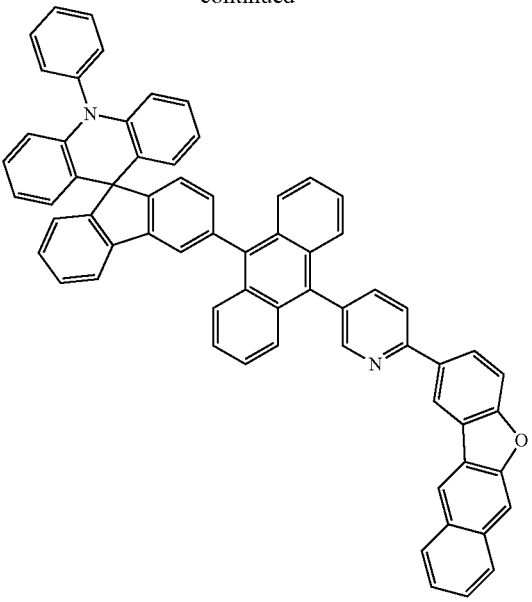

R372

In a nitrogen atmosphere, Compound A22 (14.4 g, 18.3 mmol), 2-bromobenzo[b]naphtho[2,3-d]furan (6.0 g, 20.1 mmol), Pd(PPh$_3$)$_4$ (1.0 g, 5 mol %), and potassium carbonate (7.6 g, 54.8 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R372 (12.0 g, 13.7 mmol, yield: 75%).

GC-Mass (Calcd.: 877.04 g/mol, Found: 877 g/mol).

[Synthesis Example 30] Synthesis of Compound R375

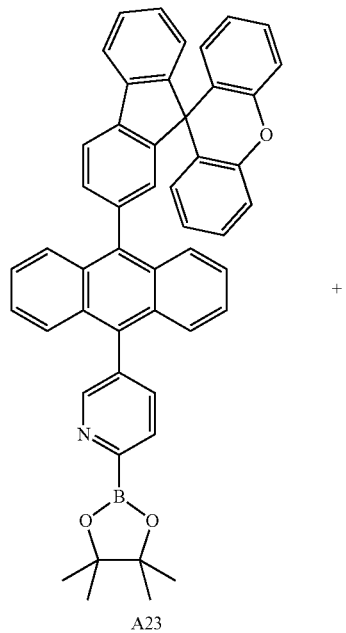

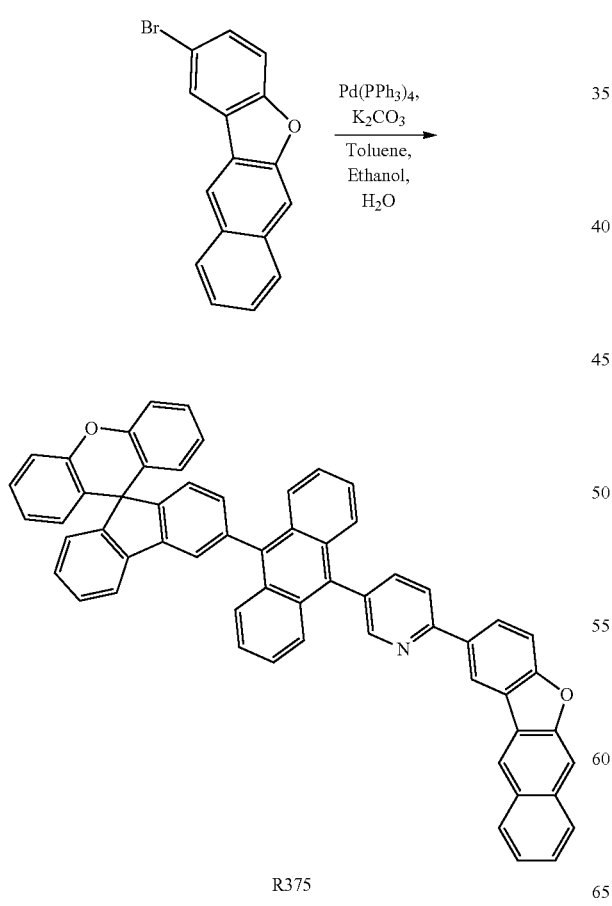

In a nitrogen atmosphere, Compound A23 (13.0 g, 18.3 mmol), 2-bromobenzo[b]naphtho[2,3-d]furan (6.0 g, 20.1 mmol), Pd(PPh$_3$)$_4$ (1.0 g, 5 mol %), and potassium carbonate (7.6 g, 54.8 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R375 (11.0 g, 14.7 mmol, yield: 75%).

GC-Mass (Calcd.: 801.93 g/mol, Found: 801 g/mol).

[Synthesis Example 31] Synthesis of Compound R378

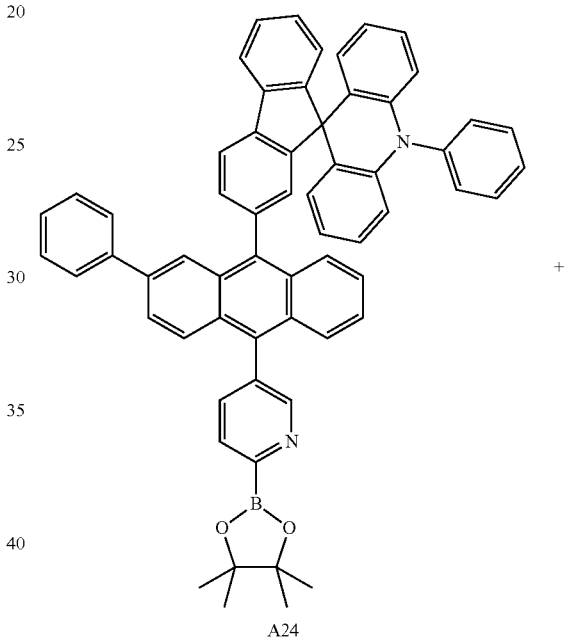

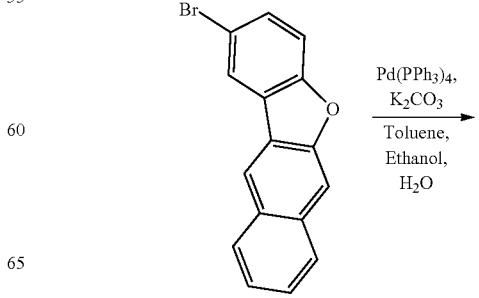

257
-continued

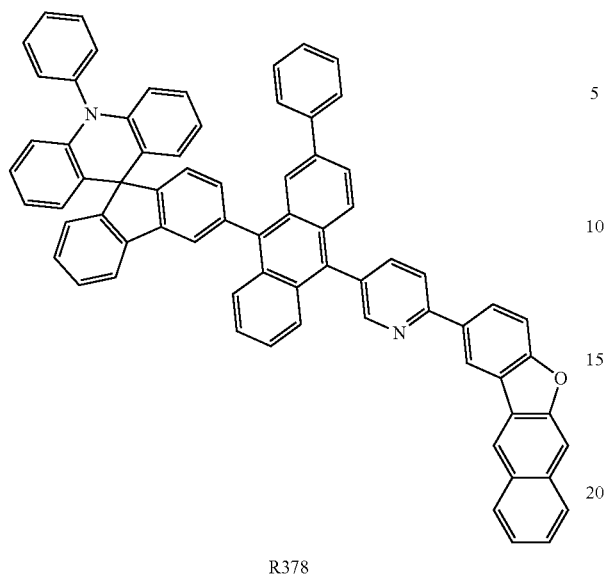
R378

In a nitrogen atmosphere, Compound A24 (16.1 g, 18.3 mmol), 2-bromobenzo[b]naphtho[2,3-d]furan (6.0 g, 20.1 mmol), Pd(PPh$_3$)$_4$ (1.0 g, 5 mol %), and potassium carbonate (7.6 g, 54.8 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R378 (13.1 g, 13.7 mmol, yield: 75%).

GC-Mass (Calcd.: 953.13 g/mol, Found: 953 g/mol).

[Synthesis Example 32] Synthesis of Compound R381

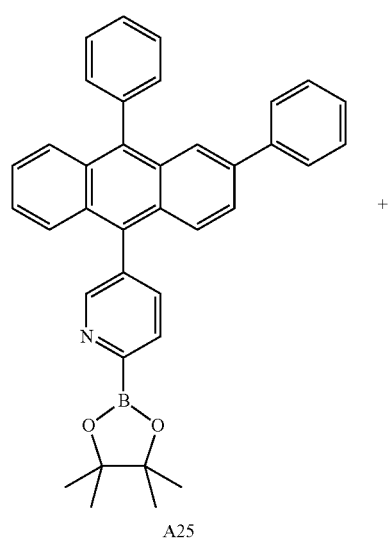
A25

+

258
-continued

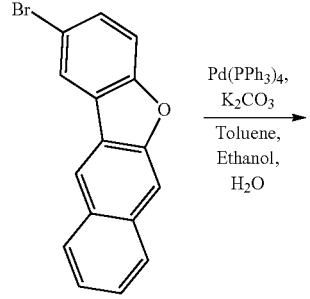

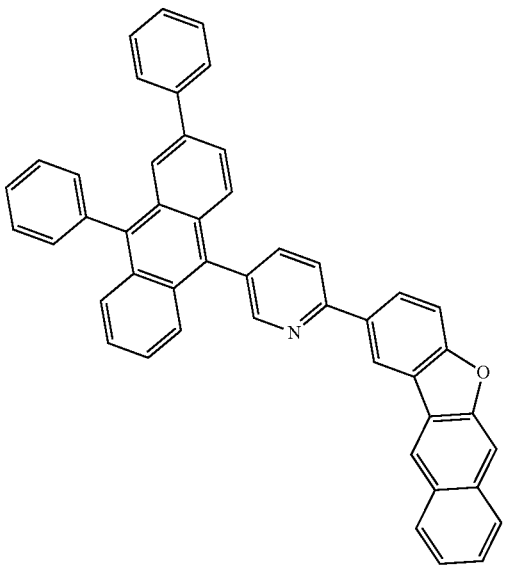
R381

In a nitrogen atmosphere, Compound A25 9.4 g, (17.5 mmol), 2-bromobenzo[b]naphtho[2,3-d]furan (5.7 g, 19.3 mmol), Pd(PPh$_3$)$_4$ (1.0 g, 5 mol %), and potassium carbonate (7.3 g, 52.6 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R381 (8.2 g, 13.2 mmol, yield: 75%).

GC-Mass (Calcd.: 623.74 g/mol, Found: 624 g/mol).

[Synthesis Example 33] Synthesis of Compound R384

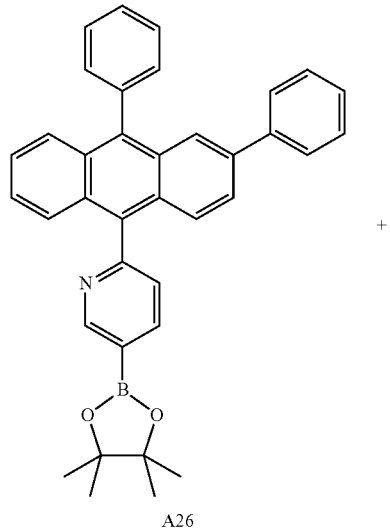

A26

+

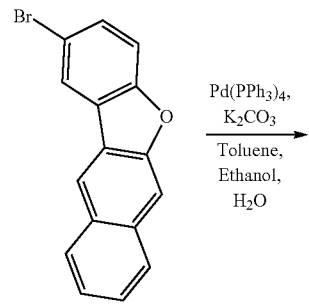

Pd(PPh₃)₄, K₂CO₃
Toluene, Ethanol, H₂O
→

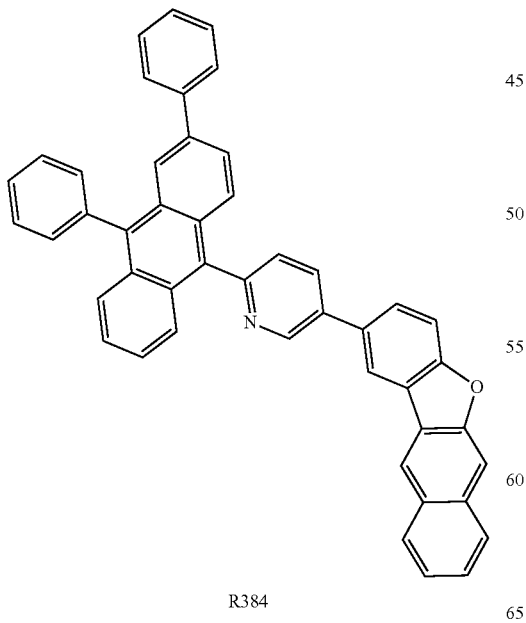

R384

In a nitrogen atmosphere, Compound A26 9.4 g, (17.5 mmol), 2-bromobenzo[b]naphtho[2,3-d]furan (5.7 g, 19.3 mmol), Pd(PPh₃)₄ (1.0 g, 5 mol %), and potassium carbonate (7.3 g, 52.6 mmol) were added to toluene/H₂O/ethanol (80 ml/40 ml/40 ml) and stirred at 110° C. for three hours.

After completion of the reaction, the organic material layer was separated using methylene chloride and dried over MgSO₄. The solvent was removed from the organic material layer, followed by purification through column chromatography to afford the object compound R384 (8.2 g, 13.2 mmol, yield: 75%).

GC-Mass (Calcd.: 623.74 g/mol, Found: 624 g/mol).

[Synthesis Example 34] Synthesis of Compound R387

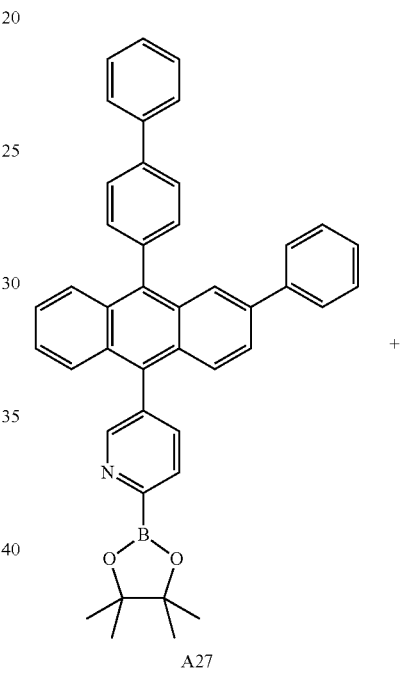

A27

+

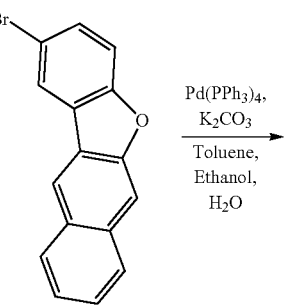

Pd(PPh₃)₄, K₂CO₃
Toluene, Ethanol, H₂O
→

-continued

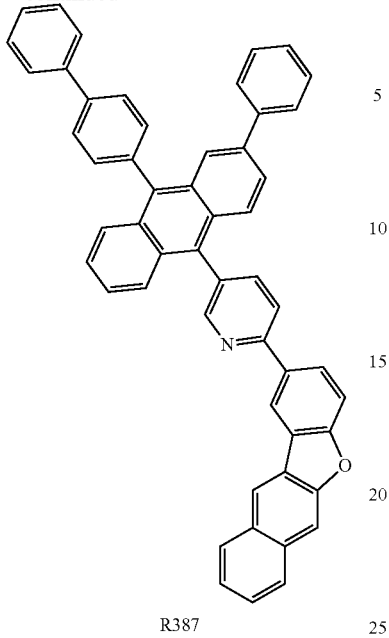

R387

In a nitrogen atmosphere, Compound A27 (9.4 g, 10.7 mmol), 2-bromobenzo[b]naphtho[2,3-d]furan (5.7 g, 19.3 mmol), Pd(PPh$_3$)$_4$ (1.0 g, 5 mol %), and potassium carbonate (7.3 g, 52.6 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R387 (9.2 g, 13.2 mmol, yield: 75%).

GC-Mass (Calcd.: 699.84 g/mol, Found: 699 g/mol).

[Synthesis Example 35] Synthesis of Compound R390

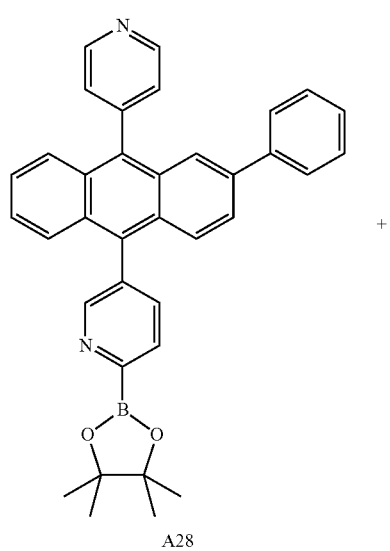

A28

+

-continued

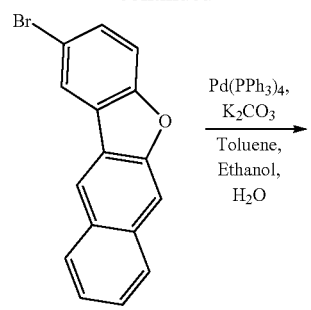

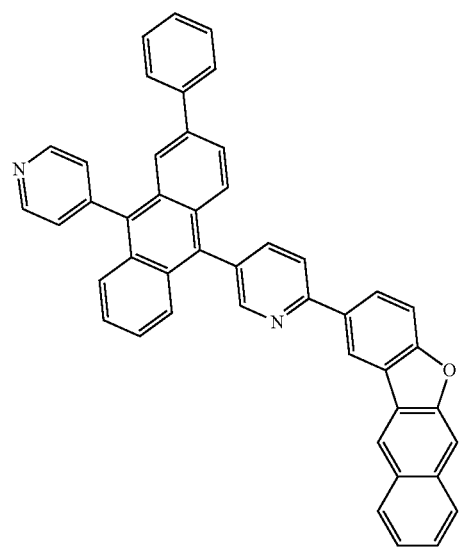

R390

In a nitrogen atmosphere, Compound A28 (9.4 g, 17.5 mmol), 2-bromobenzo[b]naphtho[2,3-d]furan (5.7 g, 19.3 mmol), Pd(PPh$_3$)$_4$ (1.0 g, 5 mol %), and potassium carbonate (7.3 g, 52.6 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R390 (8.2 g, 13.2 mmol, yield: 75%).

GC-Mass (Calcd.: 624.73 g/mol, Found: 624 g/mol).

[Synthesis Example 36] Synthesis of Compound R393

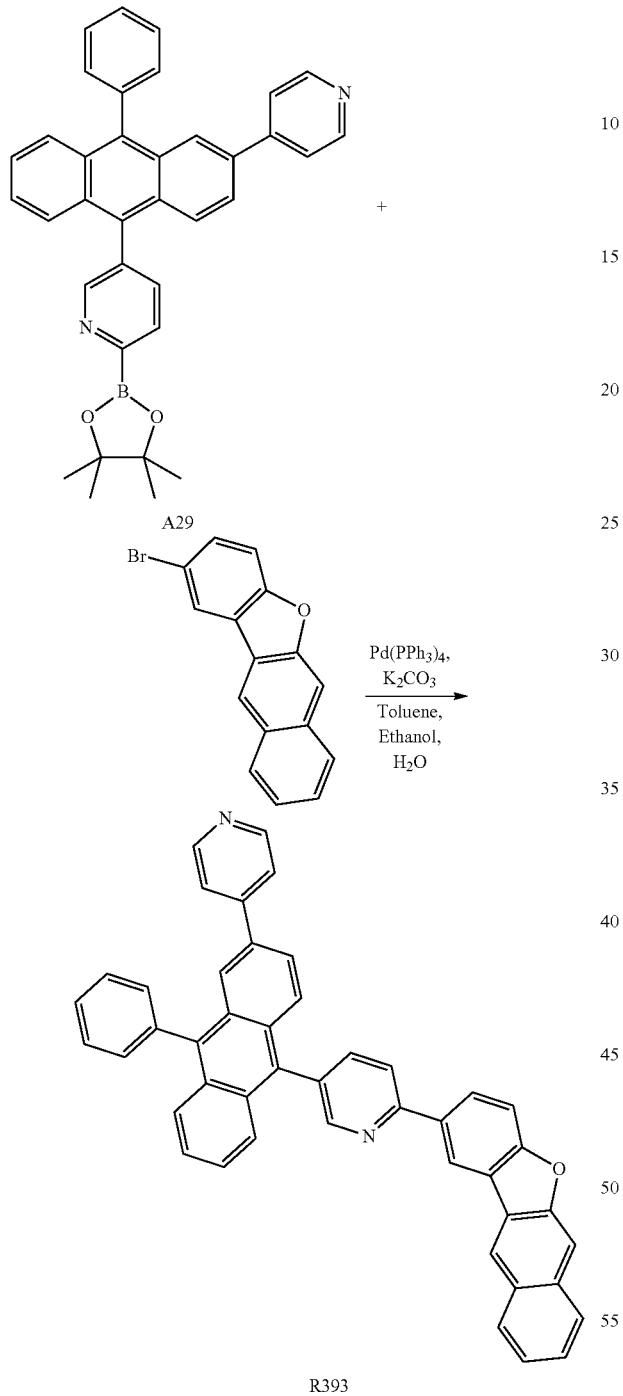

[Synthesis Example 37] Synthesis of Compound R396

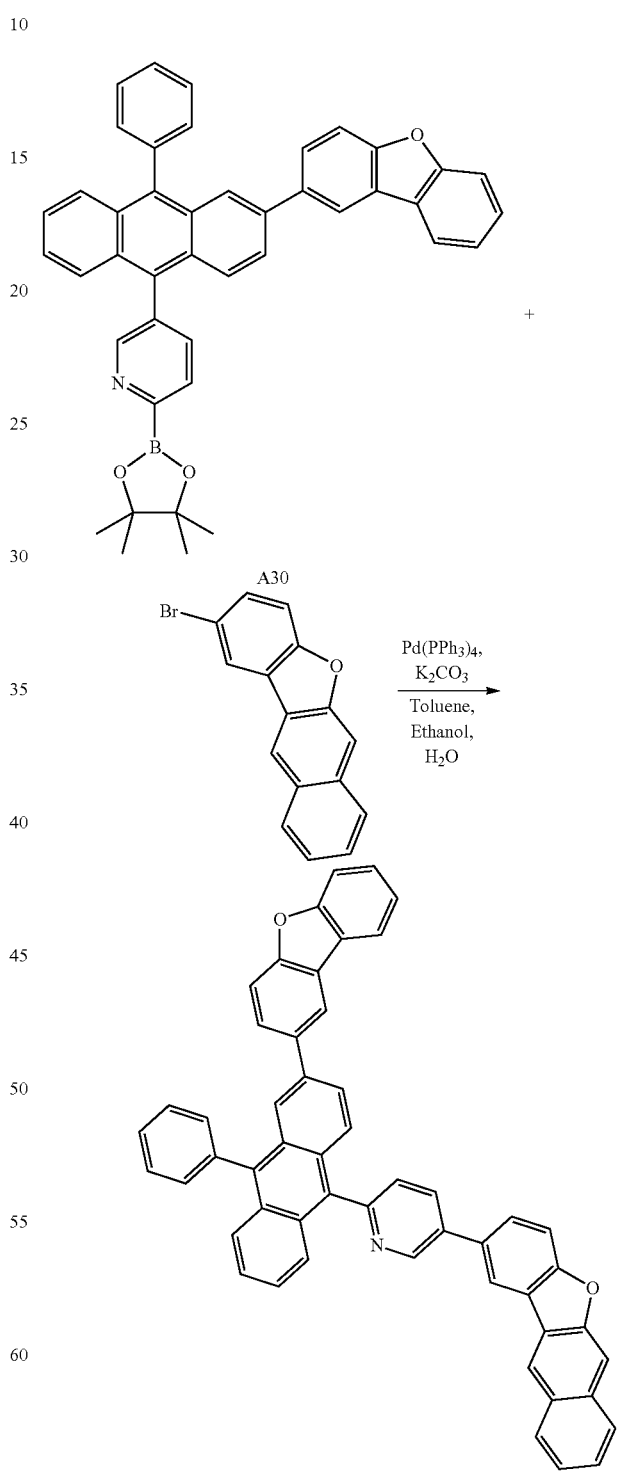

In a nitrogen atmosphere, Compound A29 (9.4 g, 17.5 mmol), 2-bromobenzo[b]naphtho[2,3-d]furan (5.7 g, 19.3 mmol), Pd(PPh$_3$)$_4$ (1.0 g, 5 mol %), and potassium carbonate (7.3 g, 52.6 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R393(8.2 g, 13.2 mmol, yield: 75%).

GC-Mass (Calcd.: 624.73 g/mol, Found: 624 g/mol).

In a nitrogen atmosphere, Compound A30 (10.9 g, 17.5 mmol), 2-bromobenzo[b]naphtho[2,3-d]furan (5.7 g, 19.3 mmol), Pd(PPh$_3$)$_4$ (1.0 g, 5 mol %), and potassium carbonate (7.3 g, 52.6 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R396 (9.4 g, 13.2 mmol, yield: 75%).

GC-Mass (Calcd.: 713.82 g/mol, Found: 713 g/mol).

[Synthesis Example 38] Synthesis of Compound R401

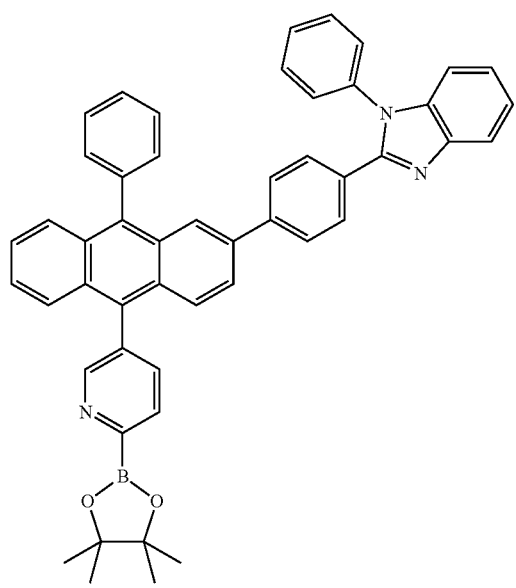

A31

+

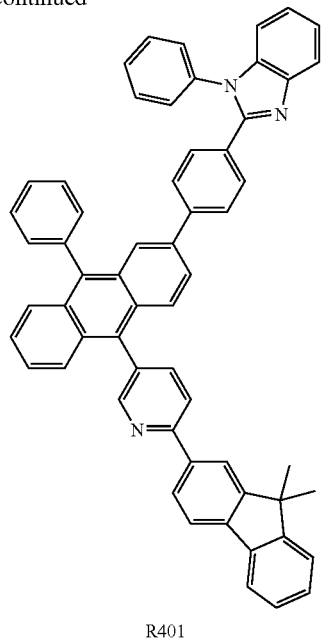

R401

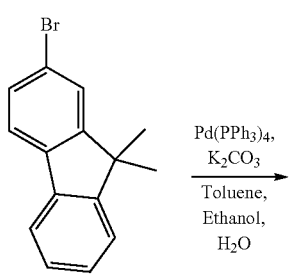

In a nitrogen atmosphere, Compound A31 (12.7 g, 17.5 mmol), 2-bromo-9,9-dimethyl-9H-fluorene (5.3 g, 19.3 mmol), Pd(PPh$_3$)$_4$ (1.0 g, 5 mol %), and potassium carbonate (7.3 g, 52.6 mmol) were added to toluene/H$_2$O/ethanol (80 ml/40 ml/40 ml) and stirred at 110° C. for three hours.

After completion of the reaction, the organic material layer was separated using methylene chloride and dried over MgSO$_4$. The solvent was removed from the organic material layer, followed by purification through column chromatography to afford the object compound R401 (9.4 g, 13.2 mmol, yield: 75%).

GC-Mass (Calcd.: 791.98 g/mol, Found: 791 g/mol).

[Synthesis Example 39] Synthesis of Compound R311

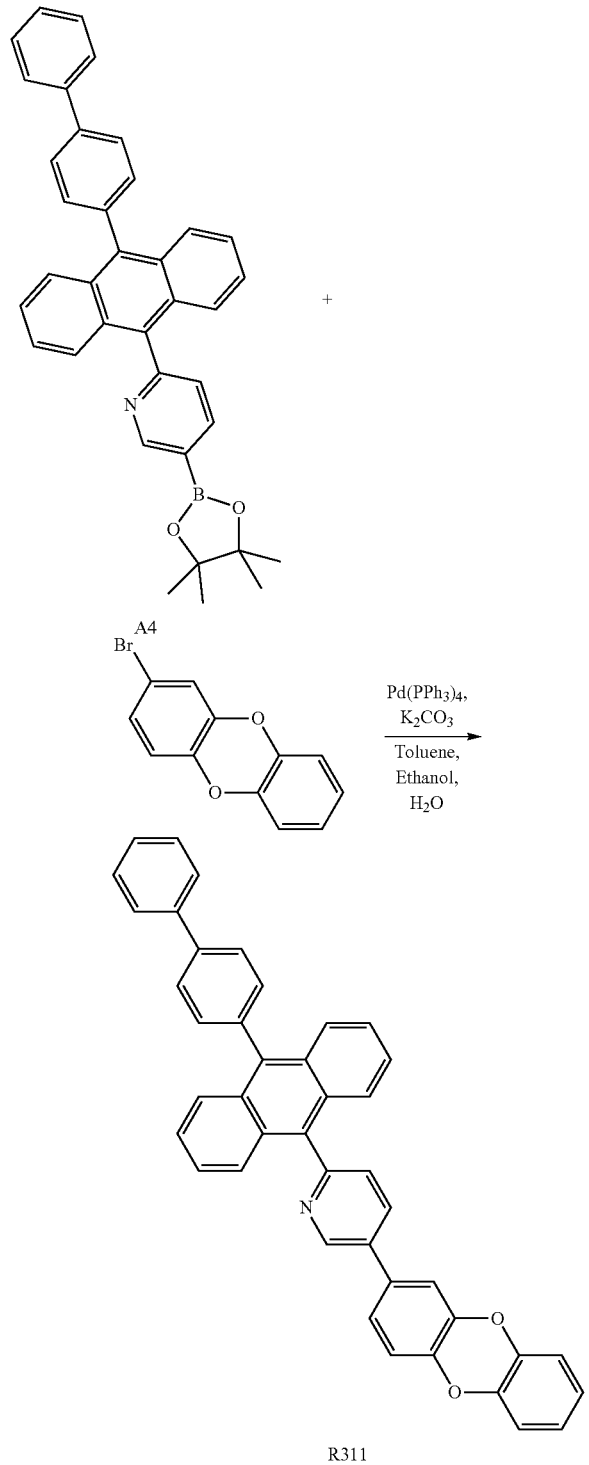

In a nitrogen atmosphere, Compound A4 (9.7 g, 18.3 mmol), 2-bromodibenzo[b,e] [1,4]dioxine (5.3 g, 20.1 mmol), Pd(PPh₃)₄ (1.0 g, 5 mol %), and potassium carbonate (7.6 g, 54.8 mmol) were added to toluene/H₂O/ethanol (80 ml/40 ml/40 ml) and stirred at 110° C. for three hours. After completion of the reaction, the organic material layer was separated using methylene chloride and dried over MgSO₄. The solvent was removed from the organic material layer, followed by purification through column chromatography to afford the object compound R311 (8.2 g, 13.9 mmol, yield: 76%).

GC-Mass (Calcd.: 598.68 g/mol, Found: 598 g/mol).

[Example 1] Fabrication of Blue Organic Electroluminescent Device

Compound R13 synthesized in Synthesis Example 1 was purified to high purity by a typically known sublimation method and then used for fabricating a blue electroluminescent device as follows.

A glass substrate coated with an ITO (Indium tin oxide) thin film 1500 Å thick was cleansed by ultrasonication in distilled water and then in a solvent such as isopropyl alcohol, acetone, methanol, etc. and then dried. The glass substrate was transferred to a UV OZONE cleaner (Power sonic 405, Hwashin Tech) and cleaned for 5 min using UV, and transferred to a vacuum evaporator.

On the transparent ITO electrode thus obtained, DS-205 (Doosan Corporation) (80 nm)/NPB (15 nm)/Compound R13 of Synthesis Example 1+5% DS-405 (Doosan Corporation) (30 nm)/Alq₃ (25 nm)/LiF (1 nm)/Al (200 nm) were deposited in that order to fabricate an organic electroluminescent device.

Structures of NPB and Alq₃ used are as follows:

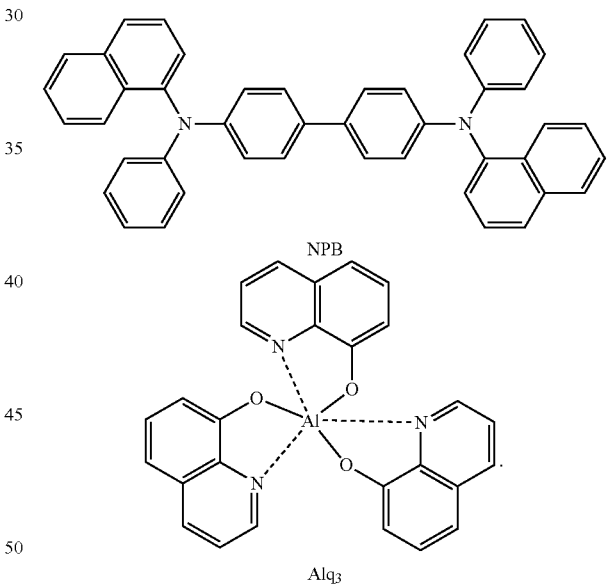

[Examples 2~30] Fabrication of Blue Organic Electroluminescent Devices

Blue organic electroluminescent devices were fabricated in the same manner as in Example 1, with the exception of using the compounds listed in Table 1, instead of Compound R13, as host materials for the light-emitting layer, respectively.

[Comparative Example 1] Fabrication of Blue Organic Electroluminescent Device

A blue organic electroluminescent device was fabricated in the same manner as in Example 1, with the exception of using the blue host material ADN, instead of Compound R13, for the light-emitting layer. The structure of ADN used is as follows:

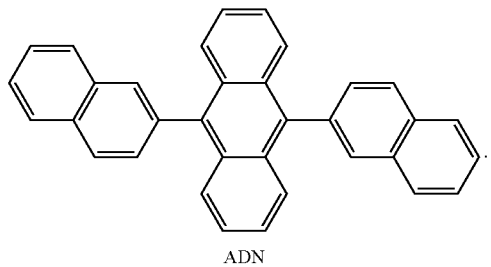 [SMILES: c1ccc2cc(-c3c4ccccc4c(-c4ccc5ccccc5c4)c4ccccc34)ccc2c1]

ADN

Evaluation Example 1

The organic electroluminescent devices fabricated in Examples 1 to 30 and Comparative Example 1 were measured for driving voltage, current efficiency, and emitting peak at a current density of 10 mA/cm², and the results are summarized in Table 1, below.

TABLE 1

| Sample | Light-Emitting Layer | Driving Volt. (V) | Current Efficiency (cd/A) | Emitting Peak (nm) |
|---|---|---|---|---|
| Example 1 | R13 | 3.3 | 12.5 | 458 |
| Example 2 | R15 | 3.4 | 11.0 | 458 |
| Example 3 | R17 | 3.3 | 10.8 | 458 |
| Example 4 | R33 | 4.0 | 8.8 | 458 |
| Example 5 | R58 | 4.0 | 8.9 | 458 |
| Example 6 | R67 | 3.0 | 7.5 | 458 |
| Example 7 | R75 | 3.1 | 7.1 | 458 |
| Example 8 | R78 | 3.2 | 7.8 | 458 |
| Example 9 | R93 | 3.5 | 11.2 | 458 |
| Example 10 | R173 | 3.8 | 11.6 | 458 |
| Example 11 | R252 | 4.1 | 12.5 | 458 |
| Example 12 | R321 | 4.2 | 11.8 | 458 |
| Example 13 | R324 | 3.5 | 11.5 | 458 |
| Example 14 | R327 | 3.9 | 10.5 | 458 |
| Example 15 | R330 | 4.2 | 10.1 | 458 |
| Example 16 | R333 | 3.9 | 11.9 | 458 |
| Example 17 | R336 | 4.2 | 10.8 | 458 |
| Example 18 | R339 | 3.2 | 10.5 | 458 |
| Example 19 | R344 | 4.3 | 12.9 | 458 |
| Example 20 | R345 | 3.8 | 9.8 | 458 |
| Example 21 | R348 | 3.2 | 8.8 | 458 |
| Example 22 | R351 | 4.4 | 12.0 | 458 |
| Example 23 | R354 | 4.1 | 12.5 | 458 |
| Example 24 | R357 | 3.9 | 10.5 | 458 |
| Example 25 | R360 | 4.2 | 9.9 | 458 |
| Example 26 | R363 | 3.2 | 11.2 | 458 |
| Example 27 | R366 | 3.3 | 10.5 | 458 |
| Example 28 | R369 | 3.5 | 11.1 | 458 |
| Example 29 | R372 | 3.2 | 9.8 | 458 |
| Example 30 | R375 | 3.0 | 10.4 | 458 |
| C. Example1 | ADN | 4.7 | 5.6 | 458 |

As shown in Table 1, the blue organic electroluminescent devices of Examples 1-30, each employing the compounds (R13-R375) according to the present disclosure as host materials for the light-emitting layer, were observed to be lower in driving voltage and higher in current efficiency than the device of Comparative Example 1 in the related art in which the AND is used. An identical level of emitting peak was measured between the devices of Examples 1-10 and the device of Comparative Example 1.

[Example 31] Fabrication of Blue Organic Electroluminescent Device

Compound R13 synthesized in Synthesis Example 1 was purified to high purity by a typically known sublimation method and then used for fabricating a blue electroluminescent device as follows.

A glass substrate coated with an ITO (Indium tin oxide) thin film 1500 Å thick was cleansed by ultrasonication in distilled water and then in a solvent such as isopropyl alcohol, acetone, methanol, etc. and then dried. The glass substrate was transferred to a UV OZONE cleaner (Power sonic 405, Hwashin Tech) and cleaned for 5 min using UV, and transferred to a vacuum evaporator.

On the transparent ITO electrode thus obtained, DS-205 (Doosan Corporation) (80 nm)/NPB (15 nm)/ADN+5% DS-405 (Doosan Corporation) (30 nm)/Compound R13/Alq₃ (25 nm)/LiF (1 nm)/Al (200 nm) were deposited in that order to fabricate an organic electroluminescent device.

Structures of NPB, ADN and Alq₃ used are as follows:

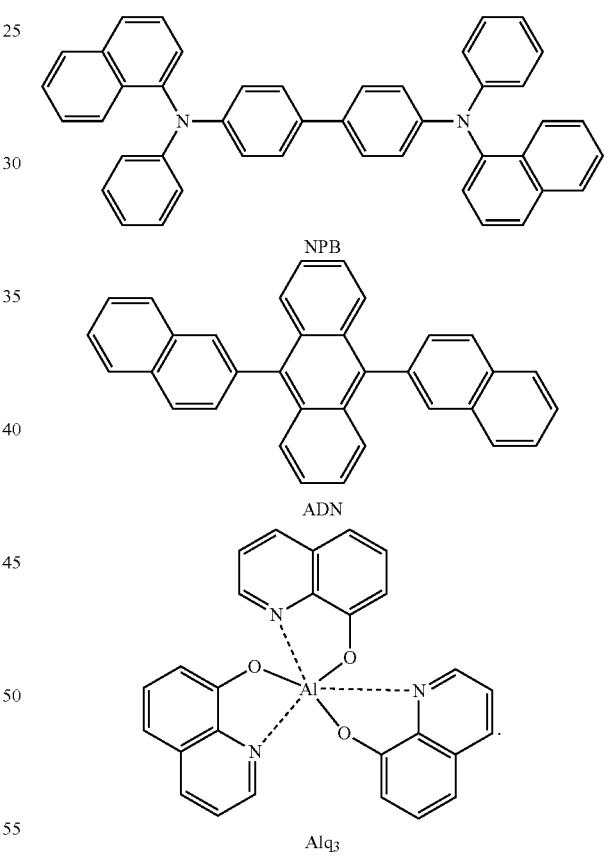

NPB

ADN

Alq₃

[Examples 32-45] Fabrication of Blue Organic Electroluminescent Devices

Blue electroluminescent devices were fabricated in the same manner as in Example 31, with the exception of using the compounds listed in Table 2, instead of Compound R13, as materials for the electron transport auxiliary layer, respectively.

[Comparative Example 2] Fabrication of Blue Organic Electroluminescent Device A blue electroluminescent device was fabricated in the same manner as in Example 31, with the exception of using the following Compound C3, instead of Compound R13, as a material for the electron transport auxiliary layer. The structure of Compound C3 used is as follows:

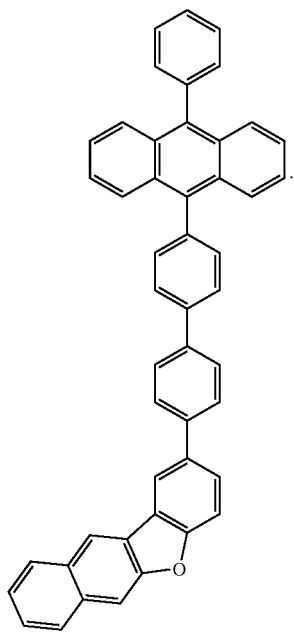

C3

[Comparative Example 3] Fabrication of Blue Organic Electroluminescent Device A blue electroluminescent device was fabricated in the same manner as in example 31, with the exception that Compound R13 was not used.

Evaluation Example 2

The organic electroluminescent devices fabricated in Examples 31 to 45 and Comparative Examples 2 and 3 were measured for driving voltage, current efficiency, and emitting peak at a current density of 10 mA/cm², and the results are summarized in Table 2, below.

TABLE 2

| Sample | Electron transport auxiliary layer | Driving Volt. (V) | Current Efficiency (cd/A) |
| --- | --- | --- | --- |
| Example 31 | R13 | 3.0 | 7.8 |
| Example 32 | R58 | 3.3 | 8.6 |
| Example 33 | R67 | 3.9 | 11.2 |
| Example 34 | R75 | 3.6 | 10.8 |
| Example 35 | R78 | 3.7 | 12.1 |
| Example 36 | R151 | 3.2 | 8.6 |
| Example 37 | R357 | 3.3 | 8.5 |
| Example 38 | R360 | 4.0 | 10.8 |
| Example 39 | R363 | 4.1 | 10.9 |
| Example 40 | R366 | 3.9 | 11.0 |
| Example 41 | R369 | 3.5 | 9.9 |
| Example 42 | R372 | 3.8 | 9.8 |
| Example 43 | R375 | 3.7 | 11.1 |
| Example 44 | R378 | 3.8 | 11.8 |
| Example 45 | R401 | 3.1 | 7.8 |
| C. Example 2 | C3 | 3.5 | 6.0 |
| C. Example 3 | — | 4.7 | 5.6 |

As shown in Table 2, the blue electroluminescent devices of Examples 31-45, each employing the compound (R13-R401) according to the present disclosure as a material for the electron transport auxiliary layer, were observed to be superior to that of Comparative Example 3, which lacked an electron transport auxiliary layer, in terms of driving voltage and emission efficiency and to that of Comparative Example 2, which employed Compound C3, in terms of current efficiency.

[Example 46] Fabrication of Green Organic Electroluminescent Device

Compound R311 synthesized in Synthesis Example 31 was purified to high purity by a typically known sublimation method and then used for fabricating a green electroluminescent device as follows.

A glass substrate coated with an ITO (Indium tin oxide) thin film 1500 Å thick was cleansed by ultrasonication in distilled water and then in a solvent such as isopropyl alcohol, acetone, methanol, etc. and then dried. The glass substrate was transferred to a UV OZONE cleaner (Power sonic 405, Hwashin Tech) and cleaned for 5 min using UV, and transferred to a vacuum evaporator.

On the transparent ITO electrode thus obtained, DS-205 (Doosan Corporation) (80 nm)/NPB (15 nm)/Alq₃ (25 nm)+ 5% C-545T (30 nm)/Compound R311/Alq₃ (25 nm)/LiF (1 nm)/Al (200 nm) were deposited in that order to fabricate an organic electroluminescent device.

Structures of NPB, C-545T, and Alq₃ used are as follows:

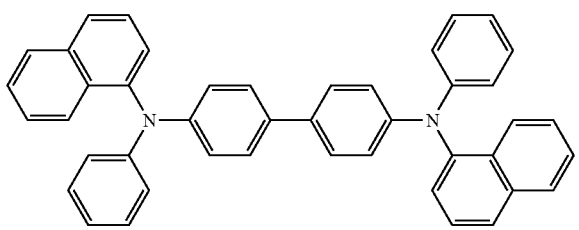

NPB

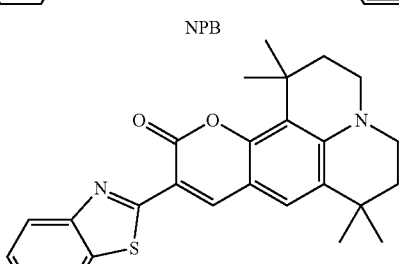

C-545T

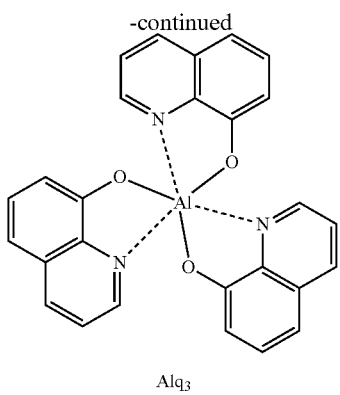

Alq3

[Examples 47-53] Fabrication of Green Organic Electroluminescent Devices

A green electroluminescent device was fabricated in the same manner as in Example 46, with the exception of using the compounds listed in Table 3, instead of Compound R311, as materials for the electron transport auxiliary layer.

[Comparative Example 4] Fabrication of Green Organic Electroluminescent Device

A green electroluminescent device was fabricated in the same manner as in Example 46, with the exception that Compound R311 was not used.

Evaluation Example 3

The organic electroluminescent devices fabricated in Examples 46 to 54 and Comparative Example 4 were measured for driving voltage, current efficiency, and emitting peak at a current density of 10 mA/cm², and the results are summarized in Table 3, below.

TABLE 3

| Sample | Electron transport auxiliary layer | Driving Volt. (V) | Current Efficiency (cd/A) | Emitting Peak (nm) |
|---|---|---|---|---|
| Example 46 | R311 | 3.2 | 12.1 | 520 |
| Example 47 | R378 | 3.0 | 12.5 | 520 |
| Example 48 | R381 | 3.9 | 15.2 | 520 |
| Example 49 | R384 | 3.8 | 13.8 | 520 |
| Example 50 | R387 | 3.9 | 14.1 | 520 |
| Example 51 | R390 | 3.8 | 13.5 | 520 |
| Example 52 | R393 | 3.5 | 12.9 | 520 |
| Example 53 | R396 | 3.4 | 12.8 | 520 |
| Example 54 | R401 | 3.9 | 14.8 | 520 |
| C. Example 4 | — | 4.7 | 11.7 | 520 |

As shown in Table 3, the green organic electroluminescent devices of Examples 46-54, each employing the compound (R311~R401) according to the present disclosure as a material for the electron transport auxiliary layer, were observed to be lower in driving voltage and higher in emission efficiency than that of Comparative Example 3, which lacked an electron transport auxiliary layer. In addition, an identical level of emitting peak was measured between the devices of Examples 46-54 and that of Comparative Example 4.

The invention claimed is:

1. A compound represented by the following Formula 2:

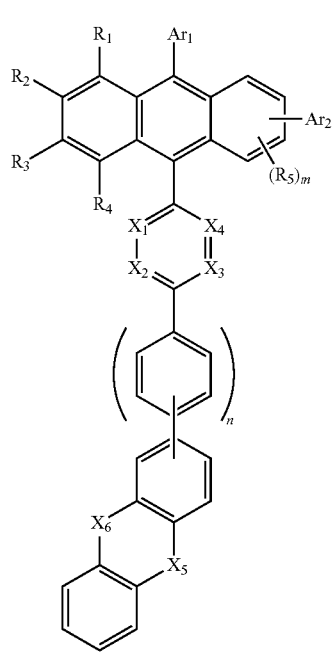

Formula 2 wherein, $X_1$ to $X_4$, which are the same or different from each other, are each independently $C(Ar_3)$ or N, with the proviso that at least one of $X_1$ to $X_4$ is N, wherein $Ar_3$ is present in a plural number, the plural $Ar_3$'s are the same or different from each other;

n is an integer of 0 to 3;

$X_5$ is selected from the group consisting of S, O, $N(Ar_4)$, and $C(Ar_5)(Ar_6)$;

$X_6$ represents a single bond or is selected from the group consisting of S, O, $N(Ar_7)$, and $C(Ar_8)(Ar_9)$;

$Ar_1$ is selected from the group consisting of a $C_6$-$C_{60}$ aryl group and a heteroaryl group having 5 to 60 nucleus atoms or optionally combines with an adjacent group to form a fused aromatic ring or fused heteroaromatic ring;

$Ar_2$ is selected from the group consisting of hydrogen, a $C_6$-$C_{60}$ aryl group, and a heteroaryl group having 5 to 60 nucleus atoms or combines with an adjacent group to form a fused aromatic ring or fused heteroaromatic ring;

$Ar_3$ to $Ar_9$ are the same or different from each other, and are each independently selected from the group consisting of hydrogen, deuterium (D), halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nucleus atoms, a $C_6$-$C_{60}$ aryl group, a heteroaryl group having 5 to 60 nucleus atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_6$-$C_{60}$ mono- or diarylphosphinyl group, and a $C_6$-$C_{60}$ arylamine group or each independently combine with an adjacent group to form a fused aromatic ring or fused heteroaromatic ring;

$R_1$ to $R_5$ are the same or different from each other, and are each independently selected from the group consisting of hydrogen, deuterium (D), halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nucleus atoms, a $C_6$-$C_{60}$ aryl group, a heteroaryl group having 5 to 60 nucleus atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_6$-$C_{60}$ arylphosphine group, a $C_6$-$C_{60}$ mono- or diarylphosphinyl group, and a $C_6$-$C_{60}$ arylamine group or each independently combine with an adjacent group to form a fused aromatic ring or fused heteroaromatic ring; and m is an integer of 1 to 3;

wherein the aryl group and the heteroaryl group in $Ar_1$ and $Ar_2$ are each independently unsubstituted or substituted with one or more substituent selected from the group consisting of a $C_1$-$C_{40}$ alkyl group, a $C_6$-$C_{60}$ aryl group, and a heteroaryl group having 5 to 60 nucleus atoms wherein the two or more substituents, if present, are the same or different from each other.

2. The compound of claim 1, wherein the compound represented by Formula 2 is a compound represented by the following Formula 6:

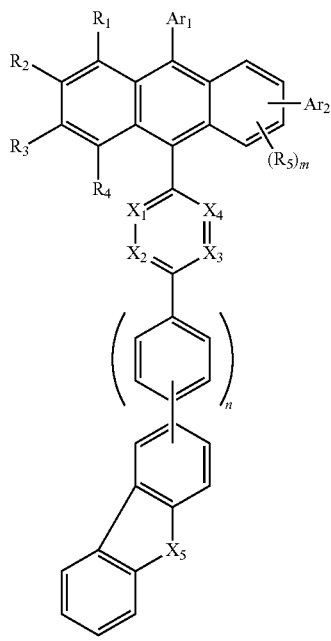

Formula 6 wherein, $R_1$ to $R_5$, $X_1$ to $X_5$, $Ar_1$, $Ar_2$, m, and n are each the same as those defined in claim 1.

3. The compound of claim 2, wherein the compound represented by Formula 6 is a compound represented by the following Formula 7:

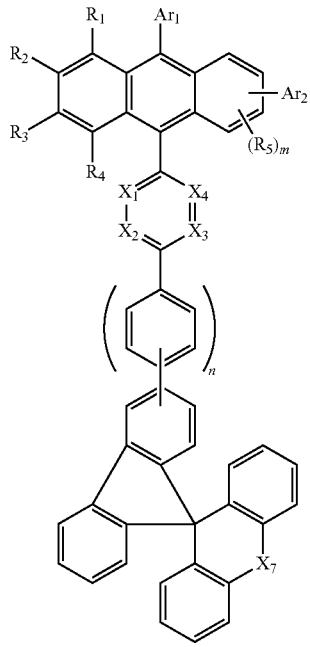

Formula 7 wherein, $R_1$ to $R_5$, $X_1$ to $X_4$, $Ar_1$, $Ar_2$, m, and n are each the same as those defined in claim 1, $X_7$ represents a single bond or is selected from the group consisting of S, O, $N(Ar_{10})$, and $C(Ar_{11})(Ar_{12})$, and $Ar_{10}$ to $Ar_{12}$ are the same or different from each other, and are each independently selected from the group consisting of hydrogen, deuterium (D), halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nucleus atoms, a $C_6$-$C_{60}$ aryl group, a heteroaryl group having 5 to 60 nucleus atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_6$-$C_{60}$ mono- or diarylphosphinyl group, and a $C_6$-$C_{60}$ arylamine group.

4. An organic electroluminescent device, comprising an anode, a cathode, and one or more organic material layers interposed between the anode and the cathode, wherein at least one of the one or more organic material layers comprises a compound represented by the following Formula 2:

Formula 2

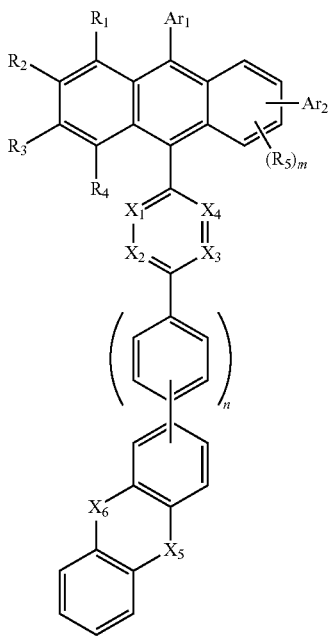

wherein, $X_1$ to $X_4$, which are the same or different from each other, are each independently $C(Ar_3)$ or N, with the proviso that at least one of $X_1$ to $X_4$ is N, wherein $Ar_3$ is present in a plural number, the plural $Ar_3$'s are the same or different from each other;

n is an integer of 0 to 3;

$X_5$ is selected from the group consisting of S, O, $N(Ar_4)$, and $C(Ar_5)(Ar_6)$;

$X_6$ represents a single bond or is selected from the group consisting of S, O, $N(Ar_7)$, and $C(Ar_8)(Ar_9)$;

$Ar_1$ is selected from the group consisting of a $C_6$-$C_{60}$ aryl group and a heteroaryl group having 5 to 60 nucleus atoms or optionally combines with an adjacent group to form a fused aromatic ring or fused heteroaromatic ring;

$Ar_2$ is selected from the group consisting of hydrogen, a $C_6$-$C_{60}$ aryl group, and a heteroaryl group having 5 to 60 nucleus atoms or combines with an adjacent group to form a fused aromatic ring or fused heteroaromatic ring;

$Ar_3$ to $Ar_9$ are the same or different from each other, and are each independently selected from the group consisting of hydrogen, deuterium (D), halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nucleus atoms, a $C_6$-$C_{60}$ aryl group, a heteroaryl group having 5 to 60 nucleus atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_6$-$C_{60}$ mono- or diarylphosphinyl group, and a $C_6$-$C_{60}$ arylamine group or each independently combine with an adjacent group to form a fused aromatic ring or fused heteroaromatic ring;

$R_1$ to $R_5$ are the same or different from each other, and are each independently selected from the group consisting of hydrogen, deuterium (D), halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nucleus atoms, a $C_6$-$C_{60}$ aryl group, a heteroaryl group having 5 to 60 nucleus atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_6$-$C_{60}$ arylphosphine group, a $C_6$-$C_{60}$ mono- or diarylphosphinyl group, and a $C_6$-$C_{60}$ arylamine group or each independently combine with an adjacent group to form a fused aromatic ring or fused heteroaromatic ring; and m is an integer of 1 to 3;

wherein the aryl group and the heteroaryl group in $Ar_1$ and $Ar_2$ are each independently unsubstituted or substituted with one or more substituent selected from the group consisting of a $C_1$-$C_{40}$ alkyl group, a $C_6$-$C_{60}$ aryl group, and a heteroaryl group having 5 to 60 nucleus atoms wherein the two or more substituents, if present, are the same or different from each other.

5. The organic electroluminescent device of claim 4, wherein the one or more organic material layers comprise a hole injection layer, a hole transport layer, a light-emitting layer, an electron transport layer, and an electron injection layer, the light-emitting layer including the compound therein.

6. The organic electroluminescent device of claim 4, wherein the one or more organic material layers comprise a hole transport layer, a hole injection layer, a light-emitting layer, an electron transport auxiliary layer, an electron transport layer, and an electron injection layer, the electron transport auxiliary layer including the compound therein.

7. The organic electroluminescent device of claim 4, wherein the compound represented by Formula 2 is a compound represented by the following Formula 6:

Formula 6

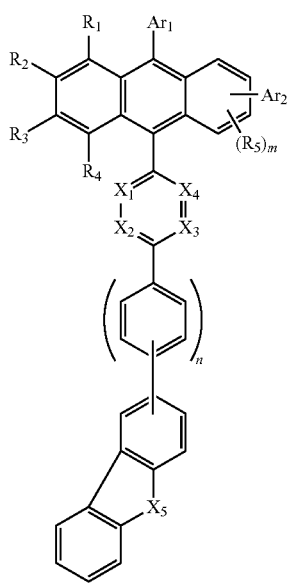

wherein, $R_1$ to $R_5$, $X_1$ to $X_5$, $Ar_1$, $Ar_2$, m, and n are each the same as those defined in claim 4.

8. The organic electroluminescent device of claim 7, wherein the compound represented by Formula 6 is a compound represented by the following Formula 7:

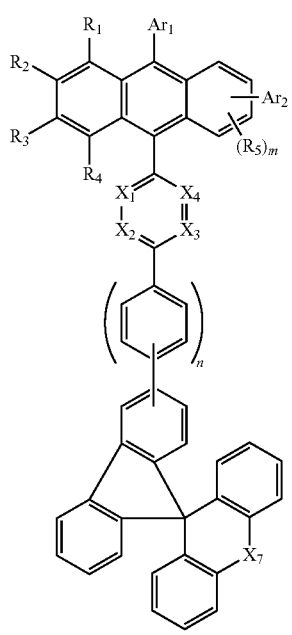

Formula 7 wherein, $R_1$ to $R_5$, $X_1$ to $X_4$, $Ar_1$, $Ar_2$, m, and n are each the same as those defined in claim 4, $X_7$ represents a single bond or is selected from the group consisting of S, O, $N(Ar_{10})$, and $C(Ar_{11})(Ar_{12})$, and $Ar_{10}$ to $Ar_{12}$ are the same or different from each other, and are each independently selected from the group consisting of hydrogen, deuterium (D), halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nucleus atoms, a $C_6$-$C_{60}$ aryl group, a heteroaryl group having 5 to 60 nucleus atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_6$-$C_{60}$ mono- or diarylphosphinyl group, and a $C_6$-$C_{60}$ arylamine group.

9. A compound represented by the following Formula 3:

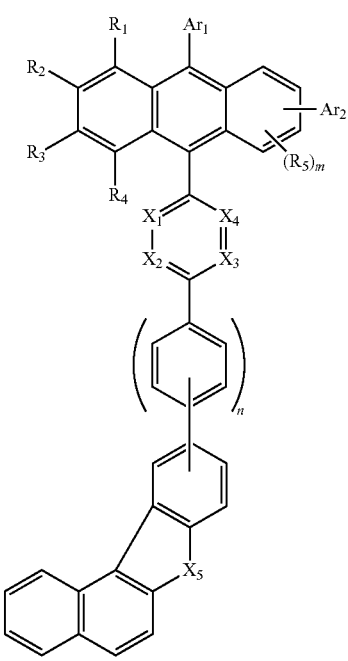

Formula 3 wherein, $X_1$ to $X_4$, which are the same or different from each other, are each independently $C(Ar_3)$ or N, with the proviso that at least one of $X_1$ to $X_4$ is N, wherein $Ar_3$ is present in a plural number, the plural $Ar_3$'s are the same or different from each other;

n is an integer of 1 to 3;

$X_5$ is S;

$Ar_1$ is selected from the group consisting of a $C_6$-$C_{60}$ aryl group and a heteroaryl group having 5 to 60 nucleus atoms or optionally combines with an adjacent group to form a fused aromatic ring or fused heteroaromatic ring;

$Ar_2$ is selected from the group consisting of hydrogen, a $C_6$-$C_{60}$ aryl group, and a heteroaryl group having 5 to 60 nucleus atoms or combines with an adjacent group to form a fused aromatic ring or fused heteroaromatic ring;

$Ar_3$ to $Ar_6$ are the same or different from each other, and are each independently selected from the group consisting of hydrogen, deuterium (D), halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nucleus atoms, a $C_6$-$C_{60}$ aryl group, a heteroaryl group having 5 to 60 nucleus atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_6$-$C_{60}$ mono- or diarylphosphinyl group, and a $C_6$-$C_{60}$ arylamine group or each independently combine with an adjacent group to form a fused aromatic ring or fused heteroaromatic ring;

$R_1$ to $R_5$ are the same or different from each other, and are each independently selected from the group consisting of hydrogen, deuterium (D), halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nucleus atoms, a $C_6$-$C_{60}$ aryl group, a heteroaryl group having 5 to 60 nucleus atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_6$-$C_{60}$ arylphosphine group, a $C_6$-$C_{60}$ mono- or diarylphosphinyl group, and a $C_6$-$C_{60}$ arylamine group or each independently combine with an adjacent group to form a fused aromatic ring or fused heteroaromatic ring; and m is an integer of 1 to 3;

wherein the aryl group and the heteroaryl group in $Ar_1$ and $Ar_2$ are each independently unsubstituted or substituted with one or more substituent selected from the group consisting of a $C_1$-$C_{40}$ alkyl group, a $C_6$-$C_{60}$ aryl group, and a heteroaryl group having 5 to 60 nucleus atoms wherein the two or more substituents, if present, are the same or different from each other.

10. An organic electroluminescent device, comprising an anode, a cathode, and one or more organic material layers interposed between the anode and the cathode, wherein at least one of the one or more organic material layers comprises a compound represented by the Formula 3 according to claim 9.

\* \* \* \* \*